US009175089B2

(12) United States Patent
Hongo et al.

(10) Patent No.: US 9,175,089 B2
(45) Date of Patent: Nov. 3, 2015

(54) ANTI-LGR5 ANTIBODIES AND IMMUNOCONJUGATES

(71) Applicant: GENENTECH INC., South San Francisco, CA (US)

(72) Inventors: Jo-Anne Hongo, Redwood City, CA (US); Weiguang Mao, San Mateo, CA (US); Paul Polakis, Mill Valley, CA (US); Andrew Polson, San Francisco, CA (US); Rajesh Vij, San Mateo, CA (US); Yan Wu, Foster City, CA (US); Wei-Ching Liang, Foster City, CA (US)

(73) Assignee: Genentech, Inc., South San Francisco, CA (US)

(*) Notice: Subject to any disclaimer, the term of this patent is extended or adjusted under 35 U.S.C. 154(b) by 50 days.

(21) Appl. No.: 13/853,620

(22) Filed: Mar. 29, 2013

(65) Prior Publication Data

US 2013/0336885 A1 Dec. 19, 2013

Related U.S. Application Data

(60) Provisional application No. 61/618,232, filed on Mar. 30, 2012, provisional application No. 61/683,048, filed on Aug. 14, 2012, provisional application No. 61/778,710, filed on Mar. 13, 2013.

(51) Int. Cl.
| | |
|---|---|
| A61K 39/395 | (2006.01) |
| A61K 39/44 | (2006.01) |
| C07K 16/28 | (2006.01) |
| C07K 16/30 | (2006.01) |
| G01N 33/68 | (2006.01) |
| A61K 51/10 | (2006.01) |
| A61K 47/48 | (2006.01) |
| A61K 39/00 | (2006.01) |

(52) U.S. Cl.
CPC ........... *C07K 16/30* (2013.01); *A61K 39/39558* (2013.01); *A61K 47/486* (2013.01); *A61K 47/48384* (2013.01); *A61K 47/48407* (2013.01); *A61K 47/48438* (2013.01); *A61K 47/48561* (2013.01); *A61K 47/48615* (2013.01); *A61K 51/1045* (2013.01); *C07K 16/28* (2013.01); *C07K 16/3046* (2013.01); *G01N 33/6893* (2013.01); *A61K 2039/505* (2013.01); *C07K 2317/24* (2013.01); *C07K 2317/33* (2013.01); *C07K 2317/73* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 3,896,111 A | 7/1975 | Kupchan et al. | |
| 4,137,230 A | 1/1979 | Hashimoto et al. | |
| 4,248,870 A | 2/1981 | Miyashita et al. | |
| 4,256,746 A | 3/1981 | Miyashita et al. | |
| 4,260,608 A | 4/1981 | Miyashita et al. | |
| 4,265,814 A | 5/1981 | Hashimoto et al. | |
| 4,294,757 A | 10/1981 | Asai | |
| 4,307,016 A | 12/1981 | Asai et al. | |
| 4,308,268 A | 12/1981 | Miyashita et al. | |
| 4,308,269 A | 12/1981 | Miyashita et al. | |
| 4,309,428 A | 1/1982 | Miyashita et al. | |
| 4,313,946 A | 2/1982 | Powell et al. | |
| 4,315,929 A | 2/1982 | Freedman et al. | |
| 4,317,821 A | 3/1982 | Miyashita et al. | |
| 4,322,348 A | 3/1982 | Asai et al. | |
| 4,331,598 A | 5/1982 | Hasegawa et al. | |
| 4,361,650 A | 11/1982 | Asai et al. | |
| 4,362,663 A | 12/1982 | Kida et al. | |
| 4,364,866 A | 12/1982 | Asai et al. | |
| 4,371,533 A | 2/1983 | Akimoto et al. | |
| 4,424,219 A | 1/1984 | Hashimoto et al. | |
| 4,450,254 A | 5/1984 | Isley et al. | |
| 4,676,980 A | 6/1987 | Segal et al. | |
| 4,737,456 A | 4/1988 | Weng et al. | |
| 4,816,567 A | 3/1989 | Cabilly et al. | |
| 5,208,020 A | 5/1993 | Chari et al. | |
| 5,362,852 A | 11/1994 | Geoghegan | |
| 5,416,064 A | 5/1995 | Chari et al. | |
| 5,500,362 A | 3/1996 | Robinson et al. | |
| 5,571,894 A | 11/1996 | Wels et al. | |
| 5,587,458 A | 12/1996 | King et al. | |
| 5,591,828 A | 1/1997 | Bosslet et al. | |
| 5,624,821 A | 4/1997 | Winter et al. | |
| 5,635,483 A | 6/1997 | Pettit et al. | |
| 5,648,237 A | 7/1997 | Carter | |
| 5,648,260 A | 7/1997 | Winter et al. | |
| 5,663,149 A | 9/1997 | Pettit et al. | |
| 5,712,374 A | 1/1998 | Kuntsmann et al. | |
| 5,714,586 A | 2/1998 | Kunstmann et al. | |

(Continued)

FOREIGN PATENT DOCUMENTS

| | | |
|---|---|---|
| EP | 328147 | 2/1989 |
| EP | 0425235 A2 | 5/1991 |

(Continued)

OTHER PUBLICATIONS

Ajani et al., "A Multi-Institutional Phase II Study of BMS-182248-01 (BR96- Doxorubicin Conjugate) Administered Every 21 Days in Patients with Advanced Gastric Adenocarcinoma" Cancer Journal 6:78-81 (2000).

Alley et al., "Antibody-drug conjugates: targeted drug delivery for cancer" Current Opinion in Chemical Biology 14:529-537 (2010).

Alley, S.C. et al., "Controlling the location of drug attachment in antibody-drug conjugates, Abstract No. 627, American Association for Cancer Research, 2004 Annual Meeting, Mar. 27-31, 2004 Proceedings of the AACR" 45:52 (2004).

(Continued)

*Primary Examiner* — Michael Pak
(74) *Attorney, Agent, or Firm* — McNeill Baur PLLC

(57) ABSTRACT

The invention provides anti-LgR5 antibodies and immunoconjugates and methods of using the same.

31 Claims, 36 Drawing Sheets

(56) References Cited

U.S. PATENT DOCUMENTS

| | | |
|---|---|---|
| 5,731,168 A | 3/1998 | Carter et al. |
| 5,739,116 A | 4/1998 | Hamann et al. |
| 5,750,373 A | 5/1998 | Garrard et al. |
| 5,767,237 A | 6/1998 | Sakakibara et al. |
| 5,767,285 A | 6/1998 | Hamann et al. |
| 5,770,429 A | 6/1998 | Lonberg et al. |
| 5,780,588 A | 7/1998 | Pettit et al. |
| 5,789,199 A | 8/1998 | Joly et al. |
| 5,821,337 A | 10/1998 | Carter et al. |
| 5,840,523 A | 11/1998 | Simmons et al. |
| 5,869,046 A | 2/1999 | Presta et al. |
| 5,959,177 A | 9/1999 | Hein et al. |
| 6,040,498 A | 3/2000 | Stomp et al. |
| 6,075,181 A | 6/2000 | Kucherlaopati et al. |
| 6,124,431 A | 9/2000 | Sakakibara et al. |
| 6,150,584 A | 11/2000 | Kucherlapati et al. |
| 6,171,586 B1 | 1/2001 | Lam et al. |
| 6,194,551 B1 | 2/2001 | Idusogie et al. |
| 6,214,345 B1 | 4/2001 | Firestone et al. |
| 6,248,516 B1 | 6/2001 | Winter et al. |
| 6,267,958 B1 | 7/2001 | Andya et al. |
| 6,333,410 B1 | 12/2001 | Chari et al. |
| 6,417,429 B1 | 7/2002 | Hein et al. |
| 6,420,548 B1 | 7/2002 | Vezina et al. |
| 6,441,163 B1 | 8/2002 | Chari et al. |
| 6,602,677 B1 | 8/2003 | Wood et al. |
| 6,602,684 B1 | 8/2003 | Umana et al. |
| 6,630,579 B2 | 10/2003 | Chari et al. |
| 6,737,056 B1 | 5/2004 | Presta |
| 6,884,799 B2 | 4/2005 | Kamal et al. |
| 6,913,748 B2 | 7/2005 | Widdison |
| 6,982,321 B2 | 1/2006 | Wiinter |
| 7,041,870 B2 | 5/2006 | Tomizuka et al. |
| 7,049,311 B1 | 5/2006 | Thurston et al. |
| RE39,151 E | 6/2006 | Chari et al. |
| 7,067,511 B2 | 6/2006 | Thurston et al. |
| 7,087,409 B2 | 8/2006 | Barbas et al. |
| 7,125,978 B1 | 10/2006 | Vezina et al. |
| 7,189,826 B2 | 3/2007 | Rodman |
| 7,265,105 B2 | 9/2007 | Thurston et al. |
| 7,276,497 B2 | 10/2007 | Chari et al. |
| 7,303,749 B1 | 12/2007 | Chari |
| 7,332,581 B2 | 2/2008 | Presta |
| 7,371,826 B2 | 5/2008 | Presta |
| 7,375,078 B2 | 5/2008 | Feng |
| 7,498,298 B2 | 3/2009 | Doronina et al. |
| 7,511,032 B2 | 3/2009 | Liu et al. |
| 7,521,541 B2 | 4/2009 | Eigenbrot et al. |
| 7,527,791 B2 | 5/2009 | Adams et al. |
| 7,528,126 B2 | 5/2009 | Howard et al. |
| 7,557,099 B2 | 7/2009 | Howard et al. |
| 7,601,354 B2 | 10/2009 | Chari |
| 7,659,241 B2 | 2/2010 | Senter et al. |
| 7,662,936 B2 | 2/2010 | Kadkhodayan et al. |
| 7,691,568 B2 | 4/2010 | Niwa et al. |
| 7,745,394 B2 | 6/2010 | Doronina et al. |
| 7,749,753 B2 | 7/2010 | Kanda et al. |
| 7,754,681 B2 | 7/2010 | Feng |
| 7,785,903 B2 | 8/2010 | Bond et al. |
| 7,829,531 B2 | 11/2010 | Senter et al. |
| 7,851,437 B2 | 12/2010 | Senter et al. |
| 7,855,275 B2 | 12/2010 | Eigenbrot et al. |
| 7,947,839 B2 | 5/2011 | Gazzard et al. |
| 7,964,566 B2 | 6/2011 | Doronina et al. |
| 7,964,597 B2 | 6/2011 | Mitchell et al. |
| 7,985,840 B2 | 7/2011 | Fuh et al. |
| 7,994,135 B2 | 8/2011 | Doronina et al. |
| 8,054,268 B2 | 11/2011 | Chen et al. |
| 8,088,387 B2 | 1/2012 | Steeves et al. |
| 8,142,784 B2 | 3/2012 | Ebens, Jr. et al. |
| 8,198,417 B2 | 6/2012 | Steeves et al. |
| 8,309,300 B2 | 11/2012 | Junutula et al. |
| 8,389,697 B2 | 3/2013 | Beria et al. |
| 8,435,488 B2 | 5/2013 | Gill et al. |
| 8,557,780 B2 | 10/2013 | Doronina et al. |
| 2002/0164328 A1 | 11/2002 | Shinkawa et al. |
| 2003/0096743 A1 | 5/2003 | Senter et al. |
| 2003/0115614 A1 | 6/2003 | Kanda et al. |
| 2003/0130189 A1 | 7/2003 | Senter et al. |
| 2003/0157108 A1 | 8/2003 | Presta |
| 2004/0093621 A1 | 5/2004 | Shitara et al. |
| 2004/0110704 A1 | 6/2004 | Yamane et al. |
| 2004/0110707 A1 | 6/2004 | Maden et al. |
| 2004/0132140 A1 | 7/2004 | Satoh et al. |
| 2005/0014934 A1 | 1/2005 | Hinton et al. |
| 2005/0031613 A1 | 2/2005 | Nakamura et al. |
| 2005/0079574 A1 | 4/2005 | Bond |
| 2005/0123536 A1 | 6/2005 | Law et al. |
| 2005/0123546 A1 | 6/2005 | Umana et al. |
| 2005/0238649 A1 | 10/2005 | Doronina et al. |
| 2005/0260186 A1 | 11/2005 | Bookbinder et al. |
| 2005/0276812 A1 | 12/2005 | Ebens et al. |
| 2006/0025576 A1 | 2/2006 | Miller et al. |
| 2006/0104968 A1 | 5/2006 | Bookbinder et al. |
| 2007/0061900 A1 | 3/2007 | Murphy et al. |
| 2007/0117126 A1 | 5/2007 | Sidhu et al. |
| 2007/0134243 A1 | 6/2007 | Gazzard et al. |
| 2007/0134759 A1 | 6/2007 | Nishiya et al. |
| 2007/0160598 A1 | 7/2007 | Dennis et al. |
| 2007/0237764 A1 | 10/2007 | Birtalan et al. |
| 2007/0292936 A1 | 12/2007 | Barthelemy et al. |
| 2008/0069820 A1 | 3/2008 | Fuh et al. |
| 2008/0171040 A1 | 7/2008 | Ebens et al. |
| 2008/0213289 A1 | 9/2008 | Francisco et al. |
| 2008/0241884 A1 | 10/2008 | Shitara et al. |
| 2009/0036431 A1 | 2/2009 | Gauzy et al. |
| 2009/0203078 A1 | 8/2009 | Ogawa et al. |
| 2009/0226465 A1 | 9/2009 | Jackson |
| 2009/0304710 A1 | 12/2009 | Park et al. |
| 2010/0034837 A1 | 2/2010 | Beria et al. |
| 2010/0047257 A1 | 2/2010 | Blanc et al. |
| 2010/0111856 A1 | 5/2010 | Gill et al. |
| 2010/0273843 A1 | 10/2010 | Feng |
| 2011/0064753 A1 | 3/2011 | Senter et al. |
| 2011/0076287 A1 | 3/2011 | Cohen et al. |
| 2011/0137017 A1 | 6/2011 | Eigenbrot et al. |
| 2011/0256157 A1 | 10/2011 | Howard et al. |
| 2011/0301334 A1 | 12/2011 | Bhakta et al. |
| 2012/0003247 A1 | 1/2012 | Doronina et al. |
| 2012/0027783 A1 | 2/2012 | Doronina et al. |
| 2012/0027784 A1 | 2/2012 | Doronina et al. |
| 2012/0034246 A1 | 2/2012 | Doronina et al. |
| 2012/0121615 A1 | 5/2012 | Flygare et al. |
| 2012/0141508 A1 | 6/2012 | Doronina et al. |
| 2012/0141509 A1 | 6/2012 | Doronina et al. |
| 2012/0141510 A1 | 6/2012 | Doronina et al. |
| 2012/0148608 A1 | 6/2012 | Doronina et al. |
| 2012/0148610 A1 | 6/2012 | Doronina et al. |
| 2012/0315645 A1 | 12/2012 | Kaur et al. |
| 2013/0028917 A1 | 1/2013 | Howard et al. |
| 2013/0216475 A1 | 8/2013 | Gill et al. |
| 2013/0266595 A1 | 10/2013 | Flygare et al. |
| 2014/0220047 A1* | 8/2014 | Doronina et al. .......... 424/181.1 |

FOREIGN PATENT DOCUMENTS

| | | |
|---|---|---|
| EP | 2216344 | 8/2010 |
| WO | 81/01145 A1 | 4/1981 |
| WO | 93/01161 A1 | 1/1993 |
| WO | 93/08829 A1 | 5/1993 |
| WO | 93/16185 A2 | 8/1993 |
| WO | 93/21232 A1 | 10/1993 |
| WO | 94/11026 A2 | 5/1994 |
| WO | 94/29351 A2 | 12/1994 |
| WO | 97/30087 A1 | 8/1997 |
| WO | 98/58964 A1 | 12/1998 |
| WO | 99/22764 A1 | 5/1999 |
| WO | 99/51642 A1 | 10/1999 |
| WO | 00/61739 A1 | 10/2000 |
| WO | 01/29246 A1 | 4/2001 |
| WO | 02/31140 A1 | 4/2002 |
| WO | 02/088172 A2 | 11/2002 |
| WO | 02/088172 A3 | 11/2002 |
| WO | 02/088172 R1 | 11/2002 |

(56) References Cited

FOREIGN PATENT DOCUMENTS

| | | |
|---|---|---|
| WO | 03/011878 A2 | 2/2003 |
| WO | 03/026577 A2 | 4/2003 |
| WO | 03/026577 A3 | 4/2003 |
| WO | 03/043583 | 5/2003 |
| WO | 03/084570 A1 | 10/2003 |
| WO | 03/085107 A1 | 10/2003 |
| WO | 03/085119 | 10/2003 |
| WO | 2004/010957 | 2/2004 |
| WO | 2004/032828 A2 | 4/2004 |
| WO | 2004/032828 A3 | 4/2004 |
| WO | 2004/056312 A2 | 7/2004 |
| WO | 2005/035586 A1 | 4/2005 |
| WO | 2005/035778 A1 | 4/2005 |
| WO | 2005/053742 A1 | 6/2005 |
| WO | 2005/081711 A2 | 9/2005 |
| WO | 2005/082023 | 9/2005 |
| WO | 2005/100402 A1 | 10/2005 |
| WO | 2005/101017 | 10/2005 |
| WO | 2005/117986 A2 | 12/2005 |
| WO | 2006/029879 A2 | 3/2006 |
| WO | 2006/034488 A2 | 3/2006 |
| WO | 2006/034488 A3 | 3/2006 |
| WO | 2006/044908 A2 | 4/2006 |
| WO | 2006/060533 | 6/2006 |
| WO | 2007/008603 A1 | 1/2007 |
| WO | 2007/008848 A2 | 1/2007 |
| WO | 2007/064345 | 6/2007 |
| WO | 2007/100385 | 9/2007 |
| WO | 2008/077546 A1 | 7/2008 |
| WO | 2009/005809 | 1/2009 |
| WO | 2009/016516 | 2/2009 |
| WO | 2009/089004 A1 | 7/2009 |
| WO | 2009/099741 A1 | 8/2009 |
| WO | 2010/009124 | 1/2010 |
| WO | 2010/016766 | 2/2010 |
| WO | 2010/099273 | 9/2010 |
| WO | 2011/056983 | 5/2011 |
| WO | 2011/130598 | 10/2011 |
| WO | 2011/153346 A1 | 12/2011 |
| WO | 2011/156328 | 12/2011 |
| WO | 2012/074757 | 6/2012 |
| WO | 2012/106587 | 8/2012 |
| WO | 2012/155019 | 11/2012 |
| WO | 2013/055987 | 4/2013 |

OTHER PUBLICATIONS

Almagro et al., "Humanization of antibodies" Frontiers in Bioscience 13:1619-1633 (Jan. 2008).
Amsberry et al., "The lactonization of 2'-hydroxyhydrocinnamic acid amides: A potential prodrug for amines" J. Org Chem 55:5867-5877 (1990).
Antonow et al., "Structure-Activity Relationships of Monomeric C2-Aryl Pyrrolo[2,1-c][1,4]benzodiazepine (PBD) Antitumor Agents" J Med Chem(53):2927-2941 (2010).
Baca et al., "Antibody humanization using monovalent phage display" J Biol Chem 272(16):10678-10684 (1997).
Bachur Anthracycline Antibiotics in Cancer Therapy "Free Radical Damage" Muggia et al., The Hague:Martinus Nijhoff,:97-102 (1981).
Boerner et al., "Production of Antigen-Specific Human Monoclonal Antibodies From In Vitro-Primed Human Splenocytes" J Immunol 147(1):86-95 (Jul. 1991).
Brennan et al., "Preparation of Biospecific Antibodies by Chemical Recombination of Monoclonal Immunoglobulin G1 Fragments" Science 229(4708):81-83 (Jul. 5, 1985).
Brodeur et al., "Mouse-human myeloma partners for the production of heterohybridomas" Monoclonal Antibody Production Techniques and Applications, pp. 51-63 (New York: Marcel Dekker, Inc.), (1987).
Brueggemann et al., "Comparison of the effector functions of human immunoglobulins using a matched set of chimeric antibodies" J. Exp. Med. 166:1351-1361 (1987).

Bubendorf et al., "Tissue microarray (TMA) technology: miniaturized pathology archives for high-throughput in situ studies" J Pathol 195:72-79 (2001).
Carter and Senter, "Antibody-drug conjugates for cancer therapy" Cancer J 14(3):154-169 (2008).
Carter et al., "Humanization of an anti-p185 HER2 antibody for human cancer therapy" P Natl Acad Sci USA :89:4285-4289 (May 1992).
Chandra et al., "A common role for various human truncated adenomatous polyposis coli isoforms in the control of beta-catenin activity and cell proliferation" PLoS One 7(4):e34479 (Apr. 3, 2012).
Chari et al., "Immunoconjugates containing novel maytansinoids: Promising anticancer drugs" Cancer Res :52:127-131 (1992).
Chari, "Targeted Cancer Therapy: Conferring Specificity to Cytotoxic Drugs" Accounts of Chemical Research :41(1):98-107 ( 2008).
Charlton, K.A., "Expression and isolation of recombinant antibody fragments in E. coli" Method Molec Biol 248:245-254 (2003).
Chen et al., "Selection and analysis of an optimized anti-VEGF antibody: crystal structure of an affinity-matured Fab in complex with antigen" J Mol Biol. 293(4):865-81 (1999).
Chothia and Lesk, "Canonical structures for the hypervariable regions of immunoglobulins" J Mol Biol 196(4):901-917 (1987).
Chowdhury, "Engineering hot spots for affinity enhancement of antibodies" Methods Molec Biol 207:179-196 (2008).
Clackson et al., "Making antibody fragments using phage display libraries" Nature 352:624-628 (Aug. 1991).
Clynes et al., "Fc receptors are required in passive and active immunity to melanoma" Proc. Natl. Acad. Sci. USA 95:652-656 (Jan. 1998).
Cragg et al., "Complement-mediated lysis by anti-CD20 mAb correlates with segregation into lipid rafts" Blood 101(3):1045-1052 (2003).
Cree et al., "Methotrexate chemosensitivity by ATP luminescence in human leukemia cell lines and in breast cancer primary cultures: comparison of the TCA-100 assay with a clonogenic assay" Anticancer Drugs 6:398-404 (1995).
Crouch et al., "The use of ATP bioluminescence as a measure of cell proliferation and cytotoxicity" J Immunol Methods 160:81-88 (1993).
Cunningham and Wells, "High-resolution epitope mapping of hGH-receptor interactions by alanine-scanning mutagenesis" Science 24:1081-1085 (Jun. 2, 1989).
Dall'Acqua et al., "Antibody humanization by framework shuffling" Methods 36:43-60 ( 2005).
de Lau et al., "Lgr5 homologues associate with Wnt receptors and mediate R-spondin signalling" Nature 476(7360):293-297 (2011).
Doronina et al., "Development of potent monoclonal antibody auristatin conjugates for cancer therapy" Nat Biotechnol 21(7):778-784 (Jul. 2003).
Doronina et al., "Enhanced activity of monomethylauristatin F through monoclonal antibody delivery: effects of linker technology on efficacy and toxicity" Bioconjug Chem 17(1):114-124 (Jan. 2006).
Dubowchik and Radia, "Monomethoxytrityl (MMT) as a versatile amino protecting group for complex prodrugs of anticancer compounds sensitive to strong acids, bases and nucleophiles" Tetrahedron Lett 38(30):5257-5260 (1997).
Dubowchik et al., "Doxorubicin immunoconjugates containing bivalent, lysosomally-cleavable dipeptide linkages" Bioorg Med Chem Lett 12:1529-32 (2002).
Duncan et al., "The binding site for C1q on IgG" Nature 322:738-740 (1988).
English Abstract of DE1033982, pp. 2 (retrieved Feb. 21, 2014).
Fellouse et al., "Synthetic antibodies from a four-amino-acid code: A dominant role for tyrosine in antigen recognition" P Natl Acad Sci USA 101(34):12467-12472 (Aug. 24, 2004).
Flatman et al., "Process analytics for purification of monoclonal antibodies" J Chromatogr 848:79-87 (2007).
Foote et al., "Antibody Framework Residues Affecting the Conformation of the Hypervariable Loops" J Mol Biol 224:487-499 (1992).

(56) References Cited

OTHER PUBLICATIONS

Fraker and Speck, "Protein and cell membrane iodinations with a sparingly soluble chloroamide, 1,3,4,6-tetrachloro-3a,6a-diphenylglycoluril" Biochem Bioph Res Co 80(4):849-857 (1978).
Francisco et al., "cAC10-vcMMAE, an anti-CD30 monomethyl auristatin E conjugate with potent and selective antitumor activity" Blood 102(4):1458-1465 (Aug. 15, 2003).
Frisch et al., "Synthesis of short polyoxyethylene-based heterobifunctional cross-linking reagents. Application to the coupling of peptides to liposomes" Bioconj Chem 7:180-186 (1996).
Gazzano-Santoro et al., "A non-radioactive complement-dependent cytotoxicity assay for anti-CD20 monoclonal antibody" J Immunol Methods 202(2):163-171 (Mar. 28, 1997).
Geoghegan and Stroh, "Site-directed conjugation of nonpeptide groups to peptides and proteins via periodate oxidation of a 2-amino alcohol. Application to modification at N-terminal serine" Bioconjugate Chem. 3:138-146 (1992).
Gerngross, T. U, "Advances in the production of human therapeutic proteins in yeasts and filamentous fungi" Nat Biotech 22(11):1409-1414 (Nov. 2004).
Graham et al., "Characteristics of a human cell line transformed by DNA from human adenovirus type 5" J Gen Virol 36(1):59-72 (Jul. 1977).
Grandi et al., "Novel anthracycline analogs" Cancer Treatment Reviews 17:133-138 (1990).
Griffiths et al., "Human anti-self antibodies with high specificity from phage display libraries" EMBO J 12(2):725-735 (1993).
Gruber et al., "Efficient tumor cell lysis mediated by a bispecific single chain antibody expressed in *Escherichia coli*" J Immunol 152:5368-5374 (1994).
Guyer et al., "Immunoglobulin binding by mouse intestinal epithelial cell receptors" J Immunol 117(2):587-593 (Aug. 1976).
Hamann, "Monoclonal antibody-drug conjugates" Expert Opin Ther Patents 15(9):1087-1103 (2005).
Hamblett et al., "Effect of drug loading on the pharmacology, pharmacokinetics and toxicity of an anti-CD30 antibody-drug conjugate," Abstract No. 624, American Association for Cancer Research; 2004 Annual Meeting, Mar. 27-31, 2004, Proceeding of the AACR' 45:52 (2004).
Hamblett et al., "Effects of drug loading on the antitumor activity of a monoclonal antibody drug conjugate" Clin Cancer Res 10:7063-7070 (2004).
Hartley et al., "SG2285, a novel C2-aryl-substituted pyrrolobenzodiazepine dimer prodrug that cross-links DNA and exerts highly potent antitumor activity" Cancer Res. 70(17):6849-6858 (2010).
Hay et al., "A 2-nitroimidazole carbamate prodrug of 5-amino-1-(chloromethyl)-3-[(5,6,7-trimethoxyindol-2-YL)carbonyl]-1,2-dihydro-3H-benz[E]indole (amino-seco-DB1-TMI) for use with ADEPT and GDEPT" Bioorg Med Chem Lett 9:2237-2242 (1999).
Hellstrom et al., "Antitumor effects of L6, an IgG2a antibody that reacts with most human carcinomas" P Natl Acad Sci USA 83:7059-7063 (Sep. 1986).
Hellstrom et al., "Strong antitumor activities of IgG3 antibodies to a human melanoma-associated ganglioside" P Natl Acad Sci USA 82:1499-1502 (Mar. 1985).
Hinman et al., "Preparation and characterization of monoclonal antibody conjugates of the calicheamicins: A novel and potent family of antitumor antibiotics" Cancer Res 53:3336-3342 (1993).
Hollinger et al., ""Diabodies": Small Bivalent and Bispecific Antibody Fragments" Proc. Natl. Acad. Sci. USA 90:6444-6448 (Jul. 1993).
Holmes et al., "Identification of Heregulin, A Specific Activator of p185[erbB2]" Science 256:1205-1210 (May 22, 1992).
Hoogenboom et al., "By-passing Immunisation; Human Antibodies from Synthetic Repertoires of Germline $V_H$ Gene Segments Rearranged in Vitro" J Mol Biol 227:381-388 (1992).
Hoogenboom et al., "Overview of antibody phage-display technology and its applications" Methods Mol Biol 178:1-37 (2002).

Howard et al., "Synthesis of a novel C2/C2'-aryl-substituted pyrrolo[2,1-c][1,4]benzodiazepine dimer prodrug with improved water solubility and reduced DNA reaction rate" Bioorg Med Chem Lett 19(22):6463-6466 (2009).
Hudson et al., "Engineered antibodies" Nature Medicine 9(1):129-134 (Jan. 2003).
Hurley et al., "Covalent Binding of Antitumor Antibiotics in the Minor Groove of DNA. Mechanism of Action of CC-1065 and the Pyrrolo(1,4)benzodiazepines" Acc Chem Res 19:230-237 (1986).
Idusogie et al., "Mapping of the C1q Binding Site on Rituxan, A Chimeric Antibody with a Human IgG1 Fc" J. Immunol 164(8):4178-4184 (2000).
Iyer & Kadambi, "Antibody drug conjugates—Trojan horses in the war on cancer" Journal of Pharmacological and Toxicological Methods 64:207-212 (2011).
Jeffrey et al., "Dipeptide-based highly potent doxorubicin antibody conjugates" Bioorganic Med Chem Letters 16:358-362 (2006).
Jubb et al., "Quantitative In Situ Hybridization of Tissue Microarrays" Methods in Molecular Biology 326:255-264 (2006).
Kam et al., "Carbon nanotubes as multifunctional biological transporters and near-infrared agents for selective cancer cell destruction" P Natl Acad Sci USA 102(33):11600-11605 (Aug. 2005).
Kanda et al., "Comparison of cell lines for stable production of fucose-negative antibodies with enhanced ADCC" Biotechnol Bioeng 94(4):680-688 (Jul. 5, 2006).
Kashmiri et al., "SDR grafting—a new approach to antibody humanization" Methods 36:25-34 (2005).
Kim et al., "Localization of the site of the murine IgG1 molecule that is involved in binding to the murine intestinal Fc receptor" Eur. J. Immunol 24:2429-2434 (1994).
Kindt et al. Kuby Immunology "Antigens and Antibodies Chapter 4" 6th ed edition, N.Y,:W.H. Freeman and Co,:p. 91 (2007).
King et al., "Monoclonal antibody conjugates of doxorubicin prepared with branched peptide linkers: Inhibition of aggregation by methoxytriethyleneglycol chains" Journal of Medical Chemistry 45:4336-4343 (2002).
Kingsbury et al., "A novel peptide delivery system involving peptidase activated prodrugs as antimicrobial agents. Synthesis and biological activity of peptidyl derivatives of 5-fluorouracil" J Med Chem 27:1447-1451 (1984).
Kirchhofer et al., "Tissue expression, protease specificity, and Kunitz domain functions of hepatocyte growth factor activator inhibitor-1B (HAI-1B), a new splice variant of HAI-1" J Biol Chem 278(38):36341-36349 (2003).
Klimka et al., "Human anti-CD30 recombinant antibodies by guided phage antibody selection using cell panning" Br J Cancer 83(2):252-260 (2000).
Klussman et al., "Secondary mAb-vcMMAE conjugates are highly sensitive reporters of antibody internalization via the lysosome pathway" Bioconjugate Chem 15:765-773 (2004).
Kohler et al., "Functional definition of the mutation cluster region of adenomatous polyposis coli in colorectal tumours" Hum Mol Genet 17(13):1978-1987 (2008).
Kohn Antibiotics "Anthramycin" Corcoran et al., New York, NY:Springer-Verlag, vol. 3:3-11 (1975).
Kostelny et al., "Formation of a bispecific antibody by the use of leucine zippers" J Immunol 148:1547-1553 (Mar. 1, 1992).
Kozbor et al., "A human hybrid myeloma for production of human monoclonal antibodies" J Immunol :133(6):3001-3005 (Dec. 1984).
Kratz et al., "Prodrugs of anthracyclines in cancer chemotherapy" Curr Med Chem 13:477-523 (2006).
Lee et al., "Bivalent antibody phage display mimics natural immunoglobulin" J Immunol Methods :284(1-2):119-132 (2004).
Lee et al., "High-affinity human antibodies from phage-displayed synthetic Fab libraries with a single framework scaffold" J Mol Biol 340(5):1073-1093 (2004).
Leimgruber et al., "Isolation and characterization of anthramycin, a new antitumor antibiotic" J Am Chem Soc 87(24):5791-5793 (1965).
Leimgruber et al., "The structure of anthramycin" J Am Chem Soc 87(24):5793-5795 (1965).
Li et al., "Human antibodies for immunotherapy development generated via a human B cell hybridoma technology" Proc Natl Acad Sci USA 103:3557-3562 (2006).

(56) References Cited

OTHER PUBLICATIONS

Li et al., "Optimization of humanized IgGs in glycoengineered Pichia pastoris" Nat Biotechnol 24(2):210-215 (Feb. 2006).
Liang et al., "Function blocking antibodies to neuropilin-1 generated from a designed human synthetic antibody phage library" J. Mol. Biol. 366:815-829 (2007).
Liu et al., "Eradication of Large Colon Tumor Xenografts by Targeted Delivery of Maytansinoids." P Natl Acad Sci USA 93:8618-8623 (1996).
Lode et al., "Targeted therapy with a novel enediyne antibiotic calicheamicin V11 effectively suppresses growth and dissemination of liver metastases in a syngeneic model of murine neuroblastoma" Cancer Res 58:2925-2928 (1998).
Lonberg, "Fully human antibodies from transgenic mouse and phage display platforms" Current Opin. Immunol 20:450-459 (2008).
Lonberg, N., "Human antibodies from transgenic animals" Nat Biotechnol 23(9):1117-11125 (2005).
Lyon et al., "Conjugation of anticancer drugs through endogenous monoclonal antibody cysteine residues" :Methods Enzymol 502:123-138 (2012).
MacCallum et al. et al., "Antibody-antigen Interactions: Contact Analysis and Binding Site Topography" J Mol Biol 262:732-745 (1996).
Mandler et al., "Immunoconjugates of geldanamycin and Anti-HER2 monoclonal antibodies: antiproliferative activity on human breast carcinoma cell lines" J National Cancer Institute 92(19):1573-1581 (Oct. 4, 2000).
Mandler et al., "Modifications in synthesis strategy improve the yield and efficacy of geldanamycin-herceptin immunoconjugates" Bioconjugate Chem 13:786-791 (2002).
Mandler et al., "Synthesis and Evaluation of Antiproliferative Activity of a Geldanamycin-Herceptin(tm) Immunoconjugate" Bioorg Med Chem Lett 10:1025-1028 (2000).
Marks et al., "By-passing immunization, Human antibodies from V-gene libraries displayed on phage" J. Mol. Biol. 222:581-597 (1991).
Marks et al., "Selection of human antibodies from phage display libraries" Methods Mol Biol. 248:161-76 (2004).
Mather et al., "Culture of testicular cells in hormone-supplemented serum-free medium" Ann NY Acad Sci 383:44-68 (1982).
Mather, "Establishment and characterization of two distinct mouse testicular epithelial cell lines" Biol Reprod 23:243-252 (1980).
McCafferty et al., "Phage Antibodies: Filamentous Phage Displaying Antibody Variable Domains" Nature 348:552-554 (Dec. 1990).
McDonagh et al., "Engineered antibody-drug conjugates with defined sites and stoichiometries of drug attachment" Protein Eng Des Sel. 19(7):299-307 (2006).
Milstein et al., "Hybrid hybridomas and their use in immunohistochemistry" Nature 305:537-540 (Oct. 6, 1983).
Morita et al., "Neonatal Lethality of LGR5 Null Mice is Associate with Ankyloglossia and Gastrointestinal Distension" Mol Cell Biol 24(22):9736-9743 (2004).
Morrison et al., "Chimeric human antibody molecules: Mouse antigen-binding domains with human constant region domains" P Natl Acad Sci USA 81:6851-6855 (Nov. 1984).
Nagy et al., "Stability of cytotoxic luteinizing hormone-releasing hormone conjugate (AN-152) containing doxorubicin 14-O-hemiglutarate in mouse and human serum in vitro: implications for the design of preclinical studies" P Natl Acad Sci USA 97(2):829-34 (Jan. 18, 2000).
Neuberger et al., "Recombinant Antibodies Possessing Novel Effector Functions" Nature 312:604-608 (Dec. 13, 1984).
Ni, "Research progress and future perspectives in antibodomics and antibodomic drugs" Xiandai Mianyixue ((Abstract only)), 26(4):265-168 (2006).
Okazaki et al., "Fucose depletion from human IgG1 oligosaccharide enhances binding enthalpy and association rate between IgG1 and FcγRIIIa" J Molec Biol 336:1239-1249 (2004).
Osbourn et al., "From rodent reagents to human therapeutics using antibody guided selection" Methods 36:61-68 (2005).

Pacciarini et al., "Phase I/II trial of nemorubicin hydrochloride in combination with cisplatin is supported by new preclinical evidences of its mechanism of action" J Clin Oncol (Abstract from 2006 ASCO Annual Meeting Proceedings (Post-Meeting Edition)), 24( SUPPL 18S):14116 (Jun. 20, 2006).
Padlan, "A possible procedure for reducing the immunogenicity of antibody variable domains while preserving their ligand-binding properties" Mol Immunol 28(4/4):489-498 (1991).
Peterson et al. Anthracycline Antibiotics in Cancer Therapy "Transport and Storage of Anthracyclines in Experimental Systems and Human Leukemia" Muggia et al., The Hague:Martinus Nijhoff,:132-146 (1981).
Petkova et al., "Enhanced half-life of genetically engineered human IgG1 antibodies in a humanized FcRn mouse model: potential application in humorally mediated autoimmune disease" Int Immunol 18(12):1759-69 (Dec. 2006).
Pettit et al., "Dolastatins 24: synthesis of (–)-dolastatin $10^1$ X-ray molecular structure of N,N-dimethylvalyl-valyl-dolaisoleuine tert-butyl ester" J Chem Soc Perkins Trans 1:859-863 (1996).
Pettit et al., "Specific activities of dolastatin 10 and peptide derivatives against cryptococcus neoformans" Antimicrob Agents and Chemotherapy 42(11):2961-2965 (Nov. 1998).
Pettit et al., "The absolute configuration and synthesis of natural (–)-Dolastatin $10^1$" J Am Chem Soc 111:5463-5465 (1989).
Pettit et al., "The dolastatins; 18: stereospecific synthesis of dolaproine" Synthesis:719-725 (Jun. 1996).
Plaks et al., "Lgr5-expressing cells are sufficient and necessary for postnatal mammary gland organogenesis" Cell Rep 3(1):70-78 (2013).
Pluckthun, A. The Pharmacology of Monoclonal Antibodies: Handbook of Pharmacology "Antibodies from *Escherichia coli*" (Chapter 11), Rosenberg and Moore, eds., Berlin:Springer-Verlag, vol. 113:269-315 (1994).
Polakis, "Arming antibodies for cancer therapy" Curr Opin Pharm 5:382-387 (2005).
Portolano et al., "Lack of promiscuity in autoantigen-specific H and L chain combinations as revealed by human H and L chain 'Roulette'" J Immunol 150(3):880-887 (Feb. 1993).
Presta et al., "Humanization of an Antibody Directed Against IgE" J Immunol 151(5):2623-2632 (Sep. 1, 1993).
Presta et al., "Humanization of an anti-vascular endothelial growth factor monoclonal antibody for the therapy of solid tumors and other disorders" Cancer Res 57:4593-4599 (Oct. 1997).
Queen et al., "A humanized antibody that binds to the interleukin 2 receptor" P Natl Acad Sci USA :86(24):10029-10033 (Dec. 1989).
Quintieri et al., "Formation and antitumor activity of PNU-159682, a major metabolite of nemorubicin in human liver microsomes" Clin Cancer Res 11:1608-17 (Feb. 15, 2005).
Quintieri et al., "In vitro cytotoxicity, cell cycle effects and DNA-binding properties of PNU-159682" Abstract (Abs #4649) Proceedings of the American Association of Cancer Research, pp. 925 (2003).
Ravetch and Kinet, "Fc receptors" Ann Rev Immunol 9:457-492 (1991).
Remington's Pharmaceutical Sciences (Table of Contents), Osol, 16 edition, Easton, PA:Mack Publishing Company,:TOC (1980).
Remington's Pharmaceutical Sciences, Oslo et al., eds., 16th edition, Mack Publishing Co. (1980).
Ricart & Tolcher, "Technology Insight: cytotoxic drug immunoconjugates for cancer therapy" Nature Clinical Practice 4(4):245-255 (2007).
Riechmann et al., "Reshaping human antibodies for therapy" Nature 332:323-327 (Mar. 1988).
Ripamonti et al., "In vivo anti-tumour activity of FCE 23762, a methoxymorpholinyl derivative of doxorubicin active on doxorubicin-resistant tumour cells" Br J Cancer 65(5):703-707 (1992).
Ripka et al., "Two chinese hamster ovary glycosylation mutants affected in the conversion of GDP-mannose to GDP-fucose" Arch Biochem Biophys 249(2):533-545 (Sep. 1986).
Rodrigues et al., "Synthesis and β-lactamase-mediated activation of a cephalosporin-taxol prodrug" Chem Biol 2:223-227 (Apr. 1995).

(56) References Cited

OTHER PUBLICATIONS

Rosok et al., "A combinatorial library strategy for the rapid humanization of anticarcinoma BR96 Fab" J Biol Chem 271(37):22611-22618 (Sep. 13, 1996).
Saleh et al., "Phase I trial of the anti-Lewis Y drug immunoconjugate BR96-doxorubicin in patients with lewis Y-expressing epithelial tumors" J Clin Oncol 18(11):2282-2292 (2000).
Saski et al., "Establishment of a novel monoclonal antibody against LGR5" Biochem Biophys Res Comm 394:498-502 (2010).
Shields et al. et al., "High resolution mapping of the binding site on human IgG1 for Fc gamma RI, Fc gamma RII, Fc gamma RIII, and FcRn and design of IgG1 variants with improved binding to the Fc gamma R" J Biol Chem 276(9):6591-6604 (Mar. 2, 2001).
Sidhu et al., "Phage-displayed antibody libraries of synthetic heavy chain complementarity determining regions" J Mol Biol 338(2):299-310 (2004).
Sims et al., "A Humanized CD18 Antibody Can Block Function without Cell Destruction" J. Immunol. 151(4):2296-2308 (Aug. 1993).
Somers et al., "The X-ray structure of a growth hormone-prolactin receptor complex" Nature 372:478-481 (1994).
Storm et al., "Effect of small changes in orientation on reaction rate" J Am Chem Soc 94:5815-5825 (1972).
Sun et al., "Enabling ScFvs as multi-drug carriers: a dendritic approach" Bioorg Med Chem 11:1761-1768 (2003).
Sun et al., "Phase I and pharmacokinetic study of nemorubicin hydrochloride (methoxymorpholino doxorubicin; PNU-152243) administered with iodinated oil via hepatic artery (IHA) to patients (pt) with unrestectable hepatocellular carcinoma (HCC)" Abstract (Abs #1448) 39th Annual Meeting of the American Society of Clinical Oncology, Chicago, IL, pp. 361 (May 31, 2003).
Sun et al., "Syntheses of dendritic linkers containing chlorambucil residues for the preparation of antibody-multidrug immunoconjugates" Bioorg Med Chem Lett 12:2213-2215 (2002).
Teicher, "Antibody-Drug Conjugate Targets" Current Cancer Drug Targets 9:982-1004 (2009).
Thurston and Bose, "Synthesis of DNA-Interactive Pyrrolo[2,1-c][1,4]benzodiazepines" Chem Rev 94:433-465 (1994).
Tian et al., "A reserve stem cell population in small intestine renders Lgr5-positive cells dispensable" Nature 478(7368):255-259 (2011).
Toki et al., "Protease-mediated fragmentation of p-amidobenzyl ethers: A new strategy for the activation of anticancer prodrugs" J Org Chem 67:1866-1872 (2002).
Tolcher et al., "Randomized phase II study of BR96-doxorubicin conjugate in patients with metastatic breast cancer" J Clin Oncol 17(2):478-484 (1999).
Torgov et al., "Generation of an intensely potent anthracycline by a monoclonal antibody—β-galactosidase conjugate" Bioconjugate Chem 16:717-21 (2005).
Traunecker et al., "Bispecific single chain molecules (Janusins) target cytotoxic lymphocytes on HIV infected cells" EMBO J 10(12):3655-3659 (1991).
Tutt et al., "Trispecific F(ab')$_3$ derivatives that use cooperative signaling via the TCR/CD3 complex and CD2 to activate and redirect resting cytotoxic T cells" J Immunol 147(1):60-69 (Jul. 1991).
Urlaub et al., "Isolation of chinese hamster cell mutants deficient in dihydrofolate reductase activity" P Natl Acad Sci USA 77(7):4216 (Jul. 1980).
van Dijk and van de Winkel, "Human antibodies as next generation therapeutics" Curr Opin Chem Biol 5(4):368-74 (Aug. 2001).
Van Dongen et al., "Immuno-PET: A navigator in monoclonal antibody development and applications" Oncologist 12:1379-1389 (2007).
Verel et al., "$^{89}$Zr Immuno-PET: Comprehensive Procedures for the production of $^{89}$Zr-labeled monoclonal antibodies" J Nucl Med 44(8):1271-1281 (Aug. 2003).
Vollmers and Brandlein, "Death by stress: natural IgM-induced apoptosis" Methods Find Exp Clin Pharmacol 27(3):185-191 (2005).
Vollmers and Brandlein, "The 'early birds': Natural IgM antibodies and immune surveillance" Histol Histopathol 20:927-937 (2005).
Walker et al., "LGR5 Is a Negative Regulator of Tumourigenicity, Antagonizes Wnt Signalling and Regulates Cell Adhesion in Colorectal Cancer Cell Lines" PLoS One 6(7):e22733 (2011).
Walker, M., "A high yielding synthesis of N-Alkyl maleimides using a novel modifiication of the Mitsunobu reaction" J Org Chem 60:5352-5355 (1995).
Wicki et al., "Kras in metastatic colorectal cancer" Swiss Med Wkly 140:w13112 (2010).
Widdison et al., "Semisynthetic Maytansine Analogues for the Targeted Treatment of Cancer" J Med Chem 49:4392-4408 (2006).
Winter et al., "Making antibodies by phage display technology" Annu Rev Immunol 12:433-455 (1994).
Woyke et al., "In vitro activities and postantifungal effects of the potent dolastatin 10 derivative auristatin PHE" Antimicrob Agents Chemother 45(12):3580-3584 (Dec. 2001).
Wright and Morrison, "Effect of glycosylation on antibody function: Implications for genetic engineering" Trends Biotechnol 15:26-32 (1997).
Wu and Kabat, "An analysis of the sequences of the variable regions of Bence Jones proteins and myeloma light chains and their implications for antibody complementarity" J Exp Med 132(2):211-250 (1970).
Yamane-Ohnuki et al., "Establishment of FUT8 knockout Chinese hamster ovary cells: an ideal host cell line for producing completely defucosylated antibodies with enhanced antibody-dependent cellular cytotoxicity" Biotechnol Bioeng 87(5):614-622 (Sep. 5, 2004).
Yazaki and Wu Methods in Molecular Biology Lo, B.K.C. (ed.), Totowa, NJ:Humana Press, vol. 248:255-268 (2004).
Yokota, "Are KRAS/BRAF mutations potent prognostic and/or predictive biomarkers in colorectal cancers?" Anticancer Agents Med Chem 12(2):163-171 (2012).
Yu et al., "The biosynthetic gene cluster of the maytansinoid antitumor agent ansamitocin from Actinosynnema pretiosum" P Natl Acad Sci USA 99(12):7968-7973 (Jun. 11, 2002).
International Search Report and Written Opinion for PCT/US2013/034629, mailed Aug. 12, 2013, 19 pages.
Hoogenboom, "Selecting and Screening Recombinant Antibody Libraries," Nature Biotechnology (2005) 23(9): 1105-1116.
Search Report for Singapore Patent Application No. 11201405881T, mailed Jun. 10, 2015 (11 pages).
Written Opinion for Singapore Patent Application No. 11201405881T, mailed Jun. 10, 2015 (13 pages).

* cited by examiner

Anti-LgR5 Monoclonal Antibodies

| Antibody | Epitope Region | FACS | | | | IHC | Western Blot | Affinity (Biacore) | Affinity (Scatchard) |
|---|---|---|---|---|---|---|---|---|---|
| | | Human | Cyno | Rat | Mouse | | | | |
| YW353 | 22-123 | +++ | +++ | neg | neg | neg | neg | 1.6 nM | 0.2 nM |
| ch8E11 | 22-323 | +++ | +++ | ++ | +++ | neg | neg | 2.4 nM | 0.4 nM (Hu)<br>0.2 nM (Mu) |
| hu8E11.v2 | 22-323 | +++ | +++ | ++ | +++ | neg | neg | 3.1 nM | 0.3-0.7 nM (Hu)<br>0.6-0.6 nM (Mu)<br>2.4-2.8 nM (Rat) |
| 2H6 | 324-423 | ++ | n.d. | n.d. | ++ | NS | +++ | 208 nM | n.d. |
| 3G12 | 324-423 | +++ | n.d. | n.d. | + | NS | +++ | 72 nM | n.d. | n.d. = not determined
NS = some nonspecific binding

| | VL (KappaIV) | VH (Group I) | Kon($10^5 M^{-1}s^{-1}$) | Koff($10^{-4}s^{-1}$) | KD(nM) |
|---|---|---|---|---|---|
| h8E11.v1 | CDR graft | CDR graft + 71S/78V | 1.53 | 7.72 | 5.05 |
| h8E11.v2 | CDR graft | CDR graft + 67A/69F/71S/78V | 2.79 | 8.53 | 3.10 |
| h8E11.v3 | CDR graft + 68R | CDR graft + 71S/78V | 1.12 | 5.3 | 4.73 |
| h8E11.v4 | CDR graft + 68R | CDR graft + 67A/69F/71S/78V | 2.54 | 9.22 | 3.63 |
| h8E11.v5 | CDR graft | CDR graft + 71R/78A | 0.65 | 9.33 | 14.35 |
| h8E11.v6 | CDR graft | CDR graft + 71A/78A | 1.43 | 20.2 | 14.13 |
| h8E11.v7 | CDR graft + 68R | CDR graft + 71R/78A | 1.17 | 25.8 | 22.05 |
| h8E11.v8 | CDR graft + 68R | CDR graft + 71A/78A | 2.42 | 21.7 | 8.97 |
| Chimeric 8E11 | Mouse 8E11 VL | Mouse 8E11 VH | 2.1 | 6.4 | 3.00 |

```
signal sequence
LGR5_human          MDTSRLGVLLSLPVLLQLATGGSSPRSGVLLRGCPTHCHCEPDGRMLLRVDCSDLGLSEL    60
LGR5_cyno_predicted XXXXXXXXXXXXXXXXXXXXXXXXXXXXXXGCPTHCHCEPDGRMLLRVDCSDLGLSEL      60
LGR5_mouse          MDTSCVHMLLSLLALLQLVAAGSSPGPDAIPRGCPSHCHCELDGRMLLRVDCSDLGLSEL    60
LGR5_rat            MDTSRVRMLLSLLALLQLVAAGSPPRPDTMPRGCPSYCHCELDGRMLLRVDCSDLGLSEL    60
                         *::.:***     ****  *:***:.*** ******.********

LGR5_human          PSNLSVFTSYLDLSMNNISQLLPNPLPSLRFLEELRLAGNALTYIPKGAFTGLYSLKVLM   120
LGR5_cyno_predicted PSNLSVFTSYLDLSMNNISQLLPNPLPSLRFLEELRLAGNALTYIPKGAFTGLYSLKVLM   120
LGR5_mouse          PSNLSVFTSYLDLSMNNISQLPASLLHRLCFLEELRLAGNALTHIPKGAFTGLHSLKVLM   120
LGR5_rat            PSNLSVFTSYLDLSMNNISQLPASLLHRLRFLEELRLAGNALTHIPKGAFAGLHSLKVLM   120
                    ********************  * *  ************:*****:**:**:*****

LGR5_human          LQNNQLRHVPTEALQNLRSLQSIRLDANHISYVPPSCFSGLHSLRHLWLDDNALTEIPVQ   180
LGR5_cyno_predicted LQNNQLRQVPTEALQNLRSLQSIRLDANHISYVPPSCFSGLHSLRHLWLDDNALTEIPVQ   180
LGR5_mouse          LQNNQLRQVPEEALQNLRSLQSIRLDANHISYVPPSCFSGLHSLRHLWLDDNALTDVPVQ   180
LGR5_rat            LQNNQLRQVPEEALQNLRSLQSIRLDANHISYVPPSCFSGLHSLRHLWLDDNALTDVPVQ   180
                    *******:**.***************************************:**:***

LGR5_human          AFRSLSALQAMTLALNKIHHIPDYAFGNLSSLVVLHLHNNRIHSLGKKCFDGLHSLETLD   240
LGR5_cyno_predicted AFRSLSALQAMTLALNKIHHIPDYAFGNLSSLVVLHLHNNRIHSLGKKCFDGLHSLETLD   240
LGR5_mouse          AFRSLSALQAMTLALNKIHHIADYAFGNLSSLVVLHLHNNRIHSLGKKCFDGLHSLETLD   240
LGR5_rat            AFRSLSALQAMTLALNKIHHIADHAFGNLSSLVVLHLHNNRIHSLGKKCFDGLHSLETLD   240
                    *********************.*:*********************************

LGR5_human          LNYNNLDEFPTAIRTLSNLKELGFHSNNIRSIPEKAFVGNPSLITIHFYDNPIQFVGRSA   300
LGR5_cyno_predicted LNYNNLDEFPTAIRTLSNLKELGFHSNNIRSIPEKAFVGNPSLITIHFYDNPIQFVGRSA   300
LGR5_mouse          LNYNNLDEFPTAIKTLSNLKELGFHSNNIRSIPERAFVGNPSLITIHFYDNPIQFVGVSA   300
LGR5_rat            LNYNNLDEFPTAIKTLSNLKELGFHSNNIRSIPERAFVGNPSLITIHFYDNPIQFVGISA   300
                    *************:********************:********************* **

LGR5_human          FQHLPELRTLTLNGASQITEFPDLTGTANLESLLTTGAQISSLPQTVCNQLPNLQVLDLS   360
LGR5_cyno_predicted FQHLPELRTLTLNGASQITEFPDLTGTANLESLLTTGAQISSLPQTVCNQLPNLQVLDLS   360
LGR5_mouse          FQHLPELRTLTLNGASHITEFPHLTGTATLESLLTGAKISSLPQAVCDQLPNLQVLDLS   360
LGR5_rat            FQHLPELRTLTLNGASQITEFPDLTGTATLESLLTGAKISSLPQTVCDQLPNLQVLDLS   360
                    ****************:*****.*****.******.*:******.:**:***********
```

FIG. 12A

```
LGR5_human            YNLLEDLPSFSVCQKLQKIDLRHNEIYEIKVDTFQQLLSLRSLNLAWNKIAIIHPNAFST 420
LGR5_cyno_predicted   YNLLEDLPSFSVCQKLQKIDLRHNEIYEIKVDTFQQLLSLRSLNLAWNKIAIIHPNAFST 420
LGR5_mouse            YNLLEDLPSLSGCQKLQKIDLRHNEIYEIKGSTFQQLFNLRSLNLAWNKIAIIHPNAFST 420
LGR5_rat              YNLLEDLPSLSGCQKLQKIDLRHNEIYEIKGGTFQQLFNLRSLNLARNKIAIIHPNAFST 420
                      ********:*.*********************** ***:*******.************

LGR5_human            LPSLIKLDLSSNLLSSFPITGLHGLTHLKLTGNHALQSLISSENFPELKVIEMPYAYQCC 480
LGR5_cyno_predicted   LPSLIKLDLSSNLLSSFPVTGLHGLTHLKLTGNHALQSLISSENFPELKIIEMPYAYQCC 480
LGR5_mouse            LPSLIKLDLSSNLLSSFPVTGLHGLTHLKLTGNRALQSLIPSANFPELKIIEMPSAYQCC 480
LGR5_rat              LPSLIKLDLSSNLLSSFPVTGLHGLTHLKLTGNRALQSLIPSANFPELKIIEMPYAYQCC 480
                      ******************:**************:*****.*:*****::***.*****

LGR5_human            AFGVCENAYKISNQWNKGDNSSMDDLHKKDAGMFQAQDERDLEDFLLDFEEDLKALHSVQ 540
LGR5_cyno_predicted   AFGVCENAYKISNQWNKGDNSSMDDLHKKDAGMFQVQDERDLEDFLLDFEEDLKALHSVQ 540
LGR5_mouse            AFGGCENVYKISNQWNKDDGNSVDDLHKKDAGLFQVQDERDLEDFLLDFEEDLKALHSVQ 540
LGR5_rat              AFGGCENVYKIPNQWNKDDSSVDDLRKKDAGLFQVQDERDLEDFLLDFEEDLKVLHSVQ 540
                      *** *** ***.*****.*.* ***:******:**.*********************:****

LGR5_human            CSPSPGPFKPCEHLLDGWLIRIGVWTIAVLALTCNALVTSTVFRSPLYISPIKLLIGVIA 600
LGR5_cyno_predicted   CSPSPGPFKPCEHLLDGWLIRIGVWTIAVLALTCNALVTSTVFRSPLYISPIKLLIGVIA 600
LGR5_mouse            CSPSPGPFKPCEHLFGSWLIRIGVWTTAVLALSCNALVALTVFRTPLYISSIKLLIGVIA 600
LGR5_rat              CSPPPGPFKPCEHLFGSWLIRIGVWTTAVLALSCNALVAFTVFRTPLYISSIKLLIGVIA 600
                      ***.**********: *.********:*****:*****::.***:****.********

LGR5_human            AVNMLTGVSSAVLAGVDAFTFGSFARHGAWWENGVGCHVIGFLSIFASESSVFLLTLAAL 660
LGR5_cyno_predicted   VVNMLTGVSSAVLAGVDAFTFGSFARHGAWWENGVGCQVIGFLSIFASESSVFLLTLAAL 660
LGR5_mouse            VVDILMGVSSAVLAAVDAFTFGRFEAQHGAWEDGIGCQIVGFLSIFASESSIFLLTLAAL 660
LGR5_rat              VVDILMGVSSAILAVVDTFTFGSFAQHGAWEGGIGCQIVGFLSIFASESSVFLLTLAAL 660
                      .:::* ******:**.**:**** * :*****::*:***:******* **:*******

LGR5_human            ERGFSVKYSAKFETKAPFSSLKVIILLCALLALTMAAVPLLGGSKYGASPLCLPLPFGEP 720
LGR5_cyno_predicted   ERGFSVKCSAKFETKAPFSSLKVIILLCALLALTMAAVPLLGGSEYGASPLCLPLPFGEP 720
LGR5_mouse            ERGFSVKCSSKFEVKAPLFSLRAIVLLCVLLALTIATIPLLGGSKYNASPLCIPLPFGEP 720
LGR5_rat              ERGFSVKCSSKFEMKAPLSSLKAIILLCVLLAIILCVLLALTIATVPLLGGSEYNASPLCIPLPFGEP 720
                      ******* *:***:***: **:.*:***:***:  ..:::****.* ******:******
```

FIG. 12B

```
LGR5_human             STMGYMVALILLNSLCFLMMTIAYTKLYCNLDKGDLENIWDCSMVKHIALLLFTNCILNC 780
LGR5_cyno_predicted    STTGYMVALILLNSLCFLMMTIAYTKLYCNLDKGDLENIWDCSMVKHIALLLFTNCILYC 780
LGR5_mouse             STTGYMVALVLLNSLCFLIMTIAYTKLYCSLEKGELENLWDCSMVKHIALLLFANCILYC 780
LGR5_rat               STTGYMVALVLLNSLCFLIMTIAYTRLYCSLEKGELENLWDCSMVKHTALLLFTNCILYC 780
                       ** ******:*******:*:***::*** *:*  **** *******:***** ** * *

LGR5_human             PVAFLSFSSLINLTFISPEVIKFILLVVPLPACLNPLLYILFNPHFKEDLVSLRKQTYV 840
LGR5_cyno_predicted    PVAFLSFSSLLNLTFISPEVIKFILLVIVPLPACLNPLLYILFNPHFKEDLVSLGKQTYF 840
LGR5_mouse             PVAFLSFSSLLNLTFISPDVIKFILLVIVPLPSCLNPLLYIVFNPHFKEDMGSLGKHTRF 840
LGR5_rat               PVAFLSFSSLLNLTFISPEVIKFILLVIVPLPACLNPLLYIVFNPHFKEDMGSLGKQTRF 840
                       **********:*******:********::***:*******::*******: ** **:*:  .

LGR5_human             WTRSKHPSLMSINSDDVEKQSCDSTQALVTFTSSSITYDLPPSSVPSPAYPVTESCHLSS 900
LGR5_cyno_predicted    WTRSKHPSLMSINSDDVEKQSCDSTQALVTFTSSSIAYDLPPSSVPSPAYPVTESCHLSS 900
LGR5_mouse             WMRSKHASLLSINSDDVEKRSCESTQALVSFTHASIAYDLPSTSGASPAYPMTESCHLSS 900
LGR5_rat               WTRAKHPSLLSINSDDVEKRSCDSTQALVSFTHASIAYDLPSDSGSSPAYPMTESCHLSS 900
                       * *:**.**:*********.**:******:** :**:*****..  .****:*******

LGR5_human             VAFVPCL 907    SEQ ID NO: 67
LGR5_cyno_predicted    VAFVPCL 907    SEQ ID NO: 69
LGR5_mouse             VAFVPCL 907    SEQ ID NO: 72
LGR5_rat               VAFVPCL 907    SEQ ID NO: 70
                       *******
```

*FIG. 12C*

A
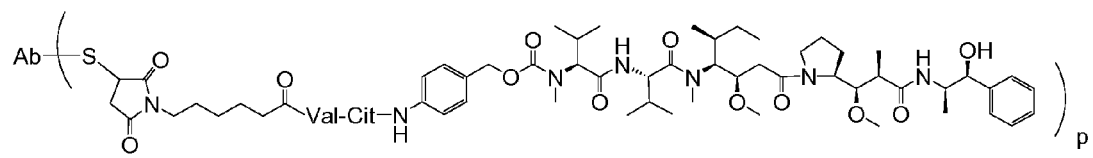
B
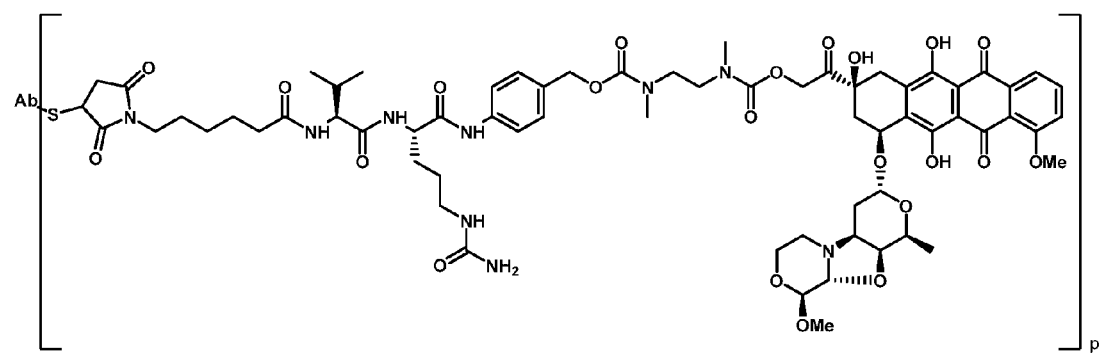
C
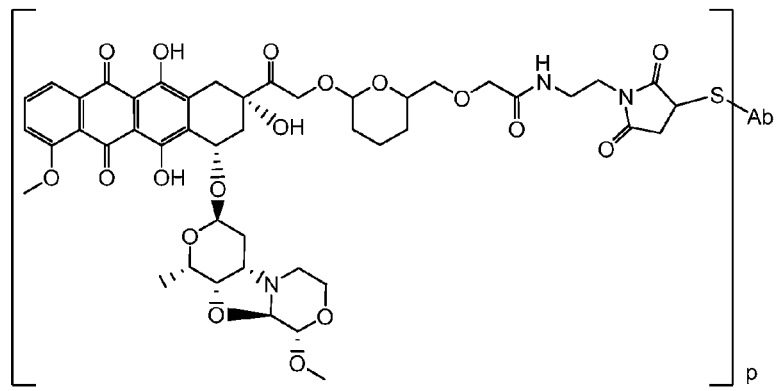
FIG. 35

D
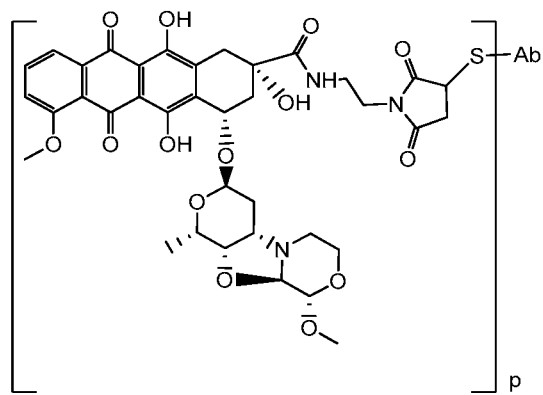
E
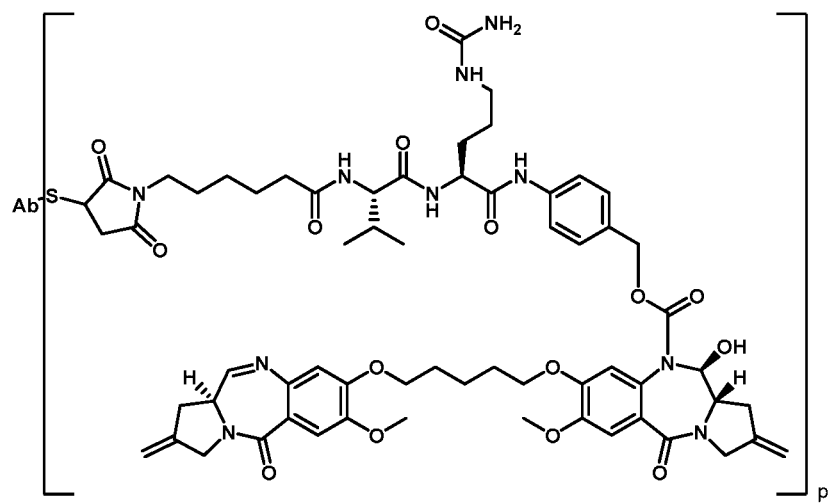
FIG. 35 (cont.)

SEQUENCE LISTING

<160> NUMBER OF SEQ ID NOS: 86

<210> SEQ ID NO 1
<211> LENGTH: 114
<212> TYPE: PRT

<213> ORGANISM: Artificial Sequence
<220> FEATURE:
<223> OTHER INFORMATION: Synthetic: hukIV

<400> SEQUENCE: 1

Asp Ile Val Met Thr Gln Ser Pro Asp Ser Leu Ala Val Ser Leu Gly
1               5                   10                  15

Glu Arg Ala Thr Ile Asn Cys Lys Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Phe Thr Phe Gly Gln Gly Thr Lys Val Glu Ile
            100                 105                 110

Lys Arg

<210> SEQ ID NO 2
<211> LENGTH: 112
<212> TYPE: PRT
<213> ORGANISM: Artificial Sequence
<220> FEATURE:
<223> OTHER INFORMATION: Synthetic: huVH1

<400> SEQUENCE: 2

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Ile
        35                  40                  45

Gly Trp Ile Asn Pro Gly Ser Gly Asn Thr Asn Tyr Ala Gln Lys Phe
50                  55                  60

Gln Gly Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Phe Asp Tyr Trp Gly Gln Gly Thr Leu Val Thr Val Ser Ser
            100                 105                 110

<210> SEQ ID NO 3
<211> LENGTH: 112
<212> TYPE: PRT
<213> ORGANISM: Artificial Sequence
<220> FEATURE:
<223> OTHER INFORMATION: Synthetic: mu8E11 light chain variable region

<400> SEQUENCE: 3

Asn Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Asn Ser Phe Met His Trp Tyr Gln Gln Lys Pro Gly Gln Pro Pro
        35                  40                  45

```
Lys Leu Leu Ile Tyr Leu Ala Ser Asn Leu Glu Ser Gly Val Pro Ala
 50                  55                  60

Arg Phe Ser Gly Ser Gly Ser Arg Thr Asp Phe Thr Leu Thr Ile Asp
 65                  70                  75                  80

Pro Val Glu Ala Asp Asp Ala Ala Thr Tyr Tyr Cys Gln Gln Asn Tyr
                 85                  90                  95

Glu Asp Pro Phe Thr Phe Gly Ser Gly Thr Lys Val Glu Ile Lys Arg
            100                 105                 110
```

<210> SEQ ID NO 4
<211> LENGTH: 118
<212> TYPE: PRT
<213> ORGANISM: Artificial Sequence
<220> FEATURE:
<223> OTHER INFORMATION: Synthetic: mu8E11 heavy chain variable region

<400> SEQUENCE: 4

```
Gln Val Gln Leu Gln Gln Ser Gly Thr Glu Leu Met Lys Pro Gly Ala
 1               5                  10                  15

Ser Val Lys Ile Ser Cys Lys Ala Thr Gly Tyr Thr Phe Ser Ala Tyr
                 20                  25                  30

Trp Ile Glu Trp Ile Lys Gln Arg Pro Gly His Gly Leu Glu Trp Ile
             35                  40                  45

Gly Glu Ile Leu Pro Gly Ser Asp Ser Thr Asp Tyr Asn Glu Lys Phe
 50                  55                  60

Lys Val Lys Ala Thr Phe Ser Ser Asp Thr Ser Ser Asn Thr Val Tyr
 65                  70                  75                  80

Ile Gln Leu Asn Ser Leu Thr Tyr Glu Asp Ser Ala Val Tyr Tyr Cys
                 85                  90                  95

Ala Arg Gly Gly His Tyr Gly Ser Leu Asp Tyr Trp Gly Gln Gly Thr
            100                 105                 110

Thr Leu Lys Val Ser Ser
        115
```

<210> SEQ ID NO 5
<211> LENGTH: 112
<212> TYPE: PRT
<213> ORGANISM: Artificial Sequence
<220> FEATURE:
<223> OTHER INFORMATION: Synthetic: hu8E11.v1 light chain variable
      region

<400> SEQUENCE: 5

```
Asp Ile Val Met Thr Gln Ser Pro Asp Ser Leu Ala Val Ser Leu Gly
 1               5                  10                  15

Glu Arg Ala Thr Ile Asn Cys Arg Ala Ser Glu Ser Val Asp Asn Tyr
                 20                  25                  30

Gly Asn Ser Phe Met His Trp Tyr Gln Gln Lys Pro Gly Gln Pro Pro
             35                  40                  45

Lys Leu Leu Ile Tyr Leu Ala Ser Asn Leu Glu Ser Gly Val Pro Asp
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln Asn Tyr
                 85                  90                  95

Glu Asp Pro Phe Thr Phe Gly Gln Gly Thr Lys Val Glu Ile Lys Arg
            100                 105                 110
```

```
<210> SEQ ID NO 6
<211> LENGTH: 118
<212> TYPE: PRT
<213> ORGANISM: Artificial Sequence
<220> FEATURE:
<223> OTHER INFORMATION: Synthetic: hu8E11.v1 heavy chain variable
      region

<400> SEQUENCE: 6

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Ala Tyr
            20                  25                  30

Trp Ile Glu Trp Val Arg Gln Ala Pro Gly Gln Gly Leu Glu Trp Ile
        35                  40                  45

Gly Glu Ile Leu Pro Gly Ser Asp Ser Thr Asp Tyr Asn Glu Lys Phe
    50                  55                  60

Lys Val Arg Val Thr Ile Thr Ser Asp Thr Ser Thr Ser Thr Val Tyr
65                  70                  75                  80

Leu Glu Leu Ser Ser Leu Arg Ser Glu Asp Thr Ala Val Tyr Tyr Cys
                85                  90                  95

Ala Arg Gly Gly His Tyr Gly Ser Leu Asp Tyr Trp Gly Gln Gly Thr
            100                 105                 110

Leu Val Thr Val Ser Ser
        115

<210> SEQ ID NO 7
<211> LENGTH: 112
<212> TYPE: PRT
<213> ORGANISM: Artificial Sequence
<220> FEATURE:
<223> OTHER INFORMATION: Synthetic: hu8E11.v2 light chain variable
      region

<400> SEQUENCE: 7

Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Ser Val Asp Asn Tyr
            20                  25                  30

Gly Asn Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Asn Tyr
                85                  90                  95

Glu Asp Pro Phe Thr Phe Gly Gln Gly Thr Lys Val Glu Ile Lys Arg
            100                 105                 110

<210> SEQ ID NO 8
<211> LENGTH: 118
<212> TYPE: PRT
<213> ORGANISM: Artificial Sequence
<220> FEATURE:
<223> OTHER INFORMATION: Synthetic: hu8E11.v2 heavy chain variable
      region

<400> SEQUENCE: 8

Glu Val Gln Leu Val Gln Ser Gly Ala Glu Val Lys Lys Pro Gly Ala
1               5                   10                  15
```

Ser Val Lys Val Ser Cys Lys Ala Ser Gly Tyr Thr Phe Ser Ala Tyr
            20                  25                  30

Trp Ile Glu Trp Val Arg Gln Ala Pro Gly Gln Gly Leu Glu Trp Ile
        35                  40                  45

Gly Glu Ile Leu Pro Gly Ser Asp Ser Thr Asp Tyr Asn Glu Lys Phe
    50                  55                  60

Lys Val Arg Ala Thr Phe Thr Ser Asp Thr Ser Thr Ser Thr Val Tyr
65                  70                  75                  80

Leu Glu Leu Ser Ser Leu Arg Ser Glu Asp Thr Ala Val Tyr Tyr Cys
                85                  90                  95

Ala Arg Gly Gly His Tyr Gly Ser Leu Asp Tyr Trp Gly Gln Gly Thr
            100                 105                 110

Leu Val Thr Val Ser Ser
        115

<210> SEQ ID NO 9
<211> LENGTH: 112
<212> TYPE: PRT
<213> ORGANISM: Artificial Sequence
<220> FEATURE:
<223> OTHER INFORMATION: Synthetic: hu8E11.v3 light chain variable
      region

<400> SEQUENCE: 9

Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Ser Val Asp Asn Tyr
            20                  25                  30

Gly Asn Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Asp
    50                  55                  60

Arg Phe Ser Gly Ser Gly Ser Arg Thr Asp Phe Thr Leu Thr Ile Ser
65                  70                  75                  80

Ser Leu Gln Ala Glu Asp Val Ala Val Tyr Tyr Cys Gln Gln Asn Tyr
                85                  90                  95

Glu Asp Pro Phe Thr Phe Gly Gln Gly Thr Lys Val Glu Ile Lys Arg
            100                 105                 110

<210> SEQ ID NO 10
<211> LENGTH: 118
<212> TYPE: PRT
<213> ORGANISM: Artificial Sequence
<220> FEATURE:
<223> OTHER INFORMATION: Synthetic: hu8E11.v3 heavy chain variable
      region

<400> SEQUENCE: 10

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Ala Tyr
            20                  25                  30

Trp Ile Glu Trp Val Arg Gln Ala Pro Gly Gln Gly Leu Glu Trp Ile
        35                  40                  45

Gly Glu Ile Leu Pro Gly Ser Asp Ser Thr Asp Tyr Asn Glu Lys Phe
    50                  55                  60

Lys Val Arg Val Thr Ile Thr Ser Asp Thr Ser Thr Ser Thr Val Tyr
65                  70                  75                  80

Leu Glu Leu Ser Ser Leu Arg Ser Glu Asp Thr Ala Val Tyr Tyr Cys
                85                  90                  95

Ala Arg Gly Gly His Tyr Gly Ser Leu Asp Tyr Trp Gly Gln Gly Thr
            100                 105                 110

Leu Val Thr Val Ser Ser
        115

<210> SEQ ID NO 11
<211> LENGTH: 112
<212> TYPE: PRT
<213> ORGANISM: Artificial Sequence
<220> FEATURE:
<223> OTHER INFORMATION: Synthetic: hu8E11.v4 light chain variable
      region

<400> SEQUENCE: 11

Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Ser Val Asp Asn Tyr
            20                  25                  30

Gly Asn Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Asp
    50                  55                  60

Arg Phe Ser Gly Ser Gly Ser Arg Thr Asp Phe Thr Leu Thr Ile Ser
65                  70                  75                  80

Ser Leu Gln Ala Glu Asp Val Ala Val Tyr Tyr Cys Gln Gln Asn Tyr
                85                  90                  95

Glu Asp Pro Phe Thr Phe Gly Gln Gly Thr Lys Val Glu Ile Lys Arg
            100                 105                 110

<210> SEQ ID NO 12
<211> LENGTH: 118
<212> TYPE: PRT
<213> ORGANISM: Artificial Sequence
<220> FEATURE:
<223> OTHER INFORMATION: Synthetic: hu8E11.v4 heavy chain variable
      region

<400> SEQUENCE: 12

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Ala Tyr
            20                  25                  30

Trp Ile Glu Trp Val Arg Gln Ala Pro Gly Gln Gly Leu Glu Trp Ile
        35                  40                  45

Gly Glu Ile Leu Pro Gly Ser Asp Ser Thr Asp Tyr Asn Glu Lys Phe
    50                  55                  60

Lys Val Arg Ala Thr Phe Thr Ser Asp Thr Ser Thr Ser Thr Val Tyr
65                  70                  75                  80

Leu Glu Leu Ser Ser Leu Arg Ser Glu Asp Thr Ala Val Tyr Tyr Cys
                85                  90                  95

Ala Arg Gly Gly His Tyr Gly Ser Leu Asp Tyr Trp Gly Gln Gly Thr
            100                 105                 110

Leu Val Thr Val Ser Ser
        115

<210> SEQ ID NO 13

```
<211> LENGTH: 112
<212> TYPE: PRT
<213> ORGANISM: Artificial Sequence
<220> FEATURE:
<223> OTHER INFORMATION: Synthetic: hu8E11.v5 light chain variable
      region

<400> SEQUENCE: 13

Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Ser Val Asp Asn Tyr
            20                  25                  30

Gly Asn Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Asn Tyr
                85                  90                  95

Glu Asp Pro Phe Thr Phe Gly Gln Gly Thr Lys Val Glu Ile Lys Arg
            100                 105                 110

<210> SEQ ID NO 14
<211> LENGTH: 118
<212> TYPE: PRT
<213> ORGANISM: Artificial Sequence
<220> FEATURE:
<223> OTHER INFORMATION: Synthetic: hu8E11.v5 heavy chain variable
      region

<400> SEQUENCE: 14

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Ala Tyr
            20                  25                  30

Trp Ile Glu Trp Val Arg Gln Ala Pro Gly Gln Gly Leu Glu Trp Ile
        35                  40                  45

Gly Glu Ile Leu Pro Gly Ser Asp Ser Thr Asp Tyr Asn Glu Lys Phe
    50                  55                  60

Lys Val Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Gly Gly His Tyr Gly Ser Leu Asp Tyr Trp Gly Gln Gly Thr
            100                 105                 110

Leu Val Thr Val Ser Ser
        115

<210> SEQ ID NO 15
<211> LENGTH: 112
<212> TYPE: PRT
<213> ORGANISM: Artificial Sequence
<220> FEATURE:
<223> OTHER INFORMATION: Synthetic: hu8E11.v6 light chain variable
      region

<400> SEQUENCE: 15

Asp Ile Val Met Thr Gln Ser Pro Asp Ser Leu Ala Val Ser Leu Gly
1               5                   10                  15
```

```
Glu Arg Ala Thr Ile Asn Cys Arg Ala Ser Glu Ser Val Asp Asn Tyr
                20                  25                  30

Gly Asn Ser Phe Met His Trp Tyr Gln Gln Lys Pro Gly Gln Pro Pro
            35                  40                  45

Lys Leu Leu Ile Tyr Leu Ala Ser Asn Leu Glu Ser Gly Val Pro Asp
        50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Asn Tyr
                85                  90                  95

Glu Asp Pro Phe Thr Phe Gly Gln Gly Thr Lys Val Glu Ile Lys Arg
            100                 105                 110
```

<210> SEQ ID NO 16
<211> LENGTH: 118
<212> TYPE: PRT
<213> ORGANISM: Artificial Sequence
<220> FEATURE:
<223> OTHER INFORMATION: Synthetic: hu8E11.v6 heavy chain variable
      region

<400> SEQUENCE: 16

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Ala Tyr
                20                  25                  30

Trp Ile Glu Trp Val Arg Gln Ala Pro Gly Gln Gly Leu Glu Trp Ile
            35                  40                  45

Gly Glu Ile Leu Pro Gly Ser Asp Ser Thr Asp Tyr Asn Glu Lys Phe
        50                  55                  60

Lys Val Arg Val Thr Ile Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Gly Gly His Tyr Gly Ser Leu Asp Tyr Trp Gly Gln Gly Thr
            100                 105                 110

Leu Val Thr Val Ser Ser
        115
```

<210> SEQ ID NO 17
<211> LENGTH: 112
<212> TYPE: PRT
<213> ORGANISM: Artificial Sequence
<220> FEATURE:
<223> OTHER INFORMATION: Synthetic: hu8E11.v7 light chain variable
      region

<400> SEQUENCE: 17

```
Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Ser Val Asp Asn Tyr
                20                  25                  30

Gly Asn Ser Phe Met His Trp Tyr Gln Gln Lys Pro Gly Gln Pro Pro
            35                  40                  45

Lys Leu Leu Ile Tyr Leu Ala Ser Asn Leu Glu Ser Gly Val Pro Asp
        50                  55                  60

Arg Phe Ser Gly Ser Gly Ser Arg Thr Asp Phe Thr Leu Thr Ile Ser
65                  70                  75                  80
```

Ser Leu Gln Ala Glu Asp Val Ala Val Tyr Tyr Cys Gln Gln Asn Tyr
            85                  90                  95

Glu Asp Pro Phe Thr Phe Gly Gln Gly Thr Lys Val Glu Ile Lys Arg
            100                 105                 110

<210> SEQ ID NO 18
<211> LENGTH: 118
<212> TYPE: PRT
<213> ORGANISM: Artificial Sequence
<220> FEATURE:
<223> OTHER INFORMATION: Synthetic: hu8E11.v7 heavy chain variable
      region

<400> SEQUENCE: 18

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Ala Tyr
            20                  25                  30

Trp Ile Glu Trp Val Arg Gln Ala Pro Gly Gln Gly Leu Glu Trp Ile
        35                  40                  45

Gly Glu Ile Leu Pro Gly Ser Asp Ser Thr Asp Tyr Asn Glu Lys Phe
    50                  55                  60

Lys Val Arg Val Thr Ile Thr Arg Asp Thr Ser Ser Thr Thr Ala Tyr
65                  70                  75                  80

Leu Glu Leu Ser Ser Leu Arg Ser Glu Asp Thr Ala Val Tyr Tyr Cys
                85                  90                  95

Ala Arg Gly Gly His Tyr Gly Ser Leu Asp Tyr Trp Gly Gln Gly Thr
            100                 105                 110

Leu Val Thr Val Ser Ser
        115

<210> SEQ ID NO 19
<211> LENGTH: 112
<212> TYPE: PRT
<213> ORGANISM: Artificial Sequence
<220> FEATURE:
<223> OTHER INFORMATION: Synthetic: hu8E11.v8 light chain variable
      region

<400> SEQUENCE: 19

Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Ser Val Asp Asn Tyr
            20                  25                  30

Gly Asn Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Asp
    50                  55                  60

Arg Phe Ser Gly Ser Gly Ser Arg Thr Asp Phe Thr Leu Thr Ile Ser
65                  70                  75                  80

Ser Leu Gln Ala Glu Asp Val Ala Val Tyr Tyr Cys Gln Gln Asn Tyr
                85                  90                  95

Glu Asp Pro Phe Thr Phe Gly Gln Gly Thr Lys Val Glu Ile Lys Arg
            100                 105                 110

<210> SEQ ID NO 20
<211> LENGTH: 118
<212> TYPE: PRT
<213> ORGANISM: Artificial Sequence
<220> FEATURE:

<223> OTHER INFORMATION: Synthetic: hu8E11.v8 heavy chain variable
      region

<400> SEQUENCE: 20

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Ala Tyr
            20                  25                  30

Trp Ile Glu Trp Val Arg Gln Ala Pro Gly Gln Gly Leu Glu Trp Ile
        35                  40                  45

Gly Glu Ile Leu Pro Gly Ser Asp Ser Thr Asp Tyr Asn Glu Lys Phe
    50                  55                  60

Lys Val Arg Val Thr Ile Thr Ala Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Arg Gly Gly His Tyr Gly Ser Leu Asp Tyr Trp Gly Gln Gly Thr
            100                 105                 110

Leu Val Thr Val Ser Ser
        115

<210> SEQ ID NO 21
<211> LENGTH: 113
<212> TYPE: PRT
<213> ORGANISM: Artificial Sequence
<220> FEATURE:
<223> OTHER INFORMATION: Synthetic: mu3G12 light chain variable region

<400> SEQUENCE: 21

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu Gln Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Ile Tyr Phe Cys Ser Gln Ser
                85                  90                  95

Thr His Phe Pro Tyr Thr Phe Gly Gly Gly Thr Lys Leu Glu Ile Lys
            100                 105                 110

Arg

<210> SEQ ID NO 22
<211> LENGTH: 115
<212> TYPE: PRT
<213> ORGANISM: Artificial Sequence
<220> FEATURE:
<223> OTHER INFORMATION: Synthetic: mu3G12 heavy chain variable region

<400> SEQUENCE: 22

Gln Val Gln Leu Gln Gln Pro Gly Ala Glu Met Val Lys Pro Gly Ala
1               5                   10                  15

Ser Val Lys Leu Ser Cys Lys Ala Ser Val Asp Thr Phe Asn Ser Tyr
            20                  25                  30

Trp Met His Trp Val Lys Gln Arg Pro Gly Gln Gly Leu Glu Trp Ile

```
                35                  40                  45
Gly Glu Ile Asn Pro Ser Asn Gly Arg Thr Asn Tyr Ile Glu Lys Phe
        50                  55                  60

Lys Asn Arg Ala Thr Val Thr Val Asp Lys Ser Ser Thr Ala Phe
 65                 70                  75                  80

Met Gln Leu Ser Ser Leu Thr Ser Glu Asp Ser Ala Val Tyr Tyr Cys
                85                  90                  95

Ala Thr Gly Trp Tyr Phe Asp Val Trp Gly Ala Gly Thr Thr Val Thr
                100                 105                 110

Val Ser Ser
        115

<210> SEQ ID NO 23
<211> LENGTH: 114
<212> TYPE: PRT
<213> ORGANISM: Artificial Sequence
<220> FEATURE:
<223> OTHER INFORMATION: Synthetic: mu2H6 light chain variable region

<400> SEQUENCE: 23

Asp Ile Val Met Thr Gln Ser Pro Ser Ser Leu Thr Val Thr Ala Gly
  1               5                  10                  15

Glu Lys Val Thr Met Ser Cys Lys Ser Ser Gln Ser Leu Leu Asn Ser
                20                  25                  30

Gly Asn Gln Lys Asn Tyr Leu Thr Trp Phe Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
 65                 70                  75                  80

Ile Ser Asn Val Gln Ala Glu Asp Leu Ala Val Tyr Tyr Cys Gln Asn
                85                  90                  95

Asp Tyr Ser Phe Pro Phe Thr Phe Gly Gln Gly Thr Lys Val Glu Ile
                100                 105                 110

Lys Arg

<210> SEQ ID NO 24
<211> LENGTH: 121
<212> TYPE: PRT
<213> ORGANISM: Artificial Sequence
<220> FEATURE:
<223> OTHER INFORMATION: Synthetic: mu2H6 heavy chain variable region

<400> SEQUENCE: 24

Glu Val Gln Leu Gln Gln Ser Gly Pro Glu Leu Val Lys Pro Gly Thr
  1               5                  10                  15

Ser Met Lys Ile Ser Cys Lys Ala Ser Gly Tyr Ser Phe Thr Gly Tyr
                20                  25                  30

Thr Met Asn Trp Val Lys Gln Ser His Lys Asn Gly Leu Glu Trp Ile
            35                  40                  45

Gly Leu Ile Asn Cys Tyr Asn Gly Thr Asn Tyr Asn Gln Lys Phe
        50                  55                  60

Lys Gly Lys Ala Thr Leu Thr Val Asp Lys Ser Ser Thr Ala Phe
 65                 70                  75                  80

Met Glu Leu Leu Ser Leu Thr Ser Glu Asp Ser Ala Val Tyr Tyr Cys
                85                  90                  95

Ala Arg Gly Gly Ser Thr Met Ile Thr Pro Arg Phe Ala Tyr Trp Gly
```

```
                    100                 105                 110
Gln Gly Thr Leu Val Thr Val Ser Ser
            115                 120

<210> SEQ ID NO 25
<211> LENGTH: 108
<212> TYPE: PRT
<213> ORGANISM: Artificial Sequence
<220> FEATURE:
<223> OTHER INFORMATION: Synthetic: YW353 light chain variable region

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Pro
                85                  90                  95

Thr Phe Gly Gln Gly Thr Lys Val Glu Ile Lys Arg
            100                 105

<210> SEQ ID NO 26
<211> LENGTH: 116
<212> TYPE: PRT
<213> ORGANISM: Artificial Sequence
<220> FEATURE:
<223> OTHER INFORMATION: Synthetic: YW353 heavy chain variable region

<400> SEQUENCE: 26

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Ser Tyr
            20                  25                  30

Ser Ile Ser Trp Val Arg Gln Ala Pro Gly Lys Gly Leu Glu Trp Val
        35                  40                  45

Ala Glu Ile Tyr Pro Pro Gly Gly Tyr Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Lys Ala Arg Leu Phe Phe Asp Tyr Trp Gly Gln Gly Thr Leu Val
            100                 105                 110

Thr Val Ser Ser
        115

<210> SEQ ID NO 27
<211> LENGTH: 15
<212> TYPE: PRT
<213> ORGANISM: Artificial Sequence
<220> FEATURE:
<223> OTHER INFORMATION: Synthetic: mu8E11 HVR L1

<400> SEQUENCE: 27
```

```
Arg Ala Ser Glu Ser Val Asp Asn Tyr Gly Asn Ser Phe Met His
1               5                   10                  15

<210> SEQ ID NO 28
<211> LENGTH: 7
<212> TYPE: PRT
<213> ORGANISM: Artificial Sequence
<220> FEATURE:
<223> OTHER INFORMATION: Synthetic: mu8E11 HVR L2

<400> SEQUENCE: 28

Leu Ala Ser Asn Leu Glu Ser
1               5

<210> SEQ ID NO 29
<211> LENGTH: 9
<212> TYPE: PRT
<213> ORGANISM: Artificial Sequence
<220> FEATURE:
<223> OTHER INFORMATION: Synthetic: mu8E11 HVR L3

<400> SEQUENCE: 29

Gln Gln Asn Tyr Glu Asp Pro Phe Thr
1               5

<210> SEQ ID NO 30
<211> LENGTH: 10
<212> TYPE: PRT
<213> ORGANISM: Artificial Sequence
<220> FEATURE:
<223> OTHER INFORMATION: Synthetic: mu8E11 HVR H1

<400> SEQUENCE: 30

Gly Tyr Thr Phe Ser Ala Tyr Trp Ile Glu
1               5                   10

<210> SEQ ID NO 31
<211> LENGTH: 17
<212> TYPE: PRT
<213> ORGANISM: Artificial Sequence
<220> FEATURE:
<223> OTHER INFORMATION: Synthetic: mu8E11 HVR H2

<400> SEQUENCE: 31

Glu Ile Leu Pro Gly Ser Asp Ser Thr Asp Tyr Asn Glu Lys Phe Lys
1               5                   10                  15
Val

<210> SEQ ID NO 32
<211> LENGTH: 9
<212> TYPE: PRT
<213> ORGANISM: Artificial Sequence
<220> FEATURE:
<223> OTHER INFORMATION: Synthetic: mu8E11 HVR H3

<400> SEQUENCE: 32

Gly Gly His Tyr Gly Ser Leu Asp Tyr
1               5

<210> SEQ ID NO 33
<211> LENGTH: 23
<212> TYPE: PRT
<213> ORGANISM: Artificial Sequence
<220> FEATURE:
<223> OTHER INFORMATION: Synthetic: Hu8E11 light chain (LC) framework 1
      (FR1)
```

```
<400> SEQUENCE: 33

Asp Ile Val Met Thr Gln Ser Pro Asp Ser Leu Ala Val Ser Leu Gly
1               5                   10                  15

Glu Arg Ala Thr Ile Asn Cys
            20

<210> SEQ ID NO 34
<211> LENGTH: 15
<212> TYPE: PRT
<213> ORGANISM: Artificial Sequence
<220> FEATURE:
<223> OTHER INFORMATION: Synthetic: Hu8E11 LC FR2

<400> SEQUENCE: 34

Trp Tyr Gln Gln Lys Pro Gly Gln Pro Pro Lys Leu Leu Ile Tyr
1               5                   10                  15

<210> SEQ ID NO 35
<211> LENGTH: 32
<212> TYPE: PRT
<213> ORGANISM: Artificial Sequence
<220> FEATURE:
<223> OTHER INFORMATION: Synthetic: Hu8E11.v1 LC FR3/Hu8E11.v2 LC
      FR3/Hu8E11.v5 LC FR3/Hu8E11.v6 LC FR3

<400> SEQUENCE: 35

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 36
<211> LENGTH: 32
<212> TYPE: PRT
<213> ORGANISM: Artificial Sequence
<220> FEATURE:
<223> OTHER INFORMATION: Synthetic: Hu8E11.v3 LC FR3/Hu8E11.v4 LC
      FR3/Hu8E11.v7 LC FR3/Hu8E11.v8 LC FR3

<400> SEQUENCE: 36

Gly Val Pro Asp Arg Phe Ser Gly Ser Gly Ser Arg Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 37
<211> LENGTH: 11
<212> TYPE: PRT
<213> ORGANISM: Artificial Sequence
<220> FEATURE:
<223> OTHER INFORMATION: Synthetic: Hu8E11 LC FR4

<400> SEQUENCE: 37

Phe Gly Gln Gly Thr Lys Val Glu Ile Lys Arg
1               5                   10

<210> SEQ ID NO 38
<211> LENGTH: 25
<212> TYPE: PRT
<213> ORGANISM: Artificial Sequence
<220> FEATURE:
<223> OTHER INFORMATION: Synthetic: Hu8E11 heavy chain (HC) framework1
      (FR1)

<400> SEQUENCE: 38
```

```
Glu Val Gln Leu Val Gln Ser Gly Ala Glu Val Lys Lys Pro Gly Ala
1               5                   10                  15

Ser Val Lys Val Ser Cys Lys Ala Ser
            20                  25

<210> SEQ ID NO 39
<211> LENGTH: 14
<212> TYPE: PRT
<213> ORGANISM: Artificial Sequence
<220> FEATURE:
<223> OTHER INFORMATION: Synthetic: Hu8E11 HC FR2

<400> SEQUENCE: 39

Trp Val Arg Gln Ala Pro Gly Gln Gly Leu Glu Trp Ile Gly
1               5                   10

<210> SEQ ID NO 40
<211> LENGTH: 32
<212> TYPE: PRT
<213> ORGANISM: Artificial Sequence
<220> FEATURE:
<223> OTHER INFORMATION: Synthetic: Hu8E11.v1 HC FR3/Hu8E11.v3 HC FR3

<400> SEQUENCE: 40

Arg Val Thr Ile Thr Ser Asp Thr Ser Thr Ser Thr Val Tyr Leu Glu
1               5                   10                  15

Leu Ser Ser Leu Arg Ser Glu Asp Thr Ala Val Tyr Tyr Cys Ala Arg
            20                  25                  30

<210> SEQ ID NO 41
<211> LENGTH: 32
<212> TYPE: PRT
<213> ORGANISM: Artificial Sequence
<220> FEATURE:
<223> OTHER INFORMATION: Synthetic: Hu8E11.v2 HC FR3/Hu8E11.v4 HC FR3

<400> SEQUENCE: 41

Arg Ala Thr Phe Thr Ser Asp Thr Ser Thr Ser Thr Val Tyr Leu Glu
1               5                   10                  15

Leu Ser Ser Leu Arg Ser Glu Asp Thr Ala Val Tyr Tyr Cys Ala Arg
            20                  25                  30

<210> SEQ ID NO 42
<211> LENGTH: 32
<212> TYPE: PRT
<213> ORGANISM: Artificial Sequence
<220> FEATURE:
<223> OTHER INFORMATION: Synthetic: Hu8E11.v5 HC FR3/Hu8E11.v7 HC FR3

<400> SEQUENCE: 42

Arg Val Thr Ile Thr Arg Asp Thr Ser Thr Ser Thr Ala Tyr Leu Glu
1               5                   10                  15

Leu Ser Ser Leu Arg Ser Glu Asp Thr Ala Val Tyr Tyr Cys Ala Arg
            20                  25                  30

<210> SEQ ID NO 43
<211> LENGTH: 32
<212> TYPE: PRT
<213> ORGANISM: Artificial Sequence
<220> FEATURE:
<223> OTHER INFORMATION: Synthetic: Hu8E11.v6 HC FR3/Hu8E11.v8 HC FR3

<400> SEQUENCE: 43

Arg Val Thr Ile Thr Ala Asp Thr Ser Thr Ser Thr Ala Tyr Leu Glu
```

```
                 1               5                  10                  15
Leu Ser Ser Leu Arg Ser Glu Asp Thr Ala Val Tyr Tyr Cys Ala Arg
                 20                  25                  30
```

<210> SEQ ID NO 44
<211> LENGTH: 11
<212> TYPE: PRT
<213> ORGANISM: Artificial Sequence
<220> FEATURE:
<223> OTHER INFORMATION: Synthetic: Hu8E11 HC FR4

<400> SEQUENCE: 44

```
Trp Gly Gln Gly Thr Leu Val Thr Val Ser Ser
1               5                  10
```

<210> SEQ ID NO 45
<211> LENGTH: 16
<212> TYPE: PRT
<213> ORGANISM: Artificial Sequence
<220> FEATURE:
<223> OTHER INFORMATION: Synthetic: mu3G12 HVR L1

<400> SEQUENCE: 45

```
Arg Ser Ser Gln Ser Leu Val His Ser Asn Gly Asn Thr Tyr Leu Gln
1               5                  10                  15
```

<210> SEQ ID NO 46
<211> LENGTH: 7
<212> TYPE: PRT
<213> ORGANISM: Artificial Sequence
<220> FEATURE:
<223> OTHER INFORMATION: Synthetic: mu3G12 HVR L2

<400> SEQUENCE: 46

```
Lys Val Ser Asn Arg Phe Ser
1               5
```

<210> SEQ ID NO 47
<211> LENGTH: 9
<212> TYPE: PRT
<213> ORGANISM: Artificial Sequence
<220> FEATURE:
<223> OTHER INFORMATION: Synthetic: mu3G12 HVR L3

<400> SEQUENCE: 47

```
Ser Gln Ser Thr His Phe Pro Tyr Thr
1               5
```

<210> SEQ ID NO 48
<211> LENGTH: 10
<212> TYPE: PRT
<213> ORGANISM: Artificial Sequence
<220> FEATURE:
<223> OTHER INFORMATION: Synthetic: mu3G12 HVR H1

<400> SEQUENCE: 48

```
Val Asp Thr Phe Asn Ser Tyr Trp Met His
1               5                  10
```

<210> SEQ ID NO 49
<211> LENGTH: 17
<212> TYPE: PRT
<213> ORGANISM: Artificial Sequence
<220> FEATURE:
<223> OTHER INFORMATION: Synthetic: mu3G12 HVR H2

<400> SEQUENCE: 49

Glu Ile Asn Pro Ser Asn Gly Arg Thr Asn Tyr Ile Glu Lys Phe Lys
1               5                   10                  15

Asn

<210> SEQ ID NO 50
<211> LENGTH: 6
<212> TYPE: PRT
<213> ORGANISM: Artificial Sequence
<220> FEATURE:
<223> OTHER INFORMATION: Synthetic: mu3G12 HVR H3

<400> SEQUENCE: 50

Gly Trp Tyr Phe Asp Val
1               5

<210> SEQ ID NO 51
<211> LENGTH: 17
<212> TYPE: PRT
<213> ORGANISM: Artificial Sequence
<220> FEATURE:
<223> OTHER INFORMATION: Synthetic: mu2H6 HVR L1

<400> SEQUENCE: 51

Lys Ser Ser Gln Ser Leu Leu Asn Ser Gly Asn Gln Lys Asn Tyr Leu
1               5                   10                  15

Thr

<210> SEQ ID NO 52
<211> LENGTH: 7
<212> TYPE: PRT
<213> ORGANISM: Artificial Sequence
<220> FEATURE:
<223> OTHER INFORMATION: Synthetic: mu2H6 HVR L2

<400> SEQUENCE: 52

Trp Ala Ser Thr Arg Glu Ser
1               5

<210> SEQ ID NO 53
<211> LENGTH: 9
<212> TYPE: PRT
<213> ORGANISM: Artificial Sequence
<220> FEATURE:
<223> OTHER INFORMATION: Synthetic: mu2H6 HVR L3

<400> SEQUENCE: 53

Gln Asn Asp Tyr Ser Phe Pro Phe Thr
1               5

<210> SEQ ID NO 54
<211> LENGTH: 10
<212> TYPE: PRT
<213> ORGANISM: Artificial Sequence
<220> FEATURE:
<223> OTHER INFORMATION: Synthetic: mu2H6 HVR H1

<400> SEQUENCE: 54

Gly Tyr Ser Phe Thr Gly Tyr Thr Met Asn
1               5                   10

<210> SEQ ID NO 55
<211> LENGTH: 17
<212> TYPE: PRT
<213> ORGANISM: Artificial Sequence
<220> FEATURE:

<223> OTHER INFORMATION: Synthetic: mu2H6 HVR H2

<400> SEQUENCE: 55

Leu Ile Asn Cys Tyr Asn Gly Gly Thr Asn Tyr Asn Gln Lys Phe Lys
1               5                   10                  15
Gly

<210> SEQ ID NO 56
<211> LENGTH: 12
<212> TYPE: PRT
<213> ORGANISM: Artificial Sequence
<220> FEATURE:
<223> OTHER INFORMATION: Synthetic: mu2H6 HVR H3

<400> SEQUENCE: 56

Gly Gly Ser Thr Met Ile Thr Pro Arg Phe Ala Tyr
1               5                   10

<210> SEQ ID NO 57
<211> LENGTH: 11
<212> TYPE: PRT
<213> ORGANISM: Artificial Sequence
<220> FEATURE:
<223> OTHER INFORMATION: Synthetic: YW353 HVR L1

<400> SEQUENCE: 57

Arg Ala Ser Gln Asp Val Ser Thr Ala Val Ala
1               5                   10

<210> SEQ ID NO 58
<211> LENGTH: 7
<212> TYPE: PRT
<213> ORGANISM: Artificial Sequence
<220> FEATURE:
<223> OTHER INFORMATION: Synthetic: YW353 HVR L2

<400> SEQUENCE: 58

Ser Ala Ser Phe Leu Tyr Ser
1               5

<210> SEQ ID NO 59
<211> LENGTH: 9
<212> TYPE: PRT
<213> ORGANISM: Artificial Sequence
<220> FEATURE:
<223> OTHER INFORMATION: Synthetic: YW353 HVR L3

<400> SEQUENCE: 59

Gln Gln Ser Tyr Thr Thr Pro Pro Thr
1               5

<210> SEQ ID NO 60
<211> LENGTH: 10
<212> TYPE: PRT
<213> ORGANISM: Artificial Sequence
<220> FEATURE:
<223> OTHER INFORMATION: Synthetic: YW353 HVR H1

<400> SEQUENCE: 60

Gly Phe Thr Phe Thr Ser Tyr Ser Ile Ser
1               5                   10

<210> SEQ ID NO 61
<211> LENGTH: 17
<212> TYPE: PRT
<213> ORGANISM: Artificial Sequence

```
<220> FEATURE:
<223> OTHER INFORMATION: Synthetic: YW353 HVR H2

<400> SEQUENCE: 61

Glu Ile Tyr Pro Pro Gly Gly Tyr Thr Asp Tyr Ala Asp Ser Val Lys
1               5                   10                  15
Gly

<210> SEQ ID NO 62
<211> LENGTH: 7
<212> TYPE: PRT
<213> ORGANISM: Artificial Sequence
<220> FEATURE:
<223> OTHER INFORMATION: Synthetic: YW353 HVR H3

<400> SEQUENCE: 62

Ala Arg Leu Phe Phe Asp Tyr
1               5

<210> SEQ ID NO 63
<211> LENGTH: 218
<212> TYPE: PRT
<213> ORGANISM: Artificial Sequence
<220> FEATURE:
<223> OTHER INFORMATION: Synthetic: hu8E11.v2 light chain

<400> SEQUENCE: 63

Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Ser Val Asp Asn Tyr
            20                  25                  30

Gly Asn Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Asn Tyr
                85                  90                  95

Glu Asp Pro Phe Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 64
<211> LENGTH: 448
<212> TYPE: PRT
```

<213> ORGANISM: Artificial Sequence
<220> FEATURE:
<223> OTHER INFORMATION: Synthetic: hu8E11.v2 heavy chain

<400> SEQUENCE: 64

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Ala Tyr
            20                  25                  30

Trp Ile Glu Trp Val Arg Gln Ala Pro Gly Gln Gly Leu Glu Trp Ile
        35                  40                  45

Gly Glu Ile Leu Pro Gly Ser Asp Ser Thr Asp Tyr Asn Glu Lys Phe
    50                  55                  60

Lys Val Arg Ala Thr Phe Thr Ser Asp Thr Ser Thr Ser Thr Val Tyr
65                  70                  75                  80

Leu Glu Leu Ser Ser Leu Arg Ser Glu Asp Thr Ala Val Tyr Tyr Cys
                85                  90                  95

Ala Arg Gly Gly His Tyr Gly Ser Leu Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
```

```
385                 390                 395                 400
Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 65
<211> LENGTH: 214
<212> TYPE: PRT
<213> ORGANISM: Artificial Sequence
<220> FEATURE:
<223> OTHER INFORMATION: Synthetic: YW353 light chain

<400> SEQUENCE: 65

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 66
<211> LENGTH: 446
<212> TYPE: PRT
<213> ORGANISM: Artificial Sequence
<220> FEATURE:
<223> OTHER INFORMATION: Synthetic: YW353 heavy chain

<400> SEQUENCE: 66

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Ser Tyr
            20                  25                  30
```

-continued

```
Ser Ile Ser Trp Val Arg Gln Ala Pro Gly Lys Gly Leu Glu Trp Val
         35                  40                  45
Ala Glu Ile Tyr Pro Pro Gly Gly Tyr Thr Asp Tyr Ala Asp Ser Val
 50                  55                  60
Lys Gly Arg Phe Thr Ile Ser Ala Asp Thr Ser Lys Asn Thr Ala Tyr
 65                  70                  75                  80
Leu Gln Met Asn Ser Leu Arg Ala Glu Asp Thr Ala Val Tyr Tyr Cys
                 85                  90                  95
Ala Lys Ala Arg Leu Phe Phe Asp Tyr Trp Gly Gln Gly Thr Leu Val
             100                 105                 110
Thr Val Ser Ser Ala Ser Thr Lys Gly Pro Ser Val Phe Pro Leu Ala
         115                 120                 125
Pro Ser Ser Lys Ser Thr Ser Gly Gly Thr Ala Ala Leu Gly Cys Leu
 130                 135                 140
Val Lys Asp Tyr Phe Pro Glu Pro Val Thr Val Ser Trp Asn Ser Gly
 145                 150                 155                 160
Ala Leu Thr Ser Gly Val His Thr Phe Pro Ala Val Leu Gln Ser Ser
                 165                 170                 175
Gly Leu Tyr Ser Leu Ser Ser Val Val Thr Val Pro Ser Ser Ser Leu
             180                 185                 190
Gly Thr Gln Thr Tyr Ile Cys Asn Val Asn His Lys Pro Ser Asn Thr
         195                 200                 205
Lys Val Asp Lys Lys Val Glu Pro Lys Ser Cys Asp Lys Thr His Thr
 210                 215                 220
Cys Pro Pro Cys Pro Ala Pro Glu Leu Leu Gly Gly Pro Ser Val Phe
 225                 230                 235                 240
Leu Phe Pro Pro Lys Pro Lys Asp Thr Leu Met Ile Ser Arg Thr Pro
                 245                 250                 255
Glu Val Thr Cys Val Val Val Asp Val Ser His Glu Asp Pro Glu Val
             260                 265                 270
Lys Phe Asn Trp Tyr Val Asp Gly Val Glu Val His Asn Ala Lys Thr
         275                 280                 285
Lys Pro Arg Glu Glu Gln Tyr Asn Ser Thr Tyr Arg Val Val Ser Val
 290                 295                 300
Leu Thr Val Leu His Gln Asp Trp Leu Asn Gly Lys Glu Tyr Lys Cys
 305                 310                 315                 320
Lys Val Ser Asn Lys Ala Leu Pro Ala Pro Ile Glu Lys Thr Ile Ser
                 325                 330                 335
Lys Ala Lys Gly Gln Pro Arg Glu Pro Gln Val Tyr Thr Leu Pro Pro
             340                 345                 350
Ser Arg Glu Glu Met Thr Lys Asn Gln Val Ser Leu Thr Cys Leu Val
         355                 360                 365
Lys Gly Phe Tyr Pro Ser Asp Ile Ala Val Glu Trp Glu Ser Asn Gly
 370                 375                 380
Gln Pro Glu Asn Asn Tyr Lys Thr Thr Pro Pro Val Leu Asp Ser Asp
 385                 390                 395                 400
Gly Ser Phe Phe Leu Tyr Ser Lys Leu Thr Val Asp Lys Ser Arg Trp
                 405                 410                 415
Gln Gln Gly Asn Val Phe Ser Cys Ser Val Met His Glu Ala Leu His
             420                 425                 430
Asn His Tyr Thr Gln Lys Ser Leu Ser Leu Ser Pro Gly Lys
         435                 440                 445
```

```
<210> SEQ ID NO 67
<211> LENGTH: 907
<212> TYPE: PRT
<213> ORGANISM: Homo sapiens
<220> FEATURE:
<221> NAME/KEY: misc_feature
<223> OTHER INFORMATION: Human LgR5 precursor; LGR5_human NP_003658;
      signal sequence = amino acids 1-21

<400> SEQUENCE: 67

Met Asp Thr Ser Arg Leu Gly Val Leu Leu Ser Leu Pro Val Leu Leu
1               5                   10                  15

Gln Leu Ala Thr Gly Gly Ser Ser Pro Arg Ser Gly Val Leu Leu Arg
            20                  25                  30

Gly Cys Pro Thr His Cys His Cys Glu Pro Asp Gly Arg Met Leu Leu
        35                  40                  45

Arg Val Asp Cys Ser Asp Leu Gly Leu Ser Glu Leu Pro Ser Asn Leu
50                  55                  60

Ser Val Phe Thr Ser Tyr Leu Asp Leu Ser Met Asn Asn Ile Ser Gln
65                  70                  75                  80

Leu Leu Pro Asn Pro Leu Pro Ser Leu Arg Phe Leu Glu Glu Leu Arg
                85                  90                  95

Leu Ala Gly Asn Ala Leu Thr Tyr Ile Pro Lys Gly Ala Phe Thr Gly
            100                 105                 110

Leu Tyr Ser Leu Lys Val Leu Met Leu Gln Asn Asn Gln Leu Arg His
        115                 120                 125

Val Pro Thr Glu Ala Leu Gln Asn Leu Arg Ser Leu Gln Ser Leu Arg
130                 135                 140

Leu Asp Ala Asn His Ile Ser Tyr Val Pro Pro Ser Cys Phe Ser Gly
145                 150                 155                 160

Leu His Ser Leu Arg His Leu Trp Leu Asp Asp Asn Ala Leu Thr Glu
                165                 170                 175

Ile Pro Val Gln Ala Phe Arg Ser Leu Ser Ala Leu Gln Ala Met Thr
            180                 185                 190

Leu Ala Leu Asn Lys Ile His His Ile Pro Asp Tyr Ala Phe Gly Asn
        195                 200                 205

Leu Ser Ser Leu Val Val Leu His Leu His Asn Asn Arg Ile His Ser
210                 215                 220

Leu Gly Lys Lys Cys Phe Asp Gly Leu His Ser Leu Glu Thr Leu Asp
225                 230                 235                 240

Leu Asn Tyr Asn Asn Leu Asp Glu Phe Pro Thr Ala Ile Arg Thr Leu
                245                 250                 255

Ser Asn Leu Lys Glu Leu Gly Phe His Ser Asn Asn Ile Arg Ser Ile
            260                 265                 270

Pro Glu Lys Ala Phe Val Gly Asn Pro Ser Leu Ile Thr Ile His Phe
        275                 280                 285

Tyr Asp Asn Pro Ile Gln Phe Val Gly Arg Ser Ala Phe Gln His Leu
290                 295                 300

Pro Glu Leu Arg Thr Leu Thr Leu Asn Gly Ala Ser Gln Ile Thr Glu
305                 310                 315                 320

Phe Pro Asp Leu Thr Gly Thr Ala Asn Leu Glu Ser Leu Thr Leu Thr
                325                 330                 335

Gly Ala Gln Ile Ser Ser Leu Pro Gln Thr Val Cys Asn Gln Leu Pro
            340                 345                 350

Asn Leu Gln Val Leu Asp Leu Ser Tyr Asn Leu Leu Glu Asp Leu Pro
        355                 360                 365
```

```
Ser Phe Ser Val Cys Gln Lys Leu Gln Lys Ile Asp Leu Arg His Asn
    370                 375                 380

Glu Ile Tyr Glu Ile Lys Val Asp Thr Phe Gln Gln Leu Leu Ser Leu
385                 390                 395                 400

Arg Ser Leu Asn Leu Ala Trp Asn Lys Ile Ala Ile His Pro Asn
                405                 410                 415

Ala Phe Ser Thr Leu Pro Ser Leu Ile Lys Leu Asp Leu Ser Ser Asn
                420                 425                 430

Leu Leu Ser Ser Phe Pro Ile Thr Gly Leu His Gly Leu Thr His Leu
            435                 440                 445

Lys Leu Thr Gly Asn His Ala Leu Gln Ser Leu Ile Ser Ser Glu Asn
    450                 455                 460

Phe Pro Glu Leu Lys Val Ile Glu Met Pro Tyr Ala Tyr Gln Cys Cys
465                 470                 475                 480

Ala Phe Gly Val Cys Glu Asn Ala Tyr Lys Ile Ser Asn Gln Trp Asn
                485                 490                 495

Lys Gly Asp Asn Ser Ser Met Asp Asp Leu His Lys Lys Asp Ala Gly
                500                 505                 510

Met Phe Gln Ala Gln Asp Glu Arg Asp Leu Glu Asp Phe Leu Leu Asp
    515                 520                 525

Phe Glu Glu Asp Leu Lys Ala Leu His Ser Val Gln Cys Ser Pro Ser
530                 535                 540

Pro Gly Pro Phe Lys Pro Cys Glu His Leu Leu Asp Gly Trp Leu Ile
545                 550                 555                 560

Arg Ile Gly Val Trp Thr Ile Ala Val Leu Ala Leu Thr Cys Asn Ala
                565                 570                 575

Leu Val Thr Ser Thr Val Phe Arg Ser Pro Leu Tyr Ile Ser Pro Ile
            580                 585                 590

Lys Leu Leu Ile Gly Val Ile Ala Ala Val Asn Met Leu Thr Gly Val
    595                 600                 605

Ser Ser Ala Val Leu Ala Gly Val Asp Ala Phe Thr Phe Gly Ser Phe
    610                 615                 620

Ala Arg His Gly Ala Trp Trp Glu Asn Gly Val Gly Cys His Val Ile
625                 630                 635                 640

Gly Phe Leu Ser Ile Phe Ala Ser Glu Ser Ser Val Phe Leu Leu Thr
                645                 650                 655

Leu Ala Ala Leu Glu Arg Gly Phe Ser Val Lys Tyr Ser Ala Lys Phe
                660                 665                 670

Glu Thr Lys Ala Pro Phe Ser Ser Leu Lys Val Ile Ile Leu Leu Cys
    675                 680                 685

Ala Leu Leu Ala Leu Thr Met Ala Ala Val Pro Leu Leu Gly Gly Ser
    690                 695                 700

Lys Tyr Gly Ala Ser Pro Leu Cys Leu Pro Leu Pro Phe Gly Glu Pro
705                 710                 715                 720

Ser Thr Met Gly Tyr Met Val Ala Leu Ile Leu Leu Asn Ser Leu Cys
                725                 730                 735

Phe Leu Met Met Thr Ile Ala Tyr Thr Lys Leu Tyr Cys Asn Leu Asp
                740                 745                 750

Lys Gly Asp Leu Glu Asn Ile Trp Asp Cys Ser Met Val Lys His Ile
            755                 760                 765

Ala Leu Leu Leu Phe Thr Asn Cys Ile Leu Asn Cys Pro Val Ala Phe
    770                 775                 780
```

```
Leu Ser Phe Ser Ser Leu Ile Asn Leu Thr Phe Ile Ser Pro Glu Val
785                 790                 795                 800

Ile Lys Phe Ile Leu Leu Val Val Pro Leu Pro Ala Cys Leu Asn
            805                 810                 815

Pro Leu Leu Tyr Ile Leu Phe Asn Pro His Phe Lys Glu Asp Leu Val
            820                 825                 830

Ser Leu Arg Lys Gln Thr Tyr Val Trp Thr Arg Ser Lys His Pro Ser
            835                 840                 845

Leu Met Ser Ile Asn Ser Asp Asp Val Glu Lys Gln Ser Cys Asp Ser
            850                 855                 860

Thr Gln Ala Leu Val Thr Phe Thr Ser Ser Ile Thr Tyr Asp Leu
865                 870                 875                 880

Pro Pro Ser Ser Val Pro Ser Pro Ala Tyr Pro Val Thr Glu Ser Cys
                885                 890                 895

His Leu Ser Ser Val Ala Phe Val Pro Cys Leu
                900                 905
```

<210> SEQ ID NO 68
<211> LENGTH: 886
<212> TYPE: PRT
<213> ORGANISM: Homo sapiens
<220> FEATURE:
<221> NAME/KEY: misc_feature
<223> OTHER INFORMATION: Human LgR5 mature, without signal sequence; amino acids 22 to 907

<400> SEQUENCE: 68

```
Gly Ser Ser Pro Arg Ser Gly Val Leu Leu Arg Gly Cys Pro Thr His
1               5                   10                  15

Cys His Cys Glu Pro Asp Gly Arg Met Leu Leu Arg Val Asp Cys Ser
                20                  25                  30

Asp Leu Gly Leu Ser Glu Leu Pro Ser Asn Leu Ser Val Phe Thr Ser
            35                  40                  45

Tyr Leu Asp Leu Ser Met Asn Asn Ile Ser Gln Leu Leu Pro Asn Pro
50                  55                  60

Leu Pro Ser Leu Arg Phe Leu Glu Glu Leu Arg Leu Ala Gly Asn Ala
65                  70                  75                  80

Leu Thr Tyr Ile Pro Lys Gly Ala Phe Thr Gly Leu Tyr Ser Leu Lys
                85                  90                  95

Val Leu Met Leu Gln Asn Asn Gln Leu Arg His Val Pro Thr Glu Ala
                100                 105                 110

Leu Gln Asn Leu Arg Ser Leu Gln Ser Leu Arg Leu Asp Ala Asn His
            115                 120                 125

Ile Ser Tyr Val Pro Pro Ser Cys Phe Ser Gly Leu His Ser Leu Arg
130                 135                 140

His Leu Trp Leu Asp Asp Asn Ala Leu Thr Glu Ile Pro Val Gln Ala
145                 150                 155                 160

Phe Arg Ser Leu Ser Ala Leu Gln Ala Met Thr Leu Ala Leu Asn Lys
                165                 170                 175

Ile His His Ile Pro Asp Tyr Ala Phe Gly Asn Leu Ser Ser Leu Val
                180                 185                 190

Val Leu His Leu His Asn Asn Arg Ile His Ser Leu Gly Lys Lys Cys
            195                 200                 205

Phe Asp Gly Leu His Ser Leu Glu Thr Leu Asp Leu Asn Tyr Asn Asn
210                 215                 220

Leu Asp Glu Phe Pro Thr Ala Ile Arg Thr Leu Ser Asn Leu Lys Glu
```

```
            225                 230                 235                 240
Leu Gly Phe His Ser Asn Asn Ile Arg Ser Ile Pro Glu Lys Ala Phe
                245                 250                 255

Val Gly Asn Pro Ser Leu Ile Thr Ile His Phe Tyr Asp Asn Pro Ile
            260                 265                 270

Gln Phe Val Gly Arg Ser Ala Phe Gln His Leu Pro Glu Leu Arg Thr
                275                 280                 285

Leu Thr Leu Asn Gly Ala Ser Gln Ile Thr Glu Phe Pro Asp Leu Thr
            290                 295                 300

Gly Thr Ala Asn Leu Glu Ser Leu Thr Leu Thr Gly Ala Gln Ile Ser
305                 310                 315                 320

Ser Leu Pro Gln Thr Val Cys Asn Gln Leu Pro Asn Leu Gln Val Leu
                325                 330                 335

Asp Leu Ser Tyr Asn Leu Leu Glu Asp Leu Pro Ser Phe Ser Val Cys
            340                 345                 350

Gln Lys Leu Gln Lys Ile Asp Leu Arg His Asn Glu Ile Tyr Glu Ile
                355                 360                 365

Lys Val Asp Thr Phe Gln Gln Leu Leu Ser Leu Arg Ser Leu Asn Leu
            370                 375                 380

Ala Trp Asn Lys Ile Ala Ile Ile His Pro Asn Ala Phe Ser Thr Leu
385                 390                 395                 400

Pro Ser Leu Ile Lys Leu Asp Leu Ser Ser Asn Leu Leu Ser Ser Phe
                405                 410                 415

Pro Ile Thr Gly Leu His Gly Leu Thr His Leu Lys Leu Thr Gly Asn
            420                 425                 430

His Ala Leu Gln Ser Leu Ile Ser Ser Glu Asn Phe Pro Glu Leu Lys
                435                 440                 445

Val Ile Glu Met Pro Tyr Ala Tyr Gln Cys Cys Ala Phe Gly Val Cys
            450                 455                 460

Glu Asn Ala Tyr Lys Ile Ser Asn Gln Trp Asn Lys Gly Asp Asn Ser
465                 470                 475                 480

Ser Met Asp Asp Leu His Lys Lys Asp Ala Gly Met Phe Gln Ala Gln
                485                 490                 495

Asp Glu Arg Asp Leu Glu Asp Phe Leu Leu Asp Phe Glu Glu Asp Leu
            500                 505                 510

Lys Ala Leu His Ser Val Gln Cys Ser Pro Ser Pro Gly Pro Phe Lys
                515                 520                 525

Pro Cys Glu His Leu Leu Asp Gly Trp Leu Ile Arg Ile Gly Val Trp
            530                 535                 540

Thr Ile Ala Val Leu Ala Leu Thr Cys Asn Ala Leu Val Thr Ser Thr
545                 550                 555                 560

Val Phe Arg Ser Pro Leu Tyr Ile Ser Pro Ile Lys Leu Leu Ile Gly
                565                 570                 575

Val Ile Ala Ala Val Asn Met Leu Thr Gly Val Ser Ser Ala Val Leu
            580                 585                 590

Ala Gly Val Asp Ala Phe Thr Phe Gly Ser Phe Ala Arg His Gly Ala
                595                 600                 605

Trp Trp Glu Asn Gly Val Gly Cys His Val Ile Gly Phe Leu Ser Ile
            610                 615                 620

Phe Ala Ser Glu Ser Ser Val Phe Leu Leu Thr Leu Ala Ala Leu Glu
625                 630                 635                 640

Arg Gly Phe Ser Val Lys Tyr Ser Ala Lys Phe Glu Thr Lys Ala Pro
                645                 650                 655
```

-continued

```
Phe Ser Ser Leu Lys Val Ile Ile Leu Leu Cys Ala Leu Leu Ala Leu
            660                 665                 670

Thr Met Ala Ala Val Pro Leu Gly Gly Ser Lys Tyr Gly Ala Ser
        675                 680                 685

Pro Leu Cys Leu Pro Leu Pro Phe Gly Glu Pro Ser Thr Met Gly Tyr
    690                 695                 700

Met Val Ala Leu Ile Leu Leu Asn Ser Leu Cys Phe Leu Met Met Thr
705                 710                 715                 720

Ile Ala Tyr Thr Lys Leu Tyr Cys Asn Leu Asp Lys Gly Asp Leu Glu
                725                 730                 735

Asn Ile Trp Asp Cys Ser Met Val Lys His Ile Ala Leu Leu Leu Phe
            740                 745                 750

Thr Asn Cys Ile Leu Asn Cys Pro Val Ala Phe Leu Ser Phe Ser Ser
        755                 760                 765

Leu Ile Asn Leu Thr Phe Ile Ser Pro Glu Val Ile Lys Phe Ile Leu
    770                 775                 780

Leu Val Val Val Pro Leu Pro Ala Cys Leu Asn Pro Leu Leu Tyr Ile
785                 790                 795                 800

Leu Phe Asn Pro His Phe Lys Glu Asp Leu Val Ser Leu Arg Lys Gln
                805                 810                 815

Thr Tyr Val Trp Thr Arg Ser Lys His Pro Ser Leu Met Ser Ile Asn
            820                 825                 830

Ser Asp Asp Val Glu Lys Gln Ser Cys Asp Ser Thr Gln Ala Leu Val
        835                 840                 845

Thr Phe Thr Ser Ser Ser Ile Thr Tyr Asp Leu Pro Pro Ser Ser Val
    850                 855                 860

Pro Ser Pro Ala Tyr Pro Val Thr Glu Ser Cys His Leu Ser Ser Val
865                 870                 875                 880

Ala Phe Val Pro Cys Leu
                885

<210> SEQ ID NO 69
<211> LENGTH: 875
<212> TYPE: PRT
<213> ORGANISM: M. cynomolgus
<220> FEATURE:
<221> NAME/KEY: misc_feature
<223> OTHER INFORMATION: Cynomolgus monkey LgR5 partial sequence,
      predicted; predicted to correspond to amino acids 33 to 907 of
      full-length precursor

<400> SEQUENCE: 69

Gly Cys Pro Thr His Cys His Cys Glu Pro Asp Gly Arg Met Leu Leu
1               5                   10                  15

Arg Val Asp Cys Ser Asp Leu Gly Leu Ser Glu Leu Pro Ser Asn Leu
            20                  25                  30

Ser Val Phe Thr Ser Tyr Leu Asp Leu Ser Met Asn Asn Ile Ser Gln
        35                  40                  45

Leu Leu Pro Asn Pro Leu Pro Ser Leu Arg Phe Leu Glu Glu Leu Arg
    50                  55                  60

Leu Ala Gly Asn Ala Leu Thr Tyr Ile Pro Lys Gly Ala Phe Thr Gly
65                  70                  75                  80

Leu Tyr Ser Leu Lys Val Leu Met Leu Gln Asn Asn Gln Leu Arg Gln
                85                  90                  95

Val Pro Thr Glu Ala Leu Gln Asn Leu Arg Ser Leu Gln Ser Leu Arg
            100                 105                 110
```

```
Leu Asp Ala Asn His Ile Ser Tyr Val Pro Pro Ser Cys Phe Ser Gly
        115                 120                 125

Leu His Ser Leu Arg His Leu Trp Leu Asp Asp Asn Ala Leu Thr Glu
    130                 135                 140

Ile Pro Val Gln Ala Phe Arg Ser Leu Ser Ala Leu Gln Ala Met Thr
145                 150                 155                 160

Leu Ala Leu Asn Lys Ile His His Ile Pro Asp Tyr Ala Phe Gly Asn
                165                 170                 175

Leu Ser Ser Leu Val Val Leu His Leu His Asn Asn Arg Ile His Ser
                180                 185                 190

Leu Gly Lys Lys Cys Phe Asp Gly Leu His Ser Leu Glu Thr Leu Asp
        195                 200                 205

Leu Asn Tyr Asn Asn Leu Asp Glu Phe Pro Thr Ala Ile Arg Thr Leu
    210                 215                 220

Ser Asn Leu Lys Glu Leu Gly Phe His Ser Asn Asn Ile Arg Ser Ile
225                 230                 235                 240

Pro Glu Lys Ala Phe Val Gly Asn Pro Ser Leu Ile Thr Ile His Phe
                245                 250                 255

Tyr Asp Asn Pro Ile Gln Phe Val Gly Arg Ser Ala Phe Gln His Leu
                260                 265                 270

Pro Glu Leu Arg Thr Leu Thr Leu Asn Gly Ala Ser Gln Ile Thr Glu
        275                 280                 285

Phe Pro Asp Leu Thr Gly Thr Ala Asn Leu Glu Ser Leu Thr Leu Thr
    290                 295                 300

Gly Ala Gln Ile Ser Ser Leu Pro Gln Thr Val Cys Asn Gln Leu Pro
305                 310                 315                 320

Asn Leu Gln Val Leu Asp Leu Ser Tyr Asn Leu Leu Glu Asp Leu Pro
                325                 330                 335

Ser Phe Ser Val Cys Gln Lys Leu Gln Lys Ile Asp Leu Arg His Asn
                340                 345                 350

Glu Ile Tyr Glu Ile Lys Val Asp Thr Phe Gln Gln Leu Leu Ser Leu
        355                 360                 365

Arg Ser Leu Asn Leu Ala Trp Asn Lys Ile Ala Ile Ile His Pro Asn
    370                 375                 380

Ala Phe Ser Thr Leu Pro Ser Leu Ile Lys Leu Asp Leu Ser Ser Asn
385                 390                 395                 400

Leu Leu Ser Ser Phe Pro Val Thr Gly Leu His Gly Leu Thr His Leu
                405                 410                 415

Lys Leu Thr Gly Asn His Ala Leu Gln Ser Leu Ile Ser Ser Glu Asn
                420                 425                 430

Phe Pro Glu Leu Lys Ile Glu Met Pro Tyr Ala Tyr Gln Cys Cys
        435                 440                 445

Ala Phe Gly Val Cys Glu Asn Ala Tyr Lys Ile Ser Asn Gln Trp Asn
450                 455                 460

Lys Gly Asp Asn Ser Ser Met Asp Asp Leu His Lys Lys Asp Ala Gly
465                 470                 475                 480

Met Phe Gln Val Gln Asp Glu Arg Asp Leu Glu Asp Phe Leu Leu Asp
                485                 490                 495

Phe Glu Glu Asp Leu Lys Ala Leu His Ser Val Gln Cys Ser Pro Ser
                500                 505                 510

Pro Gly Pro Phe Lys Pro Cys Glu His Leu Leu Asp Gly Trp Leu Ile
        515                 520                 525
```

| | | | | | | | | | | | | |
|---|---|---|---|---|---|---|---|---|---|---|---|---|
|Arg|Ile|Gly|Val|Trp|Thr|Ile|Ala|Val|Leu|Ala|Leu|Thr|Cys|Asn|Ala|
| |530| | | |535| | | |540| | | | | | |

Arg Ile Gly Val Trp Thr Ile Ala Val Leu Ala Leu Thr Cys Asn Ala
    530             535             540

Leu Val Thr Ser Thr Val Phe Arg Ser Pro Leu Tyr Ile Ser Pro Ile
545             550             555             560

Lys Leu Leu Ile Gly Val Ile Ala Val Asn Met Leu Thr Gly Val
                565             570             575

Ser Ser Ala Val Leu Ala Gly Val Asp Ala Phe Thr Phe Gly Ser Phe
            580             585             590

Ala Arg His Gly Ala Trp Trp Glu Asn Gly Val Gly Cys Gln Val Ile
        595             600             605

Gly Phe Leu Ser Ile Phe Ala Ser Glu Ser Ser Val Phe Leu Leu Thr
610             615             620

Leu Ala Ala Leu Glu Arg Gly Phe Ser Val Lys Cys Ser Ala Lys Phe
625             630             635             640

Glu Thr Lys Ala Pro Phe Ser Ser Leu Lys Val Ile Ile Leu Leu Cys
            645             650             655

Ala Leu Leu Ala Leu Thr Met Ala Ala Val Pro Leu Leu Gly Gly Ser
        660             665             670

Glu Tyr Gly Ala Ser Pro Leu Cys Leu Pro Leu Pro Phe Gly Glu Pro
    675             680             685

Ser Thr Thr Gly Tyr Met Val Ala Leu Ile Leu Leu Asn Ser Leu Cys
690             695             700

Phe Leu Met Met Thr Ile Ala Tyr Thr Lys Leu Tyr Cys Asn Leu Asp
705             710             715             720

Lys Gly Asp Leu Glu Asn Ile Trp Asp Cys Ser Met Val Lys His Ile
            725             730             735

Ala Leu Leu Leu Phe Thr Asn Cys Ile Leu Tyr Cys Pro Val Ala Phe
        740             745             750

Leu Ser Phe Ser Ser Leu Leu Asn Leu Thr Phe Ile Ser Pro Glu Val
    755             760             765

Ile Lys Phe Ile Leu Leu Val Ile Val Pro Leu Pro Ala Cys Leu Asn
770             775             780

Pro Leu Leu Tyr Ile Leu Phe Asn Pro His Phe Lys Glu Asp Leu Val
785             790             795             800

Ser Leu Gly Lys Gln Thr Tyr Phe Trp Thr Arg Ser Lys His Pro Ser
            805             810             815

Leu Met Ser Ile Asn Ser Asp Asp Val Glu Lys Gln Ser Cys Asp Ser
        820             825             830

Thr Gln Ala Leu Val Thr Phe Thr Ser Ser Ile Ala Tyr Asp Leu
    835             840             845

Pro Pro Ser Ser Val Pro Ser Pro Ala Tyr Pro Val Thr Glu Ser Cys
850             855             860

His Leu Ser Ser Val Ala Phe Val Pro Cys Leu
865             870             875

<210> SEQ ID NO 70
<211> LENGTH: 907
<212> TYPE: PRT
<213> ORGANISM: Rattus sp.
<220> FEATURE:
<221> NAME/KEY: misc_feature
<223> OTHER INFORMATION: Rat LgR5 precursor; LGR5_rat NP_001100254;
      signal sequence = amino acids 1-21

<400> SEQUENCE: 70

Met Asp Thr Ser Arg Val Arg Met Leu Leu Ser Leu Leu Ala Leu Leu

```
  1               5                  10                 15
Gln Leu Val Ala Ala Gly Ser Pro Pro Arg Pro Asp Thr Met Pro Arg
             20                  25                 30

Gly Cys Pro Ser Tyr Cys His Cys Glu Leu Asp Gly Arg Met Leu Leu
             35                  40                 45

Arg Val Asp Cys Ser Asp Leu Gly Leu Ser Glu Leu Pro Ser Asn Leu
 50                  55                  60

Ser Val Phe Thr Ser Tyr Leu Asp Leu Ser Met Asn Asn Ile Ser Gln
 65                  70                  75                 80

Leu Pro Ala Ser Leu Leu His Arg Leu Arg Phe Leu Glu Glu Leu Arg
             85                  90                 95

Leu Ala Gly Asn Ala Leu Thr His Ile Pro Lys Gly Ala Phe Ala Gly
            100                 105                110

Leu His Ser Leu Lys Val Leu Met Leu Gln Asn Asn Gln Leu Arg Gln
            115                 120                125

Val Pro Glu Glu Ala Leu Gln Asn Leu Arg Ser Leu Gln Ser Leu Arg
            130                 135                140

Leu Asp Ala Asn His Ile Ser Tyr Val Pro Pro Ser Cys Phe Ser Gly
145                 150                 155                160

Leu His Ser Leu Arg His Leu Trp Leu Asp Asp Asn Ala Leu Thr Asp
                165                 170                175

Val Pro Val Gln Ala Phe Arg Ser Leu Ser Ala Leu Gln Ala Met Thr
            180                 185                190

Leu Ala Leu Asn Lys Ile His His Ile Ala Asp His Ala Phe Gly Asn
            195                 200                205

Leu Ser Ser Leu Val Val Leu His Leu His Asn Asn Arg Ile His Ser
210                 215                 220

Leu Gly Lys Lys Cys Phe Asp Gly Leu His Ser Leu Glu Thr Leu Asp
225                 230                 235                240

Leu Asn Tyr Asn Asn Leu Asp Glu Phe Pro Thr Ala Ile Lys Thr Leu
            245                 250                255

Ser Asn Leu Lys Glu Leu Gly Phe His Ser Asn Asn Ile Arg Ser Ile
            260                 265                270

Pro Glu Arg Ala Phe Val Gly Asn Pro Ser Leu Ile Thr Ile His Phe
            275                 280                285

Tyr Asp Asn Pro Ile Gln Phe Val Gly Ile Ser Ala Phe Gln His Leu
            290                 295                300

Pro Glu Leu Arg Thr Leu Thr Leu Asn Gly Ala Ser Gln Ile Thr Glu
305                 310                 315                320

Phe Pro Asp Leu Thr Gly Thr Ala Thr Leu Glu Ser Leu Thr Leu Thr
                325                 330                335

Gly Ala Lys Ile Ser Ser Leu Pro Gln Thr Val Cys Asp Gln Leu Pro
            340                 345                350

Asn Leu Gln Val Leu Asp Leu Ser Tyr Asn Leu Leu Glu Asp Leu Pro
            355                 360                365

Ser Leu Ser Gly Cys Gln Lys Leu Gln Lys Ile Asp Leu Arg His Asn
            370                 375                380

Glu Ile Tyr Glu Ile Lys Gly Gly Thr Phe Gln Gln Leu Phe Asn Leu
385                 390                 395                400

Arg Ser Leu Asn Leu Ala Arg Asn Lys Ile Ala Ile Ile His Pro Asn
                405                 410                415

Ala Phe Ser Thr Leu Pro Ser Leu Ile Lys Leu Asp Leu Ser Ser Asn
            420                 425                430
```

```
Leu Leu Ser Ser Phe Pro Val Thr Gly Leu His Gly Leu Thr His Leu
            435                 440                 445

Lys Leu Thr Gly Asn Arg Ala Leu Gln Ser Leu Ile Pro Ser Ala Asn
    450                 455                 460

Phe Pro Glu Leu Lys Ile Ile Glu Met Pro Tyr Ala Tyr Gln Cys Cys
465                 470                 475                 480

Ala Phe Gly Gly Cys Glu Asn Val Tyr Lys Ile Pro Asn Gln Trp Asn
                485                 490                 495

Lys Asp Asp Ser Ser Val Asp Asp Leu Arg Lys Lys Asp Ala Gly
            500                 505                 510

Leu Phe Gln Val Gln Asp Glu Arg Asp Leu Glu Asp Phe Leu Leu Asp
            515                 520                 525

Phe Glu Glu Asp Leu Lys Val Leu His Ser Val Gln Cys Ser Pro Pro
530                 535                 540

Pro Gly Pro Phe Lys Pro Cys Glu His Leu Phe Gly Ser Trp Leu Ile
545                 550                 555                 560

Arg Ile Gly Val Trp Thr Thr Ala Val Leu Ala Leu Ser Cys Asn Ala
                565                 570                 575

Leu Val Ala Phe Thr Val Phe Arg Thr Pro Leu Tyr Ile Ser Ser Ile
                580                 585                 590

Lys Leu Leu Ile Gly Val Ile Ala Val Val Asp Ile Leu Met Gly Val
            595                 600                 605

Ser Ser Ala Ile Leu Ala Val Val Asp Thr Phe Thr Phe Gly Ser Phe
    610                 615                 620

Ala Gln His Gly Ala Trp Trp Glu Gly Gly Ile Gly Cys Gln Ile Val
625                 630                 635                 640

Gly Phe Leu Ser Ile Phe Ala Ser Glu Ser Ser Val Phe Leu Leu Thr
                645                 650                 655

Leu Ala Ala Leu Glu Arg Gly Phe Ser Val Lys Cys Ser Ser Lys Phe
                660                 665                 670

Glu Met Lys Ala Pro Leu Ser Ser Leu Lys Ala Ile Ile Leu Leu Cys
            675                 680                 685

Val Leu Leu Ala Leu Thr Ile Ala Thr Val Pro Leu Leu Gly Gly Ser
            690                 695                 700

Glu Tyr Asn Ala Ser Pro Leu Cys Leu Pro Leu Pro Phe Gly Glu Pro
705                 710                 715                 720

Ser Thr Thr Gly Tyr Met Val Ala Leu Val Leu Leu Asn Ser Leu Cys
                725                 730                 735

Phe Leu Ile Met Thr Ile Ala Tyr Thr Arg Leu Tyr Cys Ser Leu Glu
                740                 745                 750

Lys Gly Glu Leu Glu Asn Leu Trp Asp Cys Ser Met Val Lys His Thr
            755                 760                 765

Ala Leu Leu Leu Phe Thr Asn Cys Ile Leu Tyr Cys Pro Val Ala Phe
            770                 775                 780

Leu Ser Phe Ser Ser Leu Leu Asn Leu Thr Phe Ile Ser Pro Glu Val
785                 790                 795                 800

Ile Lys Phe Ile Leu Leu Val Ile Val Pro Leu Pro Ala Cys Leu Asn
                805                 810                 815

Pro Leu Leu Tyr Ile Val Phe Asn Pro His Phe Lys Glu Asp Met Gly
                820                 825                 830

Ser Leu Gly Lys Gln Thr Arg Phe Trp Thr Arg Ala Lys His Pro Ser
            835                 840                 845
```

```
Leu Leu Ser Ile Asn Ser Asp Asp Val Glu Lys Arg Ser Cys Asp Ser
            850                 855                 860

Thr Gln Ala Leu Val Ser Phe Thr His Ala Ser Ile Ala Tyr Asp Leu
865                 870                 875                 880

Pro Ser Asp Ser Gly Ser Ser Pro Ala Tyr Pro Met Thr Glu Ser Cys
                885                 890                 895

His Leu Ser Ser Val Ala Phe Val Pro Cys Leu
                900                 905

<210> SEQ ID NO 71
<211> LENGTH: 886
<212> TYPE: PRT
<213> ORGANISM: Rattus sp.
<220> FEATURE:
<221> NAME/KEY: misc_feature
<223> OTHER INFORMATION: Rat LgR5 mature, without signal sequence; amino
      acids 22 to 907

<400> SEQUENCE: 71

Gly Ser Pro Pro Arg Pro Asp Thr Met Pro Arg Gly Cys Pro Ser Tyr
1               5                   10                  15

Cys His Cys Glu Leu Asp Gly Arg Met Leu Arg Val Asp Cys Ser
            20                  25                  30

Asp Leu Gly Leu Ser Glu Leu Pro Ser Asn Leu Ser Val Phe Thr Ser
            35                  40                  45

Tyr Leu Asp Leu Ser Met Asn Asn Ile Ser Gln Leu Pro Ala Ser Leu
50                  55                  60

Leu His Arg Leu Arg Phe Leu Glu Glu Leu Arg Leu Ala Gly Asn Ala
65                  70                  75                  80

Leu Thr His Ile Pro Lys Gly Ala Phe Ala Gly Leu His Ser Leu Lys
                85                  90                  95

Val Leu Met Leu Gln Asn Asn Gln Leu Arg Gln Val Pro Glu Glu Ala
            100                 105                 110

Leu Gln Asn Leu Arg Ser Leu Gln Ser Leu Arg Leu Asp Ala Asn His
            115                 120                 125

Ile Ser Tyr Val Pro Pro Ser Cys Phe Ser Gly Leu His Ser Leu Arg
130                 135                 140

His Leu Trp Leu Asp Asp Asn Ala Leu Thr Asp Val Pro Val Gln Ala
145                 150                 155                 160

Phe Arg Ser Leu Ser Ala Leu Gln Ala Met Thr Leu Ala Leu Asn Lys
                165                 170                 175

Ile His His Ile Ala Asp His Ala Phe Gly Asn Leu Ser Ser Leu Val
            180                 185                 190

Val Leu His Leu His Asn Asn Arg Ile His Ser Leu Gly Lys Lys Cys
            195                 200                 205

Phe Asp Gly Leu His Ser Leu Glu Thr Leu Asp Leu Asn Tyr Asn Asn
210                 215                 220

Leu Asp Glu Phe Pro Thr Ala Ile Lys Thr Leu Ser Asn Leu Lys Glu
225                 230                 235                 240

Leu Gly Phe His Ser Asn Asn Ile Arg Ser Ile Pro Glu Arg Ala Phe
                245                 250                 255

Val Gly Asn Pro Ser Leu Ile Thr Ile His Phe Tyr Asp Asn Pro Ile
            260                 265                 270

Gln Phe Val Gly Ile Ser Ala Phe Gln His Leu Pro Glu Leu Arg Thr
            275                 280                 285

Leu Thr Leu Asn Gly Ala Ser Gln Ile Thr Glu Phe Pro Asp Leu Thr
```

-continued

```
            290                 295                 300
Gly Thr Ala Thr Leu Glu Ser Leu Thr Leu Thr Gly Ala Lys Ile Ser
305                 310                 315                 320

Ser Leu Pro Gln Thr Val Cys Asp Gln Leu Pro Asn Leu Gln Val Leu
                325                 330                 335

Asp Leu Ser Tyr Asn Leu Leu Glu Asp Leu Pro Ser Leu Ser Gly Cys
                340                 345                 350

Gln Lys Leu Gln Lys Ile Asp Leu Arg His Asn Glu Ile Tyr Glu Ile
            355                 360                 365

Lys Gly Gly Thr Phe Gln Gln Leu Phe Asn Leu Arg Ser Leu Asn Leu
370                 375                 380

Ala Arg Asn Lys Ile Ala Ile Ile His Pro Asn Ala Phe Ser Thr Leu
385                 390                 395                 400

Pro Ser Leu Ile Lys Leu Asp Leu Ser Ser Asn Leu Leu Ser Ser Phe
                405                 410                 415

Pro Val Thr Gly Leu His Gly Leu Thr His Leu Lys Leu Thr Gly Asn
                420                 425                 430

Arg Ala Leu Gln Ser Leu Ile Pro Ser Ala Asn Phe Pro Glu Leu Lys
            435                 440                 445

Ile Ile Glu Met Pro Tyr Ala Tyr Gln Cys Cys Ala Phe Gly Gly Cys
450                 455                 460

Glu Asn Val Tyr Lys Ile Pro Asn Gln Trp Asn Lys Asp Asp Ser Ser
465                 470                 475                 480

Ser Val Asp Asp Leu Arg Lys Lys Asp Ala Gly Leu Phe Gln Val Gln
                485                 490                 495

Asp Glu Arg Asp Leu Glu Asp Phe Leu Leu Asp Phe Glu Glu Asp Leu
                500                 505                 510

Lys Val Leu His Ser Val Gln Cys Ser Pro Pro Gly Pro Phe Lys
            515                 520                 525

Pro Cys Glu His Leu Phe Gly Ser Trp Leu Ile Arg Ile Gly Val Trp
            530                 535                 540

Thr Thr Ala Val Leu Ala Leu Ser Cys Asn Ala Leu Val Ala Phe Thr
545                 550                 555                 560

Val Phe Arg Thr Pro Leu Tyr Ile Ser Ser Ile Lys Leu Leu Ile Gly
                565                 570                 575

Val Ile Ala Val Val Asp Ile Leu Met Gly Val Ser Ser Ala Ile Leu
                580                 585                 590

Ala Val Val Asp Thr Phe Thr Phe Gly Ser Phe Ala Gln His Gly Ala
            595                 600                 605

Trp Trp Glu Gly Gly Ile Gly Cys Gln Ile Val Gly Phe Leu Ser Ile
610                 615                 620

Phe Ala Ser Glu Ser Ser Val Phe Leu Leu Thr Leu Ala Ala Leu Glu
625                 630                 635                 640

Arg Gly Phe Ser Val Lys Cys Ser Ser Lys Phe Glu Met Lys Ala Pro
                645                 650                 655

Leu Ser Ser Leu Lys Ala Ile Ile Leu Leu Cys Val Leu Leu Ala Leu
                660                 665                 670

Thr Ile Ala Thr Val Pro Leu Leu Gly Gly Ser Glu Tyr Asn Ala Ser
            675                 680                 685

Pro Leu Cys Leu Pro Leu Pro Phe Gly Glu Pro Ser Thr Thr Gly Tyr
            690                 695                 700

Met Val Ala Leu Val Leu Leu Asn Ser Leu Cys Phe Leu Ile Met Thr
705                 710                 715                 720
```

-continued

```
Ile Ala Tyr Thr Arg Leu Tyr Cys Ser Leu Glu Lys Gly Glu Leu Glu
            725                 730                 735

Asn Leu Trp Asp Cys Ser Met Val Lys His Thr Ala Leu Leu Leu Phe
            740                 745                 750

Thr Asn Cys Ile Leu Tyr Cys Pro Val Ala Phe Leu Ser Phe Ser Ser
            755                 760                 765

Leu Leu Asn Leu Thr Phe Ile Ser Pro Glu Val Ile Lys Phe Ile Leu
            770                 775                 780

Leu Val Ile Val Pro Leu Pro Ala Cys Leu Asn Pro Leu Leu Tyr Ile
785                 790                 795                 800

Val Phe Asn Pro His Phe Lys Glu Asp Met Gly Ser Leu Gly Lys Gln
                    805                 810                 815

Thr Arg Phe Trp Thr Arg Ala Lys His Pro Ser Leu Leu Ser Ile Asn
                    820                 825                 830

Ser Asp Asp Val Glu Lys Arg Ser Cys Asp Ser Thr Gln Ala Leu Val
                    835                 840                 845

Ser Phe Thr His Ala Ser Ile Ala Tyr Asp Leu Pro Ser Asp Ser Gly
                    850                 855                 860

Ser Ser Pro Ala Tyr Pro Met Thr Glu Ser Cys His Leu Ser Ser Val
865                 870                 875                 880

Ala Phe Val Pro Cys Leu
                    885

<210> SEQ ID NO 72
<211> LENGTH: 907
<212> TYPE: PRT
<213> ORGANISM: Mus musculus
<220> FEATURE:
<221> NAME/KEY: misc_feature
<223> OTHER INFORMATION: Mouse LgR5 precursor; LGR5_mouse NP_034325;
      signal sequence = amino acids 1-21

<400> SEQUENCE: 72

Met Asp Thr Ser Cys Val His Met Leu Leu Ser Leu Ala Leu Leu
1               5                   10                  15

Gln Leu Val Ala Ala Gly Ser Ser Pro Gly Asp Ala Ile Pro Arg
            20                  25                  30

Gly Cys Pro Ser His Cys His Cys Glu Leu Asp Gly Arg Met Leu Leu
            35                  40                  45

Arg Val Asp Cys Ser Asp Leu Gly Leu Ser Glu Leu Pro Ser Asn Leu
    50                  55                  60

Ser Val Phe Thr Ser Tyr Leu Asp Leu Ser Met Asn Asn Ile Ser Gln
65                  70                  75                  80

Leu Pro Ala Ser Leu Leu His Arg Leu Cys Phe Leu Glu Glu Leu Arg
                85                  90                  95

Leu Ala Gly Asn Ala Leu Thr His Ile Pro Lys Gly Ala Phe Thr Gly
            100                 105                 110

Leu His Ser Leu Lys Val Leu Met Leu Gln Asn Asn Gln Leu Arg Gln
            115                 120                 125

Val Pro Glu Glu Ala Leu Gln Asn Leu Arg Ser Leu Gln Ser Leu Arg
    130                 135                 140

Leu Asp Ala Asn His Ile Ser Tyr Val Pro Pro Ser Cys Phe Ser Gly
145                 150                 155                 160

Leu His Ser Leu Arg His Leu Trp Leu Asp Asp Asn Ala Leu Thr Asp
                165                 170                 175
```

```
Val Pro Val Gln Ala Phe Arg Ser Leu Ser Ala Leu Gln Ala Met Thr
                180                 185                 190

Leu Ala Leu Asn Lys Ile His His Ile Ala Asp Tyr Ala Phe Gly Asn
            195                 200                 205

Leu Ser Ser Leu Val Val Leu His Leu His Asn Asn Arg Ile His Ser
        210                 215                 220

Leu Gly Lys Lys Cys Phe Asp Gly Leu His Ser Leu Glu Thr Leu Asp
225                 230                 235                 240

Leu Asn Tyr Asn Asn Leu Asp Glu Phe Pro Thr Ala Ile Lys Thr Leu
                245                 250                 255

Ser Asn Leu Lys Glu Leu Gly Phe His Ser Asn Asn Ile Arg Ser Ile
            260                 265                 270

Pro Glu Arg Ala Phe Val Gly Asn Pro Ser Leu Ile Thr Ile His Phe
        275                 280                 285

Tyr Asp Asn Pro Ile Gln Phe Val Gly Val Ser Ala Phe Gln His Leu
        290                 295                 300

Pro Glu Leu Arg Thr Leu Thr Leu Asn Gly Ala Ser His Ile Thr Glu
305                 310                 315                 320

Phe Pro His Leu Thr Gly Thr Ala Thr Leu Glu Ser Leu Thr Leu Thr
                325                 330                 335

Gly Ala Lys Ile Ser Ser Leu Pro Gln Ala Val Cys Asp Gln Leu Pro
            340                 345                 350

Asn Leu Gln Val Leu Asp Leu Ser Tyr Asn Leu Leu Glu Asp Leu Pro
        355                 360                 365

Ser Leu Ser Gly Cys Gln Lys Leu Gln Lys Ile Asp Leu Arg His Asn
370                 375                 380

Glu Ile Tyr Glu Ile Lys Gly Ser Thr Phe Gln Gln Leu Phe Asn Leu
385                 390                 395                 400

Arg Ser Leu Asn Leu Ala Trp Asn Lys Ile Ala Ile His Pro Asn
            405                 410                 415

Ala Phe Ser Thr Leu Pro Ser Leu Ile Lys Leu Asp Leu Ser Ser Asn
        420                 425                 430

Leu Leu Ser Ser Phe Pro Val Thr Gly Leu His Gly Leu Thr His Leu
        435                 440                 445

Lys Leu Thr Gly Asn Arg Ala Leu Gln Ser Leu Ile Pro Ser Ala Asn
450                 455                 460

Phe Pro Glu Leu Lys Ile Ile Glu Met Pro Ser Ala Tyr Gln Cys Cys
465                 470                 475                 480

Ala Phe Gly Gly Cys Glu Asn Val Tyr Lys Ile Ser Asn Gln Trp Asn
            485                 490                 495

Lys Asp Asp Gly Asn Ser Val Asp Leu His Lys Lys Asp Ala Gly
            500                 505                 510

Leu Phe Gln Val Gln Asp Glu Arg Asp Leu Glu Asp Phe Leu Leu Asp
        515                 520                 525

Phe Glu Glu Asp Leu Lys Ala Leu His Ser Val Gln Cys Ser Pro Ser
530                 535                 540

Pro Gly Pro Phe Lys Pro Cys Glu His Leu Phe Gly Ser Trp Leu Ile
545                 550                 555                 560

Arg Ile Gly Val Trp Thr Thr Ala Val Leu Ala Leu Ser Cys Asn Ala
                565                 570                 575

Leu Val Ala Leu Thr Val Phe Arg Thr Pro Leu Tyr Ile Ser Ser Ile
            580                 585                 590

Lys Leu Leu Ile Gly Val Ile Ala Val Val Asp Ile Leu Met Gly Val
```

-continued

```
                595                 600                 605
Ser Ser Ala Val Leu Ala Ala Val Asp Ala Phe Thr Phe Gly Arg Phe
    610                 615                 620

Ala Gln His Gly Ala Trp Trp Glu Asp Gly Ile Gly Cys Gln Ile Val
625                 630                 635                 640

Gly Phe Leu Ser Ile Phe Ala Ser Glu Ser Ile Phe Leu Leu Thr
                645                 650                 655

Leu Ala Ala Leu Glu Arg Gly Phe Ser Val Lys Cys Ser Ser Lys Phe
                660                 665                 670

Glu Val Lys Ala Pro Leu Phe Ser Leu Arg Ala Ile Val Leu Leu Cys
                675                 680                 685

Val Leu Leu Ala Leu Thr Ile Ala Thr Ile Pro Leu Leu Gly Gly Ser
                690                 695                 700

Lys Tyr Asn Ala Ser Pro Leu Cys Leu Pro Leu Pro Phe Gly Glu Pro
705                 710                 715                 720

Ser Thr Thr Gly Tyr Met Val Ala Leu Val Leu Leu Asn Ser Leu Cys
                725                 730                 735

Phe Leu Ile Met Thr Ile Ala Tyr Thr Lys Leu Tyr Cys Ser Leu Glu
                740                 745                 750

Lys Gly Glu Leu Glu Asn Leu Trp Asp Cys Ser Met Val Lys His Ile
                755                 760                 765

Ala Leu Leu Leu Phe Ala Asn Cys Ile Leu Tyr Cys Pro Val Ala Phe
                770                 775                 780

Leu Ser Phe Ser Ser Leu Leu Asn Leu Thr Phe Ile Ser Pro Asp Val
785                 790                 795                 800

Ile Lys Phe Ile Leu Leu Val Ile Val Pro Leu Pro Ser Cys Leu Asn
                805                 810                 815

Pro Leu Leu Tyr Ile Val Phe Asn Pro His Phe Lys Glu Asp Met Gly
                820                 825                 830

Ser Leu Gly Lys His Thr Arg Phe Trp Met Arg Ser Lys His Ala Ser
                835                 840                 845

Leu Leu Ser Ile Asn Ser Asp Asp Val Glu Lys Arg Ser Cys Glu Ser
                850                 855                 860

Thr Gln Ala Leu Val Ser Phe Thr His Ala Ser Ile Ala Tyr Asp Leu
865                 870                 875                 880

Pro Ser Thr Ser Gly Ala Ser Pro Ala Tyr Pro Met Thr Glu Ser Cys
                885                 890                 895

His Leu Ser Ser Val Ala Phe Val Pro Cys Leu
                900                 905
```

<210> SEQ ID NO 73
<211> LENGTH: 886
<212> TYPE: PRT
<213> ORGANISM: Mus musculus
<220> FEATURE:
<221> NAME/KEY: misc_feature
<223> OTHER INFORMATION: Mouse LgR5 mature, without signal sequence;
      amino acids 22 to 907

<400> SEQUENCE: 73

```
Gly Ser Ser Pro Gly Pro Asp Ala Ile Pro Arg Gly Cys Pro Ser His
1               5                   10                  15

Cys His Cys Glu Leu Asp Gly Arg Met Leu Leu Arg Val Asp Cys Ser
                20                  25                  30

Asp Leu Gly Leu Ser Glu Leu Pro Ser Asn Leu Ser Val Phe Thr Ser
                35                  40                  45
```

```
Tyr Leu Asp Leu Ser Met Asn Ile Ser Gln Leu Pro Ala Ser Leu
     50                  55                  60

Leu His Arg Leu Cys Phe Leu Glu Glu Leu Arg Leu Ala Gly Asn Ala
 65              70                  75                  80

Leu Thr His Ile Pro Lys Gly Ala Phe Thr Gly Leu His Ser Leu Lys
                 85                  90                  95

Val Leu Met Leu Gln Asn Asn Gln Leu Arg Gln Val Pro Glu Glu Ala
            100                 105                 110

Leu Gln Asn Leu Arg Ser Leu Gln Ser Leu Arg Leu Asp Ala Asn His
            115                 120                 125

Ile Ser Tyr Val Pro Pro Ser Cys Phe Ser Gly Leu His Ser Leu Arg
        130                 135                 140

His Leu Trp Leu Asp Asp Asn Ala Leu Thr Asp Val Pro Val Gln Ala
145                 150                 155                 160

Phe Arg Ser Leu Ser Ala Leu Gln Ala Met Thr Leu Ala Leu Asn Lys
                165                 170                 175

Ile His His Ile Ala Asp Tyr Ala Phe Gly Asn Leu Ser Ser Leu Val
            180                 185                 190

Val Leu His Leu His Asn Asn Arg Ile His Ser Leu Gly Lys Lys Cys
        195                 200                 205

Phe Asp Gly Leu His Ser Leu Glu Thr Leu Asp Leu Asn Tyr Asn Asn
210                 215                 220

Leu Asp Glu Phe Pro Thr Ala Ile Lys Thr Leu Ser Asn Leu Lys Glu
225                 230                 235                 240

Leu Gly Phe His Ser Asn Asn Ile Arg Ser Ile Pro Glu Arg Ala Phe
                245                 250                 255

Val Gly Asn Pro Ser Leu Ile Thr Ile His Phe Tyr Asp Asn Pro Ile
            260                 265                 270

Gln Phe Val Gly Val Ser Ala Phe Gln His Leu Pro Glu Leu Arg Thr
        275                 280                 285

Leu Thr Leu Asn Gly Ala Ser His Ile Thr Glu Phe Pro His Leu Thr
    290                 295                 300

Gly Thr Ala Thr Leu Glu Ser Leu Thr Leu Thr Gly Lys Ile Ser
305                 310                 315                 320

Ser Leu Pro Gln Ala Val Cys Asp Gln Leu Pro Asn Leu Gln Val Leu
                325                 330                 335

Asp Leu Ser Tyr Asn Leu Leu Glu Asp Leu Pro Ser Leu Ser Gly Cys
            340                 345                 350

Gln Lys Leu Gln Lys Ile Asp Leu Arg His Asn Glu Ile Tyr Glu Ile
        355                 360                 365

Lys Gly Ser Thr Phe Gln Gln Leu Phe Asn Leu Arg Ser Leu Asn Leu
370                 375                 380

Ala Trp Asn Lys Ile Ala Ile Ile His Pro Asn Ala Phe Ser Thr Leu
385                 390                 395                 400

Pro Ser Leu Ile Lys Leu Asp Leu Ser Ser Asn Leu Leu Ser Ser Phe
                405                 410                 415

Pro Val Thr Gly Leu His Gly Leu Thr His Leu Lys Leu Thr Gly Asn
            420                 425                 430

Arg Ala Leu Gln Ser Leu Ile Pro Ser Ala Asn Phe Pro Glu Leu Lys
        435                 440                 445

Ile Ile Glu Met Pro Ser Ala Tyr Gln Cys Cys Ala Phe Gly Gly Cys
450                 455                 460
```

```
Glu Asn Val Tyr Lys Ile Ser Asn Gln Trp Asn Lys Asp Asp Gly Asn
465                 470                 475                 480

Ser Val Asp Asp Leu His Lys Lys Asp Ala Gly Leu Phe Gln Val Gln
                485                 490                 495

Asp Glu Arg Asp Leu Glu Asp Phe Leu Leu Asp Phe Glu Glu Asp Leu
            500                 505                 510

Lys Ala Leu His Ser Val Gln Cys Ser Pro Ser Pro Gly Pro Phe Lys
        515                 520                 525

Pro Cys Glu His Leu Phe Gly Ser Trp Leu Ile Arg Ile Gly Val Trp
    530                 535                 540

Thr Thr Ala Val Leu Ala Leu Ser Cys Asn Ala Leu Val Ala Leu Thr
545                 550                 555                 560

Val Phe Arg Thr Pro Leu Tyr Ile Ser Ser Ile Lys Leu Leu Ile Gly
                565                 570                 575

Val Ile Ala Val Val Asp Ile Leu Met Gly Val Ser Ser Ala Val Leu
            580                 585                 590

Ala Ala Val Asp Ala Phe Thr Phe Gly Arg Phe Ala Gln His Gly Ala
        595                 600                 605

Trp Trp Glu Asp Gly Ile Gly Cys Gln Ile Val Gly Phe Leu Ser Ile
    610                 615                 620

Phe Ala Ser Glu Ser Ser Ile Phe Leu Leu Thr Leu Ala Ala Leu Glu
625                 630                 635                 640

Arg Gly Phe Ser Val Lys Cys Ser Ser Lys Phe Glu Val Lys Ala Pro
                645                 650                 655

Leu Phe Ser Leu Arg Ala Ile Val Leu Leu Cys Val Leu Leu Ala Leu
            660                 665                 670

Thr Ile Ala Thr Ile Pro Leu Leu Gly Gly Ser Lys Tyr Asn Ala Ser
        675                 680                 685

Pro Leu Cys Leu Pro Leu Pro Phe Gly Glu Pro Ser Thr Thr Gly Tyr
    690                 695                 700

Met Val Ala Leu Val Leu Leu Asn Ser Leu Cys Phe Leu Ile Met Thr
705                 710                 715                 720

Ile Ala Tyr Thr Lys Leu Tyr Cys Ser Leu Glu Lys Gly Glu Leu Glu
                725                 730                 735

Asn Leu Trp Asp Cys Ser Met Val Lys His Ile Ala Leu Leu Leu Phe
            740                 745                 750

Ala Asn Cys Ile Leu Tyr Cys Pro Val Ala Phe Leu Ser Phe Ser Ser
        755                 760                 765

Leu Leu Asn Leu Thr Phe Ile Ser Pro Asp Val Ile Lys Phe Ile Leu
    770                 775                 780

Leu Val Ile Val Pro Leu Pro Ser Cys Leu Asn Pro Leu Leu Tyr Ile
785                 790                 795                 800

Val Phe Asn Pro His Phe Lys Glu Asp Met Gly Ser Leu Gly Lys His
                805                 810                 815

Thr Arg Phe Trp Met Arg Ser Lys His Ala Ser Leu Leu Ser Ile Asn
            820                 825                 830

Ser Asp Asp Val Glu Lys Arg Ser Cys Glu Ser Thr Gln Ala Leu Val
        835                 840                 845

Ser Phe Thr His Ala Ser Ile Ala Tyr Asp Leu Pro Ser Thr Ser Gly
    850                 855                 860

Ala Ser Pro Ala Tyr Pro Met Thr Glu Ser Cys His Leu Ser Ser Val
865                 870                 875                 880

Ala Phe Val Pro Cys Leu
```

<210> SEQ ID NO 74
<211> LENGTH: 218
<212> TYPE: PRT
<213> ORGANISM: Artificial Sequence
<220> FEATURE:
<223> OTHER INFORMATION: Synthetic: hu8E11.v2 V205C cysteine engineered
      light chain (Igk)

<400> SEQUENCE: 74

Asp Ile Val Met Thr Gln Ser Pro Asp Ser Leu Ala Val Ser Leu Gly
1               5                   10                  15

Glu Arg Ala Thr Ile Asn Cys Arg Ala Ser Glu Ser Val Asp Asn Tyr
            20                  25                  30

Gly Asn Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Asn Tyr
                85                  90                  95

Glu Asp Pro Phe Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Cys Thr Lys Ser Phe Asn Arg Gly Glu Cys
    210                 215

<210> SEQ ID NO 75
<211> LENGTH: 448
<212> TYPE: PRT
<213> ORGANISM: Artificial Sequence
<220> FEATURE:
<223> OTHER INFORMATION: Synthetic: hu8E11.v2 A118C cysteine engineered
      heavy chain (IgG1)

<400> SEQUENCE: 75

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Ala Tyr
            20                  25                  30

Trp Ile Glu Trp Val Arg Gln Ala Pro Gly Gln Gly Leu Glu Trp Ile
        35                  40                  45

Gly Glu Ile Leu Pro Gly Ser Asp Ser Thr Asp Tyr Asn Glu Lys Phe
    50                  55                  60

Lys Val Arg Ala Thr Phe Thr Ser Asp Thr Ser Thr Ser Thr Val Tyr

```
                65                  70                  75                  80
Leu Glu Leu Ser Ser Leu Arg Ser Glu Asp Thr Ala Val Tyr Tyr Cys
                    85                  90                  95

Ala Arg Gly Gly His Tyr Gly Ser Leu Asp Tyr Trp Gly Gln Gly Thr
                100                 105                 110

Leu Val Thr Val Ser Ser Cys Ser Thr Lys Gly Pro Ser Val Phe Pro
                115                 120                 125

Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 76
<211> LENGTH: 448
<212> TYPE: PRT
<213> ORGANISM: Artificial Sequence
<220> FEATURE:
<223> OTHER INFORMATION: Synthetic: hu8E11.v2 S400C cysteine engineered
      heavy chain (IgG1)
```

<400> SEQUENCE: 76

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Ala Tyr
            20                  25                  30

Trp Ile Glu Trp Val Arg Gln Ala Pro Gly Gln Gly Leu Glu Trp Ile
        35                  40                  45

Gly Glu Ile Leu Pro Gly Ser Asp Ser Thr Asp Tyr Asn Glu Lys Phe
    50                  55                  60

Lys Val Arg Ala Thr Phe Thr Ser Asp Thr Ser Thr Ser Thr Val Tyr
65                  70                  75                  80

Leu Glu Leu Ser Ser Leu Arg Ser Glu Asp Thr Ala Val Tyr Tyr Cys
                85                  90                  95

Ala Arg Gly Gly His Tyr Gly Ser Leu Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Cys Asp Gly Ser Phe Phe Leu Tyr Ser Lys Leu Thr Val Asp Lys Ser
```

```
                    405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
            435                 440                 445

<210> SEQ ID NO 77
<211> LENGTH: 214
<212> TYPE: PRT
<213> ORGANISM: Artificial Sequence
<220> FEATURE:
<223> OTHER INFORMATION: Synthetic: YW353 V205C cysteine engineered
      light chain (Igk)

<400> SEQUENCE: 77

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Cys Thr Lys Ser
        195                 200                 205

Phe Asn Arg Gly Glu Cys
    210

<210> SEQ ID NO 78
<211> LENGTH: 446
<212> TYPE: PRT
<213> ORGANISM: Artificial Sequence
<220> FEATURE:
<223> OTHER INFORMATION: Synthetic: YW353 A118C cysteine engineered
      heavy chain (IgG1)

<400> SEQUENCE: 78

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Ser Tyr
            20                  25                  30

Ser Ile Ser Trp Val Arg Gln Ala Pro Gly Lys Gly Leu Glu Trp Val
```

```
            35                  40                  45
Ala Glu Ile Tyr Pro Pro Gly Gly Tyr Thr Asp Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Lys Ala Arg Leu Phe Phe Asp Tyr Trp Gly Gln Gly Thr Leu Val
                100                 105                 110

Thr Val Ser Ser Cys Ser Thr Lys Gly Pro Ser Val Phe Pro Leu Ala
                115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
                260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys
        435                 440                 445

<210> SEQ ID NO 79
```

```
<211> LENGTH: 446
<212> TYPE: PRT
<213> ORGANISM: Artificial Sequence
<220> FEATURE:
<223> OTHER INFORMATION: Synthetic: YW353 S400C cysteine engineered
      heavy chain (IgG1)

<400> SEQUENCE: 79

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Ser Tyr
            20                  25                  30

Ser Ile Ser Trp Val Arg Gln Ala Pro Gly Lys Gly Leu Glu Trp Val
        35                  40                  45

Ala Glu Ile Tyr Pro Pro Gly Gly Tyr Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Lys Ala Arg Leu Phe Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
```

```
                    370                 375                 380

Gln Pro Glu Asn Asn Tyr Lys Thr Thr Pro Val Leu Asp Cys Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 80
<211> LENGTH: 106
<212> TYPE: PRT
<213> ORGANISM: Artificial Sequence
<220> FEATURE:
<223> OTHER INFORMATION: Synthetic: V205C cysteine engineered light
      chain constant region (Igk)

<400> SEQUENCE: 80

Thr Val Ala Ala Pro Ser Val Phe Ile Phe Pro Pro Ser Asp Glu Gln
1               5                   10                  15

Leu Lys Ser Gly Thr Ala Ser Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Cys Thr Lys Ser Phe Asn Arg Gly Glu Cys
            100                 105

<210> SEQ ID NO 81
<211> LENGTH: 330
<212> TYPE: PRT
<213> ORGANISM: Artificial Sequence
<220> FEATURE:
<223> OTHER INFORMATION: Synthetic: A118C cysteine engineered heavy
      chain constant region (IgG1)

<400> SEQUENCE: 81

Cys Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
```

```
              115                 120                 125
Lys Pro Lys Asp Thr Leu Met Ile Ser Arg Thr Pro Glu Val Thr Cys
        130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Glu Glu
225                 230                 235                 240
Met Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 82
<211> LENGTH: 330
<212> TYPE: PRT
<213> ORGANISM: Artificial Sequence
<220> FEATURE:
<223> OTHER INFORMATION: Synthetic: S400C cysteine engineered heavy
      chain constant region (IgG1)

<400> SEQUENCE: 82

Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
        50                  55                  60
Leu Ser Ser Val Val Thr Val Pro Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
        115                 120                 125
Lys Pro Lys Asp Thr Leu Met Ile Ser Arg Thr Pro Glu Val Thr Cys
    130                 135                 140
```

```
Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Cys Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 83
<211> LENGTH: 20
<212> TYPE: DNA
<213> ORGANISM: Artificial Sequence
<220> FEATURE:
<223> OTHER INFORMATION: Synthetic: primer

<400> SEQUENCE: 83
accaactgca tcctaaactg                                                   20

<210> SEQ ID NO 84
<211> LENGTH: 20
<212> TYPE: DNA
<213> ORGANISM: Artificial Sequence
<220> FEATURE:
<223> OTHER INFORMATION: Synthetic: primer

<400> SEQUENCE: 84
accgagtttc acctcagctc                                                   20

<210> SEQ ID NO 85
<211> LENGTH: 20
<212> TYPE: DNA
<213> ORGANISM: Artificial Sequence
<220> FEATURE:
<223> OTHER INFORMATION: Synthetic: primer

<400> SEQUENCE: 85
acattgccct gttgctcttc                                                   20

<210> SEQ ID NO 86
<211> LENGTH: 21
<212> TYPE: DNA
<213> ORGANISM: Artificial Sequence
<220> FEATURE:
<223> OTHER INFORMATION: Synthetic: primer
```

```
<400> SEQUENCE: 86
actgctctga tatactcaat c                                                   21
```

US 9,175,089 B2

ANTI-LGR5 ANTIBODIES AND IMMUNOCONJUGATES

This application claims the benefit of U.S. Provisional Application No. 61/618,232, filed Mar. 30, 2012; U.S. Provisional Application No. 61/683,048, filed Aug. 14, 2012; and U.S. Provisional Application No. 61/778,710, filed Mar. 13, 2013; each of which is incorporated by reference herein in its entirety for any purpose.

FIELD OF THE INVENTION

The present invention relates to anti-LgR5 antibodies and immunoconjugates and methods of using the same.

BACKGROUND

Leucine-rich repeat-containing G protein-coupled receptor 5 (LgR5) is a seven-transmembrane protein found on the surface of actively cycling intestinal stem cells (ISCs). LgR5-expressing ISCs are sensitive to Wnt modulation and are primarily responsible for homeostatic regeneration of the intestinal epithelium. Elimination of LgR5-expressing cells in mice does not affect homeostasis of intestinal epithelium, however, suggesting that other cell types can compensate for loss of this cell population. Tian et al., Nature 478: 255-259 (2011). R-spondins enhance WNT signaling by WNT3A, and all four R-spondins, RSPO1, RSPO2, RSPO3, and RSPO4, are able to bind to LgR5. Lau et al., Nature 476: 293-297 (2011).

Human LgR5 is a 907 amino acid protein, of which ~540 amino acids are predicted to be in the extracellular space following cleavage of the amino-terminal signal sequence. LgR5 comprises 17 imperfect leucine-rich repeat motifs in the ectodomain, and a cysteine-rich region located between the leucine-rich repeats and the first transmembrane domain.

There is a need in the art for agents that target LgR5 for the diagnosis and treatment of LgR5-associated conditions, such as cancer. The invention fulfills that need and provides other benefits.

SUMMARY

The invention provides anti-LgR5 antibodies and immunoconjugates and methods of using the same.

In some embodiments, an isolated antibody that binds to LgR5 is provided. In some embodiments, the antibody has at least one or more of the following characteristics, in any combination: (a) binds to an epitope within amino acids 22-555 of SEQ ID NO: 67 and/or binds to an epitope within amino acids 22-123 of SEQ ID NO: 67 and/or binds to an epitope within amino acids 22-323 of SEQ ID NO: 67 and/or binds to an epitope within amino acids 22-424 of SEQ ID NO: 67 and/or binds to an epitope within amino acids 324-555 of SEQ ID NO: 67 and/or binds to an epitope within amino acids 324-424 of SEQ ID NO: 67; (b) binds LgR5 with an affinity of ≤5 nM, or ≤4 nM, or ≤3 nM, or ≤2 nM, or ≤1 nM, and optionally ≥0.0001 nM, or ≥0.001 nM, or ≥0.01 nM; (c) does not significantly disrupt the binding of R-spondin (RSPO) to LgR5; (d) does not significantly disrupt beta-catenin signaling; (e) does not significantly disrupt RSPO activation of LgR5 signaling; (f) activates caspase 3 cleavage; (g) recognizes both human and rodent LgR5; (h) recognizes human LgR5 but not rodent LgR5; (i) does not significantly inhibit tumor growth in its unconjugated form; and (j) does not induce stem cell differentiation.

In some embodiments, the isolated anti-LgR5 antibody binds to an epitope within amino acids 22-323 of SEQ ID NO: 67 with an affinity of ≤5 nM, or ≤4 nM, or ≤3 nM, or ≤2 nM, or ≤1 nM, and optionally ≥0.0001 nM, or ≥0.001 nM, or ≥0.01 nM.

In some embodiments, the isolated anti-LgR5 antibody binds to an epitope within amino acids 22-123 of SEQ ID NO: 67 with an affinity of ≤5 nM, or ≤4 nM, or ≤3 nM, or ≤2 nM, or ≤1 nM, and optionally ≥0.0001 nM, or ≥0.001 nM, or ≥0.01 nM.

In some embodiments, the isolated anti-LgR5 antibody binds to an epitope within amino acids 324-424 of SEQ ID NO: 67 with an affinity of ≤5 nM, or ≤4 nM, or ≤3 nM, or ≤2 nM, or ≤1 nM, and optionally ≥0.0001 nM, or ≥0.001 nM, or ≥0.01 nM.

In some embodiments of any of the isolated anti-LgR5 antibodies, the anti-LgR5 antibody does not significantly disrupt the binding of R-spondin (RSPO) to LgR5. In some embodiments of any of the isolated anti-LgR5 antibodies, the anti-LgR5 antibody does not significantly disrupt wnt/beta-catenin signaling. In some embodiments of any of the isolated anti-LgR5 antibodies, the anti-LgR5 antibody does not significantly disrupt RSPO activation of LgR5 signaling. In some embodiments of any of the isolated anti-LgR5 antibodies, the anti-LgR5 antibody activates caspase 3 cleavage. In some embodiments of any of the isolated anti-LgR5 antibodies, the anti-LgR5 antibody recognizes both human and rodent LgR5. In some embodiments of any of the isolated anti-LgR5 antibodies, the anti-LgR5 antibody recognizes human LgR5 but not rodent LgR5. In some embodiments of any of the isolated anti-LgR5 antibodies, the anti-LgR5 antibody does not significantly inhibit tumor growth in its unconjugated form. In some embodiments of any of the isolated anti-LgR5 antibodies, the anti-LgR5 antibody does not induce stem cell differentiation.

In some embodiments of any of the isolated anti-LgR5 antibodies, the anti-LgR5 antibody is a monoclonal antibody. In some embodiments of any of the isolated anti-LgR5 antibodies, the anti-LgR5 antibody is a human, humanized, or chimeric antibody. In some embodiments of any of the isolated anti-LgR5 antibodies, the anti-LgR5 antibody antibody is an IgG1, IgG2a or IgG2b antibody. In some embodiments of any of the isolated anti-LgR5 antibodies, the anti-LgR5 antibody is an antibody fragment that binds LgR5. In some embodiments of any of the isolated anti-LgR5 antibodies, LgR5 is human LgR5 of SEQ ID NO: 67.

In some embodiments, an antibody that binds LgR5 binds an epitope within amino acids 22-323 of SEQ ID NO: 67. In some embodiments, the antibody binds to LgR5 with an affinity of ≤5 nM. In some embodiments, the antibody is a monoclonal antibody. In some embodiments, the antibody is a human, humanized, or chimeric antibody. In some embodiments, the antibody is an IgG1, IgG2a or IgG2b antibody. In some embodiments, the antibody is an antibody fragment that binds LgR5. In some embodiments, LgR5 is human LgR5 of SEQ ID NO: 67.

In some embodiments, the antibody comprises (a) HVR-H3 comprising the amino acid sequence of SEQ ID NO: 32, (b) HVR-L3 comprising the amino acid sequence of SEQ ID NO: 29, and (c) HVR-H2 comprising the amino acid sequence of SEQ ID NO: 31. In some embodiments, the antibody comprises (a) HVR-H1 comprising the amino acid sequence of SEQ ID NO: 30, (b) HVR-H2 comprising the amino acid sequence of SEQ ID NO: 31, and (c) HVR-H3 comprising the amino acid sequence of SEQ ID NO: 32. In some embodiments, the antibody further comprises a heavy chain framework FR3 sequence of SEQ ID NO: 41. In some embodiments, the antibody further comprises (a) HVR-L1 comprising the amino acid sequence of SEQ ID NO: 27, (b) HVR-L2 comprising the amino acid sequence of SEQ ID NO: 28, and (c) HVR-L3 comprising the amino acid sequence of SEQ ID NO: 29. In some embodiments, an isolated antibody comprises (a) HVR-L1 comprising the amino acid sequence of SEQ ID NO: 27, (b) HVR-L2 comprising the amino acid sequence of SEQ ID NO: 28, and (c) HVR-L3 comprising the amino acid sequence of SEQ ID NO: 29. In some embodiments, the antibody further comprises a light chain framework FR3 sequence of SEQ ID NO: 35.

In some embodiments, an isolated antibody comprises (a) a VH sequence having at least 95% sequence identity to the amino acid sequence of SEQ ID NO: 8; or (b) a VL sequence having at least 95% sequence identity to the amino acid sequence of SEQ ID NO:7; or (c) a VH sequence as in (a) and a VL sequence as in (b). In some embodiments, the antibody comprises a VH sequence of SEQ ID NO: 8. In some embodiments, the antibody comprises a VL sequence of SEQ ID NO: 7. In some embodiments, and isolated antibody comprises a VH sequence of SEQ ID NO: 8 and a VL sequence of SEQ ID NO: 7.

In some embodiments, an antibody that binds LgR5 comprises (a) HVR-H3 comprising the amino acid sequence of SEQ ID NO: 56, (b) HVR-L3 comprising the amino acid sequence of SEQ ID NO: 53, and (c) HVR-H2 comprising the amino acid sequence of SEQ ID NO: 55. In some embodiments, the antibody comprises (a) HVR-H1 comprising the amino acid sequence of SEQ ID NO: 54, (b) HVR-H2 comprising the amino acid sequence of SEQ ID NO: 55, and (c) HVR-H3 comprising the amino acid sequence of SEQ ID NO: 56. In some embodiments, the antibody further comprises (a) HVR-L1 comprising the amino acid sequence of SEQ ID NO: 51, (b) HVR-L2 comprising the amino acid sequence of SEQ ID NO: 52, and (c) HVR-L3 comprising the amino acid sequence of SEQ ID NO: 53. In some embodiments, an isolated antibody comprises (a) HVR-L1 comprising the amino acid sequence of SEQ ID NO: 51, (b) HVR-L2 comprising the amino acid sequence of SEQ ID NO: 52, and (c) HVR-L3 comprising the amino acid sequence of SEQ ID NO: 53.

In some embodiments, an isolated antibody comprises (a) a VH sequence having at least 95% sequence identity to the amino acid sequence of SEQ ID NO: 24; or (b) a VL sequence having at least 95% sequence identity to the amino acid sequence of SEQ ID NO:23; or (c) a VH sequence as in (a) and a VL sequence as in (b). In some embodiments, the antibody comprises a VH sequence of SEQ ID NO: 24. In some embodiments, the antibody comprises a VL sequence of SEQ ID NO: 23. In some embodiments, and isolated antibody comprises a VH sequence of SEQ ID NO: 24 and a VL sequence of SEQ ID NO: 23.

In some embodiments, an antibody that binds LgR5 comprises (a) HVR-H3 comprising the amino acid sequence of SEQ ID NO: 50, (b) HVR-L3 comprising the amino acid sequence of SEQ ID NO: 47, and (c) HVR-H2 comprising the amino acid sequence of SEQ ID NO:495. In some embodiments, the antibody comprises (a) HVR-H1 comprising the amino acid sequence of SEQ ID NO: 48, (b) HVR-H2 comprising the amino acid sequence of SEQ ID NO: 49, and (c) HVR-H3 comprising the amino acid sequence of SEQ ID NO: 50. In some embodiments, the antibody further comprises (a) HVR-L1 comprising the amino acid sequence of SEQ ID NO: 45, (b) HVR-L2 comprising the amino acid sequence of SEQ ID NO: 46, and (c) HVR-L3 comprising the amino acid sequence of SEQ ID NO: 47. In some embodiments, an isolated antibody comprises (a) HVR-L1 comprising the amino acid sequence of SEQ ID NO: 45, (b) HVR-L2 comprising the amino acid sequence of SEQ ID NO: 46, and (c) HVR-L3 comprising the amino acid sequence of SEQ ID NO: 47.

In some embodiments, an isolated antibody comprises (a) a VH sequence having at least 95% sequence identity to the amino acid sequence of SEQ ID NO: 22; or (b) a VL sequence having at least 95% sequence identity to the amino acid sequence of SEQ ID NO:21; or (c) a VH sequence as in (a) and a VL sequence as in (b). In some embodiments, the antibody comprises a VH sequence of SEQ ID NO: 22. In some embodiments, the antibody comprises a VL sequence of SEQ ID NO: 21. In some embodiments, and isolated antibody comprises a VH sequence of SEQ ID NO: 22 and a VL sequence of SEQ ID NO: 21.

In some embodiments, an antibody that binds LgR5 comprises (a) HVR-H3 comprising the amino acid sequence of SEQ ID NO: 62, (b) HVR-L3 comprising the amino acid sequence of SEQ ID NO: 59, and (c) HVR-H2 comprising the amino acid sequence of SEQ ID NO: 61. In some embodiments, the antibody comprises (a) HVR-H1 comprising the amino acid sequence of SEQ ID NO: 60, (b) HVR-H2 comprising the amino acid sequence of SEQ ID NO: 61, and (c) HVR-H3 comprising the amino acid sequence of SEQ ID NO: 62. In some embodiments, the antibody further comprises (a) HVR-L1 comprising the amino acid sequence of SEQ ID NO: 57, (b) HVR-L2 comprising the amino acid sequence of SEQ ID NO: 58, and (c) HVR-L3 comprising the amino acid sequence of SEQ ID NO: 59. In some embodiments, an isolated antibody comprises (a) HVR-L1 comprising the amino acid sequence of SEQ ID NO: 57, (b) HVR-L2 comprising the amino acid sequence of SEQ ID NO: 58, and (c) HVR-L3 comprising the amino acid sequence of SEQ ID NO: 59.

In some embodiments, an isolated antibody comprises (a) a VH sequence having at least 95% sequence identity to the amino acid sequence of SEQ ID NO: 26; or (b) a VL sequence having at least 95% sequence identity to the amino acid sequence of SEQ ID NO:25; or (c) a VH sequence as in (a) and a VL sequence as in (b). In some embodiments, the antibody comprises a VH sequence of SEQ ID NO: 26. In some embodiments, the antibody comprises a VL sequence of SEQ ID NO: 25. In some embodiments, and isolated antibody comprises a VH sequence of SEQ ID NO: 26 and a VL sequence of SEQ ID NO: 25.

In some embodiments, an isolated nucleic acid that encodes an antibody described herein is provided. In some embodiments, a host cell comprising the nucleic acid is provided. In some embodiments, a method of producing an antibody described herein is provided. In some embodiments, the method comprises culturing the host cell comprising the nucleic acid that encodes an antibody.

In some embodiments, immunoconjugates are provided. In some embodiments, an immunoconjugate comprises an anti-LgR5 antibody and a cytotoxic agent. In some embodiments, an immunoconjugate has the formula Ab-(L-D)p, wherein:

(a) Ab is an antibody described herein; (b) L is a linker; (c) D is a drug selected from a maytansinoid, an auristatin, a calicheamicin, a pyrrolobenzodiazepine, and a nemorubicin derivative; and (d) p ranges from 1-8. In some embodiments, D is an auristatin. In some such embodiments, D has formula $D_E$

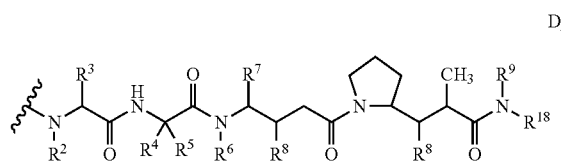

wherein $R^2$ and $R^6$ are each methyl, $R^3$ and $R^4$ are each isopropyl, $R^5$ is H, $R^7$ is sec-butyl, each $R^8$ is independently selected from $CH_3$, $O-CH_3$, OH, and H; $R^9$ is H; and $R^{18}$ is $-C(R^8)_2-C(R^8)_2-$ aryl. In some embodiments, D is MMAE having the structure:

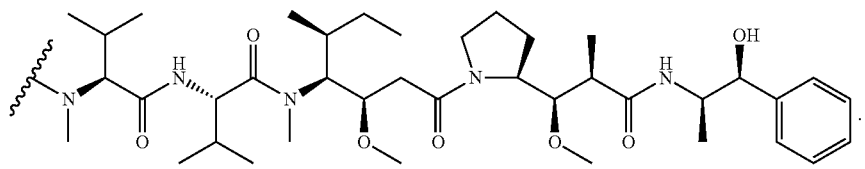 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@H](C)[C@@H](O)c1ccccc1)OC)C(C)C)C(C)C]

In some embodiments, D is a pyrrolobenzodiazepine of Formula A:

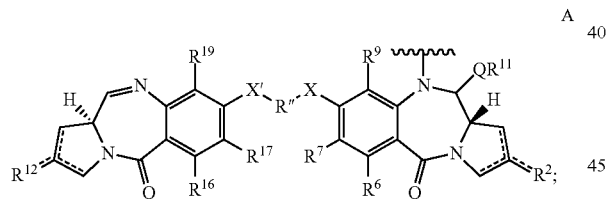

wherein the dotted lines indicate the optional presence of a double bond between C1 and C2 or C2 and C3; $R^2$ is independently selected from H, OH, =O, =$CH_2$, CN, R, OR, =CH-$R^D$, =C($R^D$)$_2$, O-$SO_2$-R, $CO_2$R and COR, and optionally further selected from halo or dihalo, wherein $R^D$ is independently selected from R, $CO_2$R, COR, CHO, $CO_2$H, and halo; $R^6$ and $R^9$ are independently selected from H, R, OH, OR, SH, SR, $NH_2$, NHR, NRR', $NO_2$, $Me_3$Sn and halo; $R^7$ is independently selected from H, R, OH, OR, SH, SR, $NH_2$, NHR, NRR', $NO_2$, $Me_3$Sn and halo; Q is independently selected from O, S and NH; $R^{11}$ is either H, or R or, where Q is O, $SO_3$M, where M is a metal cation; R and R' are each independently selected from optionally substituted $C_{1-8}$ alkyl, $C_{1-12}$ alkyl, $C_{3-8}$ heterocyclyl, $C_{3-20}$ heterocyclyl, and $C_{5-20}$ aryl groups, and optionally in relation to the group NRR', R and R' together with the nitrogen atom to which they are attached form an optionally substituted 4-, 5-, 6- or 7-membered heterocyclic ring; $R^{12}$, $R^{16}$, $R^{19}$ and $R^{17}$ are as defined for $R^2$, $R^6$, $R^9$ and $R^7$ respectively; R" is a $C_{3-12}$ alkylene group, which chain may be interrupted by one or more heteroatoms and/or aromatic rings that are optionally substituted; and X and X' are independently selected from O, S and N(H). In some such embodiments, D is

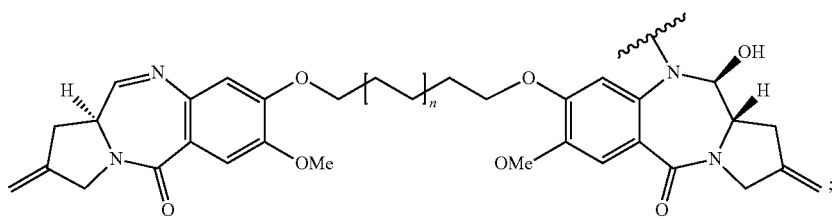

wherein n is 0 or 1.

In some embodiments, D is a nemorubicin derivative. In some embodiments, D has a structure selected from:

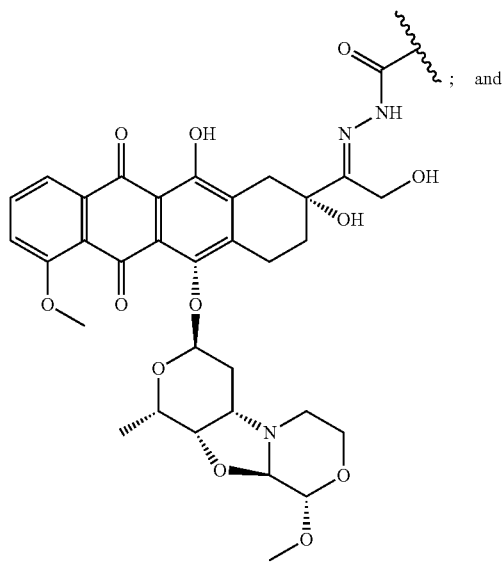

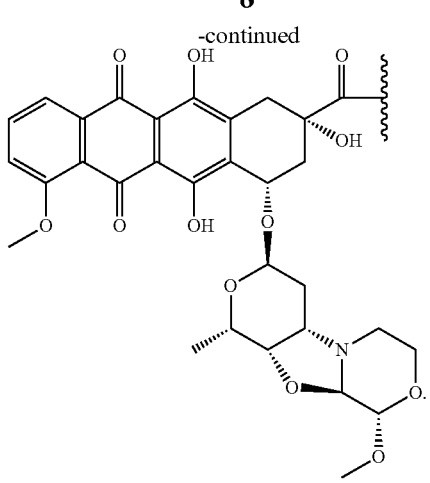

In some embodiments, an immunoconjugate comprises a linker that is cleavable by a protease. In some embodiments, the linker comprises a val-cit dipeptide or a Phe-Lys dipeptide. In some embodiments, an immunoconjugate comprises a linker that is acid-labile. In some such embodiments, the linker comprises hydrazone.

In some embodiments, an immunoconjugate has a formula selected from:

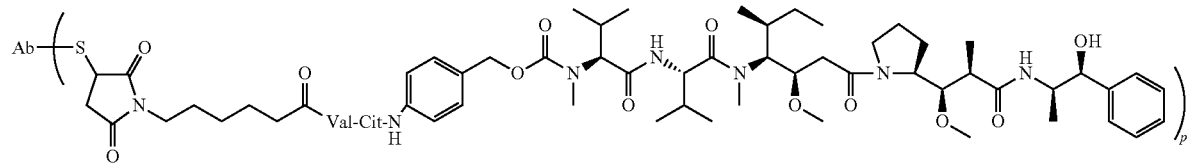

wherein S is a sulfur atom;

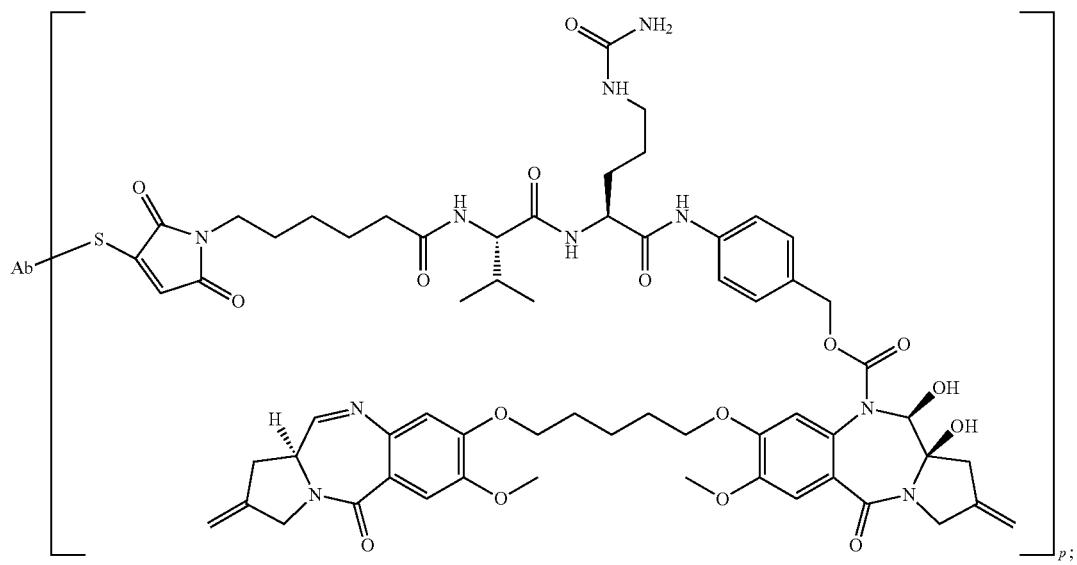

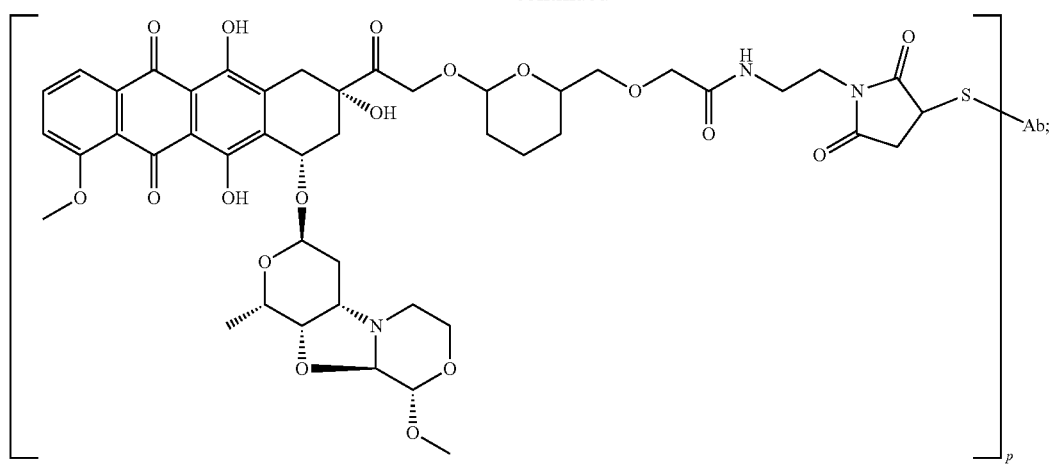
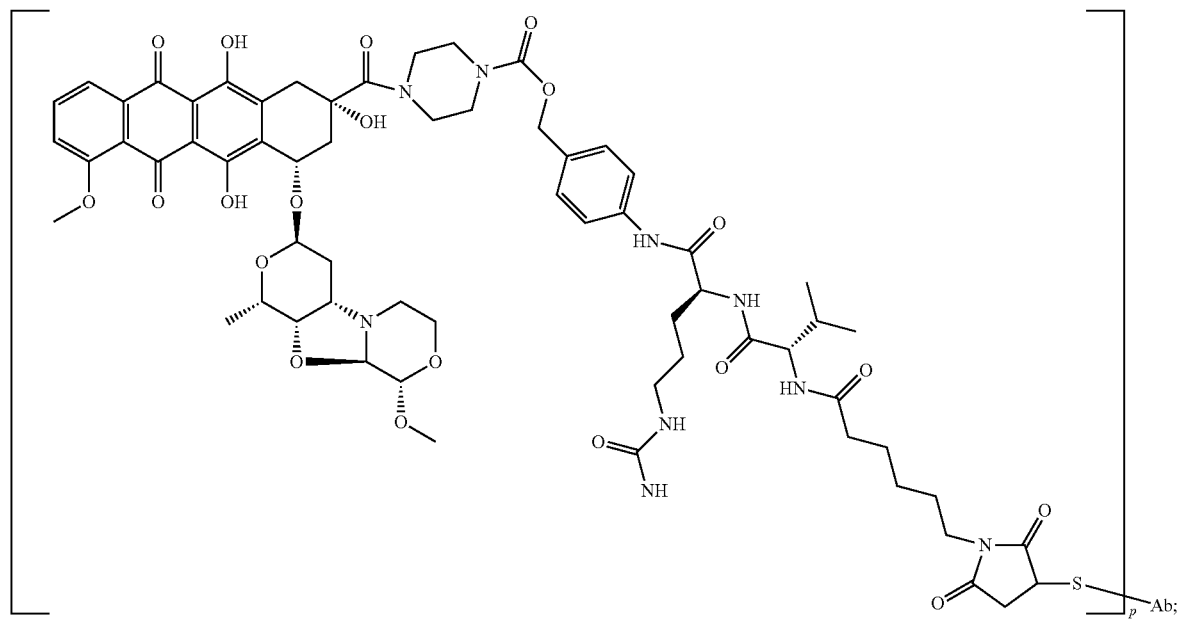
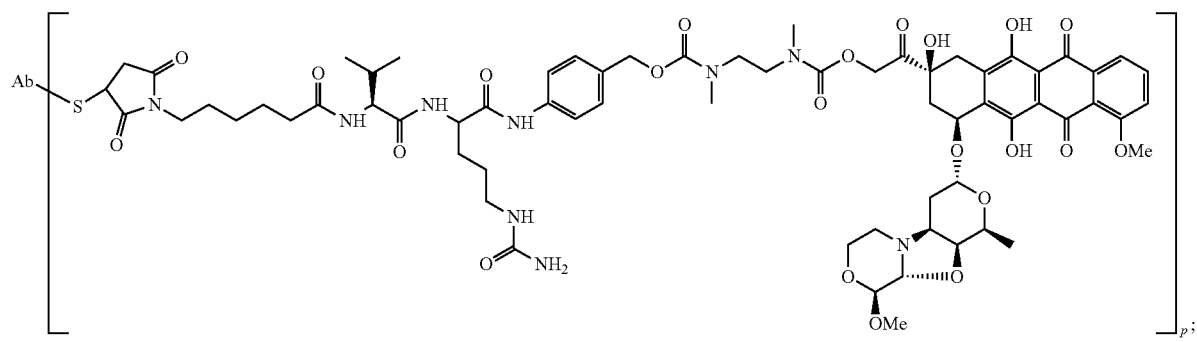

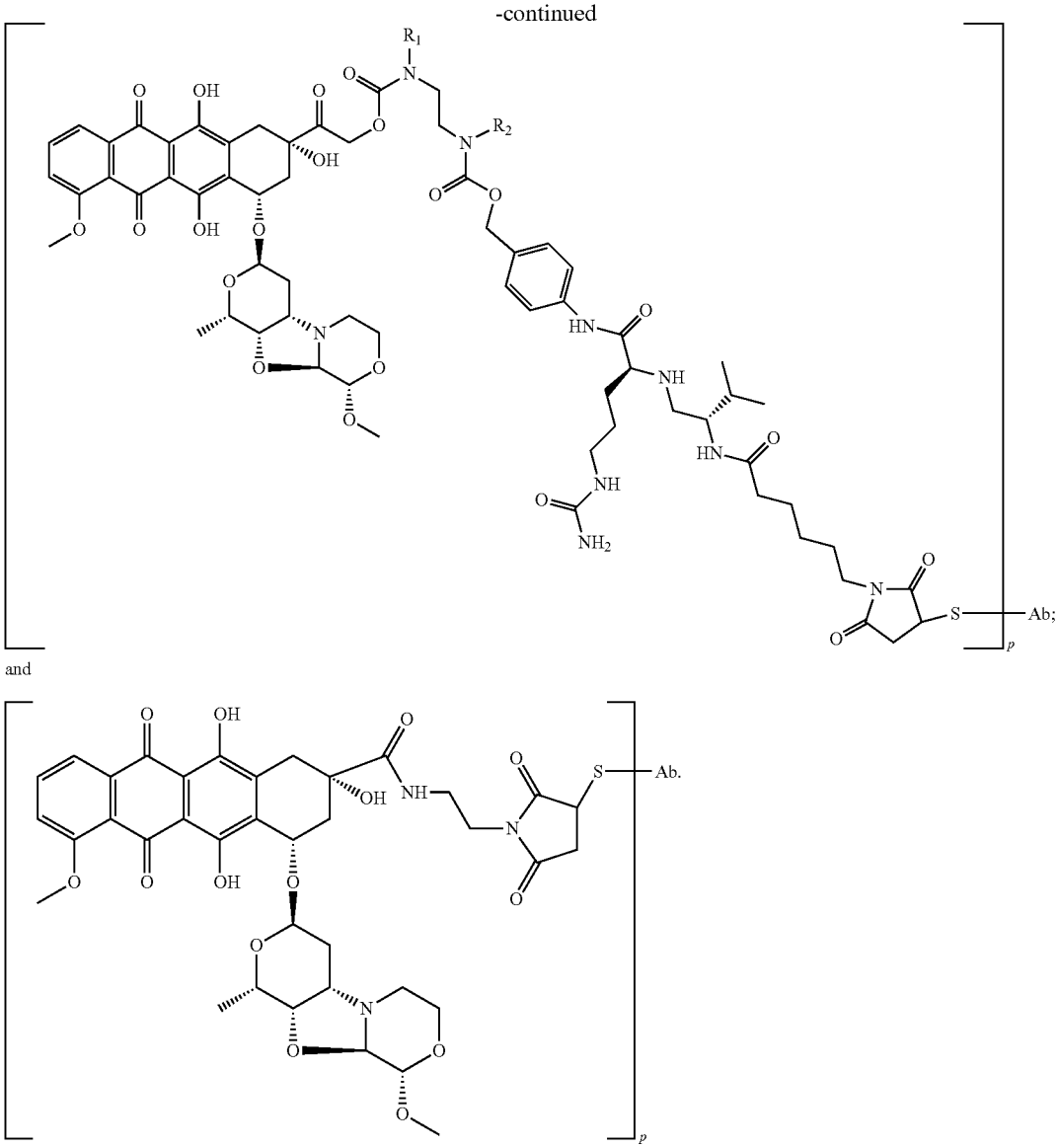

In some embodiments, p ranges from 2-5.

In some embodiments, an immunoconjugate comprises an antibody that comprises (a) HVR-H1 comprising the amino acid sequence of SEQ ID NO: 30, (b) HVR-H2 comprising the amino acid sequence of SEQ ID NO: 31, and (c) HVR-H3 comprising the amino acid sequence of SEQ ID NO: 32; (d) HVR-L1 comprising the amino acid sequence of SEQ ID NO: 27, (e) HVR-L2 comprising the amino acid sequence of SEQ ID NO: 28, and (0 HVR-L3 comprising the amino acid sequence of SEQ ID NO: 29. In some embodiments, an immunoconjugate comprises an antibody that comprises a VH sequence of SEQ ID NO: 8 and a VL sequence of SEQ ID NO: 7.

In some embodiments, pharmaceutical formulations are provided. In some such embodiments, a pharmaceutical formulation comprises an immunoconjugate comprising an antibody that binds LgR5, e.g., as described herein. In some embodiments, a pharmaceutical formulation further comprises an additional therapeutic agent. In some embodiments, the additional therapeutic agent is Avastin® (bevacizumab).

In some embodiments, methods of treating individuals having LgR5 positive cancers are provided. In some such embodiments, a method comprises administering a pharmaceutical formulation comprising an immunoconjugate comprising an antibody that binds LgR5, e.g., as described herein. In some embodiments, the LgR5-positive cancer is selected from colorectal cancer, pancreatic cancer, ovarian cancer, and endometrial cancer. In some embodiments, the LgR5-positive cancer is a small intestine cancer. In some embodiments, a small intestine cancer is a cancer of the duodenum, jejunum, and/or ilium. In some embodiments, a small intestine cancer is a cancer of the jejunum and/or ilium. In some embodiments, an LgR5-positive cancer comprises a Kras mutation, an APC mutation, or both a Kras mutation and an APC mutation (e.g., in at least a portion of the cancer cells). In some embodiments, a method comprises administering an additional therapeutic agent to the individual. In some such embodiments, the additional therapeutic agent is Avastin® (bevacizumab).

In some embodiments, methods of inhibiting proliferation of an LgR5-positive cell are provided. In some embodiments, the method comprising exposing the cell to an immunoconjugate comprising an antibody that binds LgR5 under conditions permissive for binding of the immunoconjugate to LgR5 on the surface of the cell. In some embodiments, an antibody that binds LgR5 is an antibody described herein. In some embodiments, proliferation of the cell is thereby inhibited. In some embodiments, the cell is a colorectal, small intestine, pancreatic, ovarian, or endometrial cancer cell.

In some embodiments, an antibody that binds LgR5 is conjugated to a label. In some embodiments, an antibody that binds LgR5 is an antibody described herein. In some embodiments, the label is a positron emitter. In some embodiments, the positron emitter is $^{89}$Zr.

In some embodiments, a method of detecting human LgR5 in a biological sample is provided. In some embodiments, a method comprises contacting the biological sample with an anti-LgR5 antibody under conditions permissive for binding of the anti-LgR5 antibody to a naturally occurring human LgR5, and detecting whether a complex is formed between the anti-LgR5 antibody and a naturally occurring human LgR5 in the biological sample. In some embodiments, an anti-LgR5 antibody is an antibody described herein. In some embodiments, the biological sample is a colorectal cancer sample, small intestine cancer sample, pancreatic cancer sample, ovarian cancer sample, or endometrial cancer sample.

In some embodiments, a method for detecting an LgR5-positive cancer is provided. In some such embodiments, a method comprises (i) administering a labeled anti-LgR5 antibody to a subject having or suspected of having an LgR5-positive cancer, and (ii) detecting the labeled anti-LgR5 antibody in the subject, wherein detection of the labeled anti-LgR5 antibody indicates a LgR5-positive cancer in the subject. In some embodiments, an anti-LgR5 antibody is an antibody described herein.

BRIEF DESCRIPTION OF THE FIGURES

FIG. 4 shows the properties of certain anti-LgR5 monoclonal antibodies developed as described in Examples C through F.

FIG. 5 shows an alignment of the light chain variable region sequences of murine antibody mu8E11 and humanized variants thereof (hu8E11.v1 to hu8E11.v8). The three hypervariable regions (HVRs: HVR1, HVR2, HVR3) are indicated by boxes in the sequences.

FIG. 6 shows an alignment of the heavy chain variable region sequences of murine antibody mu8E11 and humanized variants thereof (hu8E11.v1 to hu8E11.v8). The three hypervariable regions (HVRs: HVR1, HVR2, HVR3) are indicated by boxes in the sequences.

FIG. 7 shows the light chain variable region sequences of murine antibodies 3G12 and 2H6. The three hypervariable regions (HVRs: HVR1, HVR2, HVR3) are indicated by boxes in the sequences.

FIG. 8 shows the heavy chain variable region sequences of murine antibodies 3G12 and 2H6. The three hypervariable regions (HVRs: HVR1, HVR2, HVR3) are indicated by boxes in the sequences.

FIG. 9 shows affinity measurements of chimeric antibody ch8E11 and various humanized variants, as described in Example E.

FIG. 10 shows the light chain variable region sequence of human antibody YW353. The three hypervariable regions (HVRs: HVR1, HVR2, HVR3) are indicated by boxes in the sequences.

FIG. 11 shows the heavy chain variable region sequence of human antibody YW353. The three hypervariable regions (HVRs: HVR1, HVR2, HVR3) are indicated by boxes in the sequences.

FIG. 12A-C show an alignment of LgR5 from human, cynomolgus monkey, rat, and mouse.

FIG. 35 shows the structures of (A) an antibody-vcMMAE immunoconjugate, (B) an antibody-acetal-PNU immunoconjugate, (C) an antibody-acetal-PNU immunoconjugate, (D) an antibody-PNU immunoconjugate, and (E) an antibody-vcPBD immunoconjugate.

DETAILED DESCRIPTION OF CERTAIN EMBODIMENTS OF THE INVENTION

I. Definitions

Figure 1:
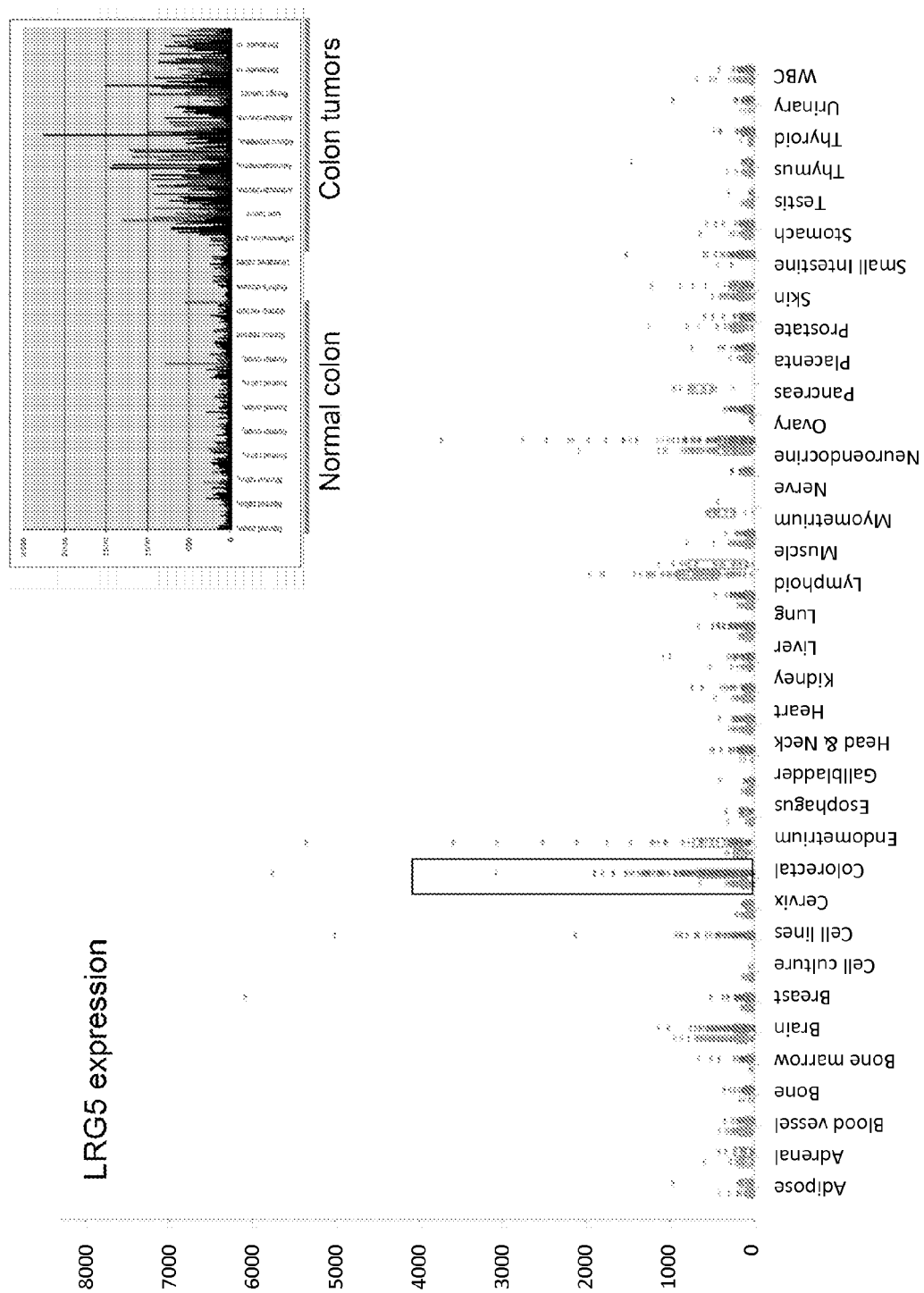
FIG. 1 shows a graphic representation of the levels of human LgR5 gene expression in various tissues, as described in Example A. The inset in FIG. 1 shows a graphic representation of the levels of human LgR5 gene expression in normal colon tissues and colon tumors, as described in Example A.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The terms "anti-LgR5 antibody" and "an antibody that binds to LgR5" refer to an antibody that is capable of binding LgR5 with sufficient affinity such that the antibody is useful as a diagnostic and/or therapeutic agent in targeting LgR5. In one embodiment, the extent of binding of an anti-LgR5 antibody to an unrelated, non-LgR5 protein is less than about 10% of the binding of the antibody to LgR5 as measured, e.g., by a radioimmunoassay (RIA). In certain embodiments, an antibody that binds to LgR5 has a dissociation constant (Kd) of $\leq 1$ μm, $\leq 100$ nM, $\leq 10$ nM, $\leq 5$ Nm, $\leq 4$ nM, $\leq 3$ nM, $\leq 2$ nM, $\leq 1$ nM, $\leq 0.1$ nM, $\leq 0.01$ nM, or $\leq 0.001$ nM (e.g., $10^{-8}$M or less, e.g. from $10^{-8}$M to $10^{-13}$M, e.g., from $10^{-9}$M to $10^{-13}$ M). In certain embodiments, an anti-LgR5 antibody binds to an epitope of LgR5 that is conserved among LgR5 from different species.

The term "antibody" is used herein in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody and that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The terms "cancer" and "cancerous" refer to or describe the physiological condition in mammals that is typically characterized by unregulated cell growth/proliferation. Examples of cancer include, but are not limited to, carcinoma, lymphoma (e.g., Hodgkin's and non-Hodgkin's lymphoma), blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioma, cervical cancer, ovarian cancer, liver cancer, bladder cancer, hepatoma, breast cancer, colon cancer, colorectal cancer, small intestine cancer, endometrial or uterine carcinoma, salivary gland carcinoma, kidney cancer, liver cancer, prostate cancer, vulval cancer, thyroid cancer, hepatic carcinoma, leukemia and other lymphoproliferative disorders, and various types of head and neck cancer.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and μ respectively.

The term "cytotoxic agent" as used herein refers to a substance that inhibits or prevents a cellular function and/or causes cell death or destruction. Cytotoxic agents include, but are not limited to, radioactive isotopes (e.g., At$^{211}$, I$^{131}$, I$^{125}$, Y$^{90}$, Re$^{186}$, Re$^{188}$, Sm$^{153}$, Bi$^{212}$, P$^{32}$, Pb$^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of an agent, e.g., a pharmaceutical formulation, refers to an amount effective, at dosages and for periods of time necessary, to achieve the desired therapeutic or prophylactic result.

The term "epitope" refers to the particular site on an antigen molecule to which an antibody binds.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest*, 5th Ed. Public Health Service, National Institutes of Health, Bethesda, Md., 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The term "glycosylated forms of LgR5" refers to naturally occurring forms of LgR5 that are post-translationally modified by the addition of carbohydrate residues.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR," as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia and Lesk, *J. Mol. Biol.* 196:901-917 (1987).) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., Sequences of Proteins of Immunological Interest, 5th Ed. Public Health Service, National Institutes of Health, Bethesda, Md. (1991).) With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, *Front. Biosci.* 13:1619-1633 (2008).) Unless otherwise indicated, HVR residues and other residues in the variable domain (e.g., FR residues) are numbered herein according to Kabat et al., supra.

An "immunoconjugate" is an antibody conjugated to one or more heterologous molecule(s), including but not limited to a cytotoxic agent.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated antibody" is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated nucleic acid" refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-LgR5 antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "LgR5," as used herein, refers to any native, mature LgR5 which results from processing of an LgR5 precursor protein in a cell. The term includes LgR5 from any vertebrate source, including mammals such as primates (e.g. humans and cynomolgus monkeys) and rodents (e.g., mice and rats), unless otherwise indicated. The term also includes naturally occurring variants of LgR5, e.g., splice variants or allelic variants. The amino acid sequence of an exemplary human LgR5 precursor protein, with signal sequence (amino acids 1-21) is shown in SEQ ID NO: 67. The amino acid sequence of an exemplary mature human LgR5 is shown in SEQ ID NO: 68. The predicted sequence for amino acids 33 to 907 of an exemplary cynomolgus monkey LgR5 is shown in SEQ ID NO: 69. The amino acid sequences for exemplary rat LgR5 precursor (with signal sequence, amino acids 1-21) and mature sequences are shown in SEQ ID NOs: 70 and 71, respectively. The amino acid sequences for exemplary mouse LgR5 precursor (with signal sequence, amino acids 1-21) and mature sequences are shown in SEQ ID NOs: 72 and 73, respectively.

The term "LgR5-positive cancer" refers to a cancer comprising cells that express LgR5 on their surface. For the purposes of determining whether a cell expresses LgR5 on the surface, LgR5 mRNA expression is considered to correlate to LgR5 expression on the cell surface. In some embodiments, expression of LgR5 mRNA is determined by a method selected from in situ hybridization and RT-PCR (including quantitative RT-PCR). Alternatively, expression of LgR5 on the cell surface can be determined, for example, using antibodies to LgR5 in a method such as immunohistochemistry, FACS, etc.

The term "LgR5-positive cell" refers to a cell that expresses LgR5 on its surface.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6$^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

"Alkyl" is $C_1$-$C_{18}$ hydrocarbon containing normal, secondary, tertiary or cyclic carbon atoms. Examples are methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$).

The term "$C_1$-$C_8$ alkyl," as used herein refers to a straight chain or branched, saturated or unsaturated hydrocarbon having from 1 to 8 carbon atoms. Representative "$C_1$-$C_8$ alkyl" groups include, but are not limited to, -methyl, -ethyl, -n-propyl, -n-butyl, -n-pentyl, -n-hexyl, -n-heptyl, -n-octyl, -n-nonyl and -n-decyl; while branched $C_1$-$C_8$ alkyls include, but are not limited to, -isopropyl, -sec-butyl, -isobutyl, -tert-butyl, -isopentyl, 2-methylbutyl, unsaturated $C_1$-$C_8$ alkyls include, but are not limited to, -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl-2-butenyl, 1-hexyl, 2-hexyl, 3-hexyl, -acetylenyl, -propynyl, -1-butynyl, -2-butynyl, -1-pentynyl, -2-pentynyl, -3-methyl-1 butynyl. A $C_1$-$C_8$ alkyl group can be unsubstituted or substituted with one or more groups including, but not limited to, —$C_1$-$C_8$ alkyl, —O—($C_1$-$C_8$ alkyl), -aryl, —C(O)R', —OC(O)R', —C(O)OR', —C(O)$NH_2$, —C(O)NHR', —C(O)N(R')$_2$—NHC(O)R', —$SO_3$R', —S(O)$_2$R', —S(O)R', —OH, -halogen, —$N_3$, —$NH_2$, —NH(R'), —N(R')$_2$ and —CN; where each R' is independently selected from H, —$C_1$-$C_8$ alkyl and aryl.

The term "$C_1$-$C_{12}$ alkyl," as used herein refers to a straight chain or branched, saturated or unsaturated hydrocarbon having from 1 to 12 carbon atoms. A $C_1$-$C_{12}$ alkyl group can be unsubstituted or substituted with one or more groups including, but not limited to, —$C_1$-$C_8$ alkyl, —O—($C_1$-$C_8$ alkyl), -aryl, —C(O)R', —OC(O)R', —C(O)OR', —C(O)$NH_2$, —C(O)NHR', —C(O)N(R')$_2$—NHC(O)R', —$SO_3$R', —S(O)$_2$R', —S(O)R', —OH, -halogen, —$N_3$, —$NH_2$, —NH(R'), —N(R')$_2$ and —CN; where each R' is independently selected from H, —$C_1$-$C_8$ alkyl and aryl.

The term "$C_1$-$C_6$ alkyl," as used herein refers to a straight chain or branched, saturated or unsaturated hydrocarbon having from 1 to 6 carbon atoms. Representative "$C_1$-$C_6$ alkyl" groups include, but are not limited to, -methyl, -ethyl, -n- propyl, -n-butyl, -n-pentyl, -and n-hexyl; while branched $C_1$-$C_6$ alkyls include, but are not limited to, -isopropyl, -sec-butyl, -isobutyl, -tert-butyl, -isopentyl, and 2-methylbutyl; unsaturated $C_1$-$C_6$ alkyls include, but are not limited to, -vinyl, -allyl, -1-butenyl, -2-butenyl, and -isobutylenyl, -1-pentenyl, -2-pentenyl, -3-methyl-1-butenyl, -2-methyl-2-butenyl, -2,3-dimethyl-2-butenyl, 1-hexyl, 2-hexyl, and 3-hexyl. A $C_1$-$C_6$ alkyl group can be unsubstituted or substituted with one or more groups, as described above for $C_1$-$C_8$ alkyl group.

The term "$C_1$-$C_4$ alkyl," as used herein refers to a straight chain or branched, saturated or unsaturated hydrocarbon having from 1 to 4 carbon atoms. Representative "$C_1$-$C_4$ alkyl" groups include, but are not limited to, -methyl, -ethyl, -n-propyl, -n-butyl; while branched $C_1$-$C_4$ alkyls include, but are not limited to, -isopropyl, -sec-butyl, -isobutyl, -tert-butyl; unsaturated $C_1$-$C_4$ alkyls include, but are not limited to, -vinyl, -allyl, -1-butenyl, -2-butenyl, and -isobutylenyl. A $C_1$-$C_4$ alkyl group can be unsubstituted or substituted with one or more groups, as described above for $C_1$-$C_8$ alkyl group.

"Alkoxy" is an alkyl group singly bonded to an oxygen. Exemplary alkoxy groups include, but are not limited to, methoxy (—$OCH_3$) and ethoxy (—$OCH_2CH_3$). A "$C_1$-$C_5$ alkoxy" is an alkoxy group with 1 to 5 carbon atoms. Alkoxy groups may can be unsubstituted or substituted with one or more groups, as described above for alkyl groups.

"Alkenyl" is $C_2$-$C_{18}$ hydrocarbon containing normal, secondary, tertiary or cyclic carbon atoms with at least one site of unsaturation, i.e. a carbon-carbon, $sp^2$ double bond. Examples include, but are not limited to: ethylene or vinyl (—CH=$CH_2$), allyl (—$CH_2$CH=$CH_2$), cyclopentenyl (—$C_5H_7$), and 5-hexenyl (—$CH_2CH_2CH_2CH_2$CH=$CH_2$). A "$C_2$-$C_8$ alkenyl" is a hydrocarbon containing 2 to 8 normal, secondary, tertiary or cyclic carbon atoms with at least one site of unsaturation, i.e. a carbon-carbon, $sp^2$ double bond.

"Alkynyl" is $C_2$-$C_{18}$ hydrocarbon containing normal, secondary, tertiary or cyclic carbon atoms with at least one site of unsaturation, i.e. a carbon-carbon, sp triple bond. Examples include, but are not limited to: acetylenic (—C≡CH) and propargyl (—$CH_2$C≡CH). A "$C_2$-$C_8$ alkynyl" is a hydrocarbon containing 2 to 8 normal, secondary, tertiary or cyclic carbon atoms with at least one site of unsaturation, i.e. a carbon-carbon, sp triple bond.

"Alkylene" refers to a saturated, branched or straight chain or cyclic hydrocarbon radical of 1-18 carbon atoms, and having two monovalent radical centers derived by the removal of two hydrogen atoms from the same or two different carbon atoms of a parent alkane. Typical alkylene radicals include, but are not limited to: methylene (—$CH_2$—) 1,2-ethyl (—$CH_2CH_2$—), 1,3-propyl (—$CH_2CH_2CH_2$—), 1,4-butyl (—$CH_2CH_2CH_2CH_2$—), and the like.

A "$C_1$-$C_{10}$ alkylene" is a straight chain, saturated hydrocarbon group of the formula —$(CH_2)_{1-10}$—. Examples of a $C_1$-$C_{10}$ alkylene include methylene, ethylene, propylene, butylene, pentylene, hexylene, heptylene, ocytylene, nonylene and decalene.

"Alkenylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkene. Typical alkenylene radicals include, but are not limited to: 1,2-ethylene (—CH=CH—).

"Alkynylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkyne. Typical alkynylene radicals include, but are not limited to: acetylene (—C≡C—), propargyl (—$CH_2$C≡C—), and 4-pentynyl (—$CH_2CH_2CH_2$C≡C—).

"Aryl" refers to a carbocyclic aromatic group. Examples of aryl groups include, but are not limited to, phenyl, naphthyl and anthracenyl. A carbocyclic aromatic group or a heterocyclic aromatic group can be unsubstituted or substituted with one or more groups including, but not limited to, —$C_1$-$C_8$ alkyl, —O—($C_1$-$C_8$ alkyl), -aryl, —C(O)R', —OC(O)R', —C(O)OR', —C(O)$NH_2$, —C(O)NHR', —C(O)N(R')$_2$—NHC(O)R', —S(O)$_2$R', —S(O)R', —OH, -halogen, —$N_3$, —$NH_2$, —NH(R'), —N(R')$_2$ and —CN; wherein each R' is independently selected from H, —$C_1$-$C_8$ alkyl and aryl.

A "$C_5$-$C_{20}$ aryl" is an aryl group with 5 to 20 carbon atoms in the carbocyclic aromatic rings. Examples of $C_5$-$C_{20}$ aryl groups include, but are not limited to, phenyl, naphthyl and anthracenyl. A $C_5$-$C_{20}$ aryl group can be substituted or unsubstituted as described above for aryl groups. A "$C_5$-$C_{14}$ aryl" is an aryl group with 5 to 14 carbon atoms in the carbocyclic aromatic rings. Examples of $C_5$-$C_{14}$ aryl groups include, but are not limited to, phenyl, naphthyl and anthracenyl. A $C_5$-$C_{14}$ aryl group can be substituted or unsubstituted as described above for aryl groups.

An "arylene" is an aryl group which has two covalent bonds and can be in the ortho, meta, or para configurations as shown in the following structures:

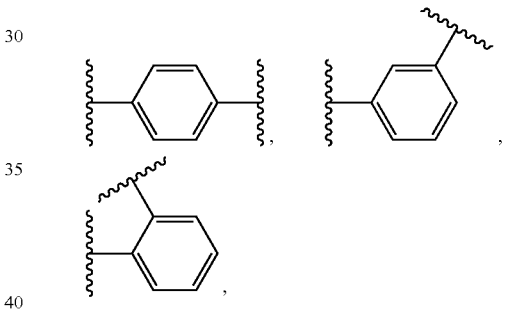

in which the phenyl group can be unsubstituted or substituted with up to four groups including, but not limited to, —$C_1$-$C_8$ alkyl, —O—($C_1$-$C_8$ alkyl), -aryl, —C(O)R', —OC(O)R', —C(O)OR', —C(O)$NH_2$, —C(O)NHR', —C(O)N(R')$_2$—NHC(O)R', —S(O)$_2$R', —S(O)R', —OH, -halogen, —$N_3$, —$NH_2$, —NH(R'), —N(R')$_2$ and —CN; wherein each R' is independently selected from H, —$C_1$-$C_8$ alkyl and aryl.

"Arylalkyl" refers to an acyclic alkyl radical in which one of the hydrogen atoms bonded to a carbon atom, typically a terminal or $sp^3$ carbon atom, is replaced with an aryl radical. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. The arylalkyl group comprises 6 to 20 carbon atoms, e.g. the alkyl moiety, including alkanyl, alkenyl or alkynyl groups, of the arylalkyl group is 1 to 6 carbon atoms and the aryl moiety is 5 to 14 carbon atoms.

"Heteroarylalkyl" refers to an acyclic alkyl radical in which one of the hydrogen atoms bonded to a carbon atom, typically a terminal or $sp^3$ carbon atom, is replaced with a heteroaryl radical. Typical heteroarylalkyl groups include, but are not limited to, 2-benzimidazolylmethyl, 2-furylethyl, and the like. The heteroarylalkyl group comprises 6 to 20 carbon atoms, e.g. the alkyl moiety, including alkanyl, alkenyl or alkynyl groups, of the heteroarylalkyl group is 1 to 6 carbon atoms and the heteroaryl moiety is 5 to 14 carbon atoms and 1 to 3 heteroatoms selected from N, O, P, and S. The heteroaryl moiety of the heteroarylalkyl group may be a monocycle having 3 to 7 ring members (2 to 6 carbon atoms or a bicycle having 7 to 10 ring members (4 to 9 carbon atoms and 1 to 3 heteroatoms selected from N, O, P, and S), for example: a bicyclo [4,5], [5,5], [5,6], or [6,6] system.

"Substituted alkyl," "substituted aryl," and "substituted arylalkyl" mean alkyl, aryl, and arylalkyl respectively, in which one or more hydrogen atoms are each independently replaced with a substituent. Typical substituents include, but are not limited to, —X, —R, —O$^-$, —OR, —SR, —S$^-$, —NR$_2$, —NR$_3$, =NR, —CX$_3$, —CN, —OCN, —SCN, —N=C=O, —NCS, —NO, —NO$_2$, =N$_2$, —N$_3$, NC(=O) R, —C(=O)R, —C(=O)NR$_2$, —SO$_3^-$, —SO$_3$H, —S(=O)$_2$R, —OS(=O)$_2$OR, —S(=O)$_2$NR, —S(=O)R, —OP(=O)(OR)$_2$, —P(O)(OR)$_2$, —PO$_3$, —PO$_3$, H$_2$, —C(=O)R, —C(=O)X, —C(=S)R, —CO$_2$R, —CO$_2^-$, —C(=S)OR, —C(=O)SR, —C(=S)SR, —C(=O)NR$_2$, —C(=S)NR$_2$, —C(=NR)NR$_2$, where each X is independently a halogen: F, Cl, Br, or I; and each R is independently —H, $C_2$-$C_{18}$ alkyl, $C_6$-$C_{20}$ aryl, $C_3$-$C_{14}$ heterocycle, protecting group or prodrug moiety. Alkylene, alkenylene, and alkynylene groups as described above may also be similarly substituted.

"Heteroaryl" and "heterocycle" refer to a ring system in which one or more ring atoms is a heteroatom, e.g. nitrogen, oxygen, and sulfur. The heterocycle radical comprises 3 to 20 carbon atoms and 1 to 3 heteroatoms selected from N, O, P, and S. A heterocycle may be a monocycle having 3 to 7 ring members (2 to 6 carbon atoms and 1 to 3 heteroatoms selected from N, O, P, and S) or a bicycle having 7 to 10 ring members (4 to 9 carbon atoms and 1 to 3 heteroatoms selected from N, O, P, and S), for example: a bicyclo [4,5], [5,5], [5,6], or [6,6] system.

Exemplary heterocycles are described, e.g., in Paquette, Leo A., "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and *J. Am. Chem. Soc.* (1960) 82:5566.

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl.

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

A "$C_3$-$C_8$ heterocycle" refers to an aromatic or non-aromatic $C_3$-$C_8$ carbocycle in which one to four of the ring carbon atoms are independently replaced with a heteroatom from the group consisting of O, S and N. Representative examples of a $C_3$-$C_8$ heterocycle include, but are not limited to, benzofuranyl, benzothiophene, indolyl, benzopyrazolyl, coumarinyl, isoquinolinyl, pyrrolyl, thiophenyl, furanyl, thiazolyl, imidazolyl, pyrazolyl, triazolyl, quinolinyl, pyrimidinyl, pyridinyl, pyridonyl, pyrazinyl, pyridazinyl, isothiazolyl, isoxazolyl and tetrazolyl. A $C_3$-$C_8$ heterocycle can be unsubstituted or substituted with up to seven groups including, but not limited to, —$C_1$-$C_8$ alkyl, —O—($C_1$-$C_8$ alkyl), -aryl, —C(O)R', —OC(O)R', —C(O)OR', —C(O)NH$_2$, —C(O) NHR', —C(O)N(R')$_2$—NHC(O)R', —S(O)$_2$R', —S(O)R', —OH, -halogen, —N$_3$, —NH$_2$, —NH(R'), —N(R')$_2$ and —CN; wherein each R' is independently selected from H, —$C_1$-$C_8$ alkyl and aryl.

"$C_3$-$C_8$ heterocyclo" refers to a $C_3$-$C_8$ heterocycle group defined above wherein one of the heterocycle group's hydrogen atoms is replaced with a bond. A $C_3$-$C_8$ heterocyclo can be unsubstituted or substituted with up to six groups including, but not limited to, —$C_1$-$C_8$ alkyl, —O—($C_1$-$C_8$ alkyl), -aryl, —C(O)R', —OC(O)R', —C(O)OR', —C(O)NH$_2$, —C(O)NHR', —C(O)N(R')$_2$—NHC(O)R', —S(O)$_2$R', —S(O)R', —OH, -halogen, —N$_3$, —NH$_2$, —NH(R'), —N(R')$_2$ and —CN; wherein each R' is independently selected from H, —$C_1$-$C_8$ alkyl and aryl.

A "$C_3$-$C_{20}$ heterocycle" refers to an aromatic or non-aromatic $C_3$-$C_8$ carbocycle in which one to four of the ring carbon atoms are independently replaced with a heteroatom from the group consisting of O, S and N. A $C_3$-$C_{20}$ heterocycle can be unsubstituted or substituted with up to seven groups including, but not limited to, —$C_1$-$C_8$ alkyl, —O—($C_1$-$C_8$ alkyl), -aryl, —C(O)R', —OC(O)R', —C(O)OR', —C(O)NH$_2$, —C(O)NHR', —C(O)N(R')$_2$—NHC(O)R', —S(O)$_2$R', —S(O)R', —OH, -halogen, —N$_3$, —NH$_2$, —NH (R'), —N(R')$_2$ and —CN; wherein each R' is independently selected from H, —$C_1$-$C_8$ alkyl and aryl.

"$C_3$-$C_{20}$ heterocyclo" refers to a $C_3$-$C_{20}$ heterocycle group defined above wherein one of the heterocycle group's hydrogen atoms is replaced with a bond.

"Carbocycle" means a saturated or unsaturated ring having 3 to 7 carbon atoms as a monocycle or 7 to 12 carbon atoms as a bicycle. Monocyclic carbocycles have 3 to 6 ring atoms, still more typically 5 or 6 ring atoms. Bicyclic carbocycles have 7 to 12 ring atoms, e.g. arranged as a bicyclo [4,5], [5,5], [5,6] or [6,6] system, or 9 or 10 ring atoms arranged as a bicyclo [5,6] or [6,6] system. Examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cycloheptyl, and cyclooctyl.

A "$C_3$-$C_8$ carbocycle" is a 3-, 4-, 5-, 6-, 7- or 8-membered saturated or unsaturated non-aromatic carbocyclic ring. Representative $C_3$-$C_8$ carbocycles include, but are not limited to, -cyclopropyl, -cyclobutyl, -cyclopentyl, -cyclopentadienyl, -cyclohexyl, -cyclohexenyl, -1,3-cyclohexadienyl, -1,4-cyclohexadienyl, -cycloheptyl, -1,3-cycloheptadienyl, -1,3,5-cycloheptatrienyl, -cyclooctyl, and -cyclooctadienyl. A $C_3$-$C_8$ carbocycle group can be unsubstituted or substituted with one or more groups including, but not limited to, —$C_1$-$C_8$ alkyl, —O—($C_1$-$C_8$ alkyl), -aryl, —C(O)R', —OC(O)R', —C(O)OR', —C(O)$NH_2$, —C(O)NHR', —C(O)N(R')$_2$— NHC(O)R', —S(O)$_2$R', —S(O)R', —OH, -halogen, —$N_3$, —$NH_2$, —NH(R'), —N(R')$_2$ and —CN; where each R' is independently selected from H, —$C_1$-$C_8$ alkyl and aryl.

A "$C_3$-$C_8$ carbocyclo" refers to a $C_3$-$C_8$ carbocycle group defined above wherein one of the carbocycle groups' hydrogen atoms is replaced with a bond.

"Linker" refers to a chemical moiety comprising a covalent bond or a chain of atoms that covalently attaches an antibody to a drug moiety. In various embodiments, linkers include a divalent radical such as an alkyldiyl, an aryldiyl, a heteroaryldiyl, moieties such as: —($CR_2$)$_n$O($CR_2$)$_n$—, repeating units of alkyloxy (e.g. polyethylenoxy, PEG, polymethyleneoxy) and alkylamino (e.g. polyethyleneamino, Jeffamine™); and diacid ester and amides including succinate, succinamide, diglycolate, malonate, and caproamide. In various embodiments, linkers can comprise one or more amino acid residues, such as valine, phenylalanine, lysine, and homolysine.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

"Leaving group" refers to a functional group that can be substituted by another functional group. Certain leaving groups are well known in the art, and examples include, but are not limited to, a halide (e.g., chloride, bromide, iodide), methanesulfonyl (mesyl), p-toluenesulfonyl (tosyl), trifluoromethylsulfonyl (triflate), and trifluoromethylsulfonate.

The term "protecting group" refers to a substituent that is commonly employed to block or protect a particular functionality while reacting other functional groups on the compound. For example, an "amino-protecting group" is a substituent attached to an amino group that blocks or protects the amino functionality in the compound. Suitable amino-protecting groups include, but are not limited to, acetyl, trifluoroacetyl, t-butoxycarbonyl (BOC), benzyloxycarbonyl (CBZ) and 9-fluorenylmethylenoxycarbonyl (Fmoc). For a general description of protecting groups and their use, see T. W. Greene, Protective Groups in Organic Synthesis, John Wiley & Sons, New York, 1991, or a later edition.

II. Compositions and Methods

In one aspect, the invention is based, in part, on antibodies that bind to LgR5 and immunoconjugates comprising such antibodies. Antibodies and immunoconjugates of the invention are useful, e.g., for the diagnosis or treatment of LgR5-positive cancers.

A. Exemplary Anti-LgR5 Antibodies

In some embodiments, the invention provides isolated antibodies that bind to LgR5. LgR5 is a seven-transmembrane protein found, for example, on the surface of actively cycling intestinal stem cells. As demonstrated herein, LgR5 is expressed in about 77% of colon tumor sections examined.

An exemplary naturally occurring human LgR5 precursor protein sequence, with signal sequence (amino acids 1-21) is provided in SEQ ID NO: 67, and the corresponding mature LgR5 protein sequence is shown in SEQ ID NO: 68 (corresponding to amino acids 22-907 of SEQ ID NO: 67).

In certain embodiments, an anti-LgR5 antibody has at least one or more of the following characteristics, in any combination: (a) binds to an epitope within amino acids 22-555 of SEQ ID NO: 67; (b) binds LgR5 with an affinity of ≤5 nM, or ≤4 nM, or ≤3 nM, or ≤2 nM, or ≤1 nM, and optionally ≥0.0001 nM, or ≥0.001 nM, or ≥0.01 nM; (c) does not significantly disrupt the binding of R-spondin (RSPO) to LgR5; (d) does not significantly disrupt beta-catenin signaling; (e) does not significantly disrupt RSPO activation of LgR5 signaling; (f) activates caspase 3 cleavage; (g) recognizes both human and rodent LgR5; (h) recognizes human LgR5 but not rodent LgR5; (i) does not significantly inhibit tumor growth in its unconjugated form; and (j) does not induce stem cell differentiation. In some embodiments, the anti-LgR5 antibody is 8E11 and humanized variants thereof, such as hu8E11.v2; YW353; 2H6; and 3G12. In some embodiments, LgR5 is human LgR5. In some embodiments, LgR5 is selected from human, cynomolgus monkey, mouse, and rat LgR5.

(a) Binds to an Epitope within Amino Acids 22-555 of SEQ ID NO: 67

Methods of determining whether an anti-LgR5 antibody binds to an epitope of LgR5 are known in the art. In some embodiments, binding of an anti-LgR5 antibody to an epitope of LgR5 (e.g., within amino acids 22-555 of SEQ ID NO: 67) may be determined by expressing LgR5 polypeptides with N- and C-terminal deletions in 293 cells and testing by FACS as described in Example I binding of the antibody to the truncated polypeptides. In some embodiments, a substantial reduction (≥70% reduction) or elimination of binding of the antibody to a truncated polypeptide relative to binding to full-length LgR5 expressed in 293 cells indicates that the antibody does not bind to that truncated polypeptide. In some embodiments, LgR5 is human LgR5. In some embodiments, LgR5 is human LgR5 or cynomolgus monkey LgR5.

In some embodiments, the epitope of LgR5 comprises the lucine rich N-terminal domain of LgR5 (e.g., amino acid residues 25-66 of SEQ ID NO:67). In some embodiments, the epitope of LgR5 comprises one or more lucine rich repeats (LRR) of LgR5 (e.g., amino acid residues 67-446 of SEQ ID NO:67; LRRs 1-16 of LgR5).). In some embodiments, the epitope of LgR5 comprises LRR 1 of LgR5 (e.g., amino acid residues 67-90 of SEQ ID NO:67). In some embodiments, the epitope of LgR5 comprises LRR 2 of LgR5 (e g, amino acid residues 91-112 of SEQ ID NO:67). In some embodiments, the epitope of LgR5 comprises LRR 3 of LgR5 (e.g., amino acid residues 115-136 of SEQ ID NO:67). In some embodiments, the epitope of LgR5 comprises LRR 4 of LgR5 (e.g., amino acid residues 139-160 of SEQ ID NO:67). In some embodiments, the epitope of LgR5 comprises LRR 5 of LgR5 (e.g., amino acid residues 163-184 of SEQ ID NO:67). In some embodiments, the epitope of LgR5 comprises LRR 6 of LgR5 (e.g., amino acid residues 187-208 of SEQ ID NO:67). In some embodiments, the epitope of LgR5 comprises LRR 7 of LgR5 (e.g., amino acid residues 211-232 of SEQ ID NO:67). In some embodiments, the epitope of LgR5 comprises LRR 8 of LgR5 (e.g., amino acid residues 235-256 of SEQ ID NO:67). In some embodiments, the epitope of LgR5 comprises LRR 9 of LgR5 (e.g., amino acid residues 258-279 of SEQ ID NO:67). In some embodiments, the epitope of LgR5 comprises LRR 10 of LgR5 (e.g., amino acid residues 282-303 of SEQ ID NO:67). In some embodiments, the epitope of LgR5 comprises LRR 11 of LgR5 (e.g., amino acid residues 306-328 of SEQ ID NO:67). In some embodiments, the epitope of LgR5 comprises LRR 12 of LgR5 (e.g., amino acid residues 329-350 of SEQ ID NO:67). In some embodiments, the epitope of LgR5 comprises LRR 13 of LgR5 (e.g., amino acid residues 353-374 of SEQ ID NO:67). In some embodiments, the epitope of LgR5 comprises LRR 14 of LgR5 (e.g., amino acid residues 375-396 of SEQ ID NO:67). In some embodiments, the epitope of LgR5 comprises LRR 15 of LgR5 (e.g., amino acid residues 399-420 of SEQ ID NO:67). In some embodiments, the epitope of LgR5 comprises LRR 16 of LgR5 (e.g., amino acid residues 423-446 of SEQ ID NO:67). In some embodiments, the epitope of LgR5 comprises any of LRR1 to LRR11, LRR2 to LRR11, LRR3 to LRR11, LLR1 to LLR3, LLR2 to LLR3, LLR2 to LLR8, LLR3 to LL7, or LLR4 to LLR6.

In some embodiments, the epitope of LgR5 comprises an epitope within amino acids 22-555 of SEQ ID NO: 67. In some embodiments, the epitope of LgR5 comprises an epitope within amino acids 22-424 of SEQ ID NO: 67. In some embodiments, the epitope of LgR5 comprises an epitope within amino acids 22-123 of SEQ ID NO: 67. In some embodiments, the epitope of LgR5 comprises an epitope within amino acids 22-323 of SEQ ID NO: 67. In some embodiments, the epitope of LgR5 comprises an epitope within amino acids 324-555 of SEQ ID NO: 67. In some embodiments, the epitope of LgR5 comprises an epitope within amino acids 324-424 of SEQ ID NO: 67.

It is understood that aspect and embodiments described herein include "consisting" and/or "consisting effectively of" aspects and embodiments.

(b) Binds LgR5 with an Affinity of ≤5 nM, or ≤4 nM, or ≤3 nM, or ≤2 nM, or ≤1 nM, and Optionally ≥0.0001 nM, or ≥0.001 nM, or ≥0.01 nM Methods of determining binding affinity are known in the art. In some embodiments, the binding affinity may be determined according to a BIAcore® assay as described herein in Example E. Specifically, in some embodiments, Kd may be measured using surface plasmon resonance assays using a BIACORE®-3000 (BIAcore, Inc., Piscataway, N.J.). BIAcore™ research grade CM5 chips may be activated with 1-ethyl-3-(3-dimethylaminopropyl) carbodiimide (EDC) and N-hydroxysuccinimide (NHS) reagents according to the supplier's instructions. Goat anti-human Fc IgGs may be coupled to the chips to achieve approximately 10,000 response units (RU) in each flow cell. Unreacted coupling groups may be blocked with 1M ethanolamine. For kinetics measurements, anti-LGR5 antibodies may be captured to achieve approximately 300 RU. Two-fold serial dilutions of human LgR5 ECD (for example, amino acids 22-557 (or a similar fragment, such as 22-555) fused to His-Fc expressed in a baculovirus system, or amino acids 22-558 (or a similar fragment, such as 22-555) fused to Fc expressed from CHO cells; 125 nM to 0.49 nM) may be injected in HBS-P buffer (0.01M HEPES pH7.4, 0.15M NaCl, 0.005% surfactant P20) at 25° C. with a flow rate of 30 µl/min. Association rates ($k_{on}$) and dissociation rates ($k_{off}$) may be calculated using a 1:1 Langmuir binding model (BIAcore™ Evaluation Software version 3.2). The equilibrium dissociation constant (Kd) may be calculated as the ratio $k_{off}/k_{on}$. If the on-rate exceeds $10^6$ $M^{-1}$ $s^{-1}$ by the surface plasmon resonance assay above, then the on-rate may be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-Aminco® spectrophotometer (ThermoSpectronic) with a stirred cuvette.

In some embodiments, the anti-LgR5 antibody binds LgR5 with an affinity of about any of ≤5 nM, or ≤4 nM, or ≤3 nM, or ≤2 nM, or ≤1 nM. In some embodiments, the anti-LgR5 antibody binds LgR5 with an affinity of about ≤5. In some embodiments, the anti-LgR5 antibody binds LgR5 with an affinity of about ≤4 nM. In some embodiments, the anti-LgR5 antibody binds LgR5 with an affinity of about ≤3 nM. In some embodiments, the anti-LgR5 antibody binds LgR5 with an affinity of about ≤2 nM. In some embodiments, LgR5 is human LgR5. In some embodiments, LgR5 is human LgR5 or cynomolgus monkey LgR5.

As is understood by one skilled in the art, reference to "about" a value or parameter includes (and describes) embodiments that are direct to that value or parameter per se. For example, description referring to "about X" includes description of "X".

(c) Does not Significantly Disrupt the Binding of R-Spondin (RSPO) to LgR5

Methods of determining the ability of an anti-LgR5 antibody to disrupt the binding of an RSPO to LgR5 are known in the art. In some embodiments, the ability of an anti-LgR5 antibody to significantly disrupt the binding of an R-spondin (RSPO) to LgR5 may be determined by flow cytometry. In some embodiments, for example, 293 cells expressing LgR5 may be contacted with fluorescently-labeled RSPO, such as RSPO1, RSPO2, RSPO3, and/or RSPO4, in the presence and absence of an anti-LgR5 antibody. Binding of RSPO to the 293 cells may be detected using fluorescence-activated cell sorting (FACS). In some embodiments, a decrease in RSPO binding in the presence of an anti-LgR5 antibody of less than about 25% relative to RSPO binding in the presence of a control antibody, indicates that the anti-LgR5 antibody does not significantly disrupt binding of RSPO to LgR5.

In some embodiments, the ability of an anti-LgR5 antibody to significantly disrupt the binding of an R-spondin (RSPO) to LgR5 may be determined by BIAcore assay. In some embodiments, for example, LgR5 extracellular domain may be immobilized on CM5 chips, e.g., as described herein, and binding of RSPO, such as RSPO1, RSPO2, RSPO3, and/or RSPO4, to the immobilized LgR5 may be determined in the presence and absence of an anti-LgR5 antibody. In some embodiments, a decrease in RSPO binding in the presence of an anti-LgR5 antibody of less than about 25% relative to RSPO binding in the presence of a control antibody, indicates that the anti-LgR5 antibody does not significantly disrupt binding of RSPO to LgR5.

In some embodiments, the RSPO is selected from RSPO1, RSPO2, RSPO3, and RSPO4. In some embodiments, the antibody disrupts binding by less than about 25%, less than about 20%, less than about 15%, or less than about 10%. In some embodiments, the antibody does not detectably disrupt binding of an RSPO to LgR5. In some embodiments, LgR5 is human LgR5. In some embodiments, LgR5 is human LgR5 or cynomolgus monkey LgR5.

(d) Does not Significantly Disrupt Wnt/Beta-Catenin Signaling

Methods of determining ability of an anti-LgR5 antibody to disrupt wnt/beta-catenin signaling are known in the art. In some embodiments, the ability of an anti-LgR5 antibody to significantly disrupt wnt/beta-catenin signaling may be determined using a reporter gene assay. In some embodiments, for example, a reporter construct comprising a reporter gene (such as, for example, a luciferase gene) under the control of a wnt/beta-catenin responsive promoter (such as, for example, a promoter comprising multimerized TCF/LEF DNA-binding sites) may be transfected into cells that express LgR5. The cells are then contacted with a Wnt ligand, such as Wnt3a, and an RSPO, such as RSPO1, RSPO2, RSPO3, and/or RSPO4, in the presence and absence of an anti-LgR5 antibody, and luciferase expression is measured. In some embodiments, a decrease in luciferase expression in the presence of antibody of less than about 25% relative to luciferase expression in the presence of a control antibody, indicates that the anti-LgR5 antibody does not significantly disrupt beta-catenin signaling.

In some embodiments, the antibody disrupts beta-catenin signaling by less than about 25%, less than about 20%, less than about 15%, or less than about 10%. In some embodiments, the antibody does not detectably disrupt beta-catenin signaling. In some embodiments, LgR5 is human LgR5. In some embodiments, LgR5 is human LgR5 or cynomolgus monkey LgR5.

(e) does not Significantly Disrupt RSPO Activation of LgR5 Signaling

Methods of determining ability of an anti-LgR5 antibody to disrupt RSPO activation of LgR5 are known in the art. In some embodiments, the ability of an anti-LgR5 antibody to significantly disrupt RSPO activation of LgR5 signaling may be determined using a reporter gene assay. In some embodiments, for example, a reporter construct comprising a reporter gene (such as, for example, a luciferase gene) under the control of a beta-catenin responsive promoter (such as, for example, a promoter comprising multimerized TCF/LEF DNA-binding sites) may be transfected into cells that express LgR5. The cells may be then contacted with a Wnt ligand, such as Wnt3a, in the presence and absence of an RSPO, such as RSPO1, RSPO2, RSPO3, and/or RSPO4, and the activation of LgR5 signaling may be measured as the increase in luciferase expression in the presence of the RSPO. The activation of LgR5 signaling may also be measured in the presence and absence of an anti-LgR5 antibody. In some embodiments, a decrease in the activation of LgR5 signaling in the presence of RSPO1, RSPO2, RSPO3, and/or RSPO4 of less than about 25% when the cells are contacted with an anti-LgR5 antibody versus a control antibody, indicates that the anti-LgR5 antibody does not significantly disrupt RSPO activation of LgR5 signaling.

In some embodiments, the RSPO is selected from RSPO1, RSPO2, RSPO3, and RSPO4. In some embodiments, the antibody disrupts RSPO activation of LgR5 signaling by less than about 25%, less than about 20%, less than about 15%, or less than about 10%. In some embodiments, the antibody does not detectably disrupt RSPO activation of LgR5 signaling. In some embodiments, LgR5 is human LgR5. In some embodiments, LgR5 is human LgR5 or cynomolgus monkey LgR5.

(f) Activates Caspase 3 Cleavage

Methods of determining ability of an anti-LgR5 antibody to activate caspase 3 cleavage are known in the art. In some embodiments, the ability of an anti-LgR5 antibody to activate caspase 3 cleavage may be determined in a rodent xenograft model, e.g., as described in Example N. In some embodiments, the presence of cleaved caspase 3 may be measured as a function of tumor area, for example, in formalin fixed paraffin embedded (FFPE) small intestine and colon tissue collected from intestinal tumorogenesis model mice that were administered an anti-LgR5 antibody. The presence of cleaved caspase 3 may be determined, in some embodiments, using immunohistochemistry. Further, in some embodiments, caspase 3 cleavage may be determined as a percent positive tumor area, e.g., as shown in Example N and FIG. 18.

In some embodiments, an anti-LgR5 antibody increases the percentage of caspase 3 positive tumor area according to the assay described in Example N by about any of at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% (i.e., the percentage of positive tumor area doubles).

(g) Recognizes Both Human and Rodent LgR5

Methods of determining the ability of an anti-LgR5 antibody to bind human and rodent LgR5 are known in the art. In some embodiments, human and rodent LgR5 polypeptides are expressed in 293 cells and binding of the antibody to the LgR5-expressing 293 cells is tested by FACS as described in Example G. In some embodiments, rodent LgR5 is mouse or rat LgR5. In some embodiments, rodent LgR5 is mouse LgR5.

(h) Recognizes Human LgR5 but not Rodent LgR5

Methods of determining the ability of an anti-LgR5 antibody to bind human but not rodent LgR5 are known in the art. In some embodiments, human and rodent LgR5 polypeptides are expressed in 293 cells and binding of the antibody to the LgR5-expressing 293 cells is tested by FACS as described in Example G. In some embodiments, rodent LgR5 is mouse or rat LgR5. In some embodiments, rodent LgR5 is mouse LgR5.

(i) Does not Significantly Inhibit Tumor Growth in its Unconjugated Form

Methods of determining the ability of an anti-LgR5 antibody to inhibit tumor growth in its unconjugated form are known in the art. In some embodiments, a rodent xenograft model such as the D5124 pancreatic cancer xenograft model described in Example M is used. In some embodiments, an anti-LgR5 antibody does not significantly inhibit tumor growth in its unconjugated form in a LoVo colon cancer cell line xenograft model, for example, as described in Example L. In some embodiments, an anti-LgR5 antibody does not significantly inhibit tumor growth in its unconjugated form in a murine intestinal tumorigenesis model, for example, as described in Example N. Inhibition of tumor growth in a xenograft model or murine intestinal tumorigenesis model is determined relative to a vehicle control or control antibody.

In some embodiments, an anti-LgR5 antibody inhibits tumor growth in its unconjugated form by less than about 25%, less than about 20%, less than about 15%, or less than about 10%. In some embodiments, an anti-LgR5 antibody does not detectably inhibit tumor growth in its unconjugated form.

(j) Does not Induce Stem Cell Differentiation

Methods of determining the ability of an anti-LgR5 antibody to induce stem cell differentiation are known in the art. In some embodiments, stem cell differentiation may be assayed by determining ability to differentiation of crypt base columnar cells (CBCs), which are fast-cycling stem cells in the small intestine that express LgR5, into, for example, enterocytes, goblet cells, and/or enteroendocrine cells, in the presence and absence of an anti-LgR5 antibody In some embodiments, an anti-LgR5 antibody is considered to not induce stem cell differentiation if about any of less than 25%, less than 20%, less than 15%, or less than 10% of a population of CBCs differentiates in the presence of the anti-LgR5 antibody under conditions in which a control antibody also induces stem cell differentiation in less than about 25% of a population of CBCs.

In some embodiments, an anti-LgR5 antibody immunoconjugate inhibits tumor growth through a primary mechanism that is not inducing stem cell differentiation. In some such embodiments, the anti-LgR5 antibody immunoconjugate inhibits tumor growth through cytotoxic activity mediated through a cytotoxic agent conjugated to the antibody in the immunoconjugate.

Antibody 8E11 and Other Embodiments

In some embodiments, the invention provides an anti-LgR5 antibody comprising at least one, two, three, four, five, or six HVRs selected from (a) HVR-H1 comprising the amino acid sequence of SEQ ID NO: 30; (b) HVR-H2 comprising the amino acid sequence of SEQ ID NO: 31; (c) HVR-H3 comprising the amino acid sequence of SEQ ID NO: 32; (d) HVR-L1 comprising the amino acid sequence of SEQ ID NO: 27; (e) HVR-L2 comprising the amino acid sequence of SEQ ID NO: 28; and (f) HVR-L3 comprising the amino acid sequence of SEQ ID NO: 29.

In one aspect, the invention provides an antibody comprising at least one, at least two, or all three VH HVR sequences selected from (a) HVR-H1 comprising the amino acid sequence of SEQ ID NO: 30; (b) HVR-H2 comprising the amino acid sequence of SEQ ID NO: 31; and (c) HVR-H3 comprising the amino acid sequence of SEQ ID NO: 32. In one embodiment, the antibody comprises HVR-H3 comprising the amino acid sequence of SEQ ID NO: 32. In another embodiment, the antibody comprises HVR-H3 comprising the amino acid sequence of SEQ ID NO: 32 and HVR-L3 comprising the amino acid sequence of SEQ ID NO: 29. In a further embodiment, the antibody comprises HVR-H3 comprising the amino acid sequence of SEQ ID NO: 32, HVR-L3 comprising the amino acid sequence of SEQ ID NO: 29, and HVR-H2 comprising the amino acid sequence of SEQ ID NO: 31. In a further embodiment, the antibody comprises (a) HVR-H1 comprising the amino acid sequence of SEQ ID NO: 30; (b) HVR-H2 comprising the amino acid sequence of SEQ ID NO: 31; and (c) HVR-H3 comprising the amino acid sequence of SEQ ID NO: 32.

In another aspect, the invention provides an antibody comprising at least one, at least two, or all three VL HVR sequences selected from (a) HVR-L1 comprising the amino acid sequence of SEQ ID NO: 27; (b) HVR-L2 comprising the amino acid sequence of SEQ ID NO: 28; and (c) HVR-L3 comprising the amino acid sequence of SEQ ID NO: 29. In one embodiment, the antibody comprises (a) HVR-L1 comprising the amino acid sequence of SEQ ID NO: 27; (b) HVR-L2 comprising the amino acid sequence of SEQ ID NO: 28; and (c) HVR-L3 comprising the amino acid sequence of SEQ ID NO: 29.

In another aspect, an antibody of the invention comprises (a) a VH domain comprising at least one, at least two, or all three VH HVR sequences selected from (i) HVR-H1 comprising the amino acid sequence of SEQ ID NO: 30, (ii) HVR-H2 comprising the amino acid sequence of SEQ ID NO: 31, and (iii) HVR-H3 comprising an amino acid sequence selected from SEQ ID NO: 32; and (b) a VL domain comprising at least one, at least two, or all three VL HVR sequences selected from (i) HVR-L1 comprising the amino acid sequence of SEQ ID NO: 27, (ii) HVR-L2 comprising the amino acid sequence of SEQ ID NO: 28, and (c) HVR-L3 comprising the amino acid sequence of SEQ ID NO: 29.

In another aspect, the invention provides an antibody comprising (a) HVR-H1 comprising the amino acid sequence of SEQ ID NO: 30; (b) HVR-H2 comprising the amino acid sequence of SEQ ID NO: 31; (c) HVR-H3 comprising the amino acid sequence of SEQ ID NO: 32; (d) HVR-L1 comprising the amino acid sequence of SEQ ID NO: 27; (e) HVR-L2 comprising the amino acid sequence of SEQ ID NO: 28; and (0 HVR-L3 comprising the amino acid sequence of SEQ ID NO: 29.

In any of the above embodiments, an anti-LgR5 antibody is humanized. In one embodiment, an anti-LgR5 antibody comprises HVRs as in any of the above embodiments, and further comprises a human acceptor framework, e.g. a human immunoglobulin framework or a human consensus framework. In certain embodiments, the human acceptor framework is the human VL kappa IV consensus ($VL_{KIV}$) framework and/or the VH framework $VH_1$. In certain embodiments, the human acceptor framework is the human VL kappa IV consensus ($VL_{KIV}$) framework and/or the VH framework $VH_1$ comprising an R71S mutation and an A78V mutation in heavy chain framework region FR3.

In some embodiments, an anti-LgR5 antibody comprises HVRs as in any of the above embodiments, and further comprises a heavy chain framework FR3 sequence selected from SEQ ID NOs: 40 to 43. In some embodiments, an anti-LgR5 antibody comprises HVRs as in any of the above embodiments, and further comprises a heavy chain framework FR3 sequence of SEQ ID NO: 41. In some such embodiments, the heavy chain variable domain framework is a modified human $VH_1$ framework having an FR3 sequence selected from SEQ ID NOs: 40 to 43. In some such embodiments, the heavy chain variable domain framework is a modified human $VH_1$ framework having an FR3 sequence of SEQ ID NO: 41.

In some embodiments, an anti-LgR5 antibody comprises HVRs as in any of the above embodiments, and further comprises a light chain framework FR3 sequence of SEQ ID NO: 36. In some such embodiments, the heavy chain variable domain framework is a modified VL kappa IV consensus ($VL_{KIV}$) framework having an FR3 sequence of SEQ ID NO: 36.

In another aspect, an anti-LgR5 antibody comprises a heavy chain variable domain (VH) sequence having at least 90%, 91%, 92%, 93%, 94%, 95%, 96%, 97%, 98%, 99%, or 100% sequence identity to an amino acid sequence selected from SEQ ID NOs: 6, 8, 10, 12, 14, 16, 18, and 20. In certain embodiments, a VH sequence having at least 90%, 91%, 92%, 93%, 94%, 95%, 96%, 97%, 98%, or 99% identity to an amino acid sequence selected from SEQ ID NOs: 6, 8, 10, 12, 14, 16, 18, and 20 contains substitutions (e.g., conservative substitutions), insertions, or deletions relative to the reference sequence, but an anti-LgR5 antibody comprising that sequence retains the ability to bind to LgR5. In certain embodiments, a total of 1 to 10 amino acids have been substituted, inserted and/or deleted in a sequence selected from SEQ ID NOs: 6, 8, 10, 12, 14, 16, 18, and 20. In certain embodiments, a total of 1 to 5 amino acids have been substituted, inserted and/or deleted in a sequence selected from SEQ ID NOs: 6, 8, 10, 12, 14, 16, 18, and 20. In certain embodiments, substitutions, insertions, or deletions occur in regions outside the HVRs (i.e., in the FRs).

In some embodiments, an anti-LgR5 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 6. In some embodiments, an anti-LgR5 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 8. In some embodiments, an anti-LgR5 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 10. In some embodiments, an anti-LgR5 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 12. In some embodiments, an anti-LgR5 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 14. In some embodiments, an anti-LgR5 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 16. In some embodiments, an anti-LgR5 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 18. In some embodiments, an anti-LgR5 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 20.

Optionally, the anti-LgR5 antibody comprises the VH sequence selected from SEQ ID NOs: 6, 8, 10, 12, 14, 16, 18, and 20, including post-translational modifications of that sequence. In a particular embodiment, the VH comprises one, two or three HVRs selected from: (a) HVR-H1 comprising the amino acid sequence of SEQ ID NO: 30, (b) HVR-H2 comprising the amino acid sequence of SEQ ID NO: 31, and (c) HVR-H3 comprising the amino acid sequence of SEQ ID NO: 32.

In another aspect, an anti-LgR5 antibody is provided, wherein the antibody comprises a light chain variable domain (VL) having at least 90%, 91%, 92%, 93%, 94%, 95%, 96%, 97%, 98%, 99%, or 100% sequence identity to an amino acid sequence selected from SEQ ID NOs: 5, 7, 9, 11, 13, 15, 17, and 19. In certain embodiments, a VL sequence having at least 90%, 91%, 92%, 93%, 94%, 95%, 96%, 97%, 98%, or 99% identity to an amino acid sequence selected from SEQ ID NOs: 5, 7, 9, 11, 13, 15, 17, and 19 contains substitutions (e.g., conservative substitutions), insertions, or deletions relative to the reference sequence, but an anti-LgR5 antibody comprising that sequence retains the ability to bind to LgR5. In certain embodiments, a total of 1 to 10 amino acids have been substituted, inserted and/or deleted in an amino acid sequence selected from SEQ ID NOs: 5, 7, 9, 11, 13, 15, 17, and 19. In certain embodiments, a total of 1 to 5 amino acids have been substituted, inserted and/or deleted in an amino acid sequence selected from SEQ ID NOs: 5, 7, 9, 11, 13, 15, 17, and 19. In certain embodiments, the substitutions, insertions, or deletions occur in regions outside the HVRs (i.e., in the FRs).

In some embodiments, an anti-LgR5 antibody comprises a light chain variable domain (VL) sequence having at least 90%, 91%, 92%, 93%, 94%, 95%, 96%, 97%, 98%, 99%, or 100% sequence identity to the amino acid sequence of SEQ ID NO: 5. In some embodiments, an anti-LgR5 antibody comprises a light chain variable domain (VL) sequence having at least 90%, 91%, 92%, 93%, 94%, 95%, 96%, 97%, 98%, 99%, or 100% sequence identity to the amino acid sequence of SEQ ID NO: 7. In some embodiments, an anti-LgR5 antibody comprises a light chain variable domain (VL) sequence having at least 90%, 91%, 92%, 93%, 94%, 95%, 96%, 97%, 98%, 99%, or 100% sequence identity to the amino acid sequence of SEQ ID NO: 9. In some embodiments, an anti-LgR5 antibody comprises a light chain variable domain (VL) sequence having at least 90%, 91%, 92%, 93%, 94%, 95%, 96%, 97%, 98%, 99%, or 100% sequence identity to the amino acid sequence of SEQ ID NO: 11. In some embodiments, an anti-LgR5 antibody comprises a light chain variable domain (VL) sequence having at least 90%, 91%, 92%, 93%, 94%, 95%, 96%, 97%, 98%, 99%, or 100% sequence identity to the amino acid sequence of SEQ ID NO: 13. In some embodiments, an anti-LgR5 antibody comprises a light chain variable domain (VL) sequence having at least 90%, 91%, 92%, 93%, 94%, 95%, 96%, 97%, 98%, 99%, or 100% sequence identity to the amino acid sequence of SEQ ID NO: 15. In some embodiments, an anti-LgR5 antibody comprises a light chain variable domain (VL) sequence having at least 90%, 91%, 92%, 93%, 94%, 95%, 96%, 97%, 98%, 99%, or 100% sequence identity to the amino acid sequence of SEQ ID NO: 17. In some embodiments, an anti-LgR5 antibody comprises a light chain variable domain (VL) sequence having at least 90%, 91%, 92%, 93%, 94%, 95%, 96%, 97%, 98%, 99%, or 100% sequence identity to the amino acid sequence of SEQ ID NO: 19.

Optionally, the anti-LgR5 antibody comprises the VL sequence of an amino acid sequence selected from SEQ ID NOs: 5, 7, 9, 11, 13, 15, 17, and 19, including post-translational modifications of that sequence. In a particular embodiment, the VL comprises one, two or three HVRs selected from (a) HVR-L1 comprising the amino acid sequence of SEQ ID NO: 27; (b) HVR-L2 comprising the amino acid sequence of SEQ ID NO: 28; and (c) HVR-L3 comprising the amino acid sequence of SEQ ID NO: 29.

In another aspect, an anti-LgR5 antibody is provided, wherein the antibody comprises a VH as in any of the embodiments provided above, and a VL as in any of the embodiments provided above. In one embodiment, the antibody comprises the VH and VL sequences in SEQ ID NO: 6 and SEQ ID NO: 5, respectively, including post-translational modifications of those sequences. In one embodiment, the antibody comprises the VH and VL sequences in SEQ ID NO: 8 and SEQ ID NO: 7, respectively, including post-translational modifications of those sequences. In one embodiment, the antibody comprises the VH and VL sequences in SEQ ID NO: 10 and SEQ ID NO: 9, respectively, including post-translational modifications of those sequences. In one embodiment, the antibody comprises the VH and VL sequences in SEQ ID NO: 12 and SEQ ID NO: 11, respectively, including post-translational modifications of those sequences. In one embodiment, the antibody comprises the VH and VL sequences in SEQ ID NO: 14 and SEQ ID NO: 13, respectively, including post-translational modifications of those sequences. In one embodiment, the antibody comprises the VH and VL sequences in SEQ ID NO: 16 and SEQ ID NO: 15, respectively, including post-translational modifications of those sequences. In one embodiment, the antibody comprises the VH and VL sequences in SEQ ID NO: 18 and SEQ ID NO: 17, respectively, including post-translational modifications of those sequences. In one embodiment, the antibody comprises the VH and VL sequences in SEQ ID NO: 20 and SEQ ID NO: 19, respectively, including post-translational modifications of those sequences.

In a further aspect, the invention provides an antibody that binds to the same epitope as an anti-LgR5 antibody provided herein. For example, in certain embodiments, an antibody is provided that binds to the same epitope as an anti-LgR5 antibody comprising a VH sequence of SEQ ID NO: 8 and a VL sequence of SEQ ID NO: 7. In certain embodiments, an antibody is provided that binds to an epitope of SEQ ID NO: 67 from, within, or overlapping amino acids 22-323. In some embodiments, an antibody is provided that binds to an epitope of SEQ ID NO: 68 from, within, or overlapping amino acids 1-312.

In a further aspect of the invention, an anti-LgR5 antibody according to any of the above embodiments is a monoclonal antibody, including a chimeric, humanized or human antibody. In one embodiment, an anti-LgR5 antibody is an antibody fragment, e.g., a Fv, Fab, Fab', scFv, diabody, or F(ab')$_2$ fragment. In another embodiment, the antibody is a substantially full length antibody, e.g., an IgG1 antibody or other antibody class or isotype as defined herein.

In a further aspect, an anti-LgR5 antibody according to any of the above embodiments may incorporate any of the features, singly or in combination, as described in Sections 1-7 below.

Antibody YW353 and Other Embodiments

In one aspect, the invention provides an anti-LgR5 antibody comprising at least one, two, three, four, five, or six HVRs selected from (a) HVR-H1 comprising the amino acid sequence of SEQ ID NO: 60; (b) HVR-H2 comprising the amino acid sequence of SEQ ID NO: 61; (c) HVR-H3 comprising the amino acid sequence of SEQ ID NO: 62; (d) HVR-L1 comprising the amino acid sequence of SEQ ID NO: 57; (e) HVR-L2 comprising the amino acid sequence of SEQ ID NO: 58; and (f) HVR-L3 comprising the amino acid sequence of SEQ ID NO: 59.

In one aspect, the invention provides an antibody comprising at least one, at least two, or all three VH HVR sequences selected from (a) HVR-H1 comprising the amino acid sequence of SEQ ID NO: 60; (b) HVR-H2 comprising the amino acid sequence of SEQ ID NO: 61; and (c) HVR-H3 comprising the amino acid sequence of SEQ ID NO: 62. In one embodiment, the antibody comprises HVR-H3 comprising the amino acid sequence of SEQ ID NO: 62. In another embodiment, the antibody comprises HVR-H3 comprising the amino acid sequence of SEQ ID NO: 62, and HVR-L3 comprising the amino acid sequence of SEQ ID NO: 59. In a further embodiment, the antibody comprises HVR-H3 comprising the amino acid sequence of SEQ ID NO: 62, HVR-L3 comprising the amino acid sequence of SEQ ID NO: 59, and HVR-H2 comprising the amino acid sequence of SEQ ID NO: 61. In a further embodiment, the antibody comprises (a) HVR-H1 comprising the amino acid sequence of SEQ ID NO: 60; (b) HVR-H2 comprising the amino acid sequence of SEQ ID NO: 61; and (c) HVR-H3 comprising the amino acid sequence of SEQ ID NO:62.

In another aspect, the invention provides an antibody comprising at least one, at least two, or all three VL HVR sequences selected from (a) HVR-L1 comprising the amino acid sequence of SEQ ID NO: 57; (b) HVR-L2 comprising the amino acid sequence of SEQ ID NO: 58; and (c) HVR-L3 comprising the amino acid sequence of SEQ ID NO: 59. In one embodiment, the antibody comprises (a) HVR-L1 comprising the amino acid sequence of SEQ ID NO: 57; (b) HVR-L2 comprising the amino acid sequence of SEQ ID NO: 58; and (c) HVR-L3 comprising the amino acid sequence of SEQ ID NO: 59.

In another aspect, an antibody of the invention comprises (a) a VH domain comprising at least one, at least two, or all three VH HVR sequences selected from (i) HVR-H1 comprising the amino acid sequence of SEQ ID NO: 60, (ii) HVR-H2 comprising the amino acid sequence of SEQ ID NO: 61, and (iii) HVR-H3 comprising the amino acid sequence of SEQ ID NO: 62; and (b) a VL domain comprising at least one, at least two, or all three VL HVR sequences selected from (i) HVR-L1 comprising the amino acid sequence of SEQ ID NO: 57, (ii) HVR-L2 comprising the amino acid sequence of SEQ ID NO: 58, and (c) HVR-L3 comprising the amino acid sequence of SEQ ID NO: 59.

In another aspect, the invention provides an antibody comprising (a) HVR-H1 comprising the amino acid sequence of SEQ ID NO: 60; (b) HVR-H2 comprising the amino acid sequence of SEQ ID NO: 61; (c) HVR-H3 comprising the amino acid sequence of SEQ ID NO: 62; (d) HVR-L1 comprising the amino acid sequence of SEQ ID NO: 57; (e) HVR-L2 comprising the amino acid sequence of SEQ ID NO: 58; and (f) HVR-L3 comprising an amino acid sequence selected from SEQ ID NO: 59.

In any of the above embodiments, an anti-LgR5 antibody is a human antibody.

In another aspect, an anti-LgR5 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 26. In certain embodiments, a VH sequence having at least 90%, 91%, 92%, 93%, 94%, 95%, 96%, 97%, 98%, or 99% identity to the amino acid sequence of SEQ ID NO: 26 contains substitutions (e.g., conservative substitutions), insertions, or deletions relative to the reference sequence, but an anti-LgR5 antibody comprising that sequence retains the ability to bind to LgR5. In certain embodiments, a total of 1 to 10 amino acids have been substituted, inserted and/or deleted in SEQ ID NO: 26. In certain embodiments, a total of 1 to 5 amino acids have been substituted, inserted and/or deleted in SEQ ID NO: 26. In certain embodiments, substitutions, insertions, or deletions occur in regions outside the HVRs (i.e., in the FRs). Optionally, the anti-LgR5 antibody comprises the VH sequence of SEQ ID NO: 26, including post-translational modifications of that sequence. In a particular embodiment, the VH comprises one, two or three HVRs selected from: (a) HVR-H1 comprising the amino acid sequence of SEQ ID NO: 60, (b) HVR-H2 comprising the amino acid sequence of SEQ ID NO: 61, and (c) HVR-H3 comprising the amino acid sequence of SEQ ID NO: 62.

In another aspect, an anti-LgR5 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 25. In certain embodiments, a VL sequence having at least 90%, 91%, 92%, 93%, 94%, 95%, 96%, 97%, 98%, or 99% identity to the amino acid sequence of SEQ ID NO: 25 contains substitutions (e.g., conservative substitutions), insertions, or deletions relative to the reference sequence, but an anti-LgR5 antibody comprising that sequence retains the ability to bind to LgR5. In certain embodiments, a total of 1 to 5 amino acids have been substituted, inserted and/or deleted in SEQ ID NO: 25. In certain embodiments, a total of 1 to 10 amino acids have been substituted, inserted and/or deleted in SEQ ID NO: 25. In certain embodiments, the substitutions, insertions, or deletions occur in regions outside the HVRs (i.e., in the FRs). Optionally, the anti-LgR5 antibody comprises the VL sequence of SEQ ID NO: 25, including post-translational modifications of that sequence. In a particular embodiment, the VL comprises one, two or three HVRs selected from (a) HVR-L1 comprising the amino acid sequence of SEQ ID NO: 57; (b) HVR-L2 comprising the amino acid sequence of SEQ ID NO: 58; and (c) HVR-L3 comprising the amino acid sequence of SEQ ID NO: 59.

In another aspect, an anti-LgR5 antibody is provided, wherein the antibody comprises a VH as in any of the embodiments provided above, and a VL as in any of the embodiments provided above. In one embodiment, the antibody comprises the VH and VL sequences in SEQ ID NO: 26 and SEQ ID NO: 25, respectively, including post-translational modifications of those sequences.

In a further aspect, the invention provides an antibody that binds to the same epitope as an anti-LgR5 antibody provided herein. For example, in certain embodiments, an antibody is provided that binds to the same epitope as an anti-LgR5 antibody comprising a VH sequence of SEQ ID NO: 26 and a VL sequence of SEQ ID NO: 25. In certain embodiments, an antibody is provided that binds to an epitope of SEQ ID NO: 67 from, within, or overlapping amino acids 22-123. In certain embodiments, an antibody is provided that binds to an epitope of SEQ ID NO: 68 from, within, or overlapping amino acids 1-102.

In a further aspect of the invention, an anti-LgR5 antibody according to any of the above embodiments is a monoclonal antibody, including a human antibody. In one embodiment, an anti-LgR5 antibody is an antibody fragment, e.g., a Fv, Fab, Fab', scFv, diabody, or F(ab')$_2$ fragment. In another embodiment, the antibody is a substantially full length antibody, e.g., an IgG2a antibody or other antibody class or isotype as defined herein.

In a further aspect, an anti-LgR5 antibody according to any of the above embodiments may incorporate any of the features, singly or in combination, as described in Sections 1-7 below.

Antibody 3G12 and Other Embodiments

In some embodiments, the invention provides an anti-LgR5 antibody comprising at least one, two, three, four, five, or six HVRs selected from (a) HVR-H1 comprising the amino acid sequence of SEQ ID NO: 48; (b) HVR-H2 comprising the amino acid sequence of SEQ ID NO: 49; (c) HVR-H3 comprising the amino acid sequence of SEQ ID NO: 50; (d) HVR-L1 comprising the amino acid sequence of SEQ ID NO: 45; (e) HVR-L2 comprising the amino acid sequence of SEQ ID NO: 46; and (f) HVR-L3 comprising the amino acid sequence of SEQ ID NO: 47.

In one aspect, the invention provides an antibody comprising at least one, at least two, or all three VH HVR sequences selected from (a) HVR-H1 comprising the amino acid sequence of SEQ ID NO: 48; (b) HVR-H2 comprising the amino acid sequence of SEQ ID NO: 49; and (c) HVR-H3 comprising the amino acid sequence of SEQ ID NO: 50. In one embodiment, the antibody comprises HVR-H3 comprising the amino acid sequence of SEQ ID NO: 50. In another embodiment, the antibody comprises HVR-H3 comprising the amino acid sequence of SEQ ID NO: 50 and HVR-L3 comprising the amino acid sequence of SEQ ID NO: 47. In a further embodiment, the antibody comprises HVR-H3 comprising the amino acid sequence of SEQ ID NO: 50, HVR-L3 comprising the amino acid sequence of SEQ ID NO: 47, and HVR-H2 comprising the amino acid sequence of SEQ ID NO: 49. In a further embodiment, the antibody comprises (a) HVR-H1 comprising the amino acid sequence of SEQ ID NO: 48; (b) HVR-H2 comprising the amino acid sequence of SEQ ID NO: 49; and (c) HVR-H3 comprising the amino acid sequence of SEQ ID NO: 50.

In another aspect, the invention provides an antibody comprising at least one, at least two, or all three VL HVR sequences selected from (a) HVR-L1 comprising the amino acid sequence of SEQ ID NO: 45; (b) HVR-L2 comprising the amino acid sequence of SEQ ID NO: 46; and (c) HVR-L3 comprising the amino acid sequence of SEQ ID NO: 47. In one embodiment, the antibody comprises (a) HVR-L1 comprising the amino acid sequence of SEQ ID NO: 45; (b) HVR-L2 comprising the amino acid sequence of SEQ ID NO: 46; and (c) HVR-L3 comprising the amino acid sequence of SEQ ID NO: 47.

In another aspect, an antibody of the invention comprises (a) a VH domain comprising at least one, at least two, or all three VH HVR sequences selected from (i) HVR-H1 comprising the amino acid sequence of SEQ ID NO: 48, (ii) HVR-H2 comprising the amino acid sequence of SEQ ID NO: 49, and (iii) HVR-H3 comprising an amino acid sequence selected from SEQ ID NO: 50; and (b) a VL domain comprising at least one, at least two, or all three VL HVR sequences selected from (i) HVR-L1 comprising the amino acid sequence of SEQ ID NO: 45, (ii) HVR-L2 comprising the amino acid sequence of SEQ ID NO: 46, and (c) HVR-L3 comprising the amino acid sequence of SEQ ID NO: 47.

In another aspect, the invention provides an antibody comprising (a) HVR-H1 comprising the amino acid sequence of SEQ ID NO: 48; (b) HVR-H2 comprising the amino acid sequence of SEQ ID NO: 49; (c) HVR-H3 comprising the amino acid sequence of SEQ ID NO: 50; (d) HVR-L1 comprising the amino acid sequence of SEQ ID NO: 45; (e) HVR-L2 comprising the amino acid sequence of SEQ ID NO: 46; and (f) HVR-L3 comprising the amino acid sequence of SEQ ID NO: 47.

In any of the above embodiments, an anti-LgR5 antibody is humanized. In one embodiment, an anti-LgR5 antibody comprises HVRs as in any of the above embodiments, and further comprises a human acceptor framework, e.g. a human immunoglobulin framework or a human consensus framework. In certain embodiments, the human acceptor framework is the human VL kappa consensus ($VL_K$) framework and/or the human VH subgroup 3 consensus ($VH_3$) framework.

In another aspect, an anti-LgR5 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 22. In certain embodiments, a VH sequence having at least 90%, 91%, 92%, 93%, 94%, 95%, 96%, 97%, 98%, or 99% identity to the amino acid sequence of SEQ ID NO: 22 contains substitutions (e.g., conservative substitutions), insertions, or deletions relative to the reference sequence, but an anti-LgR5 antibody comprising that sequence retains the ability to bind to LgR5. In certain embodiments, a total of 1 to 10 amino acids have been substituted, inserted and/or deleted in the amino acid sequence of SEQ ID NO: 22. In certain embodiments, a total of 1 to 5 amino acids have been substituted, inserted and/or deleted in the amino acid sequence of SEQ ID NO: 22. In certain embodiments, substitutions, insertions, or deletions occur in regions outside the HVRs (i.e., in the FRs).

Optionally, the anti-LgR5 antibody comprises the VH sequence of SEQ ID NO: 22, including post-translational modifications of that sequence. In a particular embodiment, the VH comprises one, two or three HVRs selected from: (a) HVR-H1 comprising the amino acid sequence of SEQ ID NO: 48, (b) HVR-H2 comprising the amino acid sequence of SEQ ID NO: 49, and (c) HVR-H3 comprising the amino acid sequence of SEQ ID NO: 50.

In another aspect, an anti-LgR5 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 21. In certain embodiments, a VL sequence having at least 90%, 91%, 92%, 93%, 94%, 95%, 96%, 97%, 98%, or 99% identity to the amino acid sequence of SEQ ID NO: 21 contains substitutions (e.g., conservative substitutions), insertions, or deletions relative to the reference sequence, but an anti-LgR5 antibody comprising that sequence retains the ability to bind to LgR5. In certain embodiments, a total of 1 to 10 amino acids have been substituted, inserted and/or deleted in the amino acid sequence of SEQ ID NO: 21. In certain embodiments, a total of 1 to 5 amino acids have been substituted, inserted and/or deleted in the amino acid sequence of SEQ ID NO: 21. In certain embodiments, the substitutions, insertions, or deletions occur in regions outside the HVRs (i.e., in the FRs).

Optionally, the anti-LgR5 antibody comprises the VL sequence of SEQ ID NO: 21, including post-translational modifications of that sequence. In a particular embodiment, the VL comprises one, two or three HVRs selected from (a) HVR-L1 comprising the amino acid sequence of SEQ ID NO: 45; (b) HVR-L2 comprising the amino acid sequence of SEQ ID NO: 46; and (c) HVR-L3 comprising the amino acid sequence of SEQ ID NO: 47.

In another aspect, an anti-LgR5 antibody is provided, wherein the antibody comprises a VH as in any of the embodiments provided above, and a VL as in any of the embodiments provided above. In one embodiment, the antibody comprises the VH and VL sequences in SEQ ID NO: 22 and SEQ ID NO: 21, respectively, including post-translational modifications of those sequences.

In a further aspect, the invention provides an antibody that binds to the same epitope as an anti-LgR5 antibody provided herein. For example, in certain embodiments, an antibody is provided that binds to the same epitope as an anti-LgR5 antibody comprising a VH sequence of SEQ ID NO: 22 and a VL sequence of SEQ ID NO: 21. In certain embodiments, an antibody is provided that binds to an epitope of SEQ ID NO: 67 from, within, or overlapping amino acids 324-423. In some embodiments, an antibody is provided that binds to an epitope of SEQ ID NO: 68 from, within, or overlapping amino acids 303-402. In certain embodiments, an antibody is provided that binds to an epitope of SEQ ID NO: 67 from, within, or overlapping amino acids 324-555. In some embodiments, an antibody is provided that binds to an epitope of SEQ ID NO: 68 from, within, or overlapping amino acids 303-534.

In a further aspect of the invention, an anti-LgR5 antibody according to any of the above embodiments is a monoclonal antibody, including a chimeric, humanized or human antibody. In one embodiment, an anti-LgR5 antibody is an antibody fragment, e.g., a Fv, Fab, Fab', scFv, diabody, or $F(ab')_2$ fragment. In another embodiment, the antibody is a substantially full length antibody, e.g., an IgG1 antibody or other antibody class or isotype as defined herein.

In a further aspect, an anti-LgR5 antibody according to any of the above embodiments may incorporate any of the features, singly or in combination, as described in Sections 1-7 below.

Antibody 2H6 and Other Embodiments

In some embodiments, the invention provides an anti-LgR5 antibody comprising at least one, two, three, four, five, or six HVRs selected from (a) HVR-H1 comprising the amino acid sequence of SEQ ID NO: 54; (b) HVR-H2 comprising the amino acid sequence of SEQ ID NO: 55; (c) HVR-H3 comprising the amino acid sequence of SEQ ID NO: 56; (d) HVR-L1 comprising the amino acid sequence of SEQ ID NO: 51; (e) HVR-L2 comprising the amino acid sequence of SEQ ID NO: 52; and (f) HVR-L3 comprising the amino acid sequence of SEQ ID NO: 53.

In one aspect, the invention provides an antibody comprising at least one, at least two, or all three VH HVR sequences selected from (a) HVR-H1 comprising the amino acid sequence of SEQ ID NO: 54; (b) HVR-H2 comprising the amino acid sequence of SEQ ID NO: 55; and (c) HVR-H3 comprising the amino acid sequence of SEQ ID NO: 56. In one embodiment, the antibody comprises HVR-H3 comprising the amino acid sequence of SEQ ID NO: 56. In another embodiment, the antibody comprises HVR-H3 comprising the amino acid sequence of SEQ ID NO: 56 and HVR-L3 comprising the amino acid sequence of SEQ ID NO: 53. In a further embodiment, the antibody comprises HVR-H3 comprising the amino acid sequence of SEQ ID NO: 56, HVR-L3 comprising the amino acid sequence of SEQ ID NO: 53, and HVR-H2 comprising the amino acid sequence of SEQ ID NO: 55. In a further embodiment, the antibody comprises (a) HVR-H1 comprising the amino acid sequence of SEQ ID NO: 54; (b) HVR-H2 comprising the amino acid sequence of SEQ ID NO: 55; and (c) HVR-H3 comprising the amino acid sequence of SEQ ID NO: 56.

In another aspect, the invention provides an antibody comprising at least one, at least two, or all three VL HVR sequences selected from (a) HVR-L1 comprising the amino acid sequence of SEQ ID NO: 51; (b) HVR-L2 comprising the amino acid sequence of SEQ ID NO: 52; and (c) HVR-L3 comprising the amino acid sequence of SEQ ID NO: 53. In one embodiment, the antibody comprises (a) HVR-L1 comprising the amino acid sequence of SEQ ID NO: 51; (b)

HVR-L2 comprising the amino acid sequence of SEQ ID NO: 52; and (c) HVR-L3 comprising the amino acid sequence of SEQ ID NO: 53.

In another aspect, an antibody of the invention comprises (a) a VH domain comprising at least one, at least two, or all three VH HVR sequences selected from (i) HVR-H1 comprising the amino acid sequence of SEQ ID NO: 54, (ii) HVR-H2 comprising the amino acid sequence of SEQ ID NO: 55, and (iii) HVR-H3 comprising an amino acid sequence selected from SEQ ID NO: 56; and (b) a VL domain comprising at least one, at least two, or all three VL HVR sequences selected from (i) HVR-L1 comprising the amino acid sequence of SEQ ID NO: 51, (ii) HVR-L2 comprising the amino acid sequence of SEQ ID NO: 52, and (c) HVR-L3 comprising the amino acid sequence of SEQ ID NO: 53.

In another aspect, the invention provides an antibody comprising (a) HVR-H1 comprising the amino acid sequence of SEQ ID NO: 54; (b) HVR-H2 comprising the amino acid sequence of SEQ ID NO: 55; (c) HVR-H3 comprising the amino acid sequence of SEQ ID NO: 56; (d) HVR-L1 comprising the amino acid sequence of SEQ ID NO: 51; (e) HVR-L2 comprising the amino acid sequence of SEQ ID NO: 52; and (0 HVR-L3 comprising the amino acid sequence of SEQ ID NO: 53.

In any of the above embodiments, an anti-LgR5 antibody is humanized. In one embodiment, an anti-LgR5 antibody comprises HVRs as in any of the above embodiments, and further comprises a human acceptor framework, e.g. a human immunoglobulin framework or a human consensus framework. In certain embodiments, the human acceptor framework is the human VL kappa consensus (VL$_K$) framework and/or the human VH subgroup 3 (VH$_3$) framework.

In another aspect, an anti-LgR5 antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 24. In certain embodiments, a VH sequence having at least 90%, 91%, 92%, 93%, 94%, 95%, 96%, 97%, 98%, or 99% identity to the amino acid sequence of SEQ ID NO: 24 contains substitutions (e.g., conservative substitutions), insertions, or deletions relative to the reference sequence, but an anti-LgR5 antibody comprising that sequence retains the ability to bind to LgR5. In certain embodiments, a total of 1 to 10 amino acids have been substituted, inserted and/or deleted in the amino acid sequence of SEQ ID NO: 24. In certain embodiments, a total of 1 to 5 amino acids have been substituted, inserted and/or deleted in the amino acid sequence of SEQ ID NO: 24. In certain embodiments, substitutions, insertions, or deletions occur in regions outside the HVRs (i.e., in the FRs).

Optionally, the anti-LgR5 antibody comprises the VH sequence of SEQ ID NO: 24, including post-translational modifications of that sequence. In a particular embodiment, the VH comprises one, two or three HVRs selected from: (a) HVR-H1 comprising the amino acid sequence of SEQ ID NO: 54, (b) HVR-H2 comprising the amino acid sequence of SEQ ID NO: 55, and (c) HVR-H3 comprising the amino acid sequence of SEQ ID NO: 56.

In another aspect, an anti-LgR5 antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 23. In certain embodiments, a VL sequence having at least 90%, 91%, 92%, 93%, 94%, 95%, 96%, 97%, 98%, or 99% identity to the amino acid sequence of SEQ ID NO: 23 contains substitutions (e.g., conservative substitutions), insertions, or deletions relative to the reference sequence, but an anti-LgR5 antibody comprising that sequence retains the ability to bind to LgR5. In certain embodiments, a total of 1 to 10 amino acids have been substituted, inserted and/or deleted in the amino acid sequence of SEQ ID NO: 23. In certain embodiments, a total of 1 to 5 amino acids have been substituted, inserted and/or deleted in the amino acid sequence of SEQ ID NO: 23. In certain embodiments, the substitutions, insertions, or deletions occur in regions outside the HVRs (i.e., in the FRs).

Optionally, the anti-LgR5 antibody comprises the VL sequence of the amino acid sequence of SEQ ID NO: 23, including post-translational modifications of that sequence. In a particular embodiment, the VL comprises one, two or three HVRs selected from (a) HVR-L1 comprising the amino acid sequence of SEQ ID NO: 51; (b) HVR-L2 comprising the amino acid sequence of SEQ ID NO: 52; and (c) HVR-L3 comprising the amino acid sequence of SEQ ID NO: 53.

In another aspect, an anti-LgR5 antibody is provided, wherein the antibody comprises a VH as in any of the embodiments provided above, and a VL as in any of the embodiments provided above. In one embodiment, the antibody comprises the VH and VL sequences in SEQ ID NO: 24 and SEQ ID NO: 23, respectively, including post-translational modifications of those sequences.

In a further aspect, the invention provides an antibody that binds to the same epitope as an anti-LgR5 antibody provided herein. For example, in certain embodiments, an antibody is provided that binds to the same epitope as an anti-LgR5 antibody comprising a VH sequence of SEQ ID NO: 24 and a VL sequence of SEQ ID NO: 23. In certain embodiments, an antibody is provided that binds to an epitope of SEQ ID NO: 67 from, within, or overlapping amino acids 324-423. In some embodiments, an antibody is provided that binds to an epitope of SEQ ID NO: 68 from, within, or overlapping amino acids 303-402. In certain embodiments, an antibody is provided that binds to an epitope of SEQ ID NO: 67 from, within, or overlapping amino acids 324-555. In some embodiments, an antibody is provided that binds to an epitope of SEQ ID NO: 68 from, within, or overlapping amino acids 303-534.

In a further aspect of the invention, an anti-LgR5 antibody according to any of the above embodiments is a monoclonal antibody, including a chimeric, humanized or human antibody. In one embodiment, an anti-LgR5 antibody is an antibody fragment, e.g., a Fv, Fab, Fab', scFv, diabody, or F(ab')$_2$ fragment. In another embodiment, the antibody is a substantially full length antibody, e.g., an IgG1 antibody or other antibody class or isotype as defined herein.

In a further aspect, an anti-LgR5 antibody according to any of the above embodiments may incorporate any of the features, singly or in combination, as described in Sections 1-7 below.

1. Antibody Affinity

In certain embodiments, an antibody provided herein has a dissociation constant (Kd) of ≤1 μM, ≤100 nM, ≤10 nM, ≤1 nM, ≤0.1 nM, ≤0.01 nM, or ≤0.001 nM, and optionally is ≥10$^{-13}$ M. (e.g. 10$^{-8}$M or less, e.g. from 10$^{-8}$M to 10$^{-13}$M, e.g., from 10$^{-9}$M to 10$^{-13}$ M).

In one embodiment, Kd is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., J. Mol. Biol. 293:865-881 (1999)). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 µM or 26 µM antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20) in PBS. When the plates have dried, 150 µl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, Kd is measured using surface plasmon resonance assays using a BIACORE®-2000 or a BIACORE®-3000 (BIAcore, Inc., Piscataway, N.J.) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm bandpass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. *Nat. Med.* 9:129-134 (2003). For a review of scFv fragments, see, e.g., Pluckthün, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g. *E. coli* or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al., *Proc. Natl. Acad. Sci. USA,* 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing SDR (a-CDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.*, 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

4. Human Antibodies

In certain embodiments, an antibody provided herein is a human antibody. Human antibodies can be produced using various techniques known in the art. Human antibodies are described generally in van Dijk and van de Winkel, *Curr. Opin. Pharmacol.* 5:368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENOMOUSE™ technology; U.S. Pat. No. 5,770,429 describing HuMAB® technology; U.S. Pat. No. 7,041,870 describing K-M MOUSE® technology, and U.S. Patent Application Publication No. US 2007/0061900, describing VELOCIMOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor. *J. Immunol.*, 133: 3001 (1984); Brodeur et al., *Monoclonal Antibody Production Techniques and Applications*, pp. 51-63 (Marcel Dekker, Inc., New York, 1987); and Boerner et al., *J. Immunol.*, 147: 86 (1991).) Human antibodies generated via human B-cell hybridoma technology are also described in Li et al., *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, *Xiandai Mianyixue*, 26(4):265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178:1-37 (O'Brien et al., ed., Human Press, Totowa, N.J., 2001) and further described, e.g., in the McCafferty et al., *Nature* 348: 552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101 (34): 12467-12472 (2004); and Lee et al., *J. Immunol. Methods* 284(1-2): 119-132 (2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.*, 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J,* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.*, 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for LgR5 and the other is for any other antigen. In certain embodiments, one of the binding specificities is for LgR5 and the other is for CD3. See, e.g., U.S. Pat. No. 5,821,337. In certain embodiments, bispecific antibodies may bind to two different epitopes of LgR5. Bispecific antibodies may also be used to localize cytotoxic agents to cells which express LgR5. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J* 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science,* 229: 81 (1985)); using leucine zippers to produce bi-specific antibodies (see, e.g., Kostelny et al., *J. Immunol.,* 148(5):1547-1553 (1992); using "diabody" technology for making bispecific antibody fragments (see, e.g., Hollinger et al., *Proc. Natl. Acad. Sci. USA,* 90:6444-6448 (1993)); and using single-chain Fv (sFv) dimers (see, e.g. Gruber et al., *J. Immunol.,* 152:5368 (1994)); and preparing trispecific antibodies as described, e.g., in Tuft et al. J. Immunol. 147: 60 (1991).

Engineered antibodies with three or more functional antigen binding sites, including "Octopus antibodies," are also included herein (see, e.g. US 2006/0025576A1).

The antibody or fragment herein also includes a "Dual Acting FAb" or "DAF" comprising an antigen binding site that binds to LgR5 as well as another, different antigen (see, US 2008/0069820, for example).

7. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "preferred substitutions." More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
   (1) hydrophobic: Norleucine, Met, Ala, Val, Leu, Ile;
   (2) neutral hydrophilic: Cys, Ser, Thr, Asn, Gln;
   (3) acidic: Asp, Glu;
   (4) basic: His, Lys, Arg;
   (5) residues that influence chain orientation: Gly, Pro;
   (6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science,* 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex is used to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

c) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express Fc(RI, Fc(RII and Fc(RIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737, 056; WO 2004/056312, and Shields et al., *J. Biol. Chem.* 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. No. 5,648,260; U.S. Pat. No. 5,624,821; and WO 94/29351 concerning other examples of Fc region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

An exemplary hu8E11.v2 light chain (LC) V205C thiomab has the heavy chain and light chain sequences of SEQ ID NOs: 64 and 74, respectively. An exemplary hu8E11.v2 heavy chain (HC) A118C thiomab has the heavy chain and light chain sequences of SEQ ID NOs: 75 and 63, respectively. An exemplary hu8E11.v2 heavy chain (HC) S400C thiomab has the heavy chain and light chain sequences of SEQ ID NOs: 76 and 63, respectively.

An exemplary YW353 light chain (LC) V205C thiomab has the heavy chain and light chain sequences of SEQ ID NOs: 66 and 77, respectively. An exemplary YW353 heavy chain (HC) A118C thiomab has the heavy chain and light chain sequences of SEQ ID NOs: 78 and 65, respectively. An exemplary YW353 heavy chain (HC) S400C thiomab has the heavy chain and light chain sequences of SEQ ID NOs: 79 and 65, respectively.

Further exemplary V205C cysteine engineered thiomabs comprise a light chain comprising a variable region selected from SEQ ID NOs: 3, 5, 7, 9, 11, 13, 15, 17, 19, 21, and 23 and a constant region of SEQ ID NO: 80; and a heavy chain comprising a variable region selected from SEQ ID NOs: 4, 6, 8, 10, 12, 14, 16, 18, 20, 22 and 24 and a human heavy chain constant region, such as an IgG1. Further exemplary A118C cysteine engineered thiomabs comprise a light chain comprising a variable region selected from SEQ ID NOs: 3, 5, 7, 9, 11, 13, 15, 17, 19, 21, and 23 and a human light chain constant region, such as a kappa light chain constant region; and a heavy chain comprising a variable region selected from SEQ ID NOs: 4, 6, 8, 10, 12, 14, 16, 18, 20, 22, and 24 and a constant region of SEQ ID NO: 81. Further exemplary S400C cysteine engineered thiomabs comprise a light chain comprising a variable region selected from SEQ ID NOs: 3, 5, 7, 9, 11, 13, 15, 17, 19, 21, and 23 and a human light chain constant region, such as a kappa light chain constant region; and a heavy chain comprising a variable region selected from SEQ ID NOs: 4, 6, 8, 10, 12, 14, 16, 18, 20, 22, and 24 and a constant region of SEQ ID NO: 82.

e) Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, polypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

B. Recombinant Methods and Compositions

Antibodies may be produced using recombinant methods and compositions, e.g., as described in U.S. Pat. No. 4,816, 567. In one embodiment, isolated nucleic acid encoding an anti-LgR5 antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-LgR5 antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-LgR5 antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology*, Vol. 248 (B. K. C. Lo, ed., Humana Press, Totowa, N.J., 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TR1 cells, as described, e.g., in Mather et al., *Annals N.Y. Acad. Sci.* 383: 44-68 (1982); MRC 5 cells; and FS4 cells. Other useful mammalian host cell lines include Chinese hamster ovary (CHO) cells, including DHFR$^-$ CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology, Vol.* 248 (B. K. C. Lo, ed., Humana Press, Totowa, N.J.), pp. 255-268 (2003).

C. Assays

Anti-LgR5 antibodies provided herein may be identified, screened for, or characterized for their physical/chemical properties and/or biological activities by various assays known in the art.

In one aspect, an antibody of the invention is tested for its antigen binding activity, e.g., by known methods such as ELISA, BIACore®, FACS, or Western blot.

In another aspect, competition assays may be used to identify an antibody that competes with any of the antibodies described herein for binding to LgR5. In certain embodiments, such a competing antibody binds to the same epitope (e.g., a linear or a conformational epitope) that is bound by an antibody described herein. Detailed exemplary methods for mapping an epitope to which an antibody binds are provided in Morris (1996) "Epitope Mapping Protocols," in *Methods in Molecular Biology* vol. 66 (Humana Press, Totowa, N.J.).

In an exemplary competition assay, immobilized LgR5 is incubated in a solution comprising a first labeled antibody that binds to LgR5 (e.g., any of the antibodies described herein) and a second unlabeled antibody that is being tested for its ability to compete with the first antibody for binding to LgR5. The second antibody may be present in a hybridoma supernatant. As a control, immobilized LgR5 is incubated in a solution comprising the first labeled antibody but not the second unlabeled antibody. After incubation under conditions permissive for binding of the first antibody to LgR5, excess unbound antibody is removed, and the amount of label associated with immobilized LgR5 is measured. If the amount of label associated with immobilized LgR5 is substantially reduced in the test sample relative to the control sample, then that indicates that the second antibody is competing with the first antibody for binding to LgR5. See Harlow and Lane (1988) *Antibodies: A Laboratory Manual* ch.14 (Cold Spring Harbor Laboratory, Cold Spring Harbor, N.Y.).

D. Immunoconjugates

The invention also provides immunoconjugates comprising an anti-LgR5 antibody herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes (i.e., a radioconjugate).

Immunoconjugates allow for the targeted delivery of a drug moiety to a tumor, and, in some embodiments intracellular accumulation therein, where systemic administration of unconjugated drugs may result in unacceptable levels of toxicity to normal cells (Polakis P. (2005) *Current Opinion in Pharmacology* 5:382-387).

Antibody-drug conjugates (ADC) are targeted chemotherapeutic molecules which combine properties of both antibodies and cytotoxic drugs by targeting potent cytotoxic drugs to antigen-expressing tumor cells (Teicher, B. A. (2009) *Current Cancer Drug Targets* 9:982-1004), thereby enhancing the therapeutic index by maximizing efficacy and minimizing off-target toxicity (Carter, P. J. and Senter P. D. (2008) *The Cancer Jour.* 14(3):154-169; Chari, R. V. (2008) *Acc. Chem. Res.* 41:98-107.

The ADC compounds of the invention include those with anticancer activity. In some embodiments, the ADC compounds include an antibody conjugated, i.e. covalently attached, to the drug moiety. In some embodiments, the antibody is covalently attached to the drug moiety through a linker. The antibody-drug conjugates (ADC) of the invention selectively deliver an effective dose of a drug to tumor tissue whereby greater selectivity, i.e. a lower efficacious dose, may be achieved while increasing the therapeutic index ("therapeutic window").

The drug moiety (D) of the antibody-drug conjugates (ADC) may include any compound, moiety or group that has a cytotoxic or cytostatic effect. Drug moieties may impart their cytotoxic and cytostatic effects by mechanisms including but not limited to tubulin binding, DNA binding or intercalation, and inhibition of RNA polymerase, protein synthesis, and/or topoisomerase. Exemplary drug moieties include, but are not limited to, a maytansinoid, dolastatin, auristatin, calicheamicin, pyrrolobenzodiazepine (PBD), nemorubicin and its derivatives, PNU-159682, anthracycline, duocarmycin, vinca alkaloid, taxane, trichothecene, CC1065, camptothecin, elinafide, and stereoisomers, isosteres, analogs, and derivatives thereof that have cytotoxic activity. Nonlimiting examples of such immunoconjugates are discussed in further detail below.

1. Exemplary Antibody-Drug Conjugates

An exemplary embodiment of an antibody-drug conjugate (ADC) compound comprises an antibody (Ab) which targets a tumor cell, a drug moiety (D), and a linker moiety (L) that attaches Ab to D. In some embodiments, the antibody is attached to the linker moiety (L) through one or more amino acid residues, such as lysine and/or cysteine.

An exemplary ADC has Formula I:

   I where p is 1 to about 20. In some embodiments, the number of drug moieties that can be conjugated to an antibody is limited by the number of free cysteine residues. In some embodiments, free cysteine residues are introduced into the antibody amino acid sequence by the methods described herein. Exemplary ADC of Formula I include, but are not limited to, antibodies that have 1, 2, 3, or 4 engineered cysteine amino acids (Lyon, R. et al (2012) *Methods in Enzym.* 502:123-138). In some embodiments, one or more free cysteine residues are already present in an antibody, without the use of engineering, in which case the existing free cysteine residues may be used to conjugate the antibody to a drug. In some embodiments, an antibody is exposed to reducing conditions prior to conjugation of the antibody in order to generate one or more free cysteine residues.

a) Exemplary Linkers

A "Linker" (L) is a bifunctional or multifunctional moiety that can be used to link one or more drug moieties (D) to an antibody (Ab) to form an antibody-drug conjugate (ADC) of Formula I. In some embodiments, antibody-drug conjugates (ADC) can be prepared using a Linker having reactive functionalities for covalently attaching to the drug and to the antibody. For example, in some embodiments, a cysteine thiol of an antibody (Ab) can form a bond with a reactive functional group of a linker or a drug-linker intermediate to make an ADC.

In one aspect, a linker has a functionality that is capable of reacting with a free cysteine present on an antibody to form a covalent bond. Nonlimiting exemplary such reactive functionalities include maleimide, haloacetamides, α-haloacetyl, activated esters such as succinimide esters, 4-nitrophenyl esters, pentafluorophenyl esters, tetrafluorophenyl esters, anhydrides, acid chlorides, sulfonyl chlorides, isocyanates, and isothiocyanates. See, e.g., the conjugation method at page 766 of Klussman, et al (2004), *Bioconjugate Chemistry* 15(4):765-773, and the Examples herein.

In some embodiments, a linker has a functionality that is capable of reacting with an electrophilic group present on an antibody. Exemplary such electrophilic groups include, but are not limited to, aldehyde and ketone carbonyl groups. In some embodiments, a heteroatom of the reactive functionality of the linker can react with an electrophilic group on an antibody and form a covalent bond to an antibody unit. Nonlimiting exemplary such reactive functionalities include, but are not limited to, hydrazide, oxime, amino, hydrazine, thiosemicarbazone, hydrazine carboxylate, and arylhydrazide.

A linker may comprise one or more linker components. Exemplary linker components include 6-maleimidocaproyl ("MC"), maleimidopropanoyl ("MP"), valine-citrulline ("val-cit" or "vc"), alanine-phenylalanine ("ala-phe"), p-aminobenzyloxycarbonyl (a "PAB"), N-Succinimidyl 4-(2-pyridylthio) pentanoate ("SPP"), and 4-(N-maleimidomethyl) cyclohexane-1 carboxylate ("MCC"). Various linker components are known in the art, some of which are described below.

A linker may be a "cleavable linker," facilitating release of a drug. Nonlimiting exemplary cleavable linkers include acid-labile linkers (e.g., comprising hydrazone), protease-sensitive (e.g., peptidase-sensitive) linkers, photolabile linkers, or disulfide-containing linkers (Chari et al., Cancer Research 52:127-131 (1992); U.S. Pat. No. 5,208,020).

In certain embodiments, a linker has the following Formula II:

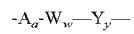   II wherein A is a "stretcher unit", and a is an integer from 0 to 1; W is an "amino acid unit", and w is an integer from 0 to 12; Y is a "spacer unit", and y is 0, 1, or 2. An ADC comprising the linker of Formula II has the Formula I(A): Ab-($A_a$-$W_w$—$Y_y$-D)$_p$, wherein Ab, D, and p are defined as above for Formula I. Exemplary embodiments of such linkers are described in U.S. Pat. No. 7,498,298, which is expressly incorporated herein by reference.

In some embodiments, a linker component comprises a "stretcher unit" (A) that links an antibody to another linker component or to a drug moiety. Nonlimiting exemplary stretcher units are shown below (wherein the wavy line indicates sites of covalent attachment to an antibody, drug, or additional linker components):

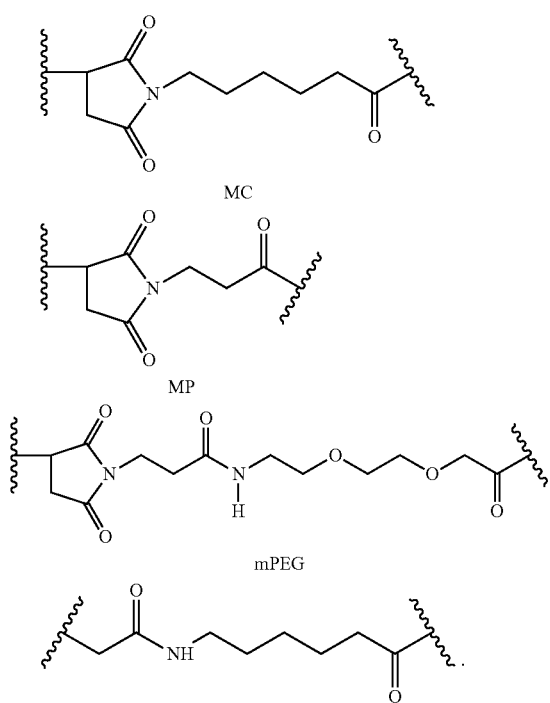

In some embodiments, a linker component comprises an "amino acid unit" (W). In some such embodiments, the amino acid unit allows for cleavage of the linker by a protease, thereby facilitating release of the drug from the immunoconjugate upon exposure to intracellular proteases, such as lysosomal enzymes (Doronina et al. (2003) *Nat. Biotechnol.* 21:778-784). Exemplary amino acid units include, but are not limited to, dipeptides, tripeptides, tetrapeptides, and pentapeptides. Exemplary dipeptides include, but are not limited to, valine-citrulline (vc or val-cit), alanine-phenylalanine (af or ala-phe); phenylalanine-lysine (fk or phe-lys); phenylalanine-homolysine (phe-homolys); and N-methyl-valine-citrulline (Me-val-cit). Exemplary tripeptides include, but are not limited to, glycine-valine-citrulline (gly-val-cit) and glycine-glycine-glycine (gly-gly-gly). An amino acid unit may comprise amino acid residues that occur naturally and/or minor amino acids and/or non-naturally occurring amino acid analogs, such as citrulline Amino acid units can be designed and optimized for enzymatic cleavage by a particular enzyme, for example, a tumor-associated protease, cathepsin B, C and D, or a plasmin protease.

Typically, peptide-type linkers can be prepared by forming a peptide bond between two or more amino acids and/or peptide fragments. Such peptide bonds can be prepared, for example, according to a liquid phase synthesis method (e.g., E. Schroder and K. Lübke (1965) "The Peptides", volume 1, pp 76-136, Academic Press).

In some embodiments, a linker component comprises a "spacer unit" (Y) that links the antibody to a drug moiety, either directly or through a stretcher unit and/or an amino acid unit. A spacer unit may be "self-immolative" or a "non-self-immolative." A "non-self-immolative" spacer unit is one in which part or all of the spacer unit remains bound to the drug moiety upon cleavage of the ADC. Examples of non-self-immolative spacer units include, but are not limited to, a glycine spacer unit and a glycine-glycine spacer unit. In some embodiments, enzymatic cleavage of an ADC containing a glycine-glycine spacer unit by a tumor-cell associated protease results in release of a glycine-glycine-drug moiety from the remainder of the ADC. In some such embodiments, the glycine-glycine-drug moiety is subjected to a hydrolysis step in the tumor cell, thus cleaving the glycine-glycine spacer unit from the drug moiety.

A "self-immolative" spacer unit allows for release of the drug moiety. In certain embodiments, a spacer unit of a linker comprises a p-aminobenzyl unit. In some such embodiments, a p-aminobenzyl alcohol is attached to an amino acid unit via an amide bond, and a carbamate, methylcarbamate, or carbonate is made between the benzyl alcohol and the drug (Hamann et al. (2005) *Expert Opin. Ther. Patents* (2005) 15:1087-1103). In some embodiments, the spacer unit comprises p-aminobenzyloxycarbonyl (PAB). In some embodiments, an ADC comprising a self-immolative linker has the structure:

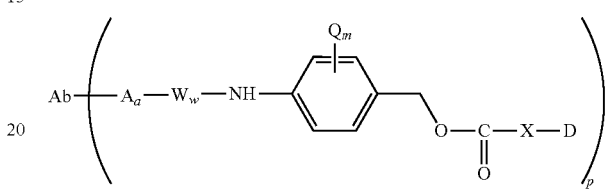

wherein Q is —$C_1$-$C_8$ alkyl, —O—($C_1$-$C_8$ alkyl), -halogen, -nitro, or -cyano; m is an integer ranging from 0 to 4; X may be one or more additional spacer units or may be absent; and p ranges from 1 to about 20. In some embodiments, p ranges from 1 to 10, 1 to 7, 1 to 5, or 1 to 4. Nonlimiting exemplary X spacer units include:

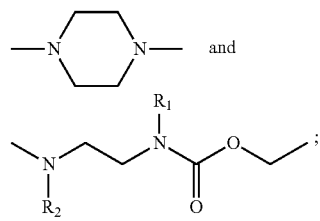

wherein $R_1$ and $R_2$ are independently selected from H and $C_1$-$C_6$ alkyl. In some embodiments, $R_1$ and $R_2$ are each —$CH_3$.

Other examples of self-immolative spacers include, but are not limited to, aromatic compounds that are electronically similar to the PAB group, such as 2-aminoimidazol-5-methanol derivatives (U.S. Pat. No. 7,375,078; Hay et al. (1999) *Bioorg. Med. Chem. Lett.* 9:2237) and ortho- or para-aminobenzylacetals. In some embodiments, spacers can be used that undergo cyclization upon amide bond hydrolysis, such as substituted and unsubstituted 4-aminobutyric acid amides (Rodrigues et al (1995) *Chemistry Biology* 2:223), appropriately substituted bicyclo[2.2.1] and bicyclo[2.2.2] ring systems (Storm et al (1972) *J. Amer. Chem. Soc.* 94:5815) and 2-aminophenylpropionic acid amides (Amsberry, et al (1990) *J. Org. Chem.* 55:5867). Linkage of a drug to the α-carbon of a glycine residue is another example of a self-immolative spacer that may be useful in ADC (Kingsbury et al (1984) *J. Med. Chem.* 27:1447).

In some embodiments, linker L may be a dendritic type linker for covalent attachment of more than one drug moiety to an antibody through a branching, multifunctional linker moiety (Sun et al (2002) *Bioorganic & Medicinal Chemistry Letters* 12:2213-2215; Sun et al (2003) *Bioorganic & Medicinal Chemistry* 11:1761-1768). Dendritic linkers can increase the molar ratio of drug to antibody, i.e. loading, which is related to the potency of the ADC. Thus, where an antibody bears only one reactive cysteine thiol group, a multitude of drug moieties may be attached through a dendritic linker.

Nonlimiting exemplary linkers are shown below in the context of an ADC of Formula I:
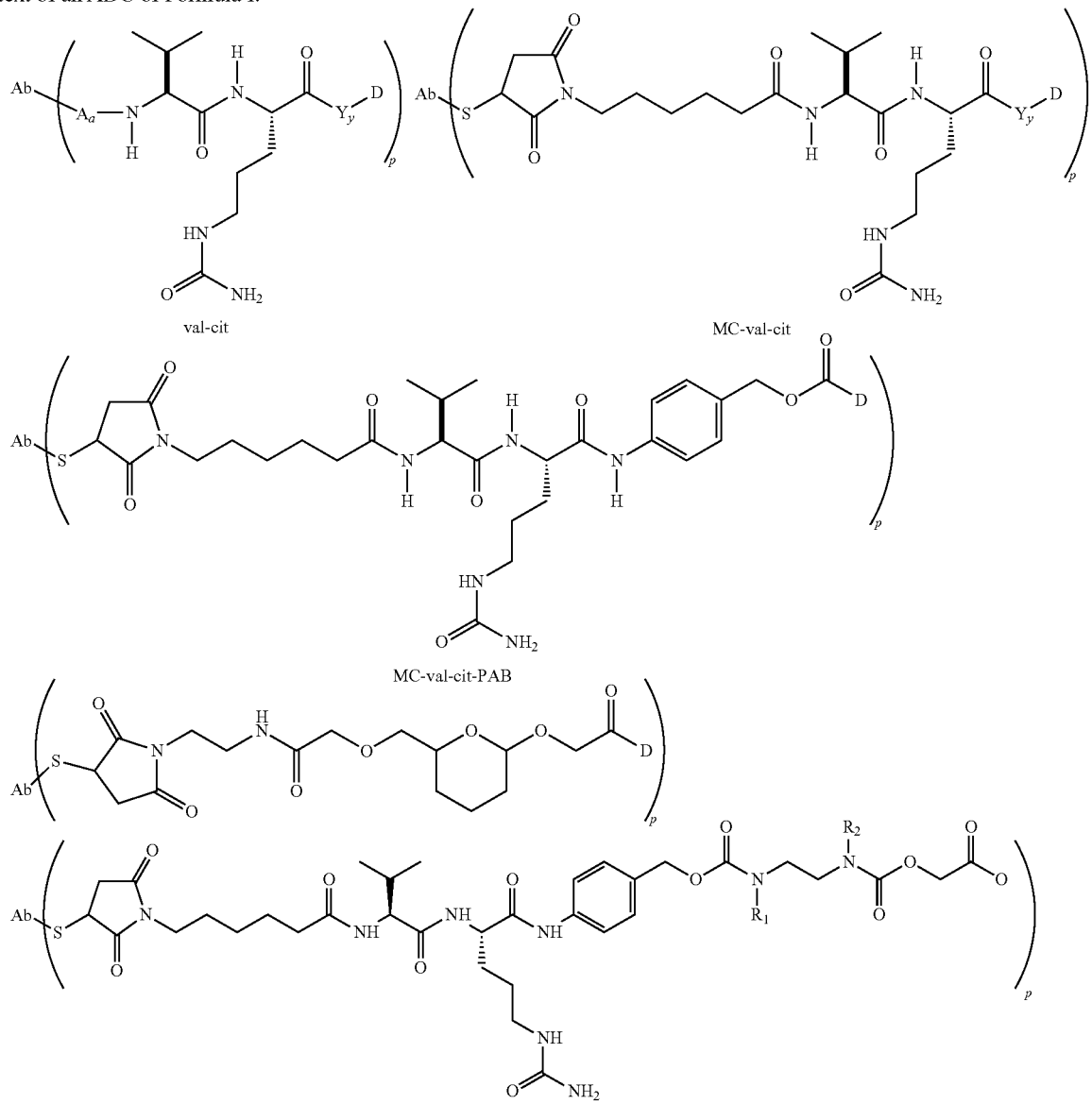
wherein $R_1$ and $R_2$ are independently selected from H and $C_1$-$C_6$ alkyl. In some embodiments, $R_1$ and $R_2$ are each —CH$_3$.
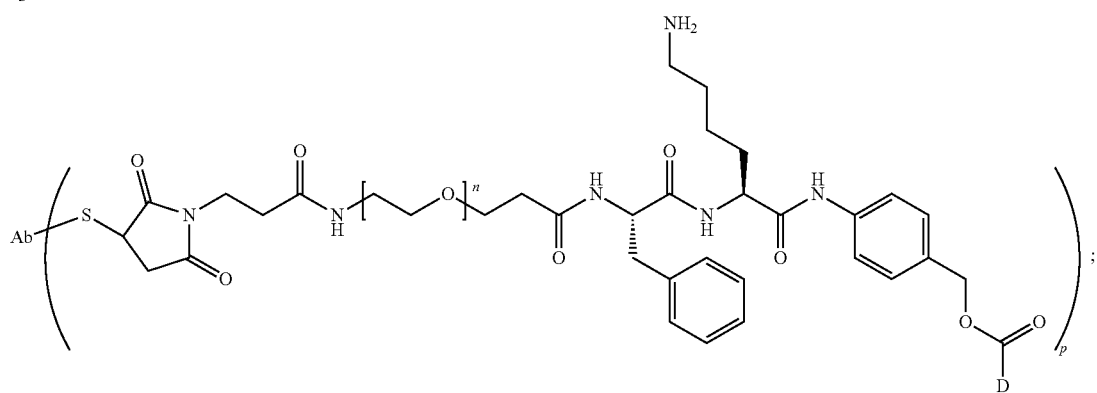
Phe-Lys-PAB-Ab wherein n is 0 to 12. In some embodiments, n is 2 to 10. In some embodiments, n is 4 to 8.

Further nonlimiting exemplary ADCs include the structures:

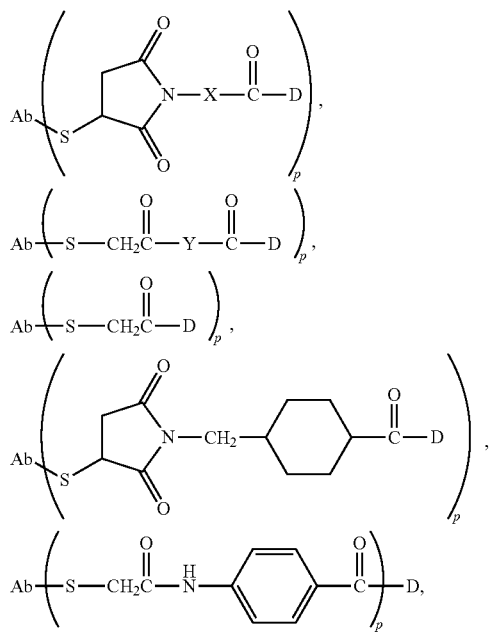

where X is:

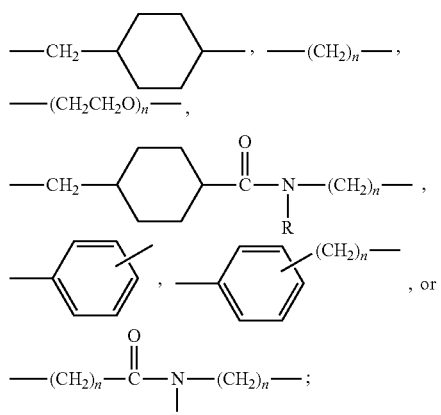

Y is:

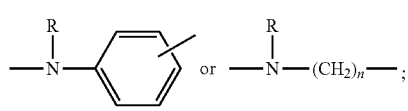

each R is independently H or $C_1$-$C_6$ alkyl; and n is 1 to 12.

In some embodiments, a linker is substituted with groups that modulate solubility and/or reactivity. As a nonlimiting example, a charged substituent such as sulfonate (—$SO_3^-$) or ammonium may increase water solubility of the linker reagent and facilitate the coupling reaction of the linker reagent with the antibody and/or the drug moiety, or facilitate the coupling reaction of Ab-L (antibody-linker intermediate) with D, or D-L (drug-linker intermediate) with Ab, depending on the synthetic route employed to prepare the ADC. In some embodiments, a portion of the linker is coupled to the antibody and a portion of the linker is coupled to the drug, and then the Ab-(linker portion)$^a$ is coupled to drug-(linker portion)$^b$ to form the ADC of Formula I.

The compounds of the invention expressly contemplate, but are not limited to, ADC prepared with the following linker reagents: bis-maleimido-trioxyethylene glycol (BMPEO), N-(β-maleimidopropyloxy)-N-hydroxy succinimide ester (BMPS), N-(ε-maleimidocaproyloxy) succinimide ester (EMCS), N-[γ-maleimidobutyryloxy]succinimide ester (GMBS), 1,6-hexane-bis-vinylsulfone (HBVS), succinimidyl 4-(N-maleimidomethyl)cyclohexane-1-carboxy-(6-amidocaproate) (LC-SMCC), m-maleimidobenzoyl-N-hydroxysuccinimide ester (MBS), 4-(4-N-Maleimidophenyl)butyric acid hydrazide (MPBH), succinimidyl 3-(bromoacetamido) propionate (SBAP), succinimidyl iodoacetate (SIA), succinimidyl (4-iodoacetyl)aminobenzoate (SIAB), N-succinimidyl-3-(2-pyridyldithio) propionate (SPDP), N-succinimidyl-4-(2-pyridylthio)pentanoate (SPP), succinimidyl 4-(N-maleimidomethyl)cyclohexane-1-carboxylate (SMCC), succinimidyl 4-(p-maleimidophenyl)butyrate (SMPB), succinimidyl 6-[(beta-maleimidopropionamido) hexanoate] (SMPH), iminothiolane (IT), sulfo-EMCS, sulfo-GMBS, sulfo-KMUS, sulfo-MBS, sulfo-SIAB, sulfo-SMCC, and sulfo-SMPB, and succinimidyl-(4-vinylsulfone) benzoate (SVSB), and including bis-maleimide reagents: dithiobismaleimidoethane (DTME), 1,4-Bismaleimidobutane (BMB), 1,4 Bismaleimidyl-2,3-dihydroxybutane (BMDB), bismaleimidohexane (BMH), bismaleimidoethane (BMOE), BM(PEG)$_2$ (shown below), and BM(PEG)$_3$ (shown below); bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). In some embodiments, bis-maleimide reagents allow the attachment of the thiol group of a cysteine in the antibody to a thiol-containing drug moiety, linker, or linker-drug intermediate. Other functional groups that are reactive with thiol groups include, but are not limited to, iodoacetamide, bromoacetamide, vinyl pyridine, disulfide, pyridyl disulfide, isocyanate, and isothiocyanate.

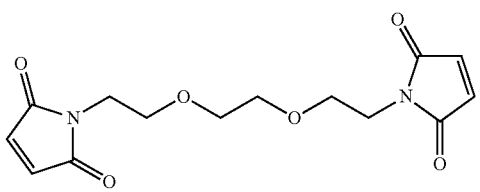

BM(PEG)$_2$

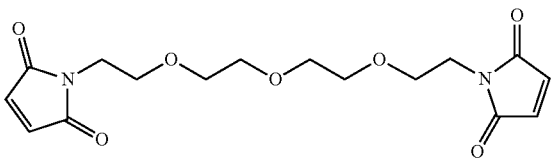

BM(PEG)$_3$

Certain useful linker reagents can be obtained from various commercial sources, such as Pierce Biotechnology, Inc. (Rockford, Ill.), Molecular Biosciences Inc. (Boulder, Colo.), or synthesized in accordance with procedures described in the art; for example, in Toki et al (2002) *J. Org. Chem.* 67:1866-1872; Dubowchik, et al. (1997) *Tetrahedron Letters*, 38:5257-60; Walker, M. A. (1995) *J. Org. Chem.* 60:5352-

5355; Frisch et al (1996) *Bioconjugate Chem.* 7:180-186; U.S. Pat. No. 6,214,345; WO 02/088172; US2003130189; US2003096743; WO 03/026577; WO 03/043583; and WO 04/032828.

Carbon-14-labeled 1-isothiocyanatobenzyl-3-methyldiethylene triaminepentaacetic acid (MX-DTPA) is an exemplary chelating agent for conjugation of radionucleotide to the antibody. See, e.g., WO94/11026.

b) Exemplary Drug Moieties (1) Maytansine and Maytansinoids

In some embodiments, an immunoconjugate comprises an antibody conjugated to one or more maytansinoid molecules. Maytansinoids are derivatives of maytansine, and are mitototic inhibitors which act by inhibiting tubulin polymerization. Maytansine was first isolated from the east African shrub Maytenus serrata (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinoids are disclosed, for example, in U.S. Pat. Nos. 4,137,230; 4,248,870; 4,256, 746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533.

Maytansinoid drug moieties are attractive drug moieties in antibody-drug conjugates because they are: (i) relatively accessible to prepare by fermentation or chemical modification or derivatization of fermentation products, (ii) amenable to derivatization with functional groups suitable for conjugation through non-disulfide linkers to antibodies, (iii) stable in plasma, and (iv) effective against a variety of tumor cell lines.

Certain maytansinoids suitable for use as maytansinoid drug moieties are known in the art and can be isolated from natural sources according to known methods or produced using genetic engineering techniques (see, e.g., Yu et al (2002) *PNAS* 99:7968-7973). Maytansinoids may also be prepared synthetically according to known methods.

Exemplary maytansinoid drug moieties include, but are not limited to, those having a modified aromatic ring, such as: C-19-dechloro (U.S. Pat. No. 4,256,746) (prepared, for example, by lithium aluminum hydride reduction of ansamytocin P2); C-20-hydroxy (or C-20-demethyl)+/−C-19-dechloro (U.S. Pat. Nos. 4,361,650 and 4,307,016) (prepared, for example, by demethylation using *Streptomyces* or *Actinomyces* or dechlorination using LAH); and C-20-demethoxy, C-20-acyloxy (—OCOR), +/−dechloro (U.S. Pat. No. 4,294,757) (prepared, for example, by acylation using acyl chlorides), and those having modifications at other positions of the aromatic ring.

Exemplary maytansinoid drug moieties also include those having modifications such as: C-9-SH (U.S. Pat. No. 4,424, 219) (prepared, for example, by the reaction of maytansinol with $H_2S$ or $P_2S_5$); C-14-alkoxymethyl(demethoxy/$CH_2OR$) (U.S. Pat. No. 4,331,598); C-14-hydroxymethyl or acyloxymethyl ($CH_2OH$ or $CH_2OAc$) (U.S. Pat. No. 4,450,254) (prepared, for example, from *Nocardia*); C-15-hydroxy/acyloxy (U.S. Pat. No. 4,364,866) (prepared, for example, by the conversion of maytansinol by *Streptomyces*); C-15-methoxy (U.S. Pat. Nos. 4,313,946 and 4,315,929) (for example, isolated from *Trewia nudlflora*); C-18-N-demethyl (U.S. Pat. Nos. 4,362,663 and 4,322,348) (prepared, for example, by the demethylation of maytansinol by *Streptomyces*); and 4,5-deoxy (U.S. Pat. No. 4,371,533) (prepared, for example, by the titanium trichloride/LAH reduction of maytansinol).

Many positions on maytansinoid compounds are useful as the linkage position. For example, an ester linkage may be formed by reaction with a hydroxyl group using conventional coupling techniques. In some embodiments, the reaction may occur at the C-3 position having a hydroxyl group, the C-14 position modified with hydroxymethyl, the C-15 position modified with a hydroxyl group, and the C-20 position having a hydroxyl group. In some embodiments, the linkage is formed at the C-3 position of maytansinol or a maytansinol analogue.

Maytansinoid drug moieties include those having the structure:

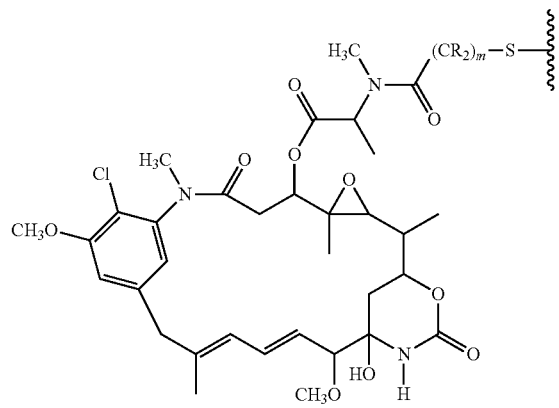

where the wavy line indicates the covalent attachment of the sulfur atom of the maytansinoid drug moiety to a linker of an ADC. Each R may independently be H or a $C_1$-$C_6$ alkyl. The alkylene chain attaching the amide group to the sulfur atom may be methanyl, ethanyl, or propyl, i.e., m is 1, 2, or 3 (U.S. Pat. No. 633,410; U.S. Pat. No. 5,208,020; Chari et al (1992) *Cancer Res.* 52:127-131; Liu et al (1996) *Proc. Natl. Acad. Sci. USA* 93:8618-8623).

All stereoisomers of the maytansinoid drug moiety are contemplated for the ADC of the invention, i.e. any combination of R and S configurations at the chiral carbons (U.S. Pat. No. 7,276,497; U.S. Pat. No. 6,913,748; U.S. Pat. No. 6,441,163; U.S. Pat. No. 633,410 (RE39151); U.S. Pat. No. 5,208,020; Widdison et al (2006) *J. Med. Chem.* 49:4392-4408, which are incorporated by reference in their entirety). In some embodiments, the maytansinoid drug moiety has the following stereochemistry:

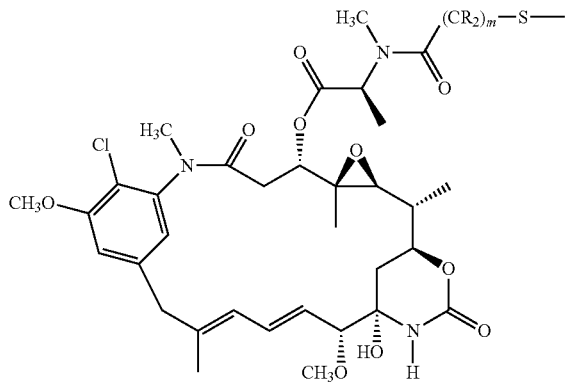

Exemplary embodiments of maytansinoid drug moieties include, but are not limited to, DM1; DM3; and DM4, having the structures:

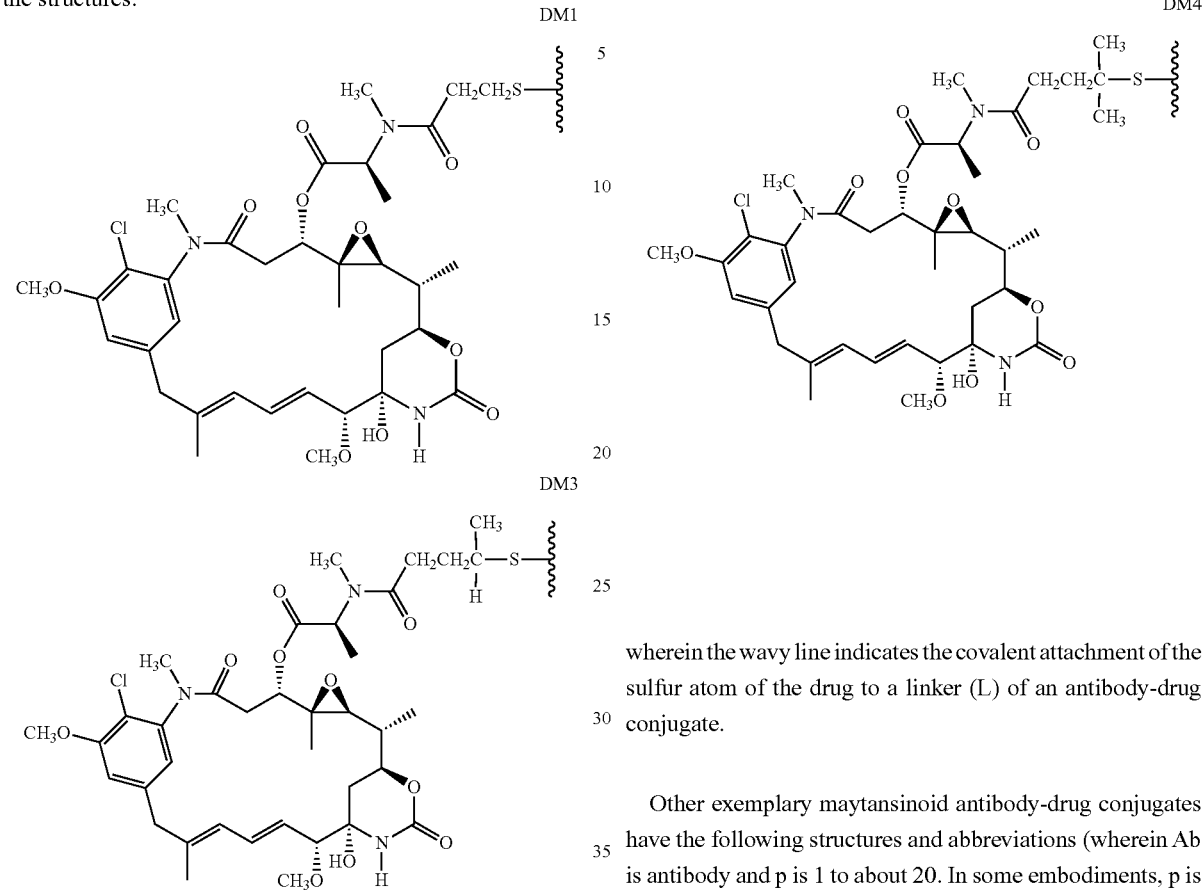

wherein the wavy line indicates the covalent attachment of the sulfur atom of the drug to a linker (L) of an antibody-drug conjugate.

Other exemplary maytansinoid antibody-drug conjugates have the following structures and abbreviations (wherein Ab is antibody and p is 1 to about 20. In some embodiments, p is 1 to 10, p is 1 to 7, p is 1 to 5, or p is 1 to 4):

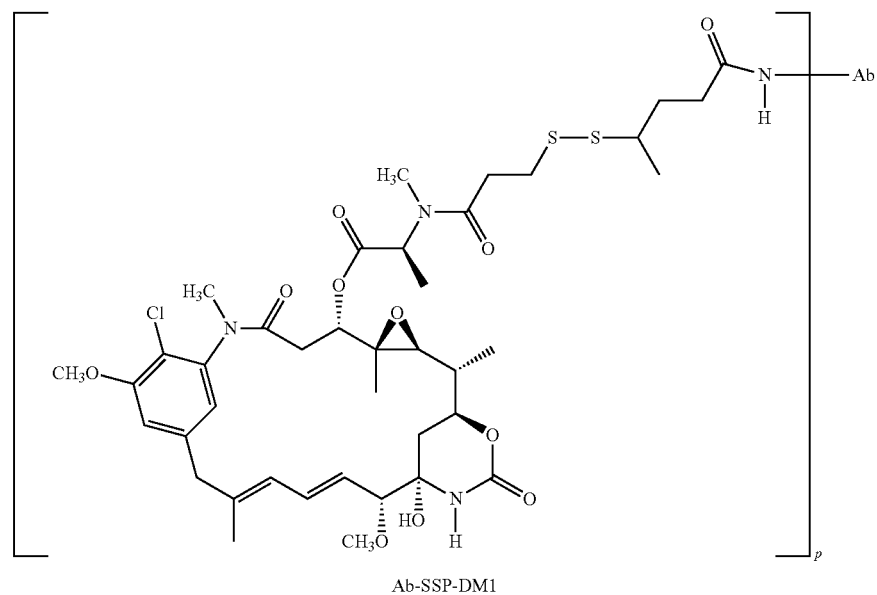

Ab-SSP-DM1

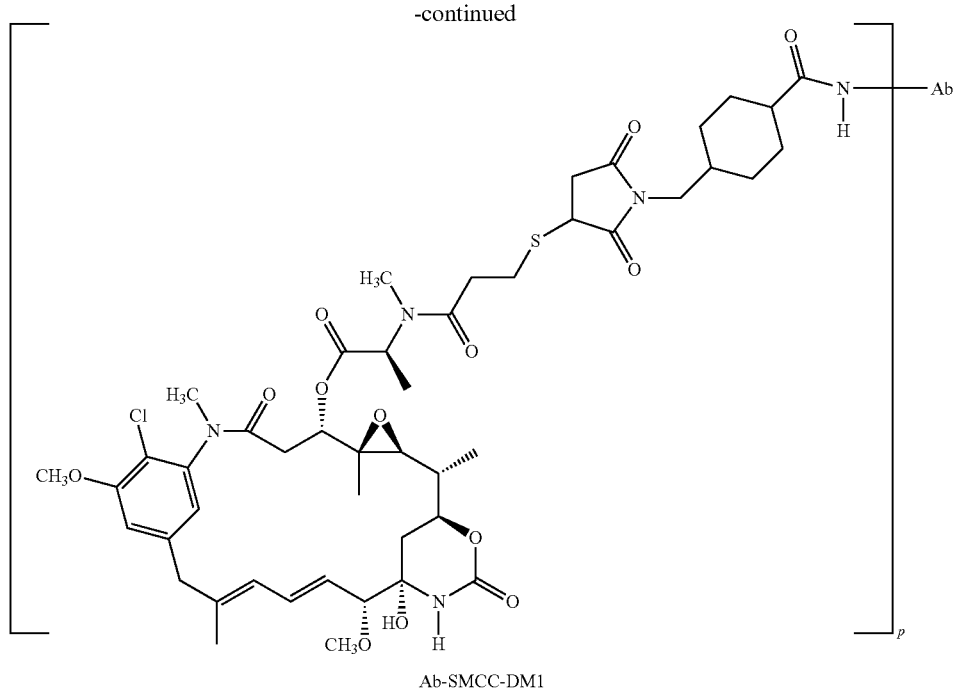

Ab-SMCC-DM1

Exemplary antibody-drug conjugates where DM1 is linked through a BMPEO linker to a thiol group of the antibody have the structure and abbreviation:

reference. See also Liu et al. *Proc. Natl. Acad. Sci. USA* 93:8618-8623 (1996); and Chari et al. *Cancer Research* 52:127-131 (1992).

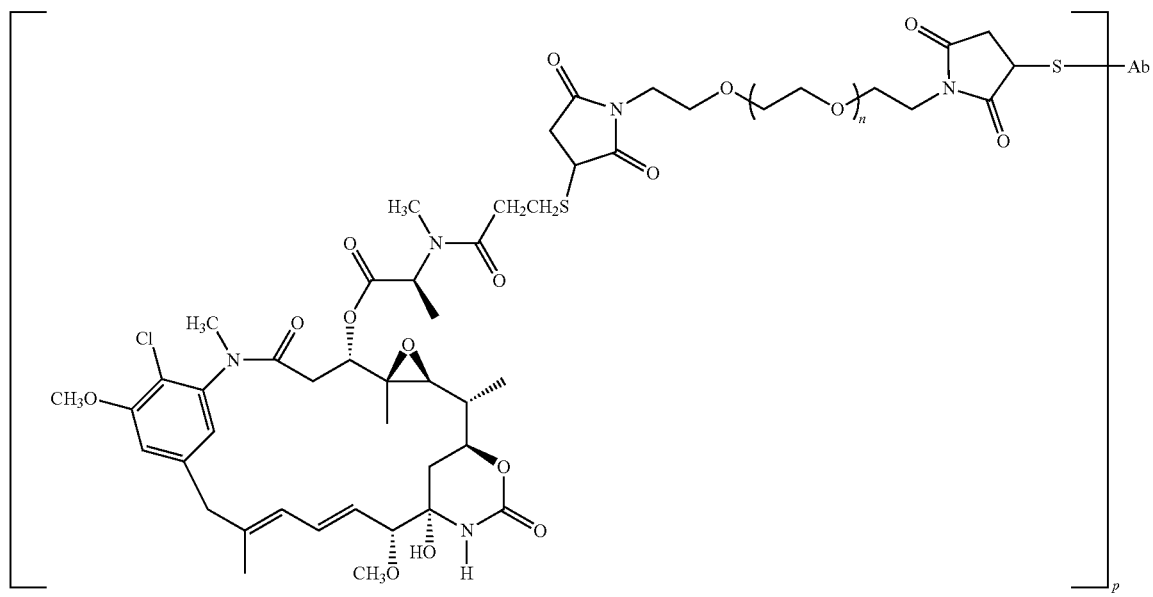

where Ab is antibody; n is 0, 1, or 2; and p is 1 to about 20. In some embodiments, p is 1 to 10, p is 1 to 7, p is 1 to 5, or p is 1 to 4.

Immunoconjugates containing maytansinoids, methods of making the same, and their therapeutic use are disclosed, for example, in U.S. Pat. Nos. 5,208,020 and 5,416,064; US 2005/0276812 A1; and European Patent EP 0 425 235 B1, the disclosures of which are hereby expressly incorporated by In some embodiments, antibody-maytansinoid conjugates may be prepared by chemically linking an antibody to a maytansinoid molecule without significantly diminishing the biological activity of either the antibody or the maytansinoid molecule. See, e.g., U.S. Pat. No. 5,208,020 (the disclosure of which is hereby expressly incorporated by reference). In some embodiments, ADC with an average of 3-4 maytansinoid molecules conjugated per antibody molecule has shown efficacy in enhancing cytotoxicity of target cells without negatively affecting the function or solubility of the antibody. In some instances, even one molecule of toxin/antibody is expected to enhance cytotoxicity over the use of naked antibody.

Exemplary linking groups for making antibody-maytansinoid conjugates include, for example, those described herein and those disclosed in U.S. Pat. No. 5,208,020; EP Patent 0 425 235 B1; Chari et al. *Cancer Research* 52:127-131 (1992); US 2005/0276812 A1; and US 2005/016993 A1, the disclosures of which are hereby expressly incorporated by reference.

(2) Auristatins and Dolastatins

Drug moieties include dolastatins, auristatins, and analogs and derivatives thereof (U.S. Pat. No. 5,635,483; U.S. Pat. No. 5,780,588; U.S. Pat. No. 5,767,237; U.S. Pat. No. 6,124,431). Auristatins are derivatives of the marine mollusk compound dolastatin-10. While not intending to be bound by any particular theory, dolastatins and auristatins have been shown to interfere with microtubule dynamics, GTP hydrolysis, and nuclear and cellular division (Woyke et al (2001) *Antimicrob. Agents and Chemother.* 45(12):3580-3584) and have anticancer (U.S. Pat. No. 5,663,149) and antifungal activity (Pettit et al (1998) *Antimicrob. Agents Chemother.* 42:2961-2965). The dolastatin/auristatin drug moiety may be attached to the antibody through the N (amino) terminus or the C (carboxyl) terminus of the peptidic drug moiety (WO 02/088172; Doronina et al (2003) *Nature Biotechnology* 21(7):778-784; Francisco et al (2003) *Blood* 102(4):1458-1465).

Exemplary auristatin embodiments include the N-terminus linked monomethylauristatin drug moieties $D_E$ and $D_F$, disclosed in U.S. Pat. No. 7,498,298 and U.S. Pat. No. 7,659,241, the disclosures of which are expressly incorporated by reference in their entirety:

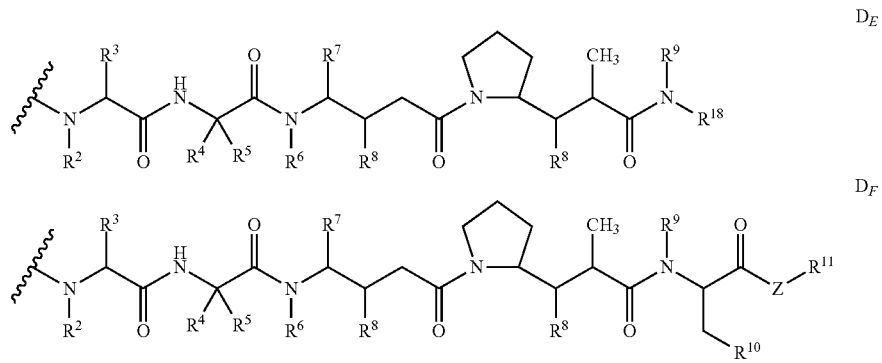

$D_E$ $D_F$ wherein the wavy line of $D_E$ and $D_F$ indicates the covalent attachment site to an antibody or antibody-linker component, and independently at each location:

$R^2$ is selected from H and $C_1$-$C_8$ alkyl;

$R^3$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

$R^4$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

$R^5$ is selected from H and methyl;

or $R^4$ and $R^5$ jointly form a carbocyclic ring and have the formula —($CR^aR^b$)$_n$— wherein $R^a$ and $R^b$ are independently selected from H, $C_1$-$C_8$ alkyl and $C_3$-$C_8$ carbocycle and n is selected from 2, 3, 4, 5 and 6;

$R^6$ is selected from H and $C_1$-$C_8$ alkyl;

$R^7$ is selected from H, $C_1$-$C_8$ alkyl, $C_3$-$C_8$ carbocycle, aryl, $C_1$-$C_8$ alkyl-aryl, $C_1$-$C_8$ alkyl-($C_3$-$C_8$ carbocycle), $C_3$-$C_8$ heterocycle and $C_1$-$C_8$ alkyl-($C_3$-$C_8$ heterocycle);

each $R^8$ is independently selected from H, OH, $C_1$-$C_8$ alkyl, $C_3$-$C_8$ carbocycle and O—($C_1$-$C_8$ alkyl);

$R^9$ is selected from H and $C_1$-$C_8$ alkyl;

$R^{10}$ is selected from aryl or $C_3$-$C_8$ heterocycle;

Z is O, S, NH, or $NR^{12}$, wherein $R^{12}$ is $C_1$-$C_8$ alkyl;

$R^{11}$ is selected from H, $C_1$-$C_{20}$ alkyl, aryl, $C_3$-$C_8$ heterocycle, —($R^{13}O$)$_m$—$R^{14}$, or —($R^{13}O$)$_m$—$CH(R^{15})_2$;

m is an integer ranging from 1-1000;

$R^{13}$ is $C_2$-$C_8$ alkyl;

$R^{14}$ is H or $C_1$-$C_8$ alkyl;

each occurrence of e is independently H, COOH, —($CH_2$)$_n$—$N(R^{16})_2$, —($CH_2$)$_n$—$SO_3H$, or —($CH_2$)$_n$—$SO_3$—$C_1$-$C_8$ alkyl;

each occurrence of e is independently H, $C_1$-$C_8$ alkyl, or —($CH_2$)$_n$—COOH;

$R^{18}$ is selected from —$C(R^8)_2$—$C(R^8)_2$-aryl, —$C(R^8)_2$—$C(R^8)_2$—($C_3$-$C_8$ heterocycle), and —$C(R^8)_2$—$C(R^8)_2$—($C_3$-$C_8$ carbocycle); and n is an integer ranging from 0 to 6.

In one embodiment, $R^3$, $R^4$ and $R^7$ are independently isopropyl or sec-butyl and $R^5$ is —H or methyl. In an exemplary embodiment, $R^3$ and $R^4$ are each isopropyl, $R^5$ is —H, and $R^7$ is sec-butyl.

In yet another embodiment, $R^2$ and $R^6$ are each methyl, and $R^9$ is —H.

In still another embodiment, each occurrence of $R^8$ is —$OCH_3$.

In an exemplary embodiment, $R^3$ and $R^4$ are each isopropyl, $R^2$ and $R^6$ are each methyl, $R^5$ is —H, $R^7$ is sec-butyl, each occurrence of $R^8$ is —$OCH_3$, and $R^9$ is —H.

In one embodiment, Z is —O— or —NH—.

In one embodiment, $R^{10}$ is aryl.

In an exemplary embodiment, $R^{10}$ is -phenyl.

In an exemplary embodiment, when Z is —O—, $R^{11}$ is —H, methyl or t-butyl.

In one embodiment, when Z is —NH, $R^{11}$ is —$CH(R^{15})_2$, wherein $R^{15}$ is —($CH_2$)$_n$—$N(R^{16})_2$, and $R^{16}$ is —$C_1$-$C_8$ alkyl or —($CH_2$)$_n$—COOH.

In another embodiment, when Z is —NH, $R^{11}$ is —$CH(R^{15})_2$, wherein $R^{15}$ is —($CH_2$)$_n$—$SO_3H$.

An exemplary auristatin embodiment of formula $D_E$ is MMAE, wherein the wavy line indicates the covalent attachment to a linker (L) of an antibody-drug conjugate:

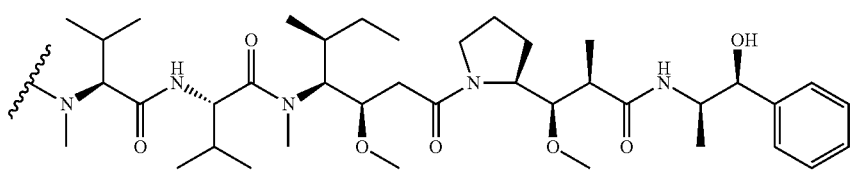

MMAE

An exemplary auristatin embodiment of formula $D_E$ is MMAF, wherein the wavy line indicates the covalent attachment to a linker (L) of an antibody-drug conjugate:

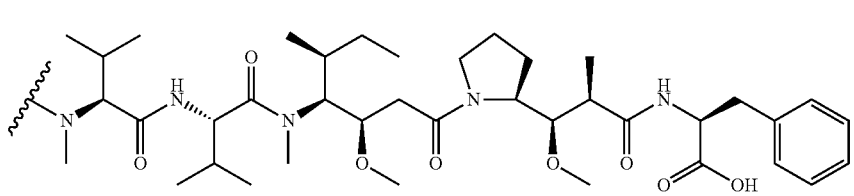

MMAF

Other exemplary embodiments include monomethylvaline compounds having phenylalanine carboxy modifications at the C-terminus of the pentapeptide auristatin drug moiety (WO 2007/008848) and monomethylvaline compounds having phenylalanine sidechain modifications at the C-terminus of the pentapeptide auristatin drug moiety (WO 2007/008603).

Nonlimiting exemplary embodiments of ADC of Formula I comprising MMAE or MMAF and various linker components have the following structures and abbreviations (wherein "Ab" is an antibody; p is 1 to about 8, "Val-Cit" is a valine-citrulline dipeptide; and "S" is a sulfur atom:

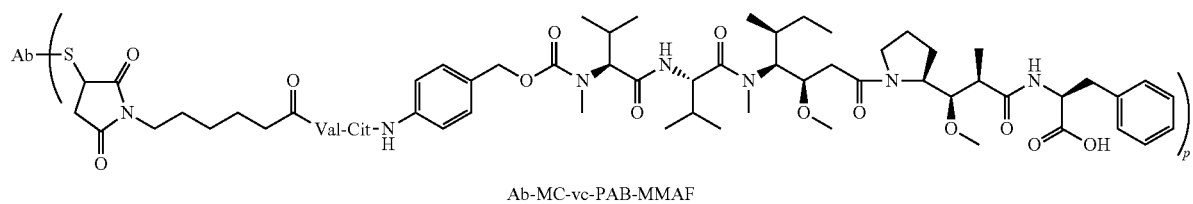

Ab-MC-vc-PAB-MMAF

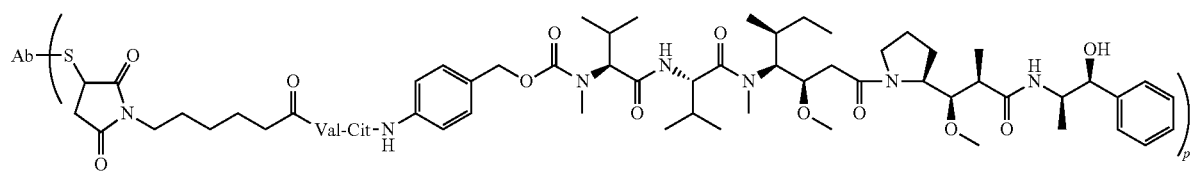

Ab-MC-vc-PAB-MMAE

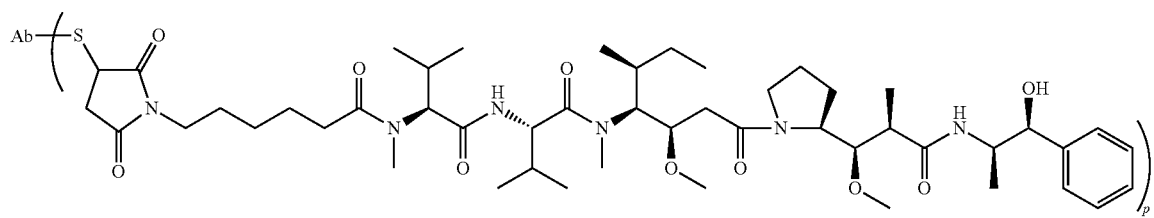

Ab-MC-MMAE

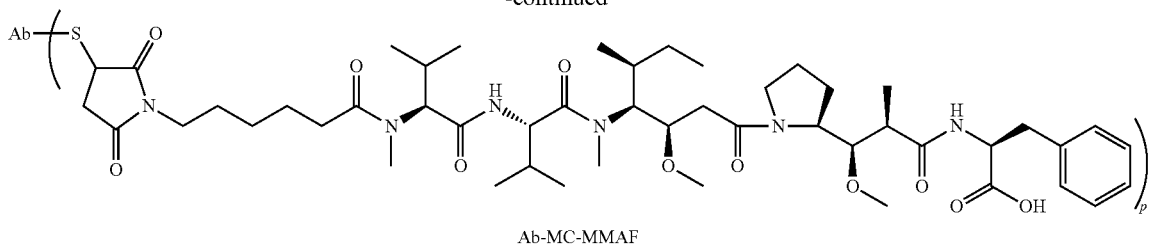

Ab-MC-MMAF

Nonlimiting exemplary embodiments of ADCs of Formula I comprising MMAF and various linker components further include Ab-MC-PAB-MMAF and Ab-PAB-MMAF. Immunoconjugates comprising MMAF attached to an antibody by a linker that is not proteolytically cleavable have been shown to possess activity comparable to immunoconjugates comprising MMAF attached to an antibody by a proteolytically cleavable linker (Doronina et al. (2006) Bioconjugate Chem. 17:114-124). In some such embodiments, drug release is believed to be effected by antibody degradation in the cell.

Typically, peptide-based drug moieties can be prepared by forming a peptide bond between two or more amino acids and/or peptide fragments. Such peptide bonds can be prepared, for example, according to a liquid phase synthesis method (see, e.g., E. Schröder and K. Lübke, "The Peptides", volume 1, pp 76-136, 1965, Academic Press). Auristatin/dolastatin drug moieties may, in some embodiments, be prepared according to the methods of: U.S. Pat. No. 7,498,298; U.S. Pat. No. 5,635,483; U.S. Pat. No. 5,780,588; Pettit et al (1989) J. Am. Chem. Soc. 111:5463-5465; Pettit et al (1998) Anti-Cancer Drug Design 13:243-277; Pettit, G. R., et al. Synthesis, 1996, 719-725; Pettit et al (1996) J. Chem. Soc. Perkin Trans. 1 5:859-863; and Doronina (2003) Nat. Biotechnol. 21(7):778-784.

In some embodiments, auristatin/dolastatin drug moieties of formulas $D_E$ such as MMAE, and $D_F$, such as MMAF, and drug-linker intermediates and derivatives thereof, such as MC-MMAF, MC-MMAE, MC-vc-PAB-MMAF, and MC-vc-PAB-MMAE, may be prepared using methods described in U.S. Pat. No. 7,498,298; Doronina et al. (2006) Bioconjugate Chem. 17:114-124; and Doronina et al. (2003) Nat. Biotech. 21:778-784 and then conjugated to an antibody of interest.

(3) Calicheamicin

In some embodiments, the immunoconjugate comprises an antibody conjugated to one or more calicheamicin molecules. The calicheamicin family of antibiotics, and analogues thereof, are capable of producing double-stranded DNA breaks at sub-picomolar concentrations (Hinman et al., (1993) Cancer Research 53:3336-3342; Lode et al., (1998) Cancer Research 58:2925-2928). Calicheamicin has intracellular sites of action but, in certain instances, does not readily cross the plasma membrane. Therefore, cellular uptake of these agents through antibody-mediated internalization may, in some embodiments, greatly enhances their cytotoxic effects. Nonlimiting exemplary methods of preparing antibody-drug conjugates with a calicheamicin drug moiety are described, for example, in U.S. Pat. No. 5,712,374; U.S. Pat. No. 5,714,586; U.S. Pat. No. 5,739,116; and U.S. Pat. No. 5,767,285.

(4) Pyrrolobenzodiazepines

In some embodiments, an ADC comprises a pyrrolobenzodiazepine (PBD). In some embodiments, PDB dimers recognize and bind to specific DNA sequences. The natural product anthramycin, a PBD, was first reported in 1965 (Leimgruber, et al., (1965)J. Am. Chem. Soc., 87:5793-5795; Leimgruber, et al., (1965)J. Am. Chem. Soc., 87:5791-5793). Since then, a number of PBDs, both naturally-occurring and analogues, have been reported (Thurston, et al., (1994) Chem. Rev. 1994, 433-465 including dimers of the tricyclic PBD scaffold (U.S. Pat. No. 6,884,799; U.S. Pat. No. 7,049,311; U.S. Pat. No. 7,067,511; U.S. Pat. No. 7,265,105; U.S. Pat. No. 7,511,032; U.S. Pat. No. 7,528,126; U.S. Pat. No. 7,557,099). Without intending to be bound by any particular theory, it is believed that the dimer structure imparts the appropriate three-dimensional shape for isohelicity with the minor groove of B-form DNA, leading to a snug fit at the binding site (Kohn, In Antibiotics III. Springer-Verlag, New York, pp. 3-11 (1975); Hurley and Needham-VanDevanter, (1986) Acc. Chem. Res., 19:230-237). Dimeric PBD compounds bearing C2 aryl substituents have been shown to be useful as cytotoxic agents (Hartley et al (2010) Cancer Res. 70(17):6849-6858; Antonow (2010) J. Med. Chem. 53(7):2927-2941; Howard et al (2009) Bioorganic and Med. Chem. Letters 19(22):6463-6466).

PBD dimers have been conjugated to antibodies and the resulting ADC shown to have anti-cancer properties. Nonlimiting exemplary linkage sites on the PBD dimer include the five-membered pyrrolo ring, the tether between the PBD units, and the N10-C11 imine group (WO 2009/016516; US 2009/304710; US 2010/047257; US 2009/036431; US 2011/0256157; WO 2011/130598).

Nonlimiting exemplary PBD dimer components of ADCs are of Formula A:

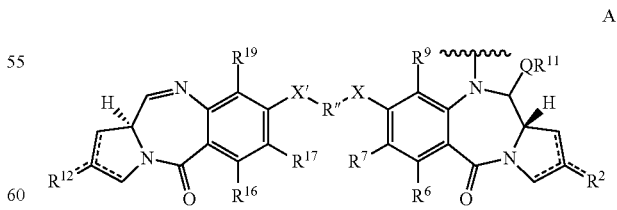

A and salts and solvates thereof, wherein:
the wavy line indicates the covalent attachment site to the linker;
the dotted lines indicate the optional presence of a double bond between C1 and C2 or C2 and C3;

$R^2$ is independently selected from H, OH, =O, =CH$_2$, CN, R, OR, =CH—R$^D$, =C(R$^D$)$_2$, O—SO$_2$—R, CO$_2$R and COR, and optionally further selected from halo or dihalo, wherein R$^D$ is independently selected from R, CO$_2$R, COR, CHO, CO$_2$H, and halo;

$R^6$ and $R^9$ are independently selected from H, R, OH, OR, SH, SR, NH$_2$, NHR, NRR', NO$_2$, Me$_3$Sn and halo;

$R^7$ is independently selected from H, R, OH, OR, SH, SR, NH$_2$, NHR, NRR', NO$_2$, Me$_3$Sn and halo;

Q is independently selected from O, S and NH;

$R^{11}$ is either H, or R or, where Q is O, SO$_3$M, where M is a metal cation;

R and R' are each independently selected from optionally substituted C$_{1-8}$ alkyl, C$_{1-12}$ alkyl, C$_{3-8}$ heterocyclyl, C$_{3-20}$ heterocycle, and C$_{5-20}$ aryl groups, and optionally in relation to the group NRR', R and R' together with the nitrogen atom to which they are attached form an optionally substituted 4-, 5-, 6- or 7-membered heterocyclic ring;

$R^{12}$, $R^{16}$, $R^{19}$ and $R^{17}$ are as defined for $R^2$, $R^6$, $R^9$ and $R^7$ respectively;

R" is a C$_{3-12}$ alkylene group, which chain may be interrupted by one or more heteroatoms, e.g. O, S, N(H), NMe and/or aromatic rings, e.g. benzene or pyridine, which rings are optionally substituted; and X and X' are independently selected from O, S and N(H).

In some embodiments, R and R' are each independently selected from optionally substituted C$_{1-12}$ alkyl, C$_{3-20}$ heterocycle, and C$_{5-20}$ aryl groups, and optionally in relation to the group NRR', R and R' together with the nitrogen atom to which they are attached form an optionally substituted 4-, 5-, 6- or 7-membered heterocyclic ring.

In some embodiments, $R^9$ and $R^{19}$ are H.

In some embodiments, $R^6$ and $R^{16}$ are H.

In some embodiments, $R^7$ are $R^{17}$ are both OR$^{7A}$, where R$^{7A}$ is optionally substituted C$_{1-4}$ alkyl. In some embodiments, R$^{7A}$ is Me. In some embodiments, R$^{7A}$ is Ch$_2$Ph, where Ph is a phenyl group.

In some embodiments, X is O.

In some embodiments, $R^{11}$ is H.

In some embodiments, there is a double bond between C2 and C3 in each monomer unit.

In some embodiments, $R^2$ and $R^{12}$ are independently selected from H and R. In some embodiments, $R^2$ and $R^{12}$ are independently R. In some embodiments, $R^2$ and $R^{12}$ are independently optionally substituted C$_{5-20}$ aryl or C$_{5-7}$ aryl or C$_{8-10}$ aryl. In some embodiments, $R^2$ and $R^{12}$ are independently optionally substituted phenyl, thienyl, napthyl, pyridyl, quinolinyl, or isoquinolinyl. In some embodiments, $R^2$ and $R^{12}$ are independently selected from =O, =CH$_2$, =CH—R$^D$, and =C(R$^D$)$_2$. In some embodiments, $R^2$ and $R^{12}$ each =CH$_2$. In some embodiments, $R^2$ and $R^{12}$ are each H. In some embodiments, $R^2$ and $R^{12}$ are each =O. In some embodiments, $R^2$ and $R^{12}$ are each =CF$_2$. In some embodiments, $R^2$ and/or $R^{12}$ are independently =C(R$^D$)$_2$. In some embodiments, $R^2$ and/or $R^{12}$ are independently =CH—R$^D$.

In some embodiments, when $R^2$ and/or $R^{12}$ is =CH—R$^D$, each group may independently have either configuration shown below:

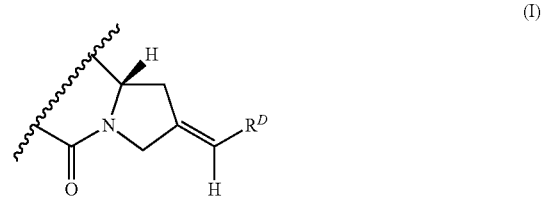

(I)

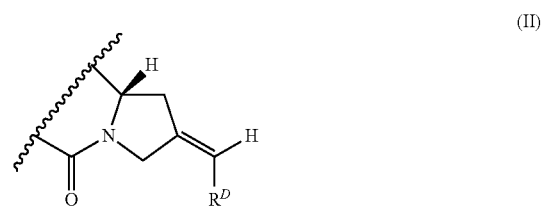

(II)

In some embodiments, a =CH—R$^D$ is in configuration (I).

In some embodiments, R" is a C$_3$ alkylene group or a C$_5$ alkylene group.

In some embodiments, an exemplary PBD dimer component of an ADC has the structure of Formula A(I):

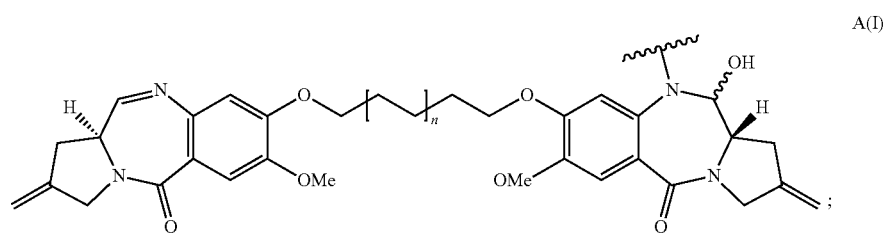

A(I)

wherein n is 0 or 1.

In some embodiments, an exemplary PBD dimer component of an ADC has the structure of Formula A(II):

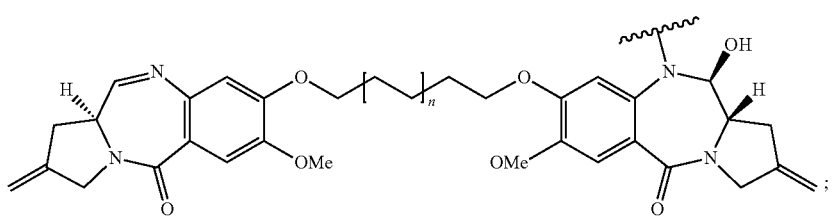

A(II)

wherein n is 0 or 1.

In some embodiments, an exemplary PBD dimer component of an ADC has the structure of Formula A(III):

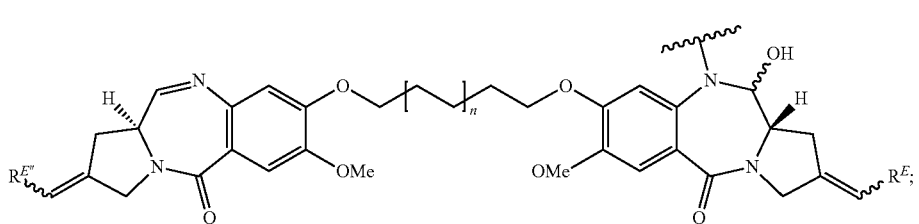

A(III)

wherein $R^E$ and $R^{E''}$ are each independently selected from H or $R^D$, wherein $R^D$ is defined as above; and
wherein n is 0 or 1.

In some embodiments, n is 0. In some embodiments, n is 1. In some embodiments, $R^E$ and/or $R^{E''}$ is H. In some embodiments, $R^E$ and $R^{E''}$ are H. In some embodiments, $R^E$ and/or $R^{E''}$ is $R^D$, wherein $R^D$ is optionally substituted $C_{1-12}$ alkyl. In some embodiments, $R^E$ and/or $R^{E''}$ is $R^D$, wherein $R^D$ is methyl.

In some embodiments, an exemplary PBD dimer component of an ADC has the structure of Formula A(IV):

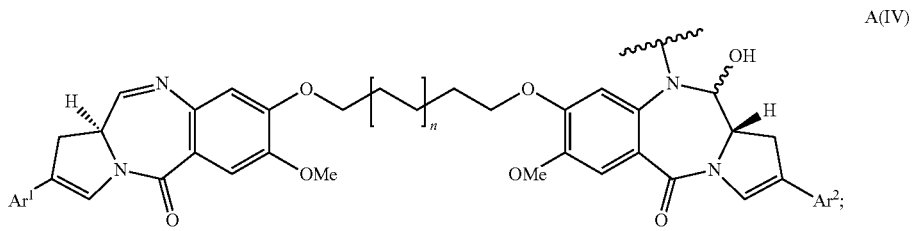

A(IV)

wherein $Ar^1$ and $Ar^2$ are each independently optionally substituted $C_{5-20}$ aryl; wherein $Ar^1$ and $Ar^2$ may be the same or different; and wherein n is 0 or 1.

In some embodiments, an exemplary PBD dimer component of an ADC has the structure of Formula A(V):

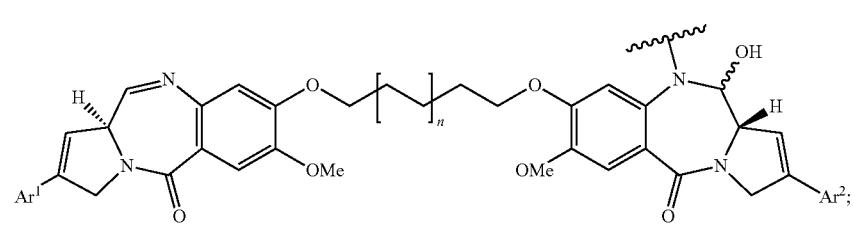

A(V)

wherein Ar¹ and Ar² are each independently optionally substituted $C_{5-20}$ aryl; wherein Ar¹ and Ar² may be the same or different; and wherein n is 0 or 1.

In some embodiments, Ar¹ and Ar² are each independently selected from optionally substituted phenyl, furanyl, thiophenyl and pyridyl. In some embodiments, Ar¹ and Ar² are each independently optionally substituted phenyl. In some embodiments, Ar¹ and Ar² are each independently optionally substituted thien-2-yl or thien-3-yl. In some embodiments, Ar¹ and Ar² are each independently optionally substituted quinolinyl or isoquinolinyl. The quinolinyl or isoquinolinyl group may be bound to the PBD core through any available ring position. For example, the quinolinyl may be quinolin-2-yl, quinolin-3-yl, quinolin-4-yl, quinolin-5-yl, quinolin-6-yl, quinolin-7-yl and quinolin-8-yl. In some embodiments, the quinolinyl is selected from quinolin-3-yl and quinolin-6-yl. The isoquinolinyl may be isoquinolin-1-yl, isoquinolin-3-yl, isoquinolin-4-yl, isoquinolin-5-yl, isoquinolin-6-yl, isoquinolin-7-yl and isoquinolin-8-yl. In some embodiments, the isoquinolinyl is selected from isoquinolin-3-yl and isoquinolin-6-yl.

Further nonlimiting exemplary PBD dimer components of ADCs are of Formula B:

and salts and solvates thereof, wherein:

the wavy line indicates the covalent attachment site to the linker;

the wavy line connected to the OH indicates the S or R configuration;

$R^{V1}$ and $R^{V2}$ are independently selected from H, methyl, ethyl and phenyl (which phenyl may be optionally substituted with fluoro, particularly in the 4 position) and $C_{5-6}$ heterocyclyl; wherein $R^{V1}$ and $R^{V2}$ may be the same or different; and n is 0 or 1.

In some embodiments, $R^{V1}$ and $R^{V2}$ are independently selected from H, phenyl, and 4-fluorophenyl.

In some embodiments, a linker may be attached at one of various sites of the PBD dimer drug moiety, including the N10 imine of the B ring, the C-2 endo/exo position of the C ring, or the tether unit linking the A rings (see structures C(I) and C(II) below).

Nonlimiting exemplary PBD dimer components of ADCs include Formulas C(I) and C(II):

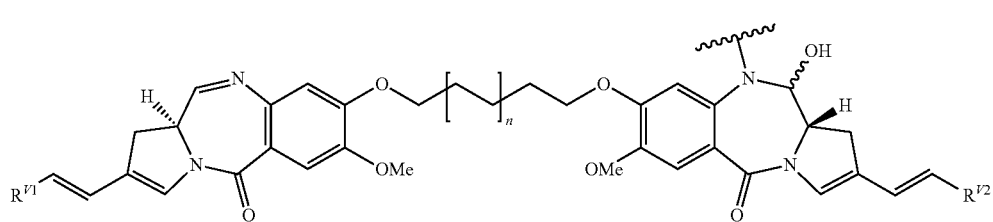

B

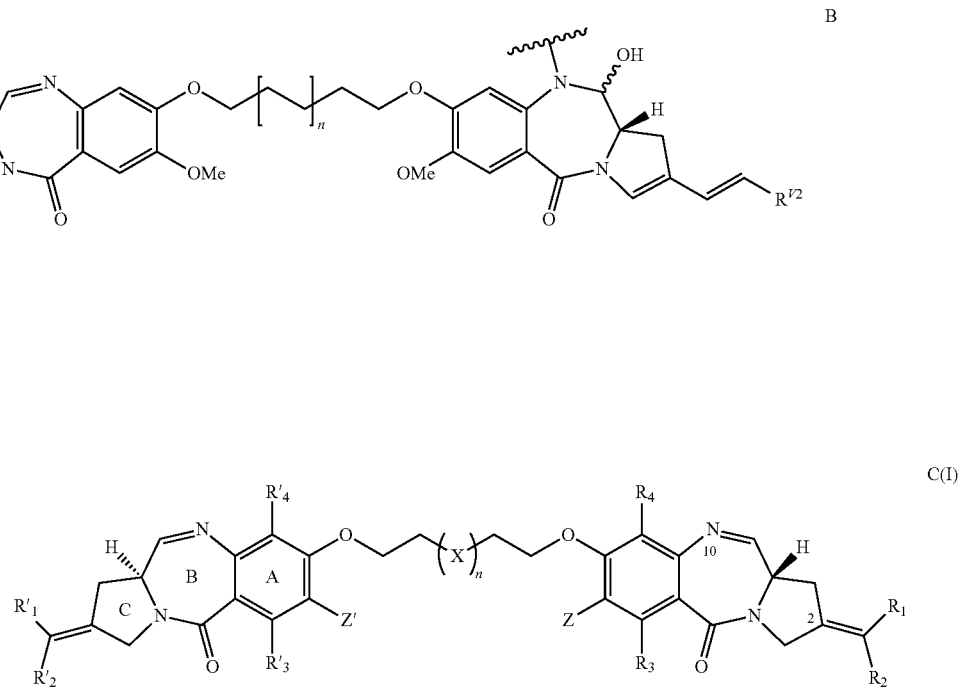

C(I)

C(II)

Formulas C(I) and C(II) are shown in their N10-C11 imine form. Exemplary PBD drug moieties also include the carbinolamine and protected carbinolamine forms as well, as shown in the table below:

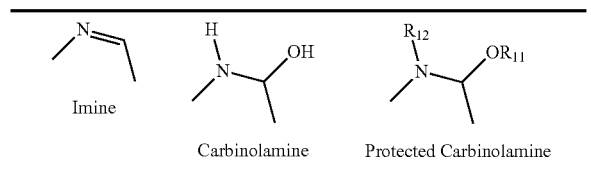

| Imine | Carbinolamine | Protected Carbinolamine | wherein:

X is $CH_2$ (n=1 to 5), N, or O;

Z and Z' are independently selected from OR and $NR_2$, where R is a primary, secondary or tertiary alkyl chain containing 1 to 5 carbon atoms;

$R_1$, $R_1'$, $R_2$ and $R_2'$ are each independently selected from H, $C_1$-$C_8$ alkyl, $C_2$-$C_8$ alkenyl, $C_2$-$C_8$ alkynyl, $C_{5-20}$ aryl (including substituted aryls), $C_{5-20}$ heteroaryl groups, $-NH_2$, $-NHMe$, $-OH$, and $-SH$, where, in some embodiments, alkyl, alkenyl and alkynyl chains comprise up to 5 carbon atoms;

$R_3$ and $R_3'$ are independently selected from H, OR, NHR, and $NR_2$, where R is a primary, secondary or tertiary alkyl chain containing 1 to 5 carbon atoms;

$R_4$ and $R_4'$ are independently selected from H, Me, and OMe;

$R_5$ is selected from $C_1$-$C_8$ alkyl, $C_2$-$C_8$ alkenyl, $C_2$-$C_8$ alkynyl, $C_{5-20}$ aryl (including aryls substituted by halo, nitro, cyano, alkoxy, alkyl, heterocyclyl) and $C_{5-20}$ heteroaryl groups, where, in some embodiments, alkyl, alkenyl and alkynyl chains comprise up to 5 carbon atoms;

$R_{11}$ is H, $C_1$-$C_8$ alkyl, or a protecting group (such as acetyl, trifluoroacetyl, t-butoxycarbonyl (BOC), benzyloxycarbonyl (CBZ), 9-fluorenylmethylenoxycarbonyl (Fmoc), or a moiety comprising a self-immolating unit such as valine-citrulline-PAB);

$R_{12}$ is H, $C_1$-$C_8$ alkyl, or a protecting group;

wherein a hydrogen of one of $R_1$, $R_1'$, $R_2$, $R_2'$, $R_5$, or $R_{12}$ or a hydrogen of the $-OCH_2CH_2(X)-CH_2CH_2O-$ spacer between the A rings is replaced with a bond connected to the linker of the ADC.

Exemplary PDB dimer portions of ADC include, but are not limited to (the wavy line indicates the site of covalent attachment to the linker):

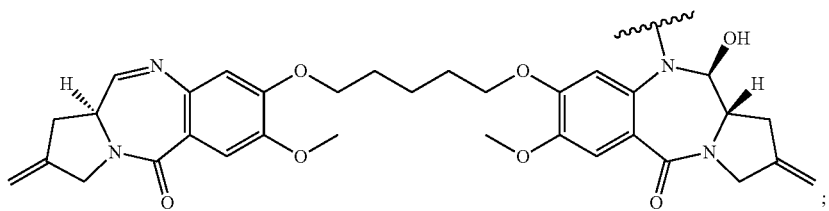

PBD dimer

Nonlimiting exemplary embodiments of ADCs comprising PBD dimers have the following structures:

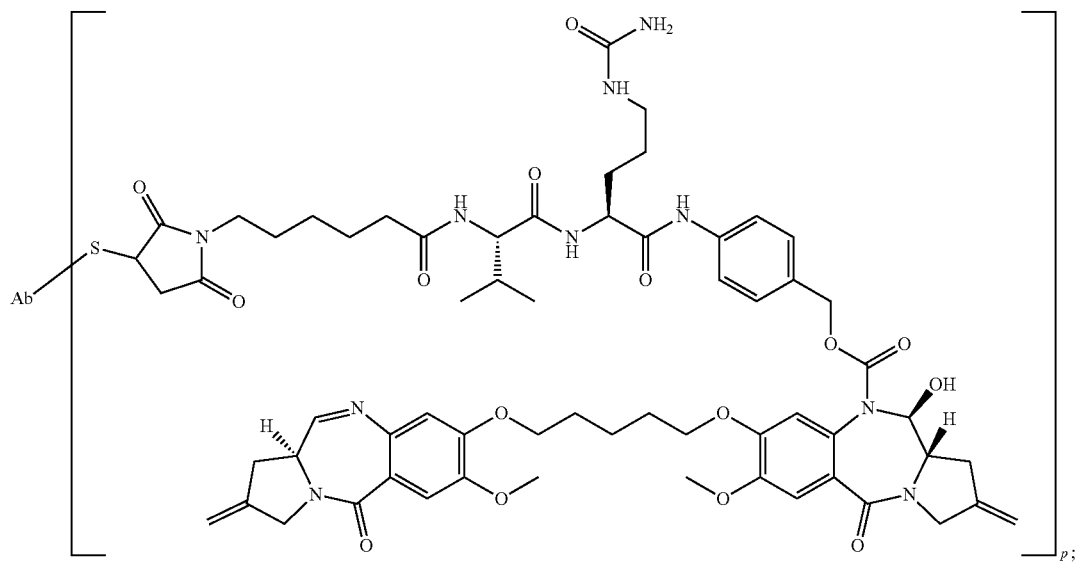

PBD dimer-val-cit-PAB-Ab

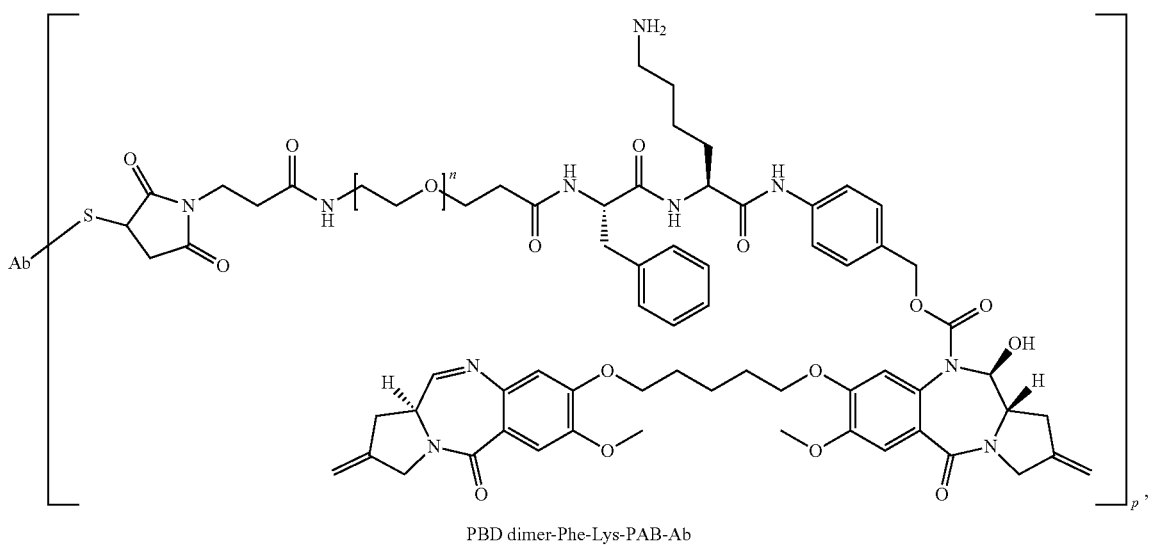

PBD dimer-Phe-Lys-PAB-Ab wherein:

n is 0 to 12. In some embodiments, n is 2 to 10. In some embodiments, n is 4 to 8. In some embodiments, n is selected from 4, 5, 6, 7, and 8.

The linkers of PBD dimer-val-cit-PAB-Ab and the PBD dimer-Phe-Lys-PAB-Ab are protease cleavable, while the linker of PBD dimer-maleimide-acetal is acid-labile.

PBD dimers and ADC comprising PBD dimers may be prepared according to methods known in the art. See, e.g., WO 2009/016516; US 2009/304710; US 2010/047257; US 2009/036431; US 2011/0256157; WO 2011/130598.

(5) Anthracyclines

In some embodiments, an ADC comprising anthracycline. Anthracyclines are antibiotic compounds that exhibit cytotoxic activity. While not intending to be bound by any particular theory, studies have indicated that anthracyclines may operate to kill cells by a number of different mechanisms, including: 1) intercalation of the drug molecules into the DNA of the cell thereby inhibiting DNA-dependent nucleic acid synthesis; 2) production by the drug of free radicals which then react with cellular macromolecules to cause damage to the cells, and/or 3) interactions of the drug molecules with the cell membrane (see, e.g., C. Peterson et al., "Transport And Storage Of Anthracycline In Experimental Systems And Human Leukemia" in *Anthracycline Antibiotics In Cancer Therapy*; N. R. Bachur, "Free Radical Damage" id. at pp. 97-102). Because of their cytotoxic potential anthracyclines have been used in the treatment of numerous cancers such as leukemia, breast carcinoma, lung carcinoma, ovarian adenocarcinoma and sarcomas (see e.g., P. H-Wiernik, in *Anthracycline: Current Status And New Developments* p 11).

Nonlimiting exemplary anthracyclines include doxorubicin, epirubicin, idarubicin, daunomycin, nemorubicin, and derivatives thereof. Immunoconjugates and prodrugs of daunorubicin and doxorubicin have been prepared and studied (Kratz et al (2006) *Current Med. Chem.* 13:477-523; Jeffrey et al (2006) *Bioorganic & Med. Chem. Letters* 16:358-362; Torgov et al (2005) *Bioconj. Chem.* 16:717-721; Nagy et al (2000) *Proc. Natl. Acad. Sci. USA* 97:829-834; Dubowchik et al (2002) *Bioorg. & Med. Chem. Letters* 12:1529-1532; King et al (2002) *J. Med. Chem.* 45:4336-4343; EP 0328147; U.S. Pat. No. 6,630,579). The antibody-drug conjugate BR96-doxorubicin reacts specifically with the tumor-associated antigen Lewis-Y and has been evaluated in phase I and II studies (Saleh et al (2000) *J. Clin. Oncology* 18:2282-2292; Ajani et al (2000) *Cancer Jour.* 6:78-81; Tolcher et al (1999) *J. Clin. Oncology* 17:478-484).

PNU-159682 is a potent metabolite (or derivative) of nemorubicin (Quintieri, et al. (2005) *Clinical Cancer Research* 11(4):1608-1617). Nemorubicin is a semisynthetic analog of doxorubicin with a 2-methoxymorpholino group on the glycoside amino of doxorubicin and has been under clinical evaluation (Grandi et al (1990) *Cancer Treat. Rev.* 17:133; Ripamonti et al (1992) *Brit. J. Cancer* 65:703;), including phase II/III trials for hepatocellular carcinoma (Sun et al (2003) *Proceedings of the American Society for Clinical Oncology* 22, Abs1448; Quintieri (2003) *Proceedings of the American Association of Cancer Research*, 44:1st Ed, Abs 4649; Pacciarini et al (2006) *Jour. Clin. Oncology* 24:14116).

A nonlimiting exemplary ADC comprising nemorubicin or nemorubicin derivatives is shown in Formula Ia:

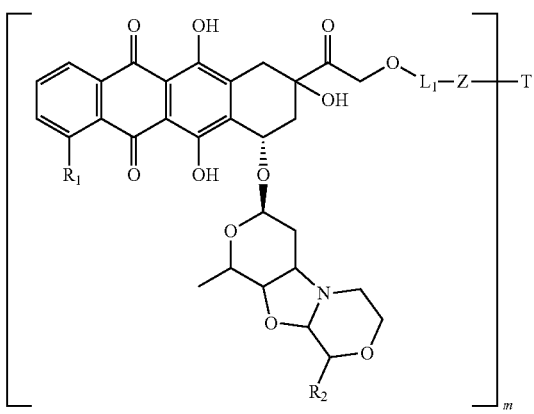

(Ia)

wherein $R_1$ is hydrogen atom, hydroxy or methoxy group and $R_2$ is a $C_1$-$C_5$ alkoxy group, or a pharmaceutically acceptable salt thereof;

$L_1$ and Z together are a linker (L) as described herein;

T is an antibody (Ab) as described herein; and m is 1 to about 20. In some embodiments, m is 1 to 10, 1 to 7, 1 to 5, or 1 to 4.

In some embodiments, $R_1$ and $R_2$ are both methoxy (—OMe).

A further nonlimiting exemplary ADC comprising nemorubicin or nemorubicin derivatives is shown in Formula Ib:

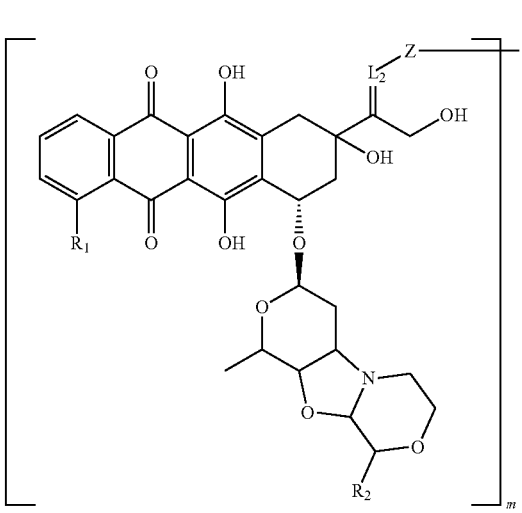

(Ib)

wherein $R_1$ is hydrogen atom, hydroxy or methoxy group and $R_2$ is a $C_1$-$C_5$ alkoxy group, or a pharmaceutically acceptable salt thereof;

$L_2$ and Z together are a linker (L) as described herein;

T is an antibody (Ab) as described herein; and m is 1 to about 20. In some embodiments, m is 1 to 10, 1 to 7, 1 to 5, or 1 to 4.

In some embodiments, $R_1$ and $R_2$ are both methoxy (—OMe).

In some embodiments, the nemorubicin component of a nemorubicin-containing ADC is PNU-159682. In some such embodiments, the drug portion of the ADC may have one of the following structures:

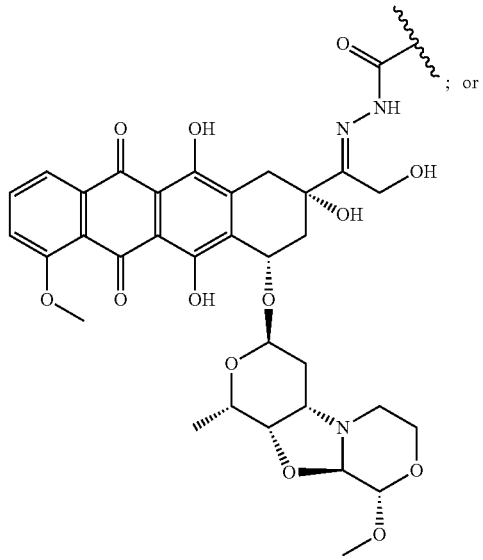

; or

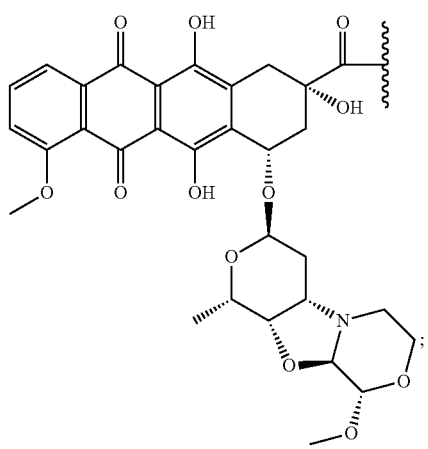

;

wherein the wavy line indicates the attachment to the linker (L).

Anthracyclines, including PNU-159682, may be conjugated to antibodies through several linkage sites and a variety of linkers (US 2011/0076287; WO2009/099741; US 2010/0034837; WO 2010/009124), including the linkers described herein.

Exemplary ADCs comprising a nemorubicin and linker include, but are not limited to:

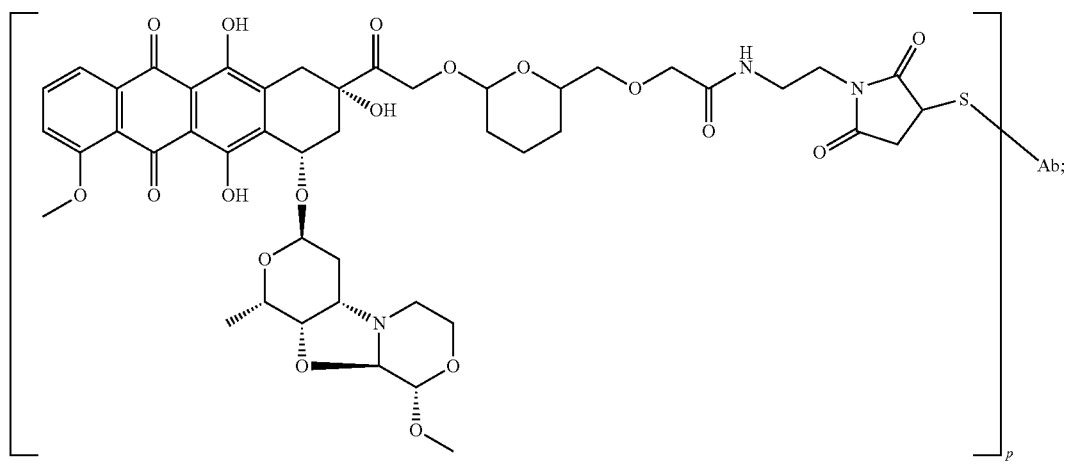
PNU-159682 maleimide acetal-Ab
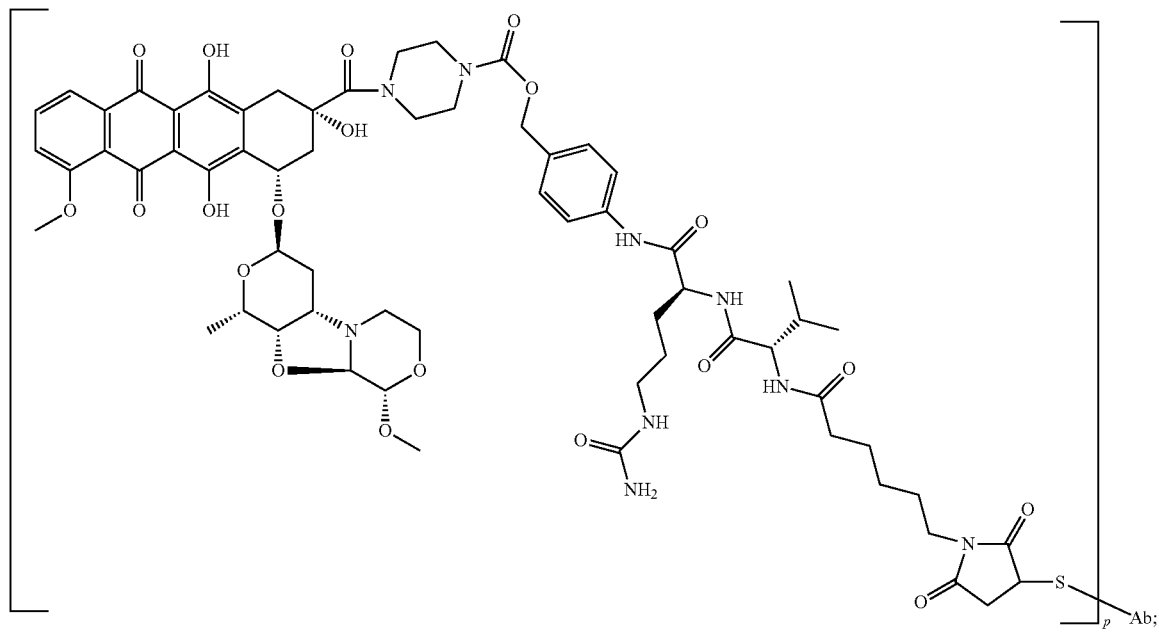
PNU-159682-val-cit-PAB-Ab
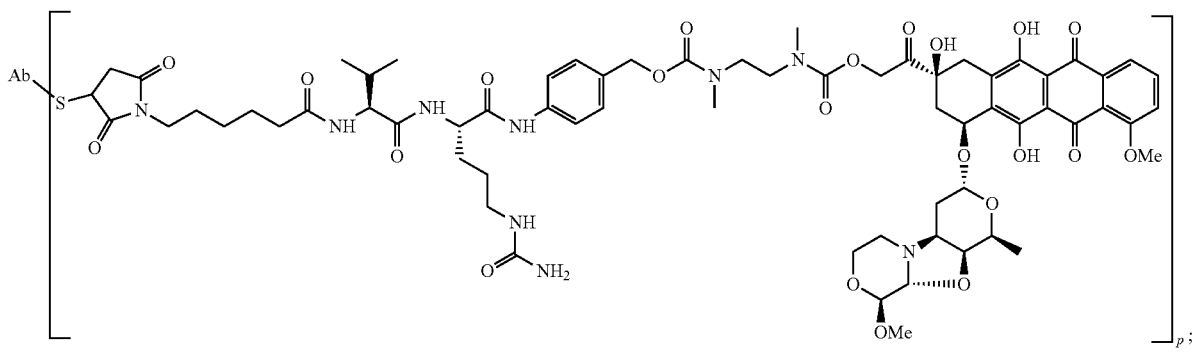
PNU-159682-val-cit-PAB-spacer-Ab

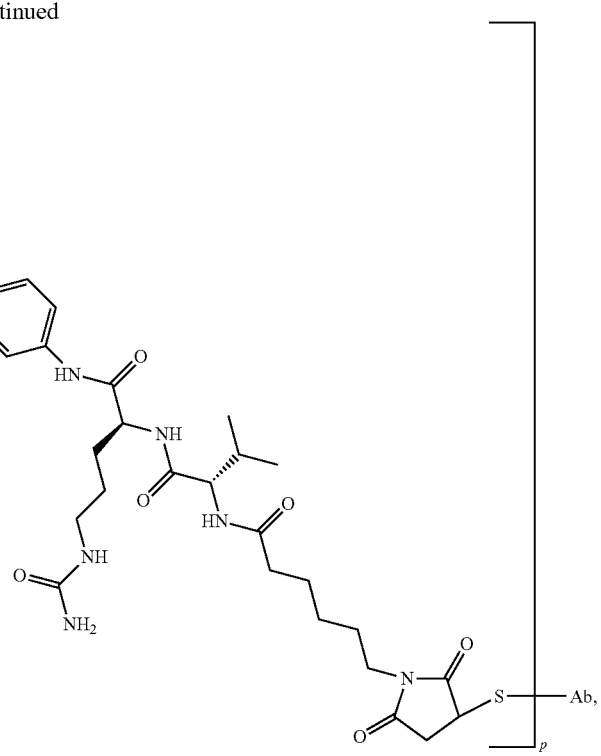

PNU-159682-val-cit-PAB-spacer(R¹R²)-Ab wherein:

R$_1$ and R$_2$ are independently selected from H and C$_1$-C$_6$ alkyl; and

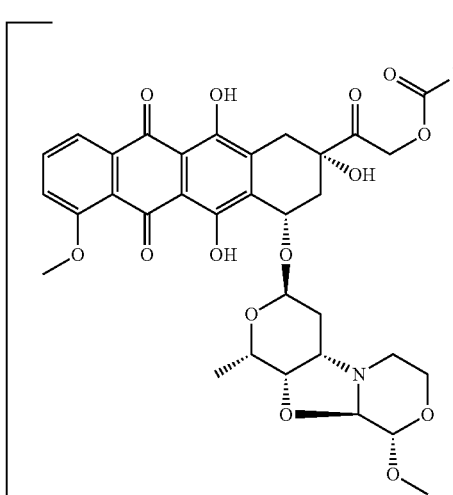

PNU-159682-maleimide-Ab

The linker of PNU-159682 maleimide acetal-Ab is acid-labile, while the linkers of PNU-159682-val-cit-PAB-Ab, PNU-159682-val-cit-PAB-spacer-Ab, and PNU-159682-val-cit-PAB-spacer(R¹R²)-Ab are protease cleavable.

(6) Other Drug Moieties

Drug moieties also include geldanamycin (Mandler et al (2000) *J. Nat. Cancer Inst.* 92(19):1573-1581; Mandler et al (2000) *Bioorganic & Med. Chem. Letters* 10:1025-1028; Mandler et al (2002) *Bioconjugate Chem.* 13:786-791); and enzymatically active toxins and fragments thereof, including, but not limited to, diphtheria A chain, nonbinding active fragments of diphtheria toxin, exotoxin A chain (from *Pseudomonas aeruginosa*), ricin A chain, abrin A chain, modeccin A chain, alpha-sarcin, Aleurites fordii proteins, dianthin proteins, *Phytolacca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin and the tricothecenes. See, e.g., WO 93/21232.

Drug moieties also include compounds with nucleolytic activity (e.g., a ribonuclease or a DNA endonuclease).

In certain embodiments, an immunoconjugate may comprise a highly radioactive atom. A variety of radioactive isotopes are available for the production of radioconjugated antibodies. Examples include At$^{211}$, I$^{131}$, I$^{125}$, Y$^{90}$, Re$^{186}$, Re$^{188}$, Sm$^{153}$, Bi$^{212}$, P$^{32}$, Pb$^{212}$ and radioactive isotopes of Lu. In some embodiments, when an immunoconjugate is used for detection, it may comprise a radioactive atom for scintigraphic studies, for example Tc$^{99}$ or I$^{123}$, or a spin label for nuclear magnetic resonance (NMR) imaging (also known as magnetic resonance imaging, MRI), such as zirconium-89, iodine-123, iodine-131, indium-111, fluorine-19, carbon-13, nitrogen-15, oxygen-17, gadolinium, manganese or iron. Zirconium-89 may be complexed to various metal chelating agents and conjugated to antibodies, e.g., for PET imaging (WO 2011/056983).

The radio- or other labels may be incorporated in the immunoconjugate in known ways. For example, a peptide may be biosynthesized or chemically synthesized using suitable amino acid precursors comprising, for example, one or more fluorine-19 atoms in place of one or more hydrogens. In some embodiments, labels such as Tc$^{99}$, I$^{123}$, Re$^{186}$, Re$^{188}$ and In$^{111}$ can be attached via a cysteine residue in the antibody. In some embodiments, yttrium-90 can be attached via a lysine residue of the antibody. In some embodiments, the IODOGEN method (Fraker et al (1978) *Biochem. Biophys. Res. Commun.* 80: 49-57 can be used to incorporate iodine- 123. "Monoclonal Antibodies in Immunoscintigraphy" (Chatal, CRC Press 1989) describes certain other methods.

In certain embodiments, an immunoconjugate may comprise an antibody conjugated to a prodrug-activating enzyme. In some such embodiments, a prodrug-activating enzyme converts a prodrug (e.g., a peptidyl chemotherapeutic agent, see WO 81/01145) to an active drug, such as an anti-cancer drug. Such immunoconjugates are useful, in some embodiments, in antibody-dependent enzyme-mediated prodrug therapy ("ADEPT"). Enzymes that may be conjugated to an antibody include, but are not limited to, alkaline phosphatases, which are useful for converting phosphate-containing prodrugs into free drugs; arylsulfatases, which are useful for converting sulfate-containing prodrugs into free drugs; cytosine deaminase, which is useful for converting non-toxic 5-fluorocytosine into the anti-cancer drug, 5-fluorouracil; proteases, such as *serratia* protease, thermolysis, subtilisin, carboxypeptidases and cathepsins (such as cathepsins B and L), which are useful for converting peptide-containing prodrugs into free drugs; D-alanylcarboxypeptidases, which are useful for converting prodrugs that contain D-amino acid substituents; carbohydrate-cleaving enzymes such as β-galactosidase and neuraminidase, which are useful for converting glycosylated prodrugs into free drugs; β-lactamase, which is useful for converting drugs derivatized with β-lactams into free drugs; and penicillin amidases, such as penicillin V amidase and penicillin G amidase, which are useful for converting drugs derivatized at their amine nitrogens with phenoxyacetyl or phenylacetyl groups, respectively, into free drugs. In some embodiments, enzymes may be covalently bound to antibodies by recombinant DNA techniques well known in the art. See, e.g., Neuberger et al., *Nature* 312:604-608 (1984).

c) Drug Loading

Drug loading is represented by p, the average number of drug moieties per antibody in a molecule of Formula I. Drug loading may range from 1 to 20 drug moieties (D) per antibody. ADCs of Formula I include collections of antibodies conjugated with a range of drug moieties, from 1 to 20. The average number of drug moieties per antibody in preparations of ADC from conjugation reactions may be characterized by conventional means such as mass spectroscopy, ELISA assay, and HPLC. The quantitative distribution of ADC in terms of p may also be determined. In some instances, separation, purification, and characterization of homogeneous ADC where p is a certain value from ADC with other drug loadings may be achieved by means such as reverse phase HPLC or electrophoresis.

For some antibody-drug conjugates, p may be limited by the number of attachment sites on the antibody. For example, where the attachment is a cysteine thiol, as in certain exemplary embodiments above, an antibody may have only one or several cysteine thiol groups, or may have only one or several sufficiently reactive thiol groups through which a linker may be attached. In certain embodiments, higher drug loading, e.g. p>5, may cause aggregation, insolubility, toxicity, or loss of cellular permeability of certain antibody-drug conjugates. In certain embodiments, the average drug loading for an ADC ranges from 1 to about 8; from about 2 to about 6; or from about 3 to about 5. Indeed, it has been shown that for certain ADCs, the optimal ratio of drug moieties per antibody may be less than 8, and may be about 2 to about 5 (U.S. Pat. No. 7,498,298).

In certain embodiments, fewer than the theoretical maximum of drug moieties are conjugated to an antibody during a conjugation reaction. An antibody may contain, for example, lysine residues that do not react with the drug-linker intermediate or linker reagent, as discussed below. Generally, antibodies do not contain many free and reactive cysteine thiol groups which may be linked to a drug moiety; indeed most cysteine thiol residues in antibodies exist as disulfide bridges. In certain embodiments, an antibody may be reduced with a reducing agent such as dithiothreitol (DTT) or tricarbonylethylphosphine (TCEP), under partial or total reducing conditions, to generate reactive cysteine thiol groups. In certain embodiments, an antibody is subjected to denaturing conditions to reveal reactive nucleophilic groups such as lysine or cysteine.

The loading (drug/antibody ratio) of an ADC may be controlled in different ways, and for example, by: (i) limiting the molar excess of drug-linker intermediate or linker reagent relative to antibody, (ii) limiting the conjugation reaction time or temperature, and (iii) partial or limiting reductive conditions for cysteine thiol modification.

It is to be understood that where more than one nucleophilic group reacts with a drug-linker intermediate or linker reagent, then the resulting product is a mixture of ADC compounds with a distribution of one or more drug moieties attached to an antibody. The average number of drugs per antibody may be calculated from the mixture by a dual ELISA antibody assay, which is specific for antibody and specific for the drug. Individual ADC molecules may be identified in the mixture by mass spectroscopy and separated by HPLC, e.g. hydrophobic interaction chromatography (see, e.g., McDonagh et al (2006) Prot. Engr. Design & Selection 19(7):299-307; Hamblett et al (2004) Clin. Cancer Res. 10:7063-7070; Hamblett, K. J., et al. "Effect of drug loading on the pharmacology, pharmacokinetics, and toxicity of an anti-CD30 antibody-drug conjugate," Abstract No. 624, American Association for Cancer Research, 2004 Annual Meeting, Mar. 27-31, 2004, Proceedings of the AACR, Volume 45, March 2004; Alley, S. C., et al. "Controlling the location of drug attachment in antibody-drug conjugates," Abstract No. 627, American Association for Cancer Research, 2004 Annual Meeting, Mar. 27-31, 2004, Proceedings of the AACR, Volume 45, March 2004). In certain embodiments, a homogeneous ADC with a single loading value may be isolated from the conjugation mixture by electrophoresis or chromatography.

d) Certain Methods of Preparing Immunoconjugates

An ADC of Formula I may be prepared by several routes employing organic chemistry reactions, conditions, and reagents known to those skilled in the art, including: (1) reaction of a nucleophilic group of an antibody with a bivalent linker reagent to form Ab-L via a covalent bond, followed by reaction with a drug moiety D; and (2) reaction of a nucleophilic group of a drug moiety with a bivalent linker reagent, to form D-L, via a covalent bond, followed by reaction with a nucleophilic group of an antibody. Exemplary methods for preparing an ADC of Formula I via the latter route are described in U.S. Pat. No. 7,498,298, which is expressly incorporated herein by reference.

Nucleophilic groups on antibodies include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; and (iii) aldehydes, ketones, carboxyl, and maleimide groups. Certain antibodies have reducible interchain disulfides, i.e. cysteine bridges. Antibodies may be made reactive for conjugation with linker reagents by treatment with a reducing agent such as DTT (dithiothreitol) or tricarbonylethylphosphine (TCEP), such that the antibody is fully or partially reduced. Each cysteine bridge will thus form, theoretically, two reactive thiol nucleophiles. Additional nucleophilic groups can be introduced into antibodies through modification of lysine residues, e.g., by reacting lysine residues with 2-iminothiolane (Traut's reagent), resulting in conversion of an amine into a thiol. Reactive thiol groups may also be introduced into an antibody by introducing one, two, three, four, or more cysteine residues (e.g., by preparing variant antibodies comprising one or more non-native cysteine amino acid residues).

Antibody-drug conjugates of the invention may also be produced by reaction between an electrophilic group on an antibody, such as an aldehyde or ketone carbonyl group, with a nucleophilic group on a linker reagent or drug. Useful nucleophilic groups on a linker reagent include, but are not limited to, hydrazide, oxime, amino, hydrazine, thiosemicarbazone, hydrazine carboxylate, and arylhydrazide. In one embodiment, an antibody is modified to introduce electrophilic moieties that are capable of reacting with nucleophilic substituents on the linker reagent or drug. In another embodiment, the sugars of glycosylated antibodies may be oxidized, e.g. with periodate oxidizing reagents, to form aldehyde or ketone groups which may react with the amine group of linker reagents or drug moieties. The resulting imine Schiff base groups may form a stable linkage, or may be reduced, e.g. by borohydride reagents to form stable amine linkages. In one embodiment, reaction of the carbohydrate portion of a glycosylated antibody with either galactose oxidase or sodium meta-periodate may yield carbonyl (aldehyde and ketone) groups in the antibody that can react with appropriate groups on the drug (Hermanson, Bioconjugate Techniques). In another embodiment, antibodies containing N-terminal serine or threonine residues can react with sodium meta-periodate, resulting in production of an aldehyde in place of the first amino acid (Geoghegan & Stroh, (1992) *Bioconjugate Chem.* 3:138-146; U.S. Pat. No. 5,362,852). Such an aldehyde can be reacted with a drug moiety or linker nucleophile.

Exemplary nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups.

Nonlimiting exemplary cross-linker reagents that may be used to prepare ADC are described herein in the section titled "Exemplary Linkers." Methods of using such cross-linker reagents to link two moieties, including a proteinaceous moiety and a chemical moiety, are known in the art. In some embodiments, a fusion protein comprising an antibody and a cytotoxic agent may be made, e.g., by recombinant techniques or peptide synthesis. A recombinant DNA molecule may comprise regions encoding the antibody and cytotoxic portions of the conjugate either adjacent to one another or separated by a region encoding a linker peptide which does not destroy the desired properties of the conjugate.

In yet another embodiment, an antibody may be conjugated to a "receptor" (such as streptavidin) for utilization in tumor pre-targeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a drug or radionucleotide).

E. Methods and Compositions for Diagnostics and Detection

In certain embodiments, any of the anti-LgR5 antibodies provided herein is useful for detecting the presence of LgR5 in a biological sample. The term "detecting" as used herein encompasses quantitative or qualitative detection. A "biological sample" comprises, e.g., a cell or tissue (e.g., biopsy material, including cancerous or potentially cancerous colon, colorectal, small intestine, endometrial, pancreatic, or ovarian tissue).

In one embodiment, an anti-LgR5 antibody for use in a method of diagnosis or detection is provided. In a further aspect, a method of detecting the presence of LgR5 in a biological sample is provided. In certain embodiments, the method comprises contacting the biological sample with an anti-LgR5 antibody as described herein under conditions permissive for binding of the anti-LgR5 antibody to LgR5, and detecting whether a complex is formed between the anti-LgR5 antibody and LgR5 in the biological sample. Such method may be an in vitro or in vivo method. In one embodiment, an anti-LgR5 antibody is used to select subjects eligible for therapy with an anti-LgR5 antibody, e.g. where LgR5 is a biomarker for selection of patients. In a further embodiment, the biological sample is a cell or tissue (e.g., biopsy material, including cancerous or potentially cancerous colon, colorectal, small intestine, endometrial, pancreatic, or ovarian tissue).

In a further embodiment, an anti-LgR5 antibody is used in vivo to detect, e.g., by in vivo imaging, an LgR5-positive cancer in a subject, e.g., for the purposes of diagnosing, prognosing, or staging cancer, determining the appropriate course of therapy, or monitoring response of a cancer to therapy. One method known in the art for in vivo detection is immuno-positron emission tomography (immuno-PET), as described, e.g., in van Dongen et al., *The Oncologist* 12:1379-1389 (2007) and Verel et al., *J. Nucl. Med.* 44:1271-1281 (2003). In such embodiments, a method is provided for detecting an LgR5-positive cancer in a subject, the method comprising administering a labeled anti-LgR5 antibody to a subject having or suspected of having an LgR5-positive cancer, and detecting the labeled anti-LgR5 antibody in the subject, wherein detection of the labeled anti-LgR5 antibody indicates an LgR5-positive cancer in the subject. In certain of such embodiments, the labeled anti-LgR5 antibody comprises an anti-LgR5 antibody conjugated to a positron emitter, such as $^{68}$Ga, $^{18}$F, $^{64}$Cu, $^{86}$Y, $^{89}$Zr, and $^{124}$I. In a particular embodiment, the positron emitter is $^{89}$Zr.

In further embodiments, a method of diagnosis or detection comprises contacting a first anti-LgR5 antibody immobilized to a substrate with a biological sample to be tested for the presence of LgR5, exposing the substrate to a second anti-LgR5 antibody, and detecting whether the second anti-LgR5 is bound to a complex between the first anti-LgR5 antibody and LgR5 in the biological sample. A substrate may be any supportive medium, e.g., glass, metal, ceramic, polymeric beads, slides, chips, and other substrates. In certain embodiments, a biological sample comprises a cell or tissue (e.g., biopsy material, including cancerous or potentially cancerous colon, colorectal, small intestine, endometrial, pancreatic or ovarian tissue). In certain embodiments, the first or second anti-LgR5 antibody is any of the antibodies described herein. In some such embodiments, the second anti-LgR5 antibody may be 8E11 or antibodies derived from 8E11, e.g., as described herein. In some such embodiments, the second anti-LgR5 antibody may be YW353 or antibodies derived from YW353, e.g., as described herein. In some embodiments, the first or second anti-LgR5 antibody is selected from 3G12 and 2H6 and antibodies derived from 3G12 and/or 2H6, e.g., as described herein.

Exemplary disorders that may be diagnosed or detected according to any of the above embodiments include LgR5-positive cancers, such as LgR5-positive colorectal cancer (including adenocarcinoma), LgR5-positive small intestine cancer (including adenocarcinoma, sarcoma (e.g., leiomyosarcoma), carcinoid tumors, gastrointestinal stromal tumor, and lymphoma) LgR5-positive ovarian cancer (including ovarian serous adenocarcinoma), LgR5-positive pancreatic cancer (including pancreatic ductal adenocarcinoma), and LgR5-positive endometrial cancer. In some embodiments, an LgR5-positive cancer is a cancer that receives an anti-LgR5 immunohistochemistry (IHC) or in situ hybridization (ISH) score greater than "0," which corresponds to very weak or no staining in >90% of tumor cells, under the conditions described herein in Example B. In another embodiment, an LgR5-positive cancer expresses LgR5 at a 1+, 2+ or 3+ level, as defined under the conditions described herein in Example B. In some embodiments, an LgR5-positive cancer is a cancer that expresses LgR5 according to a reverse-transcriptase PCR (RT-PCR) assay that detects LgR5 mRNA. In some embodiments, the RT-PCR is quantitative RT-PCR.

In certain embodiments, labeled anti-LgR5 antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}$P, $^{14}$C, $^{125}$I, $^{3}$H, and $^{131}$I, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like. In another embodiment, a label is a positron emitter. Positron emitters include but are not limited to $^{68}$Ga, $^{18}$F, $^{64}$Cu, $^{86}$Y, $^{76}$Br, $^{89}$Zr, and $^{124}$I. In a particular embodiment, a positron emitter is $^{89}$Zr.

F. Pharmaceutical Formulations

Pharmaceutical formulations of an anti-LgR5 antibody or immunoconjugate as described herein are prepared by mixing such antibody or immunoconjugate having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody or immunoconjugate formulations are described in U.S. Pat. No. 6,267,958. Aqueous antibody or immunoconjugate formulations include those described in U.S. Pat. No. 6,171,586 and WO2006/044908, the latter formulations including a histidine-acetate buffer.

The formulation herein may also contain more than one active ingredient as necessary for the particular indication being treated, preferably those with complementary activities that do not adversely affect each other. For example, in some instances, it may be desirable to further provide Avastin® (bevacizumab), e.g., for the treatment of LgR5-positive cancer such as LgR5-positive colon cancer or LgR5-positive colorectal cancer.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody or immunoconjugate, which matrices are in the form of shaped articles, e.g. films, or microcapsules.

The formulations to be used for in vivo administration are generally sterile. Sterility may be readily accomplished, e.g., by filtration through sterile filtration membranes.

G. Therapeutic Methods and Compositions

Any of the anti-LgR5 antibodies or immunoconjugates provided herein may be used in methods, e.g., therapeutic methods.

In one aspect, an anti-LgR5 antibody or immunoconjugate provided herein is used in a method of inhibiting proliferation of an LgR5-positive cell, the method comprising exposing the cell to the anti-LgR5 antibody or immunoconjugate under conditions permissive for binding of the anti-LgR5 antibody or immunoconjugate to LgR5 on the surface of the cell, thereby inhibiting the proliferation of the cell. In certain embodiments, the method is an in vitro or an in vivo method. In further embodiments, the cell is a colon, colorectal, small intestine, ovarian, pancreatic, or endometrial cell.

In some embodiments, an anti-LgR5 antibody or immunoconjugate provided herein is used in a method of treating cancer that comprises a mutation in a Kras gene and/or a mutation in an adenomatous polyposis coli (APC) gene in at least a portion of the cells of the cancer. In various embodiments, the cancer is selected from colon, colorectal, small intestine, ovarian, pancreatic, and endometrial cancer. In some embodiments, an anti-LgR5 antibody or immunoconjugate provided herein is used in a method of treating a colon or colorectal cancer that comprises a mutation in a Kras gene and/or a mutation in an APC gene in at least a portion of the cells of the cancer. Nonlimiting exemplary Kras mutations found in cancers (including colon and colorectal cancers) include mutations at Kras codon 12 (e.g., G12D, G12V, G12R, G12C, G12S, and G12A), codon 13 (e.g., G13D and G13C), codon 61 (e.g., G61H, G61L, G61E, and G61K), and codon 146. See, e.g., Yokota, *Anticancer Agents Med. Chem.*, 12: 163-171 (2012); Wicki et al., *Swiss Med. Wkly,* 140: w13112 (2010). Nonlimiting exemplary APC mutations found in cancers include mutations in the mutation cluster region (MCR), such as stop codons and frameshift mutations that result in a truncated APC gene product. See, e.g., Chandra et al., *PLoS One,* 7: e34479 (2012); and Kohler et al., *Hum. Mol. Genet.,* 17: 1978-1987 (2008).

In some embodiments, a method of treating cancer comprises administering an anti-LgR5 antibody or immunoconjugate to a subject, wherein the subject has a cancer comprising a Kras mutation and/or an APC mutation in at least a portion of the cancer cells. In some embodiments, the cancer is selected from colon, colorectal, small intestine, ovarian, pancreatic, and endometrial cancer. In some embodiments, the cancer is colon and/or colorectal cancer. In some embodiments, the subject has previously been determined to have a cancer comprising a Kras mutation and/or an APC mutation in at least a portion of the cancer cells. In some embodiments, the cancer is LgR5-positive.

Presence of various biomarkers in a sample can be analyzed by a number of methodologies, many of which are known in the art and understood by the skilled artisan, including, but not limited to, immunohistochemistry ("IHC"), Western blot analysis, immunoprecipitation, molecular binding assays, ELISA, ELIFA, fluorescence activated cell sorting ("FACS"), MassARRAY, proteomics, quantitative blood based assays (as for example Serum ELISA), biochemical enzymatic activity assays, in situ hybridization, Southern analysis, Northern analysis, whole genome sequencing, polymerase chain reaction ("PCR") including quantitative real time PCR ("qRT-PCR") and other amplification type detection methods, such as, for example, branched DNA, SISBA, TMA and the like, RNA-Seq, FISH, microarray analysis, gene expression profiling, and/or serial analysis of gene expression ("SAGE"), as well as any one of the wide variety of assays that can be performed by protein, gene, and/or tissue array analysis. Typical protocols for evaluating the status of genes and gene products are found, for example in Ausubel et al., eds., 1995, Current Protocols In Molecular Biology, Units 2 (Northern Blotting), 4 (Southern Blotting), 15 (Immunoblotting) and 18 (PCR Analysis). Multiplexed immunoassays such as those available from Rules Based Medicine or Meso Scale Discovery ("MSD") may also be used.

Inhibition of cell proliferation in vitro may be assayed using the CellTiter-Glo™ Luminescent Cell Viability Assay, which is commercially available from Promega (Madison, Wis.). That assay determines the number of viable cells in culture based on quantitation of ATP present, which is an indication of metabolically active cells. See Crouch et al. (1993) *J. Immunol. Meth.* 160:81-88, U.S. Pat. No. 6,602, 677. The assay may be conducted in 96- or 384-well format, making it amenable to automated high-throughput screening (HTS). See Cree et al. (1995) *AntiCancer Drugs* 6:398-404.

The assay procedure involves adding a single reagent (Cell-Titer-Glo® Reagent) directly to cultured cells. This results in cell lysis and generation of a luminescent signal produced by a luciferase reaction. The luminescent signal is proportional to the amount of ATP present, which is directly proportional to the number of viable cells present in culture. Data can be recorded by luminometer or CCD camera imaging device. The luminescence output is expressed as relative light units (RLU).

In another aspect, an anti-LgR5 antibody or immunoconjugate for use as a medicament is provided. In further aspects, an anti-LgR5 antibody or immunoconjugate for use in a method of treatment is provided. In certain embodiments, an anti-LgR5 antibody or immunoconjugate for use in treating LgR5-positive cancer is provided. In certain embodiments, the invention provides an anti-LgR5 antibody or immunoconjugate for use in a method of treating an individual having an LgR5-positive cancer, the method comprising administering to the individual an effective amount of the anti-LgR5 antibody or immunoconjugate. In one such embodiment, the method further comprises administering to the individual an effective amount of at least one additional therapeutic agent, e.g., as described below.

In a further aspect, the invention provides for the use of an anti-LgR5 antibody or immunoconjugate in the manufacture or preparation of a medicament. In one embodiment, the medicament is for treatment of LgR5-positive cancer. In a further embodiment, the medicament is for use in a method of treating LgR5-positive cancer, the method comprising administering to an individual having LgR5-positive cancer an effective amount of the medicament. In one such embodiment, the method further comprises administering to the individual an effective amount of at least one additional therapeutic agent, e.g., as described below.

In a further aspect, the invention provides a method for treating LgR5-positive cancer. In one embodiment, the method comprises administering to an individual having such LgR5-positive cancer an effective amount of an anti-LgR5 antibody or immunoconjugate. In one such embodiment, the method further comprises administering to the individual an effective amount of at least one additional therapeutic agent, as described below.

An LgR5-positive cancer according to any of the above embodiments may be, e.g., LgR5-positive colon or colorectal cancer (including adenocarcinoma), LgR5-positive small intestine cancer (including adenocarcinoma, sarcoma (e.g., leiomyosarcoma), carcinoid tumors, gastrointestinal stromal tumor, and lymphoma)., LgR5-positive ovarian cancer (including ovarian serous adenocarcinoma), LgR5-positive pancreatic cancer (including pancreatic ductal adenocarcinoma), and LgR5-positive endometrial cancer. In some embodiments, an LgR5-positive cancer is a cancer that receives an anti-LgR5 immunohistochemistry (IHC) or in situ hybridization (ISH) score greater than "0," which corresponds to very weak or no staining in >90% of tumor cells, under the conditions described herein in Example B. In another embodiment, an LgR5-positive cancer expresses LgR5 at a 1+, 2+ or 3+ level, as defined under the conditions described herein in Example B. In some embodiments, an LgR5-positive cancer is a cancer that expresses LgR5 according to a reverse-transcriptase PCR(RT-PCR) assay that detects LgR5 mRNA. In some embodiments, the RT-PCR is quantitative RT-PCR.

An "individual" according to any of the above embodiments may be a human.

In a further aspect, the invention provides pharmaceutical formulations comprising any of the anti-LgR5 antibodies or immunoconjugate provided herein, e.g., for use in any of the above therapeutic methods. In one embodiment, a pharmaceutical formulation comprises any of the anti-LgR5 antibodies or immunoconjugates provided herein and a pharmaceutically acceptable carrier. In another embodiment, a pharmaceutical formulation comprises any of the anti-LgR5 antibodies or immunoconjugates provided herein and at least one additional therapeutic agent, e.g., as described below.

Antibodies or immunoconjugates of the invention can be used either alone or in combination with other agents in a therapy. For instance, an antibody or immunoconjugate of the invention may be co-administered with at least one additional therapeutic agent. In certain embodiments, an additional therapeutic agent is Avastin® (bevacizumab), e.g., for the treatment of LgR5-positive cancer such as LgR5-positive colon cancer or LgR5-positive colorectal cancer.

Such combination therapies noted above encompass combined administration (where two or more therapeutic agents are included in the same or separate formulations), and separate administration, in which case, administration of the antibody or immunoconjugate of the invention can occur prior to, simultaneously, and/or following, administration of the additional therapeutic agent and/or adjuvant. Antibodies or immunoconjugates of the invention can also be used in combination with radiation therapy.

An antibody or immunoconjugate of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies or immunoconjugates of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody or immunoconjugate need not be, but is optionally formulated with one or more agents currently used to prevent or treat the disorder in question. The effective amount of such other agents depends on the amount of antibody or immunoconjugate present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody or immunoconjugate of the invention (when used alone or in combination with one or more other additional therapeutic agents) will depend on the type of disease to be treated, the type of antibody or immunoconjugate, the severity and course of the disease, whether the antibody or immunoconjugate is administered for preventive or therapeutic purposes, previous therapy, the patient's clinical history and response to the antibody or immunoconjugate, and the discretion of the attending physician. The antibody or immunoconjugate is suitably administered to the patient at one time or over a series of treatments. Depending on the type and severity of the disease, about 1 µg/kg to 15 mg/kg (e.g. 0.1 mg/kg-10 mg/kg) of antibody or immunoconjugate can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody or immunoconjugate would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. However, other dosage regimens may be useful. The progress of this therapy is easily monitored by conventional techniques and assays.

It is understood that any of the above formulations or therapeutic methods may be carried out using both an immunoconjugate of the invention and an anti-LgR5 antibody.

H. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the disorder and may have a sterile access port (for example the container may be an intravenous solution bag or a vial having a stopper pierceable by a hypodermic injection needle). At least one active agent in the composition is an antibody or immunoconjugate of the invention. The label or package insert indicates that the composition is used for treating the condition of choice. Moreover, the article of manufacture may comprise (a) a first container with a composition contained therein, wherein the composition comprises an antibody or immunoconjugate of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution or dextrose solution. It may further include other materials desirable from a commercial and user standpoint, including other buffers, diluents, filters, needles, and syringes.

III. Examples

The following are examples of methods and compositions of the invention. It is understood that various other embodiments may be practiced, given the general description provided above.

A. Human LgR5 Gene Expression

Human LgR5 gene expression was analyzed using a proprietary database containing gene expression information (GeneExpress®, Gene Logic Inc., Gaithersburg, Md.). Graphical analysis of the GeneExpress® database was conducted using a microarray profile viewer. FIG. 1 is a graphic representation of human LgR5 gene expression in various tissues. The scale on the y-axis indicates gene expression levels based on hybridization signal intensity. Dots appear both to the left and to the right of the line extending from the name of each listed tissue. The dots appearing to the left of the line represent gene expression in normal tissue, and the dots appearing to the right of the line represent gene expression in tumor and diseased tissue. FIG. 1 shows increased LgR5 gene expression in certain tumor or diseased tissues relative to their normal counterparts. In particular, LgR5 is substantially overexpressed in colorectal, endometrial, and ovarian tumors. FIG. 1, inset, shows that LgR5 is overexpressed in at least the following colon tumors: adenocarcinoma, benign tumors, and metastatic colon tumors, and also in tissue with a colon tumor content of less than 50% ("low tumor" in FIG. 1 inset); but is not overexpressed in normal colon, Crohn's disease, or ulcerative colitis. Human LgR5 expression is much lower in normal tissues, with low levels of expression in normal brain, muscle, ovarian, and placental tissues.

B. Prevalence of Human LgR5 in Colon Tumors

To evaluate the expression of LgR5 in colorectal cancer, 57 primary colorectal adenocarcinomas were acquired from multiple sources (Asterand, Detroit, Mich.; Bio-Options, Fullerton, Calif.; University of Michigan, Ann Arbor, Mich.; Cytomyx, Rockville, Md.; Cooperative Human Tissue Network, Nashville, Tenn.; Indivumed, Hamburg, Germany; ProteoGenex, Culver City, Calif.). Forty-four percent of samples were from men, and the average age of the patients was 66 years (range 31 to 93 years). Tissue microarrays (TMAs) were assembled using duplicate cores as described in Bubendorf L, et al., *J Pathol.* 2001 September; 195(1):72-9, and included five normal colorectal mucosa samples from matched cases.

LgR5 expression was determined by in situ hybridization using the oligonucleotide probes shown in Table 2. See, e.g., Jubb A M, et al., *Methods Mol Biol* 2006; 326:255-64. ISH for β-actin was used to confirm mRNA integrity in colorectal cancer tissues prior to analysis.

LgR5 hybridization intensity was scored by a trained pathologist according to the scheme below, taking into account the intensity (silver grains) as well as breadth of staining.

0 (negative): very weak or no hybridization in >90% of tumor cells

1+ (mild): predominant hybridization pattern is weak

2+ (moderate): predominant hybridization pattern is moderately strong in the majority (>50%) of neoplastic cells 3+ (strong): predominant hybridization pattern is strong in the majority (>50%) of neoplastic cells Sense probes were used to control for the specificity of hybridization.

Figure 2:
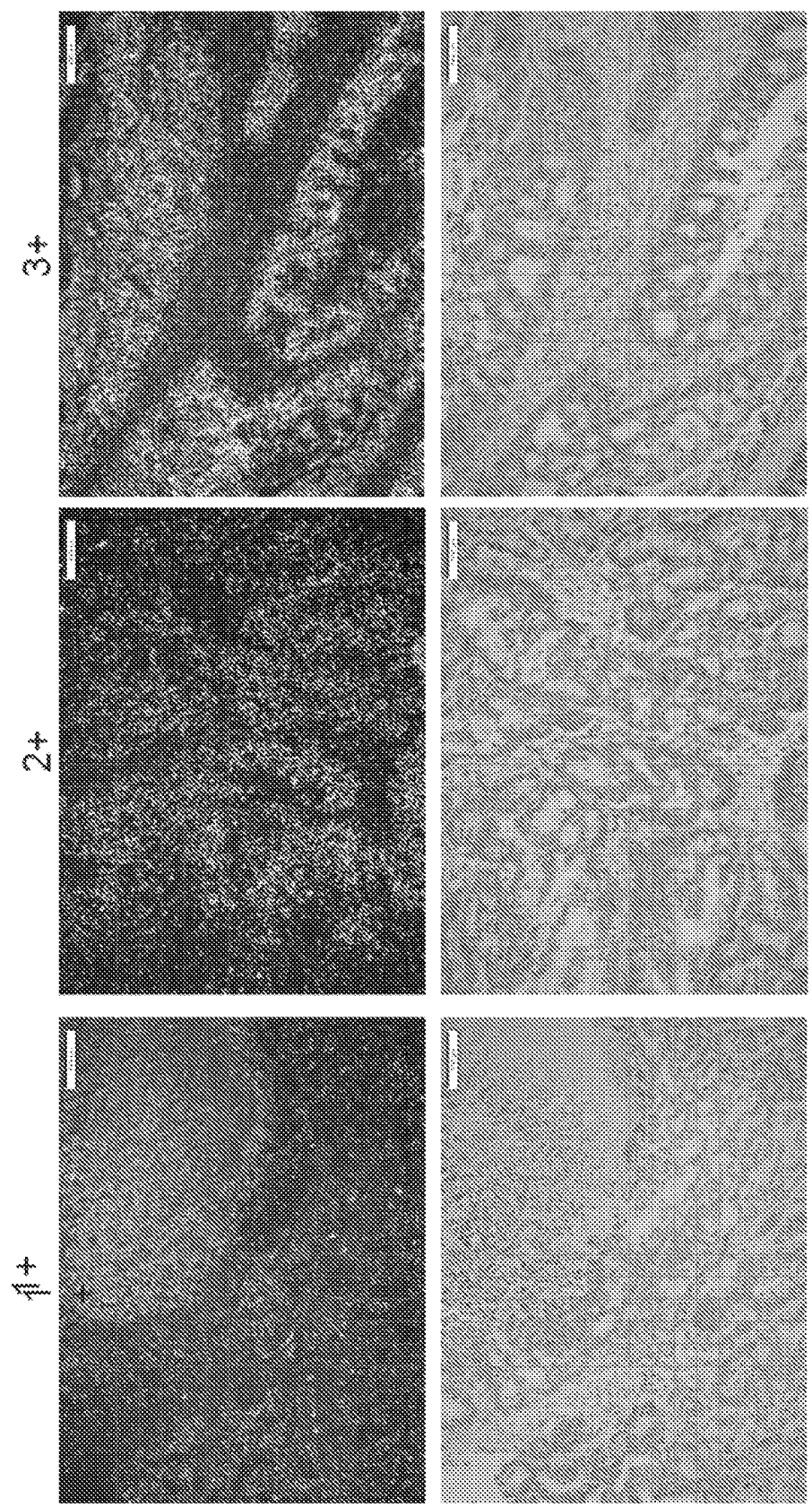
FIG. 2 shows expression of LgR5 in colon tumors by in situ hybridization, as described in Example B.

FIG. 2 shows exemplary colon tumor sections with 1+, 2+, and 3+ levels of staining. The top panels show dark field images and the bottom panels show bright field images. The deposition of silver grains in the dark field images indicates hybridization of the probe and expression of LgR5 mRNA. ~77% (41/53) of colon tumor sections analyzed were LgR5 positive, showing staining at the 1+, 2+, or 3+ levels, with 34% (18/53) showing 2+ or 3+ staining. Four of the 57 samples analyzed were noninformative for LgR5 expression.

To evaluate the significance of Lgr5 expression in colon tumors, a population-based series of patients who had undergone surgical resections for colorectal adenocarcinoma was compiled retrospectively from the pathology archives at St James' University Hospital (Leeds, UK) from 1988 to 2003. Tissue microarrays (TMAs) were constructed with one core of normal mucosa and three cores of adenocarcinoma per patient as described in Bubendorf L, et al., *J Pathol.* 2001 September; 195(1):72-9. ISH was performed and scored as described above. The heterogeneity of expression across three cores from the same tumor was also determined, and is expressed as the proportion of tumors that showed a particular level of discordance in one of the three cores. For example, if three cores had scores of +1, +3, and +3, one of the three cores from that tumor is discordant by 2.

Figure 3:
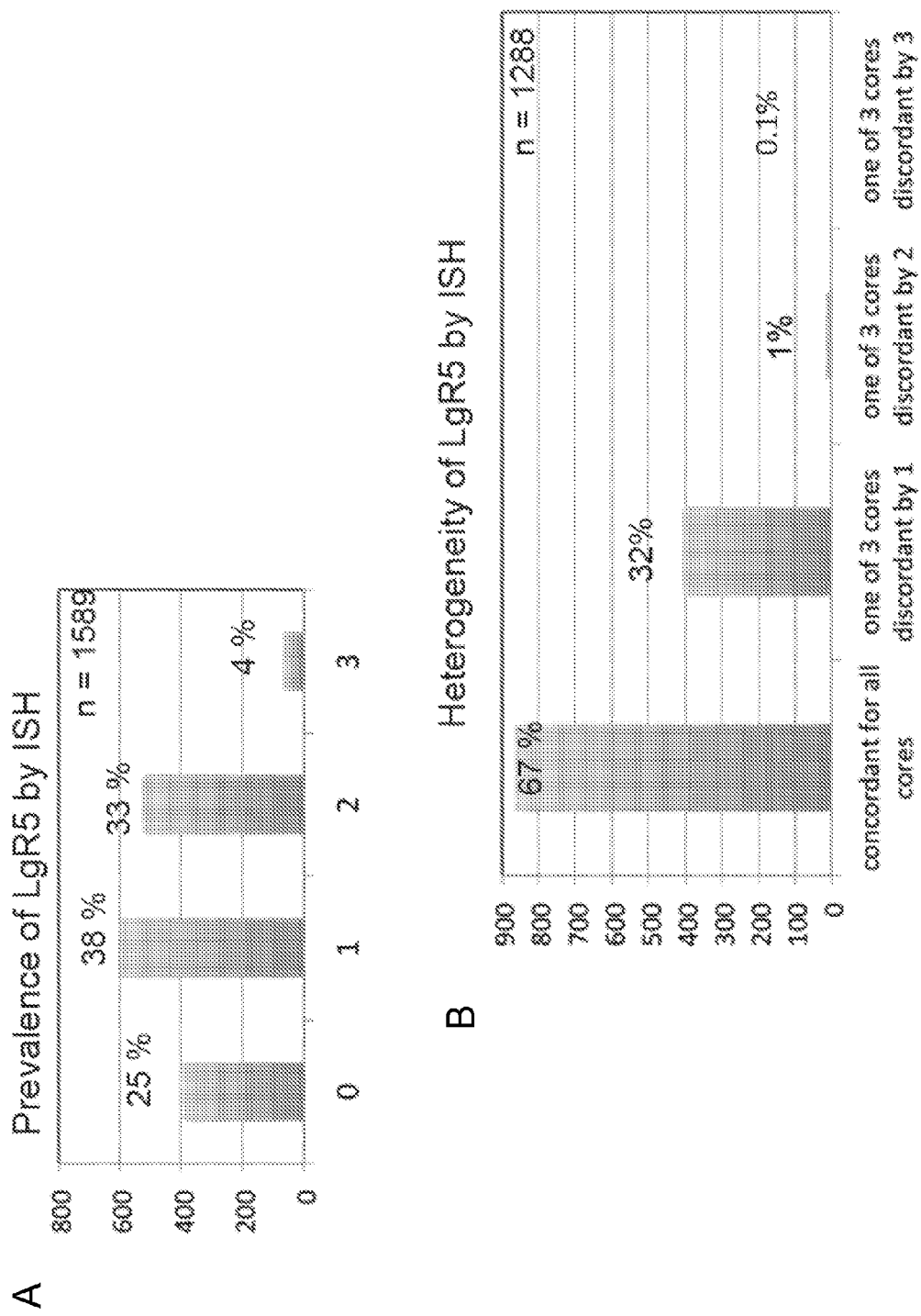
FIG. 3 shows (A) the prevalence of various levels of LgR5 expression in a colon tumor tissue microarray, and (B) the heterogeneity of LgR5 expression in three cores from each colorectal adenocarcinoma sample, both determined by in situ hybridization, as described in Example B.

FIG. 3A shows the prevalence of 0, 1+, 2+, and 3+ levels of LgR5 staining in the colon tumor tissue microarray, measured by in situ hybridization. 75% of the colon tumor tissues showed staining at the 1+, 2+, or 3+ levels, with 37% showing 2+ or 3+ staining. FIG. 3B shows the heterogeneity of LgR5 expression. 67% of tumors showed no heterogeneity across the three cores. 32% shows a discordance of 1 in one of the three cores, and only 1% showed a discordance greater than 1.

C. Mouse Monoclonal Antibody Generation

Monoclonal antibodies against human LgR5 were generated using the following procedures. Human LgR5 extracellular domain (ECD; amino acids 22-557) with a C-terminal His-tagged Fc was expressed from a baculovirus expression system, and purified on a Ni-NTA column (Qiagen), followed by gel filtration on a Superdex 200 column in 20 mM MES pH 6.0, 6M guanidine HCl as previously described (Kirchhofer et al., 2003) and dialysis into PBS for storage at −80° C.

Fifteen Balb/c mice (Charles River Laboratories International, Inc., Hollister, Calif., USA) were injected with either

TABLE 2

| | | | | |
|---|---|---|---|---|
| Primer sequences for isotopic in situ hybridization probes. | | | | |
| Gene | Genbank Accession | Nucleotides Complementary to Probe | Antisense (AS) or Sense (S) | Forward Primer (5' to 3') | Reverse Primer (5' to 3') |
| Lgr5 | NM_003667 | 508 | AS | ACCAACTGCATCCT AAACTG (SEQ ID NO: 83) | ACCGAGTTTCACCTC AGCTC (SEQ ID NO: 84) |
| Lgr5 | NM_003667 | 496 | S | ACATTGCCCTGTTGC TCTTC (SEQ ID NO: 85) | ACTGCTCTGATATAC TCAATC (SEQ ID NO: 86) | huLgR5 plasmid DNA in lactated Ringer's solution (via tail vein) or with recombinant human LgR5 ECD as described above (via rear footpads) in adjuvant containing metabolizable squalene (4% v/v), Tween 80 (0.2% v/v), trehalose 6,6-dimycolate (0.05% w/v) and monophosphoryl lipid A (0.05% w/v; Sigma Aldrich, USA). Serum titers were evaluated by standard enzyme linked immunosorbant assay (ELISA) and FACS following 6-9 injections. Splenic B cells harvested from a total of 5 mice were fused with mouse myeloma cells (X63.Ag8.653; American Type Culture Collection, Manassas, Va., USA) by electrofusion (Hybrimune; Harvard Apparatus, Inc., Holliston, Mass., USA). After 10-14 days, hybridoma supernatants were screened for antibody secretion by ELISA. All positive clones were then expanded and re-screened for binding to huLgR5 and muLgR5 by ELISA and FACS (i.e., for binding to 293-huLGR5 and 293-muLGR5 cells). Hybridoma clones 8E11.1.1 (identified from the DNA immunized mice), and 2H6.3.5 and 3G12.2.1 (both from the protein immunized mice) showed high immunobinding after two rounds of subcloning (by limiting dilution) and were scaled up for purification in INTEGRA CELLine 1000 bioreactors (INTEGRA Biosciences AG, Zizers, Switzerland). Supernatants were then purified by affinity chromatography, sterile-filtered, and stored at 4° C. in PBS. The isotypes of the mAbs were determined to be IgG1 (kappa light chain) using the Isostrip Mouse mAb Isotyping Kit (Roche Applied Biosciences, Indianapolis, Ind., USA).

FIG. 4 shows certain monoclonal antibodies generated, along with certain properties, some of which will be described in further detail below.

D. Cloning and Chimerization of Mouse Monoclonal Antibodies

Monoclonal antibodies 8E11, 3G12, and 2H6 were cloned and chimerized as follows.

Figure 5:
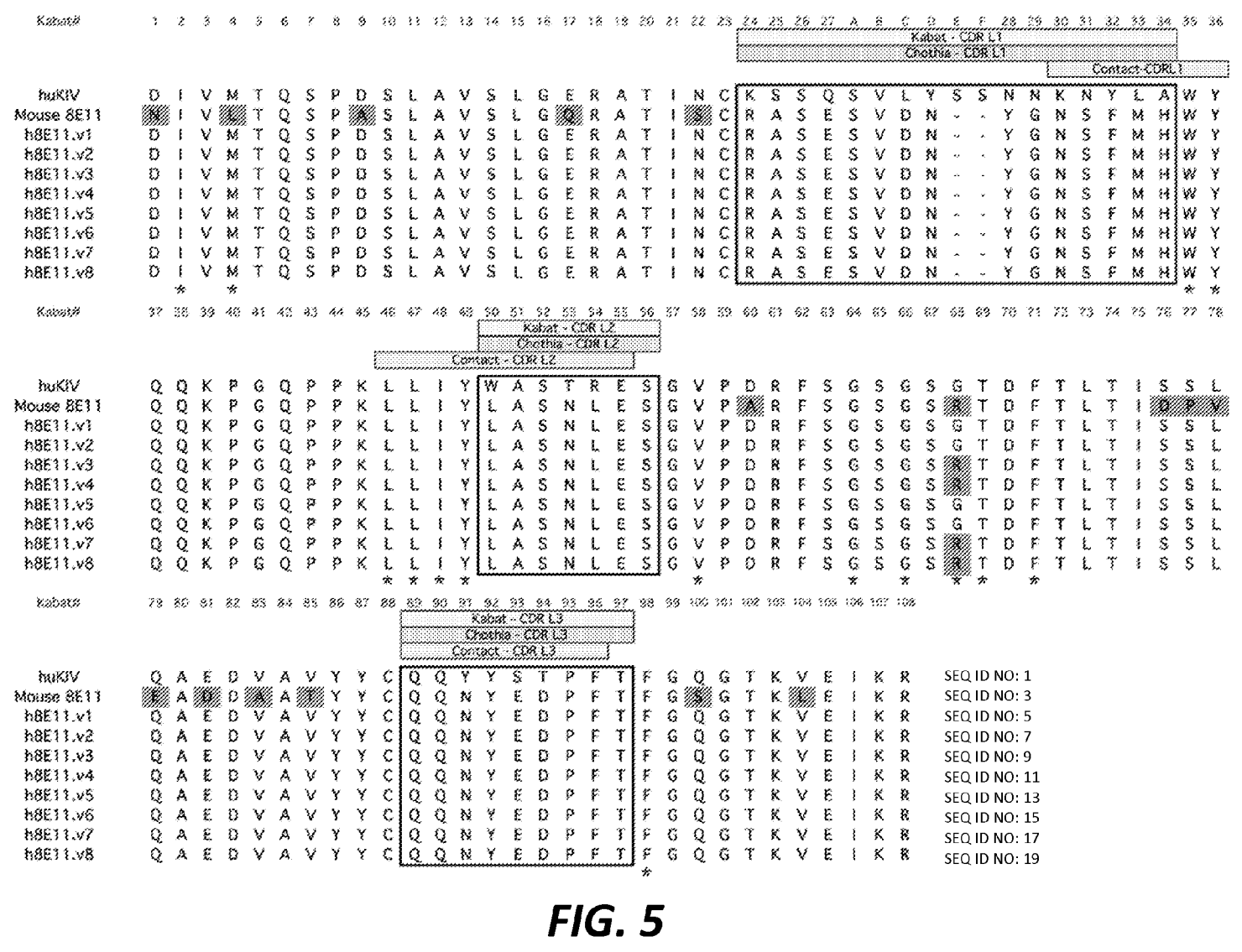
Figure 6:
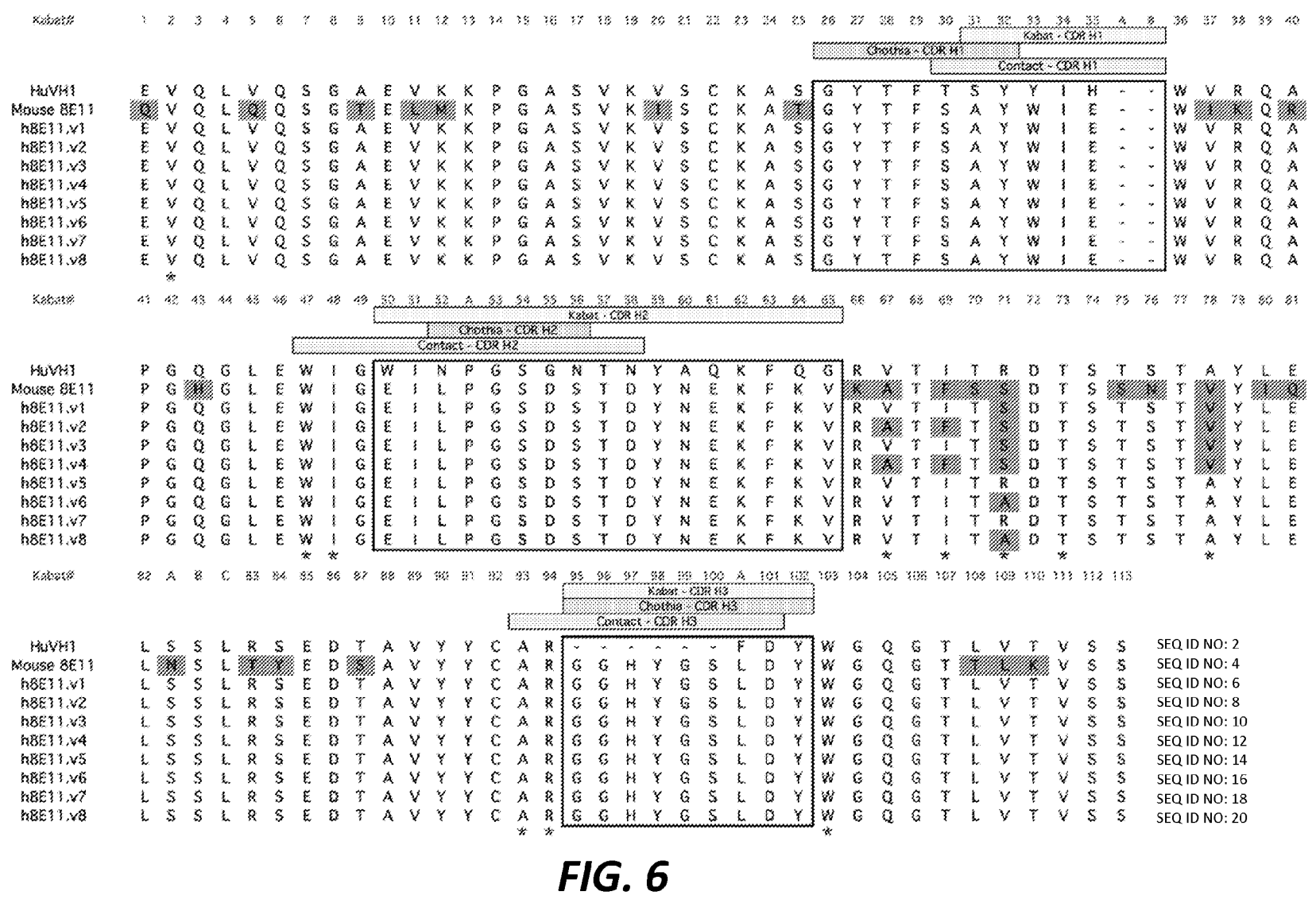
Figure 7:
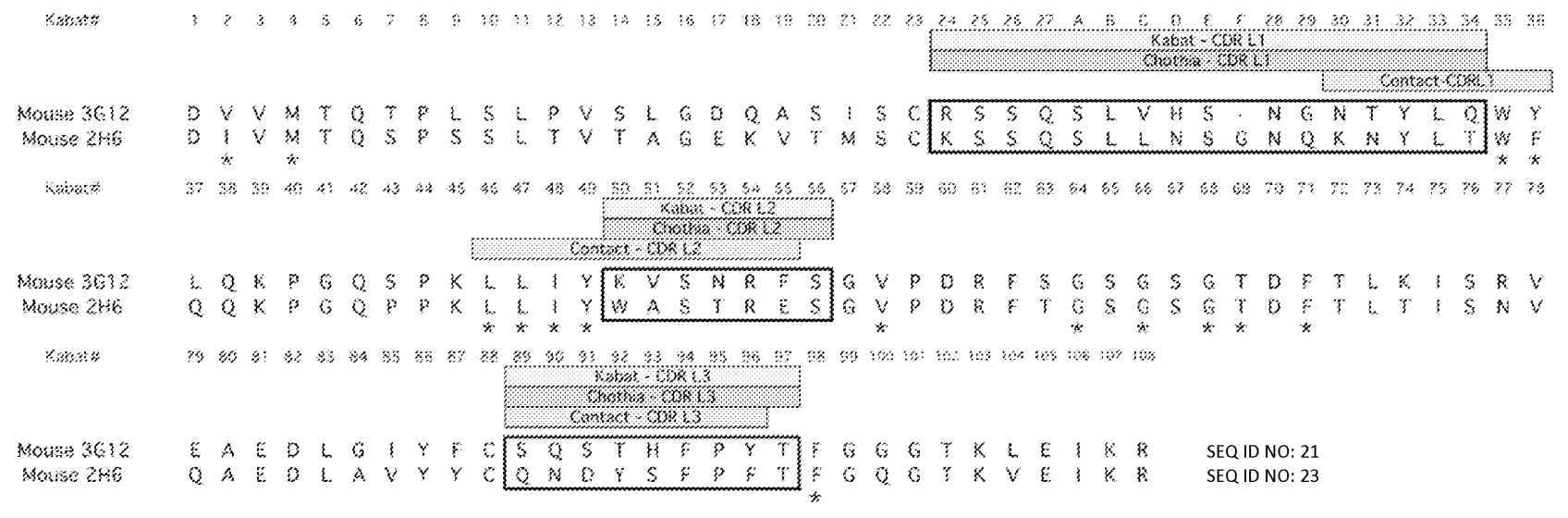
Figure 8:
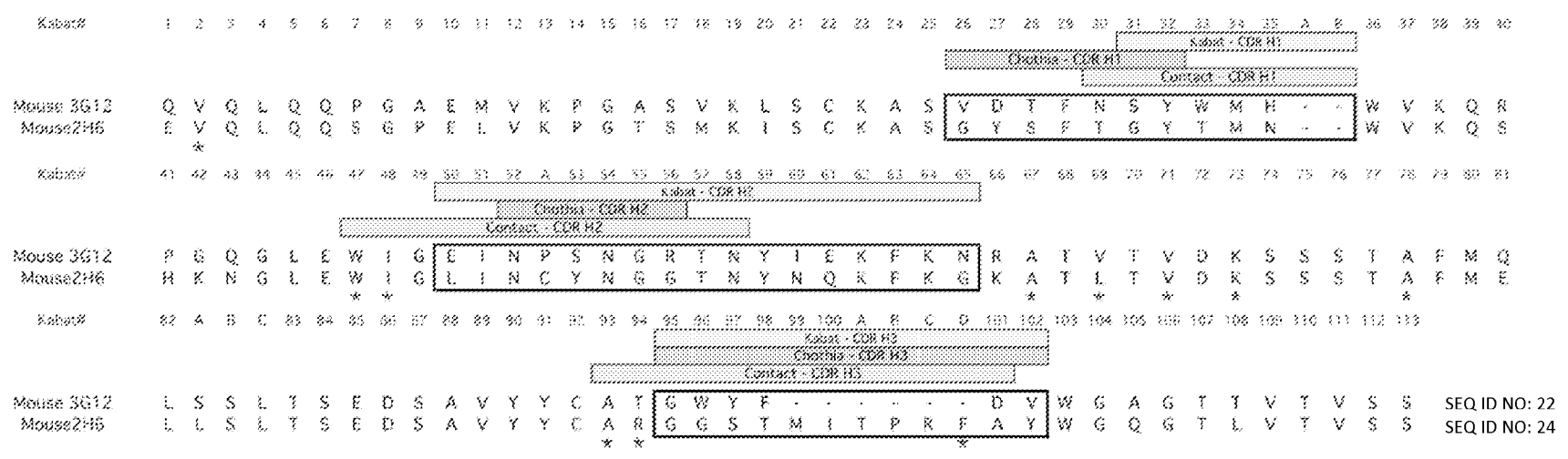

Total RNA was extracted from hybridoma cells producing murine 8E11, murine 3G12, or murine 2H6 using standard methods. The variable light (VL) and variable heavy (VH) domains were amplified using RT-PCR with degenerate primers to the heavy and light chains. The forward primers were specific for the N-terminal amino acid sequence of the VL and VH regions. Respectively, the LC and HC reverse primers were designed to anneal to a region in the constant light (CL) and constant heavy domain 1 (CH1), which are highly conserved across species. The polynucleotide sequence of the inserts was determined using routine sequencing methods. The 8E11 VL and VH amino acid sequences are shown in FIGS. 5 and 6, respectively (SEQ ID NOs: 3 and 4, respectively). The 3G12 and 2H6 VL and VH amino acid sequences are shown in FIGS. 7 and 8, respectively. The VL and VH sequences of antibody 3G12 are shown in SEQ ID NOs: 21 and 22, respectively, and the VL and VH sequences of antibody 2H6 are shown in SEQ ID NOs: 23 and 24, respectively.

Each antibody was chimerized by cloning the mouse heavy chain variable region onto a human IgG1 heavy chain constant region and cloning the light chain variable region onto a human kappa light chain constant region.

E. Humanization of 8E11

Monoclonal antibody 8E11 was humanized as described below. Residue numbers are according to Kabat et al., *Sequences of proteins of immunological interest*, 5th Ed., Public Health Service, National Institutes of Health, Bethesda, Md. (1991).

Direct Hypervariable Region Grafts onto the Acceptor Human Consensus Framework

Variants constructed during the humanization of 8E11 were assessed in the form of an IgG. The VL and VH domains from murine 8E11 were aligned with the human VL kappa IV ($VL_{KIV}$) and human VH subgroup I ($VH_I$) consensus sequences. Hypervariable regions from the murine 8E11 (mu8E11) antibody were engineered into $VL_{KIV}$ and $VH_I$ acceptor frameworks to generate 8E11.v1. Specifically, from the mu8E11 VL domain, positions 24-34 (L1), 50-56 (L2) and 89-97 (L3) were grafted into $VL_{KIV}$. From the mu8E11 VH domain, positions 26-35 (H1), 49-65 (H2) and 95-102 (H3) were grafted into $VH_I$. In addition, positions 71 and 78 in framework III of VH were retained from the mouse sequence in 8E11.v1. Those residues were found to be part of the framework residues acting as "Vernier" zone, which may adjust CDR structure and fine-tune the antigen fit. See, e.g., Foote and Winter, *J. Mol. Biol.* 224: 487-499 (1992) (FIGS. 5 and 6). These CDR definitions include positions defined by their sequence hypervariability (Wu, T. T. & Kabat, E. A. (1970)), their structural location (Chothia, C. & Lesk, A. M. (1987)) and their involvement in antigen-antibody contacts (MacCallum et al. *J. Mol. Biol.* 262: 732-745 (1996)).

Additional 8E11 variants were generated to evaluate the contributions of other Vernier positions, such as position 68 in the light chain, and positions 67 and 69 in the heavy chain. Humanized 8E11.v2 was generated by retaining two addition mouse residues, at positions 67 and 69 of the heavy chain variable region. The light chain variable region sequence and heavy chain variable region sequence for 8E11.v2, and other variants, are shown in FIGS. 5 and 6, respectively.

The humanized variants of 8E11 were generated by Kunkel mutagenesis using a separate oligonucleotide for each hypervariable region. Correct clones were identified by DNA sequencing.

Assessment of Variants

For screening purposes, IgG variants were initially produced in 293 cells. Vectors coding for VL and VH were transfected into 293 cells. IgG was purified from cell culture media by protein A affinity chromatography.

The affinity of each 8E11 IgG variant for human LgR5 was determined by surface plasmon resonance using a BIAcore™-3000. BIAcore™ research grade CM5 chips were activated with 1-ethyl-3-(3-dimethylaminopropyl) carbodiimide (EDC) and N-hydroxysuccinimide (NHS) reagents according to the supplier's instructions. Goat anti-human Fc IgGs were coupled to the chips to achieve approximately 10,000 response units (RU) in each flow cell. Unreacted coupling groups were blocked with 1M ethanolamine. For kinetics measurements, anti-LGR5 antibodies were captured to achieve approximately 300 RU. Two-fold serial dilutions of human LgR5 ECD (amino acids 22-557 fused to His-Fc expressed in a baculovirus system, or amino acids 22-558 fused to Fc expressed from CHO cells; 125 nM to 0.49 nM) were injected in HBS-P buffer (0.01M HEPES pH7.4, 0.15M NaCl, 0.005% surfactant P20) at 25° C. with a flow rate of 30 μl/min. Association rates ($k_{on}$) and dissociation rates ($k_{off}$) were calculated using a 1:1 Langmuir binding model (BIAcore™ Evaluation Software version 3.2). The equilibrium dissociation constant (Kd) was calculated as the ratio $k_{off}/k_{on}$.

Results

The human acceptor framework used for humanization of 8E11 is based on the human VL kappa IV consensus ($VL_{KIV}$) and the acceptor VH framework $VH_I$. Eight humanized variants of mu8E11 were produced and tested for LgR5 affinity by BIAcore™. The light chain variable regions and heavy chain variable regions of each of the variants is shown in FIGS. 5 and 6, respectively. The results of the affinity measurements are shown in FIG. 9.

To improve the binding affinity of 8E11.v1, position 68 in the light chain and positions of 67 and 69 in the heavy chain were changed to residues found at these positions in mu8E11.

Positions 71 and 78 in the heavy chain were changed to residues found at these positions in the human framework VH$_I$. Combinations of these altered light and heavy chains were expressed as IgG and purified as described above, and assessed for binding to human LgR5 by Biacore (FIG. 9).

Variant hu8E11.v2 was generated by changing positions 67 and 69 of the hu8E11.v1 heavy chain to the residues found at those positions in mu8E11. The affinity (K$_D$) of hu8E11.v2 was found to be about the same as the parental ch8E11 antibody.

Summary of Changes for Humanized 8E11.v2

The 6 murine 8E11 CDRs (defined as positions 24-34 (L1), 50-56 (L2) and 89-97 (L3), 26-35 (H1), 49-65 (H2) and 93-102 (H3)) were grafted into the human consensus VL$_{KIV}$ and VH$_I$ acceptor domains. Positions 67, 69, 71, and 78 were changed back to murine residues from mu8E11. Humanized 8E11.v2 has comparable affinity for LgR5 to chimeric 8E11.

Throughout this application, mouse monoclonal antibodies 8E11, 2H6, and 3G12 are referred to in the alternative as 8E11, m8E11, or mu8E11; and 2H6, m2H6 or mu2H6; and 3G12, m3G12, or mu3G12; respectively. Chimeric monoclonal antibodies 8E11, 2H6, and 3G12 are referred to as chimeric 8E11 or ch8E11; chimeric 2H6 or ch2H6; and chimeric 3G12 or ch3G12; respectively. Humanized monoclonal antibody 8E11.v2 may also be referred to as 8E11v2, h8E11v.2, or hu8E11v.2.

F. Generation of a Human Monoclonal Antibody by Phage Display

Human LgR5 ECD (amino acids 22-555) with an N-terminal FLAG was expressed in CHO cells and purified on an anti-FLAG resin overnight, and then eluted with 0.1M acetic acid, pH 2.7. The protein was then purified by gel filtration on a Superdex 200 column in PBS and then dialyzed into PBS for storage at −80° C.

Human phage antibody libraries with synthetic diversities in the selected complementary determining regions (H1, H2, H3), mimicking the natural diversity of human IgG repertoire were used for panning. The Fab fragments were displayed bivalently on the surface of M13 bacteriophage particals (Lee et al. (2004) *J Mol Biol* 340, 1073-93). Human LgR5 ECD (amino acids 22-555) produced as described above was used as an antigen. Nunc 96-well MaxiSorp immunoplates (Nunc) were coated overnight at 4° C. with LgR5 ECD protein (10 µg/ml) and blocked for 1 hour with PBST buffer (PBS, 0.05% Tween 20) supplemented with 1% BSA. The antibody phage libraries were added and incubated overnight at room temperature. The plates were washed with PBST buffer and bound phage were eluted with 50 mM HCL/500 mM NaCl for 30 minutes and neutralized with an equal volume of 1M Tris base. Recovered phages were amplified in *E. coli* XL-1 blue cells. During subsequent selection rounds, the incubation time of the phage antibodies was decreased to 2 hours and the stringency of plate washing was gradually increased (Liang et al. (2007) *J Mol Biol* 366, 815-829). Unique and specific phage antibodies that bind to human LgR5 ECD were identified by phage ELISA and DNA sequencing. Certain clones, including YW353, were reformatted to full length IgGs by cloning the VL and VH regions into LPG3 and LPG4 vectors, respectively. Antibodies were transiently expressed in mammalian cells and purified on protein A columns (Carter et al. (1992) *Proc Natl Acad Sci USA* 89, 4285-9).

Figures 10, 11:
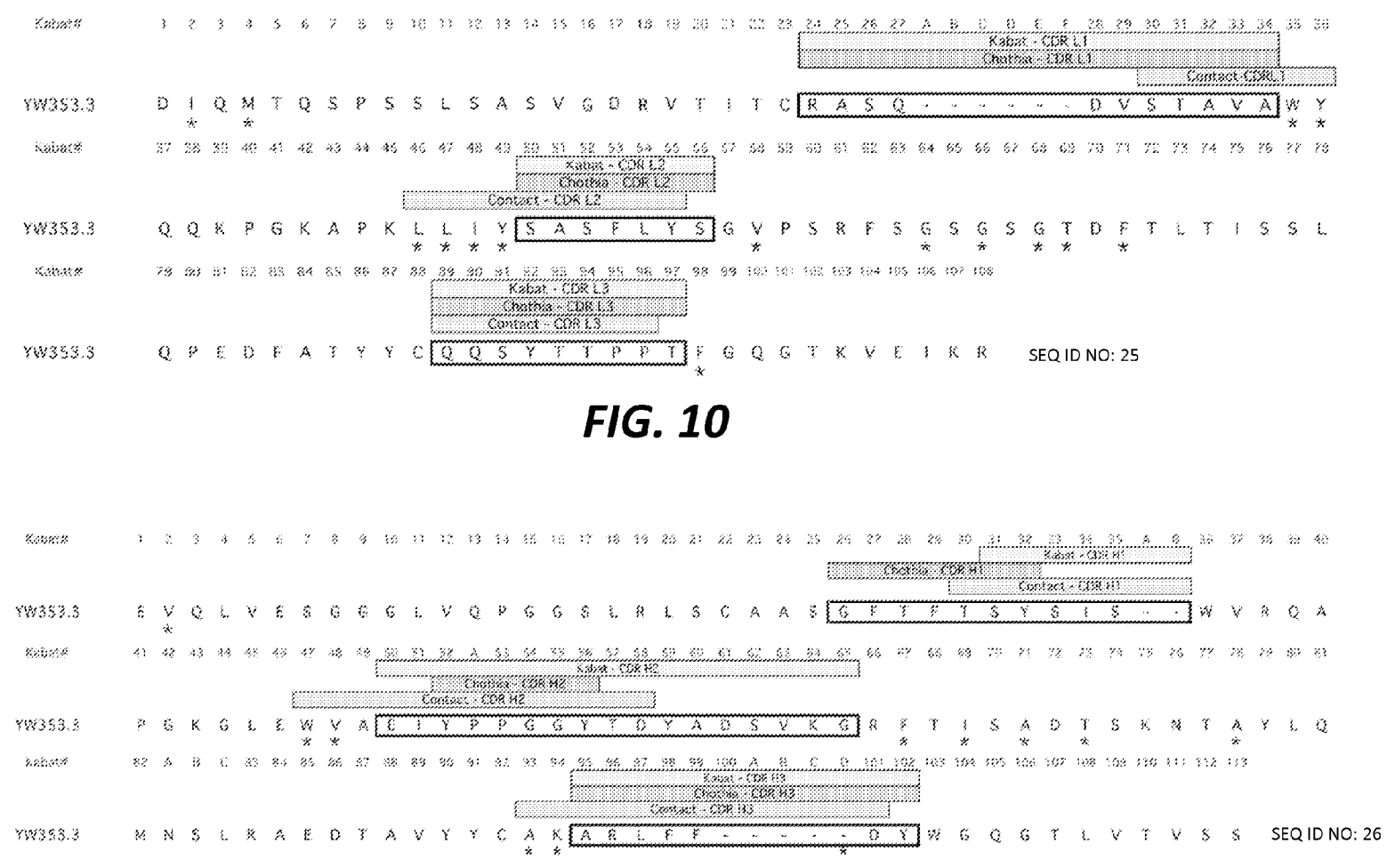

The light chain and heavy chain variable regions sequence for human antibody YW353 are shown in FIGS. 10 and 11, respectively (SEQ ID NOs: 26 and 25). IgG1 heavy chain and kappa light chain sequences for human antibody YW353 are shown in SEQ ID NOs: 66 and 65, respectively. Since YW353 was generated from a human antibody phage library, the terms "YW353" and "huYW353" are used interchangeably herein.

G. Species Cross-Reactivity

Monoclonal antibodies were tested to determine if they cross-react with LgR5 from species other than human. FIGS. 12A to C shows an alignment between human (SEQ ID NO: 67), cynomolgus monkey (SEQ ID NO: 69), rat (SEQ ID NO: 70) and mouse (SEQ ID NO: 72) LgR5. Residues that are identical among all four species are indicated by asterisks (*). FIG. 4 shows the results of FACS analysis of 293 cells stably transfected with gD epitope-tagged LgR5 (human, cynomolgus monkey, rat, or mouse LgR5); stained with 10 µg/ml YW353, ch8E11, hu8E11.v2, 2H6, or 3G12 antibody; and detected with R-Phycoerythrin conjugated goat anti-human antibody. Untransfected 293 cells do not normally express LgR5. YW353 antibody binds human and cynomolgus monkey LgR5, but not rat or mouse LgR5. Ch8E11 and hu8E11.v2 antibodies bind all four species of LgR5, although binding to rat LgR5 is not as strong as binding to human, cynomolgus monkey, or mouse LgR5. 2H6 antibody binds to human and mouse LgR5, and was not tested for binding to cynomolgus monkey or rat LgR5. 3G12 antibody shows strong binding to human LgR5, less strong binding to mouse LgR5, and was not tested for binding to cynomolgus monkey or rat LgR5.

H. Antibody Affinities

The affinity of each antibody for human LgR5 was determined by surface plasmon resonance using a BIAcore™-3000, substantially as described above in Example E.

As shown in FIG. 4, YW353 antibody bound to human LgR5 with an affinity of 1.6 nM. Ch8E11 and hu8E11.v2 antibodies bound to human LgR5 with affinities of 2.4 nm and 3.1 nm, respectively. 2H6 and 3G12 antibodies bound to human LgR5 with affinities of 208 nM and 72 nM, respectively.

Scatchard analysis was performed following standard procedures (Holmes et al., *Science* 256:1205-1210 (1992)) to determine the relative binding affinities of YW353, ch8E11 and hu8E11v2 antibodies.

Anti-Lgr5 antibodies were [I$^{125}$] labeled using the indirect Iodogen method. The [I$^{125}$] labeled anti-Lgr5 antibodies were purified from free $^{125}$I-Na by gel filtration using a NAP-5 column (GE Healthcare); the purified iodinated anti-Lgr5 antibodies had a range of specific activities of 13.92 to 19.01 µCi/µg. Competition assay mixtures of 50 µL volume containing a fixed concentration of [I$^{125}$] labeled antibody and decreasing concentrations of serially diluted, unlabeled antibody were placed into 96-well plates. 293 cells stably expressing human, rat, or mouse Lgr5 were cultured in growth media at 37° C. in 5% CO$_2$. Cells were detached from the flask using Sigma Cell Dissociation Solution and were washed with binding buffer, which consisted of Dulbecco's Modified Eagle Medium (DMEM) with 2% fetal bovine serum (FBS), 50 mM HEPES (pH 7.2) and 0.1% sodium azide. The washed cells were added to the 96 well plates at a density of 250,000 cells in 0.2 mL of binding buffer. The final concentration of the labeled antibody in each well was 200 µM. The final concentration of the unlabeled antibody in the competition assay ranged from 500 nM through ten 2-fold dilution steps to a 0 nM buffer-only assay. Competition assays were carried out in triplicate. Competition assays were incubated for 2 hours at room temperature. After the 2-hour incubation, the competition assays were transferred to a Millipore Multiscreen filter plate (Billerica, Mass.) and washed 4 times with binding buffer to separate the free from bound [I$^{125}$] labeled antibody. The filters were counted on a Wallac Wizard 1470 gamma counter (PerkinElmer Life and Analytical Sciences Inc.; Wellesley, Mass.). The binding data was evaluated using NewLigand software (Genentech), which uses the fitting algorithm of Munson and Robard to determine the binding affinity of the antibody (Munson and Robard 1980)

As shown in FIG. 4, YW353 bound to gD-tagged human LgR5 expressed on stably transfected 293 cells with an affinity of 0.2 nM. Ch8E11 bound to gD-tagged human LgR5 and gD-tagged mouse LgR5 expressed on stably transfected 293 cells with affinities of 0.4 nM and 0.2 nM, respectively. Hu8E11v2 bound to gD-tagged human LgR5, gD-tagged mouse LgR5, and gD-tagged rat LgR5 expressed on stably transfected 293 cells with affinities 0.3-0.7 nM, 0.5-0.6 nM, and 2.4-2.8 nM, respectively. These Kd values were generally lower than those determined by BIAcore®.

I. Epitope Mapping

To determine the region of LgR5 bound by each antibody, 293 cells transiently transfected with gD epitope-tagged LgR5 with various N- and/or C-terminal deletions were stained with 10 μg/ml YW353, ch8E11, hu8E11v2, 2H6, or 3G12 antibody; and binding was detected with R-Phycoerythrin conjugated goat anti-human antibody. Antibodies YW353, 8E11, 2H6, and 3G12 all bound to gD epitope-tagged full-length LgR5. Antibodies 2H6 and 3G12 bound to gD epitope-tagged LgR5$_{324-907}$ (amino acids 324-907 of SEQ ID NO: 67). Antibodies YW353 and 8E11 did not bind to gD epitope-tagged LgR5$_{324-907}$. Only antibody YW353 bound to gD epitope-tagged LgR5$_{22-123}$ (amino acids 22-123 of SEQ ID NO: 67) with a C-terminal GPI anchor. Antibodies YW353 and 8E11 both bound to gD epitope-tagged LgR5$_{22-323}$ (amino acids 22-323 of SEQ ID NO: 67) with a C-terminal GPI anchor, but antibodies 2H6 and 3G12 did not. Finally, none of the antibodies bound to gD epitope-tagged LgR5$_{424-907}$ (amino acids 424-907 of SEQ ID NO: 67).

FIG. 4 summarizes those results in the column titled "epitope region." As shown in that figure, antibody YW353 binds to an epitope in the region of amino acids 22 to 123 of SEQ ID NO: 67; antibody 8E11 and its humanized variants bind to an epitope in the region of amino acids 22 to 323 of SEQ ID NO: 67; and antibodies 2H6 and 3G12 bind to an epitope in the region of amino acids 324 to 423 of SEQ ID NO: 67.

J. Production of Anti-LgR5 Antibody Drug Conjugates

For larger scale antibody production, antibodies were produced in CHO cells. Vectors coding for VL and VH were transfected into CHO cells and IgG was purified from cell culture media by protein A affinity chromatography.

Anti-LgR5 Antibody MMAE Conjugates

Anti-LgR5 antibody-drug conjugates (ADCs) were produced by conjugating YW353 (IgG1 heavy chain and kappa light chain sequences shown in SEQ ID NOs: 66 and 65, respectively), hu8E11v2 (IgG1 heavy chain and kappa light chain sequences shown in SEQ ID NOs: 64 and 63, respectively), mu8E11, ch8E11, 2H6, ch2H6, 3G12, and ch3G12 to the drug-linker moiety MC-vc-PAB-MMAE, which is depicted herein. For convenience, the drug-linker moiety MC-vc-PAB-MMAE is sometimes referred to in these Examples and in the Figures as "vcMMAE" or "VCE." Prior to conjugation, the antibodies were partially reduced with TCEP using standard methods in accordance with the methodology described in WO 2004/010957 A2. The partially reduced antibodies were conjugated to the drug-linker moiety using standard methods in accordance with the methodology described, e.g., in Doronina et al. (2003) Nat. Biotechnol. 21:778-784 and US 2005/0238649 A1. Briefly, the partially reduced antibodies were combined with the drug-linker moiety to allow conjugation of the drug-linker moiety to reduced cysteine residues of the antibody. The conjugation reactions were quenched, and the ADCs were purified. The drug load (average number of drug moieties per antibody) for each ADC was determined and was between 3.3 and 4.0 for the anti-LgR5 antibodies. The structure of an antibody-vcMMAE immunoconjugate is shown in FIG. 35A (p=drug load).

Anti-LgR5 Antibody PNU Conjugates

Anti-LgR5 antibody-PNU drug conjugates (ADCs) were produced by conjugating YW353 A118C thioMab (IgG1 A118C heavy chain and kappa light chain sequences shown in SEQ ID NOs: 78 and 65, respectively) or hu8E11v2 thioMab (IgG1 A118C heavy chain and kappa light chain sequences shown in SEQ ID NOs: 75 and 63, respectively) to PNU drug-linker moieties. Prior to conjugation, the antibody was reduced with dithiothreitol (DTT) to remove blocking groups (e.g. cysteine) from the engineered cysteines of the thio-antibody. This process also reduces the interchain disulfide bonds of the antibody. The reduced antibody was purified to remove the released blocking groups and the interchain disulfides were reoxidized using dehydro-ascorbic acid (dhAA).

For antibody-drug conjugates comprising a val-cit linker and PNU, the intact antibody was combined with the drug-linker moiety MC-val-cit-PAB-spacer-PNU-159682 ("val-cit" may also be referred to herein as "vc") to allow conjugation of the drug-linker moiety to the engineered cysteine residues of the antibody. The conjugation reaction was quenched by adding excess N-acetyl-cysteine to react with any free linker-drug moiety, and the ADC was purified. The drug load (average number of drug moieties per antibody) for the ADC was in the range of about 1.8 to 2. The structure of an antibody-vcPNU immunoconjugate is shown in FIG. 35B (p=drug load).

For antibody drug conjugates comprising an acetal linker and PNU, the intact antibody was combined with the drug-linker moiety MC-acetal-PNU-159682 to allow conjugation of the drug-linker moiety to the engineered cysteine residues of the antibody. The conjugation reaction was quenched by adding excess N-acetyl-cysteine to react with any free linker-drug moiety, and the ADC was purified. The drug load (average number of drug moieties per antibody) for the ADC was about 1.8 to 2. The structure of an antibody-acetal-PNU immunoconjugate is shown in FIG. 35C (p=drug load).

For antibody drug conjugates comprising a noncleavable linker and PNU, the intact antibody was combined with the drug-linker moiety MC-PNU-159682 to allow conjugation of the drug-linker moiety to the engineered cysteine residues of the antibody. The conjugation reaction was quenched by adding excess N-acetyl-cysteine to react with any free linker-drug moiety, and the ADC was purified. The drug load (average number of drug moieties per antibody) for the ADC was about 1.8 to 2. The structure of an antibody-PNU immunoconjugate is shown in FIG. 35D (p=drug load).

Anti-LgR5 Antibody PBD Conjugate

Anti-LgR5 antibody-PBD drug conjugates (ADCs) were produced by conjugating YW353 A118C thioMab (IgG1 A118C heavy chain and kappa light chain sequences shown in SEQ ID NOs: 78 and 65, respectively) or hu8E11v2 thioMab (IgG1 A118C heavy chain and kappa light chain sequences shown in SEQ ID NOs: 75 and 63, respectively) to PBD drug-linker moieties. Prior to conjugation, the antibody was reduced with dithiothreitol (DTT) to remove blocking groups (e.g. cysteine) from the engineered cysteines of the thio-antibody. This process also reduces the interchain disulfide bonds of the antibody. The reduced antibody was purified to remove the released blocking groups and the interchain disulfides were reoxidized using dehydro-ascorbic acid (dhAA).

For antibody-drug conjugates comprising a val-cit linker and PBD, the intact antibody was combined with the drug-linker moiety MC-val-cit-PAB-PBD ("val-cit" may also be referred to herein as "vc") to allow conjugation of the drug-linker moiety to the engineered cysteine residues of the antibody. The conjugation reaction was quenched by adding excess N-acetyl-cysteine to react with any free linker-drug moiety, and the ADC was purified. The drug load (average number of drug moieties per antibody) for the ADC was in the range of about 1.8 to 2. The structure of an antibody-vcPBD is shown in FIG. 35E (p=drug load).

K. Toxicity of Anti-LgR5 Antibody Drug Conjugate in Rats

In order to evaluate potential toxicity of anti-LgR5 antibody 8E11.v2-vcMMAE, six male Sprague-Dawley rats were administered 12 mg/kg 8E11.v2-vcMMAE once per week for four weeks, and six male Sprague-Dawley rats were administered 20 mg/kg 8E11.v2-vcMMAE once per week for two weeks. Four male Sprague-Dawley control rats were administered vehicle alone once per week for two weeks, and four male Sprague-Dawley control rats were administered vehicle alone once per week for four weeks. The rats in the two-week groups were necropsied on day 12 and the rats in the four-week groups were necropsied on day 26.

Briefly, all rats administered 8E11.v2-vcMMAE showed reduced red cell mass (red blood cells, hematocrit, hemoglobin, and reticulocytes), neutrophils, and platelets compared to control rats. Rats administered 20 mg/kg 8E11.v2-vcMMAE also showed reduced white blood cell count and lymphocytes compared to control rats. In addition, all rats administered 8E11.v2-vcMMAE showed increases in liver enzymes ALT, AST, ALP, and GGT, and increased total billirubin compared to control rats.

Histopathologic analysis of tissues collected from the study showed cellular depletion of lymphoid and hemopoietic tissues in rats administered 8E11.v2-vcMMAE, as well as increased mitotic figures in rapidly dividing tissues. Rats administered 20 mg/kg 8E11.v2-vcMMAE also showed minimal liver necrosis, minimal increased mitotic figures and single cell cryptal necrosis/apoptosis, and minimal mild alveolar histiocytosis and type II cell hyperplasia.

The pathology changes observed were similar to pathology observed in rats administered other vcMMAE antibody-drug conjugates. There did not appear to be any evidence of LgR5 antigen-dependent toxicity in the GI tract.

L. Efficacy of Anti-LgR5 Antibody Drug Conjugates in LoVo Colon Cancer Cell Line Xenograft The efficacy of the anti-LgR5 ADCs was investigated using a LoVo colon cancer xenograft model. LoVo cells are a colorectal adenocarcinoma cell line with an APC mutation (ATCC # CCL 229). LgR5 is highly expressed in LoVo cells, and was confirmed by microarray, TaqMan® quantitative RT-PCR, in situ hybridization, FACS, and Western blot. Five million LoVo cells (LgR5-positive by FACS using YW353) in HBSS-matrigel were injected subcutaneously into the dorsal flank of NCR nude mice and six days post-inoculation mice were given a single intravenous injection of 5 mg/kg murine anti-gp120-vcMMAE control antibody-drug conjugate, human anti-gD 5B6-vcMMAE control antibody-drug conjugate, huYW353-vcMMAE antibody-drug conjugate, mu8E11-vcMMAE antibody-drug conjugate, mu2H6-vcMMAE antibody-drug conjugate, or mu3G12-vcMMAE antibody-drug conjugate; or with vehicle (PBS) alone. The presence of the antibodies was confirmed by PK bleeds one day post injection.

Figure 13:
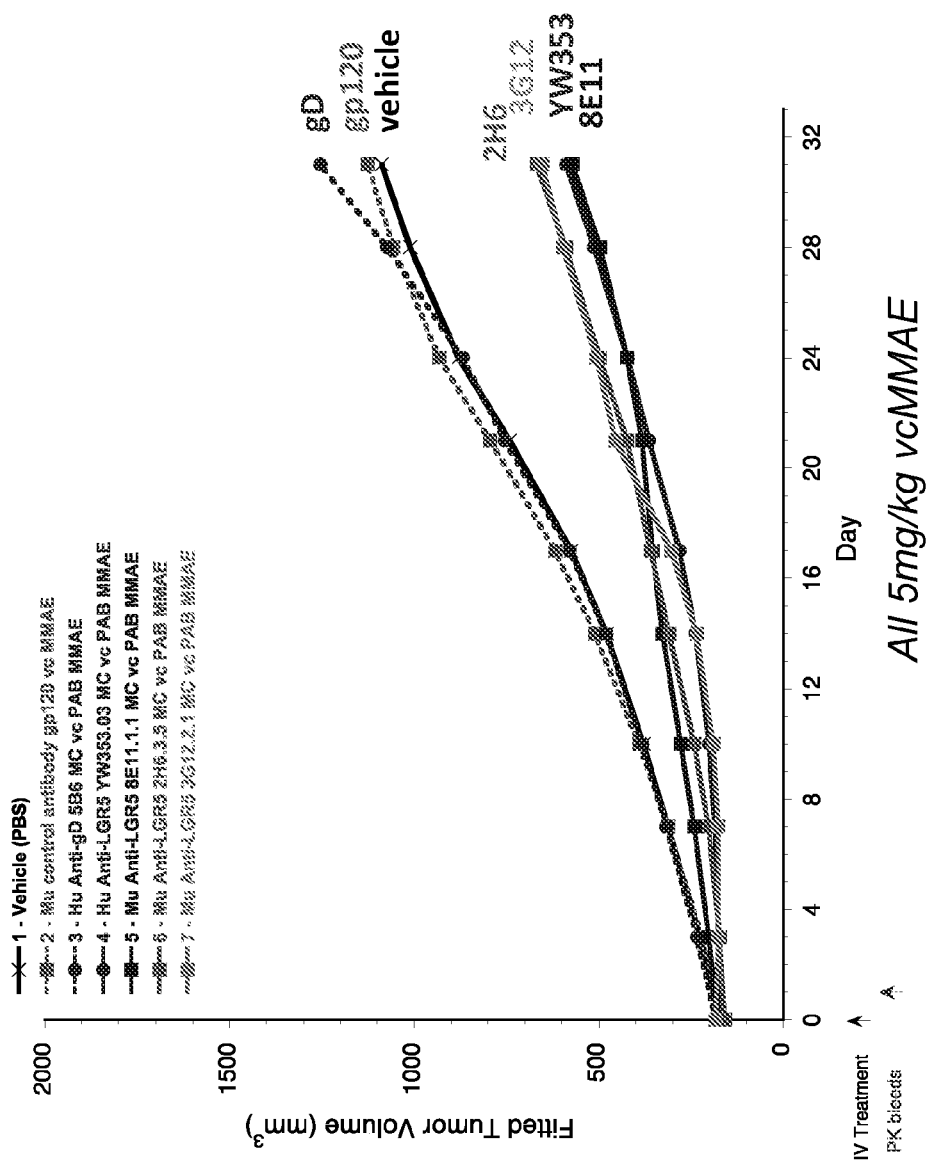
FIG. 13 shows that anti-LgR5 immunoconjugates demonstrate efficacy in LoVo colon cancer xenografts, as described in Example L.

As shown in FIG. 13, substantial tumor growth inhibition was achieved with all four anti-LgR5 antibody-drug conjugates tested.

M. Efficacy of Anti-LgR5 Antibody Drug Conjugates in D5124 Pancreatic Cancer Xenograft The efficacy of the anti-LgR5 ADCs was investigated using a D5124 pancreatic cancer xenograft model, which has a β-catenin mutation. LgR5 is highly expressed in D5124 tumors, and was confirmed by microarray, TaqMan® quantitative RT-PCR, in situ hybridization, FACS, and Western blot. Twenty to 30 mm$^3$ D5124 tumor fragments (LgR5-positive by FACS using YW353 and 8E11) were implanted subcutaneously into the dorsal flank area of NCR nude mice and 18 days post-transplantation the mice were given a single intravenous injection of 6 mg/kg human anti-gD 5B6-vcMMAE control antibody-drug conjugate, 3 mg/kg or 6 mg/kg huYW353-vcMMAE antibody-drug conjugate, 3 mg/kg or 6 mg/kg ch8E11-vcMMAE antibody-drug conjugate, 3 mg/kg or 6 mg/kg ch2H6-vcMMAE antibody-drug conjugate, or 3 mg/kg or 6 mg/kg ch3G12-vcMMAE antibody-drug conjugate; or with vehicle (histidine buffer: 20 mM histidine acetate, 240 mM sucrose, 0.02% Tween 20, pH5.5; "HB#8" in FIG. 14) alone. The presence of the antibodies was confirmed by PK bleeds one and eight days post injection.

Figure 14:
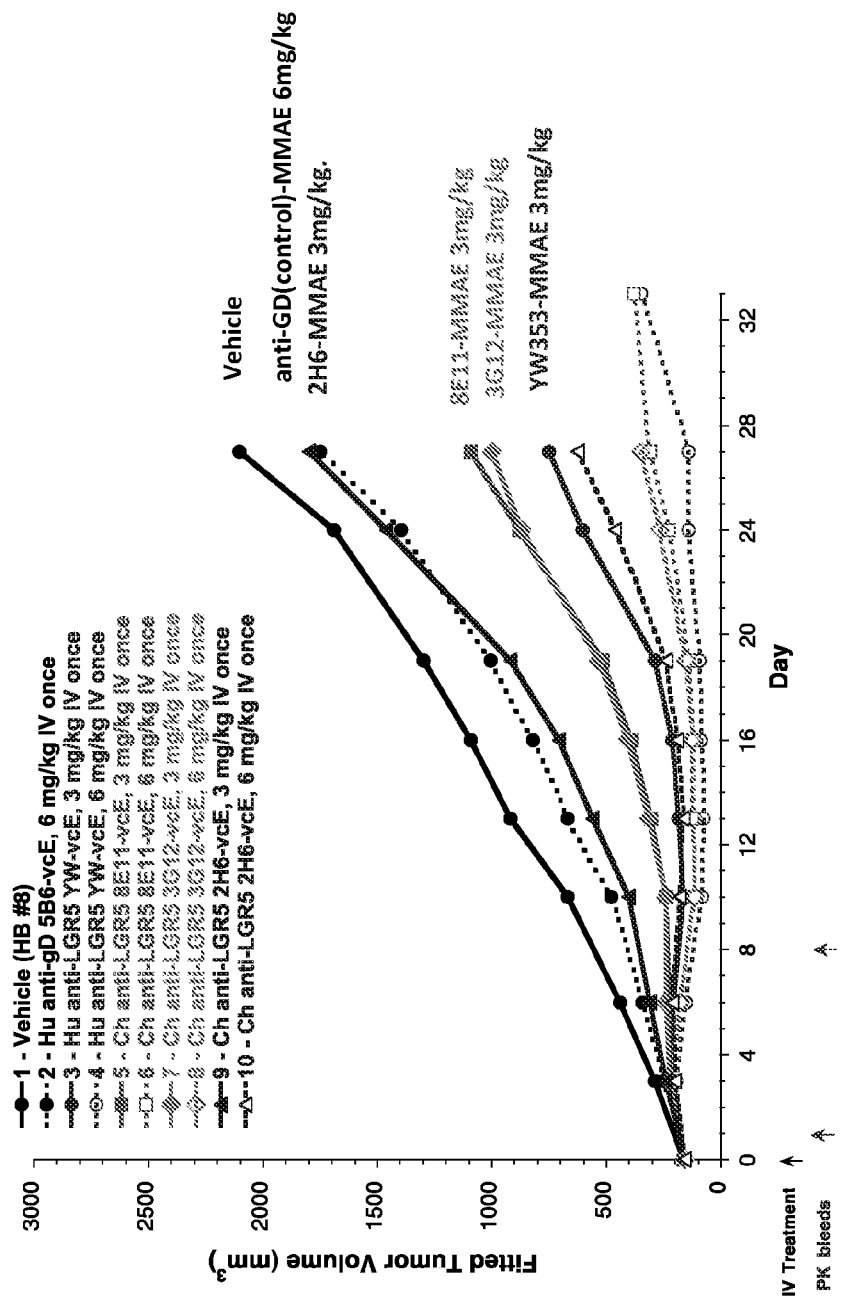
FIG. 14 shows that anti-LgR5 immunoconjugates demonstrate efficacy in D5124 pancreatic cancer xenografts, as described in Example M.

As shown in FIG. 14, substantial tumor growth inhibition was achieved at both doses of huYW353-vcMMAE, ch8E11-vcMMAE, and ch3G12-vcMMAE. Substantial tumor growth inhibition was also achieved at 6 mg/kg ch2H6-vcMMAE.

The efficacy of various doses of YW353-vcMMAE was then tested in the D5124 pancreatic cancer xenograft model described above. Twenty to 30 mm$^3$ D5124 tumor fragments (LgR5-positive by FACS using YW353 and 8E11) were implanted subcutaneously into the dorsal flank area of NCR nude mice and 23 days post-transplantation mice were given a single intravenous injection of 0.5 mg/kg, 1 mg/kg, 3 mg/kg, 6 mg/kg, or 12 mg/kg huYW353-vcMMAE antibody-drug conjugate; or 12 mg/kg huYW353; or 7.2 mg/kg or 14.4 mg/kg human anti-gD 5B6-vcMMAE control antibody-drug conjugate; or vehicle (histidine buffer: 20 mM histidine acetate, 240 mM sucrose, 0.02% Tween 20, pH5.5; "HB#8" in FIG. 15) alone. The presence of the antibodies was confirmed by PK bleeds one, four, and 14 days post injection.

Figure 15:
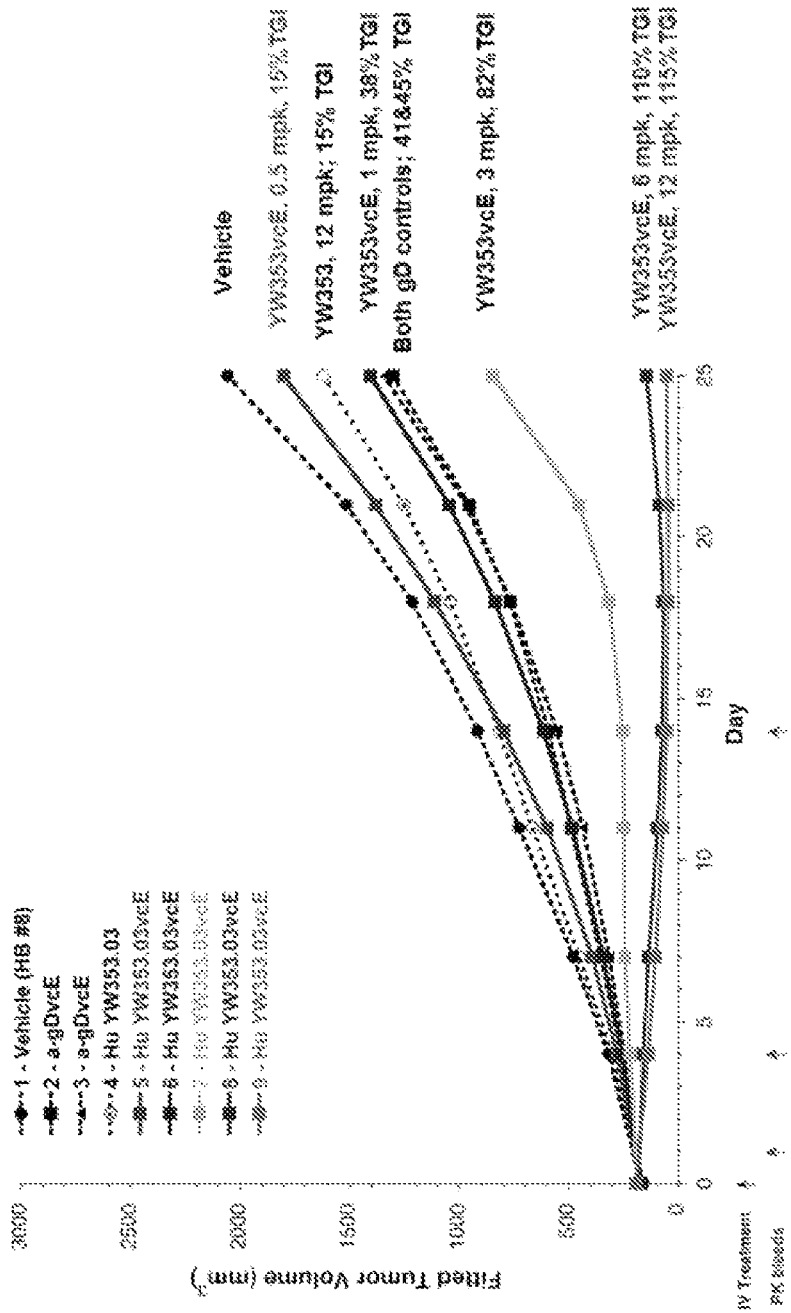
FIG. 15 shows that huYW353-vcMMAE immunoconjugate demonstrates efficacy at 3, 6, and 12 mg/kg in D5124 pancreatic cancer xenografts, as described in Example M.

As shown in FIG. 15, substantial tumor growth inhibition was achieved at 3 mg/kg huYW353-vcMMAE, and almost complete tumor growth inhibition was achieved at 6 mg/kg and 12 mg/kg huYW353-vcMMAE.

Figure 16:
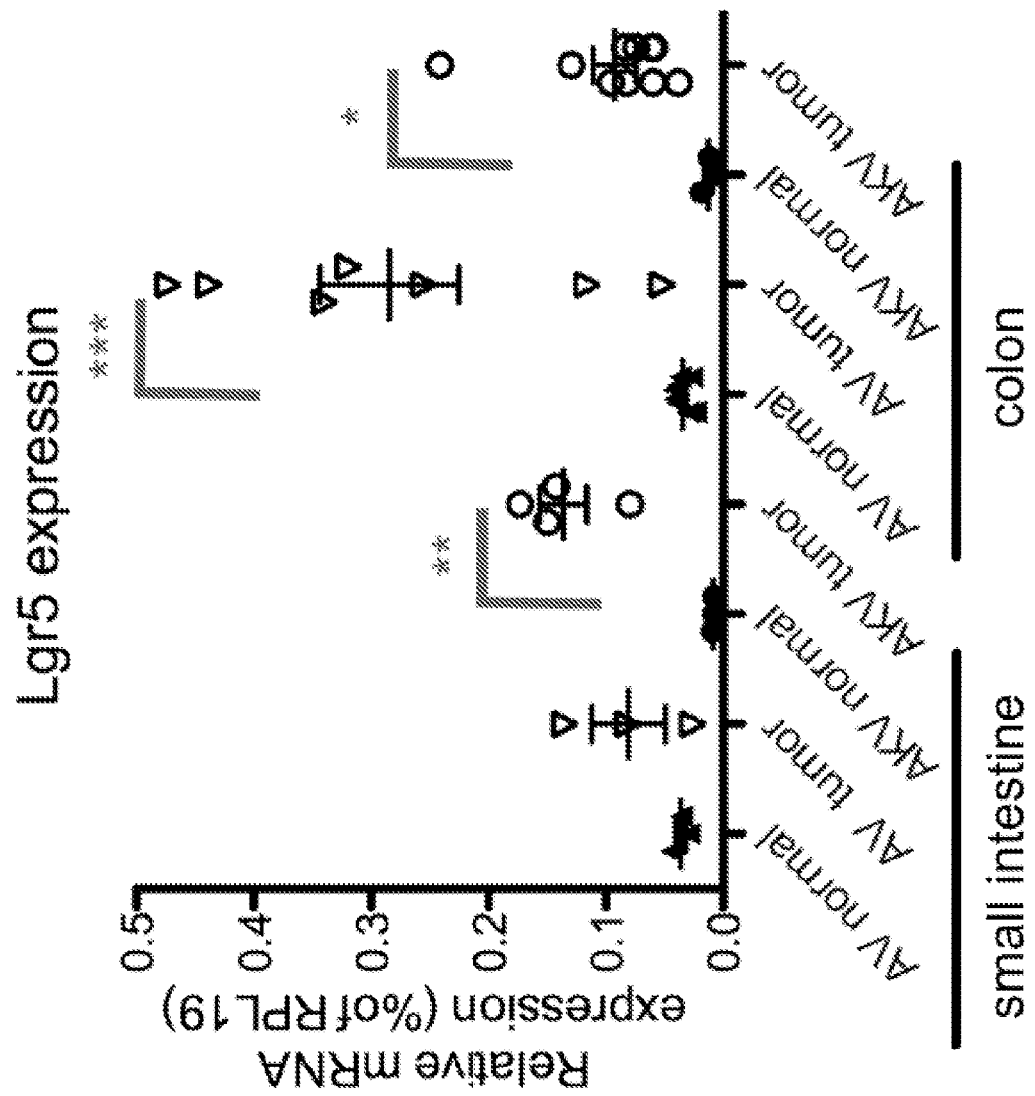
FIG. 16 shows LgR5 mRNA expression in normal tissue and polyps from colons of AV and AKV mice, as described in Example N.
Figure 20:
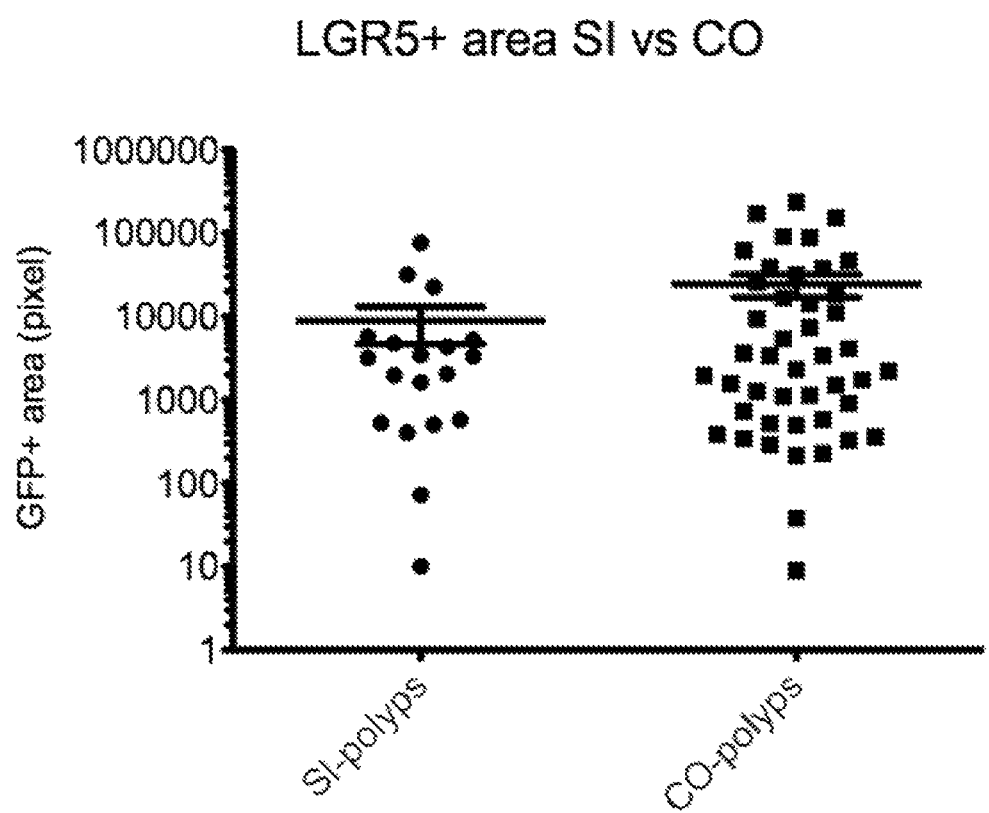
FIG. 20 shows LgR5+ area in small intestine polyps and colon polyps in AKV LgR5$^{DTR/+}$ mice, as described in Example N.

N. Efficacy of Mu8E11 and Mu8E11-vcMMAE in Murine Intestinal Tumorigenesis Model The efficacy of mu8E11 and mu8E11-vcMMAE was investigated in a murine intestinal tumorigenesis model, APC$^{min/+}$; LSL-Kras$^{G12D}$; VillinCre ("AKV mice"). AKV mice are the result of crossing APC$^{min/+}$; VillinCre ("AV mice") with LSL-Kras$^{G12D}$ mice. While AV mice develop 0-4 adenomas in the colon and 100 adenomas in the small intestine, AKV mice develop an average of 140 adenomas in the colon and 100 adenomas in the small intestine (data not shown). LgR5 mRNA expression was measured in normal tissue and polyps of AV and AKV mice, and LgR5 was found to be significantly overexpressed in polyps from both the small intestine and colon in AKV mice (FIG. 16). To visualize expression of LgR5 in the small intestine and colon of AKV mice, AKV mice were crossed with mice having a cassette containing an enhanced green fluorescent protein (EGFP) linked in frame to human diphtheria toxin receptor cDNA located in the Lgr5 gene. See Tian et al., *Nature*, 478: 255-260 (2011). The area of EGFP expression in small intestine polyps and large intestine polyps were visualized in the AKV Lgr5$^{DTR/+}$ mice. The results of that experiment are shown in FIG. 20. It was found that LgR5 expression did not significantly differ between small intestine polyps and colon polyps, and further, there was no correlation between tumor size and LgR5+ area. The mean LgR5+ area of the tumors was 8%, but varied widely between tumors. Preliminary results show that the LgR5+ area in colorectal tumors of humans may be significantly higher than in mice, suggesting that the therapeutic index of anti-LgR5 ADC therapy in humans may be even better than in mice.

Figure 23:
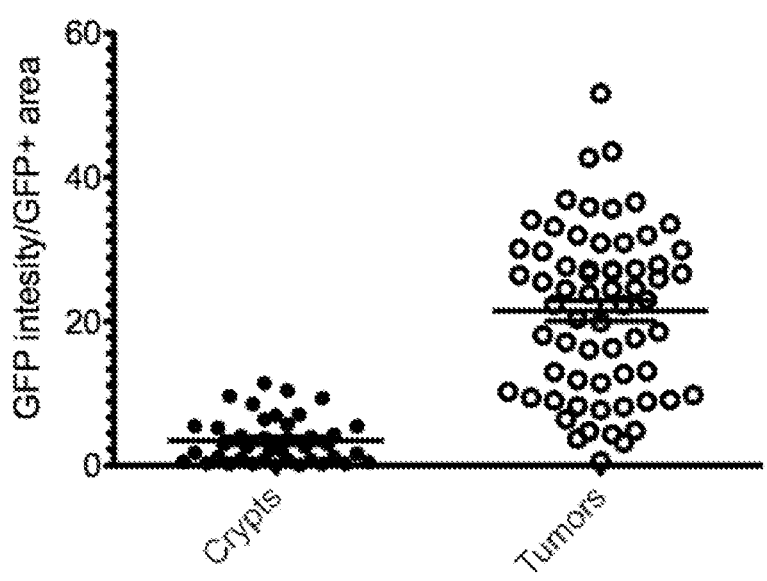
FIG. 23 shows the ratio of GFP intensity to GFP+ area in crypts and tumors of AKV LgR5$^{DTR/+}$ mice, as described in Example N.

To assess Lgr5 expression differences between intestinal crypts and tumors within these animals, intestinal tracts from AKV Lgr5$^{DTR/+}$ mice were obtained and direct visualization of GFP was performed on tissue sections. Tumors and normal crypts were thereafter quantitated for the intensity of each GFP positive pixel. To determine relative GFP intensity, the intensity score is divided by the GFP+ area. As shown in FIG. 23, LgR5 expression is higher in tumors than in intestinal crypts in of AKV Lgr5$^{DTR/+}$ mice.

An overall survival study was carried out with AKV mice to determine whether anti-LgR5 antibody can increase survival. Ten AKV mice were administered 15 mg/kg mu8E11-MC-vc-PAB-MMAE; six AKV mice were administered 15 mg/kg mu8E11, and 9 mice were administered 15 mg/kg control antibody anti-gp120-MC-vc-MMAE. The antibodies and ADCs were administered weekly beginning at 6 weeks of age until the mice either died or were deemed moribund (as determined by standard criteria related to signs of severe lethargy, weight loss and anemia), in which case the mice were sacrificed.

Figure 17:
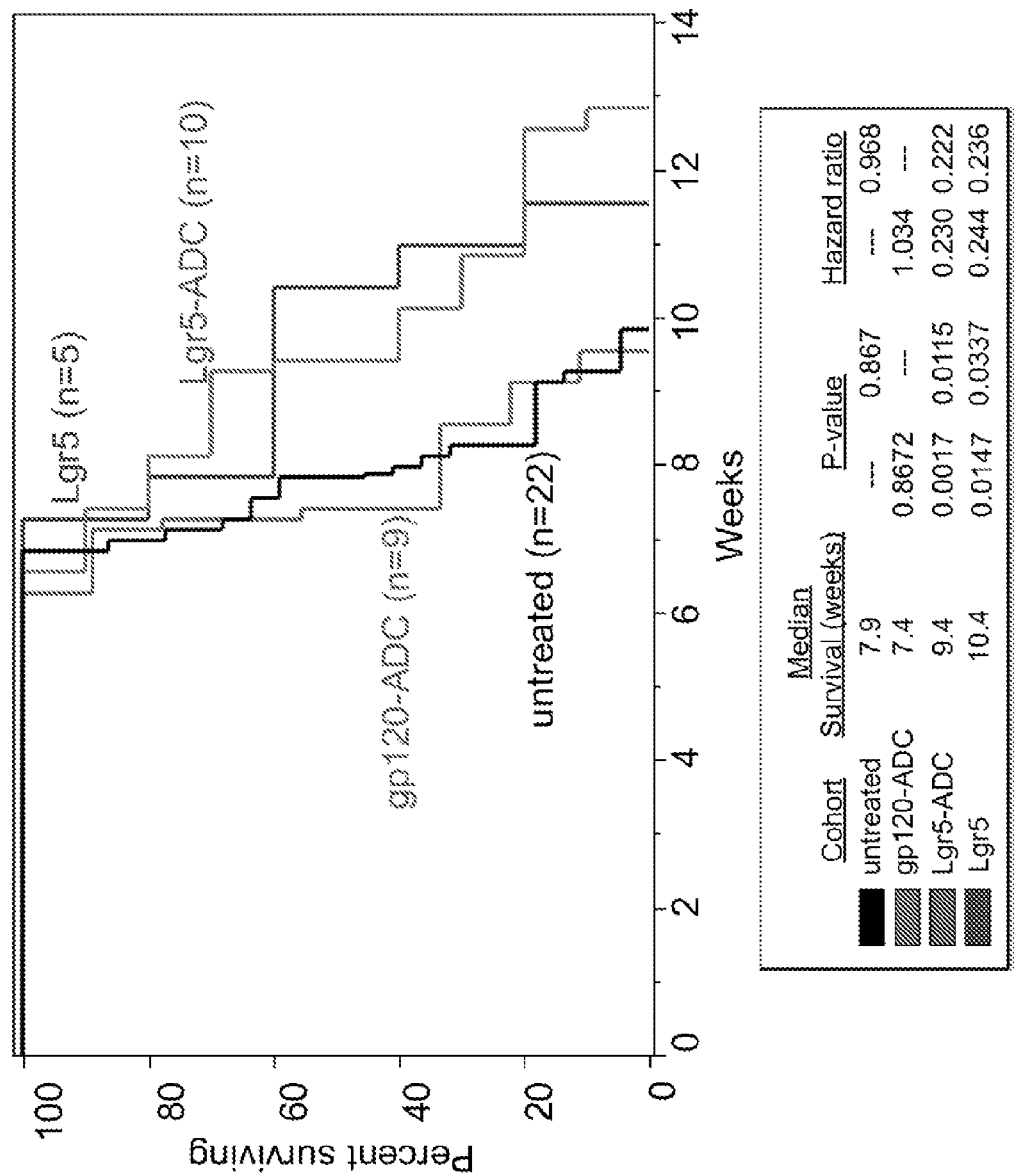
FIG. 17 shows survival of AKV mice administered anti-LgR5 antibody and anti-LgR5 antibody-drug conjugate have longer survival times than control AKV mice, as described in Example N.
Figure 19:
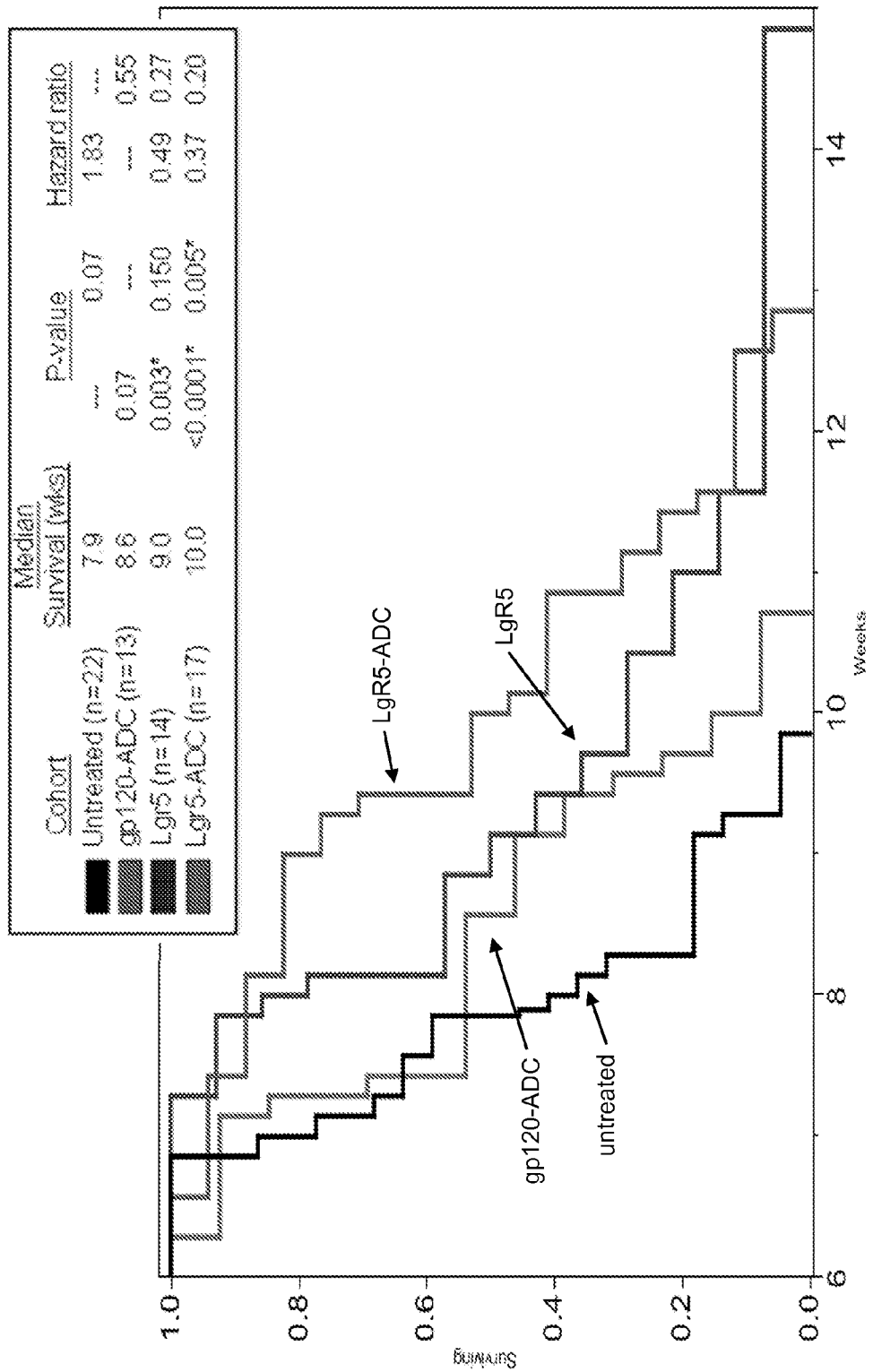
FIG. 19 shows AKV mice administered anti-LgR5 antibody-drug conjugate have longer survival times than untreated AKV mice and AKV mice administered gp120-ADC or anti-LgR5, as described in Example N.

The results of the overall survival study are shown in FIG. 17. The untreated control data represents historical survival rates for 22 AKV mice. In that experiment, AKV mice administered either mu8E11 or mu8E11-MC-vc-PAB-MMAE had significantly longer survival times than untreated AKV mice or AKV mice administered a control ADC. Based on these results, additional animals were evaluated as described above. The results of that experiment are shown in FIG. 19. In the larger experiment, AKV mice administered mu8E11-MC-vc-PAB-MMAE had significantly longer survival times than untreated AKV mice or AKV mice administered a control ADC, and also had a longer survival time than mice administered mu8E11. At the time of death, the AKV mice administered control ADC and anti-LgR5-ADC had similar numbers and sizes of polyps, suggesting that anti-LgR5-ADC may slow the disease and thereby extend survival.

In order to determine whether anti-LgR5 antibody and/or anti-LgR5 ADC caused apoptosis in the gastrointestinal tumors of AKV mice, the presence of cleaved caspase 3 was measured as a function of tumor area. Formalin fixed paraffin embedded (FFPE) small intestine and colon tissue collected at time of death were subjected to immunohistochemical staining for cleaved caspase 3 (Cell Signaling Technologies; Danvers, Mass., cat#9661L). Images of the stained slides were acquired by the Olympus Nanozoomer automated slide scanning platform and manually identified tumor-specific areas were analyzed in the Matlab software package (Mathworks, Natick, Mass.). Positively stained area and total tumor area were quantified. Although rare, cleaved caspase 3 was visible in the crypts following treatment with anti-LgR5 ADC, but was not observed in control ADC treated animals, suggesting that LgR5-expressing cells are being specifically targeted.

Figure 18:
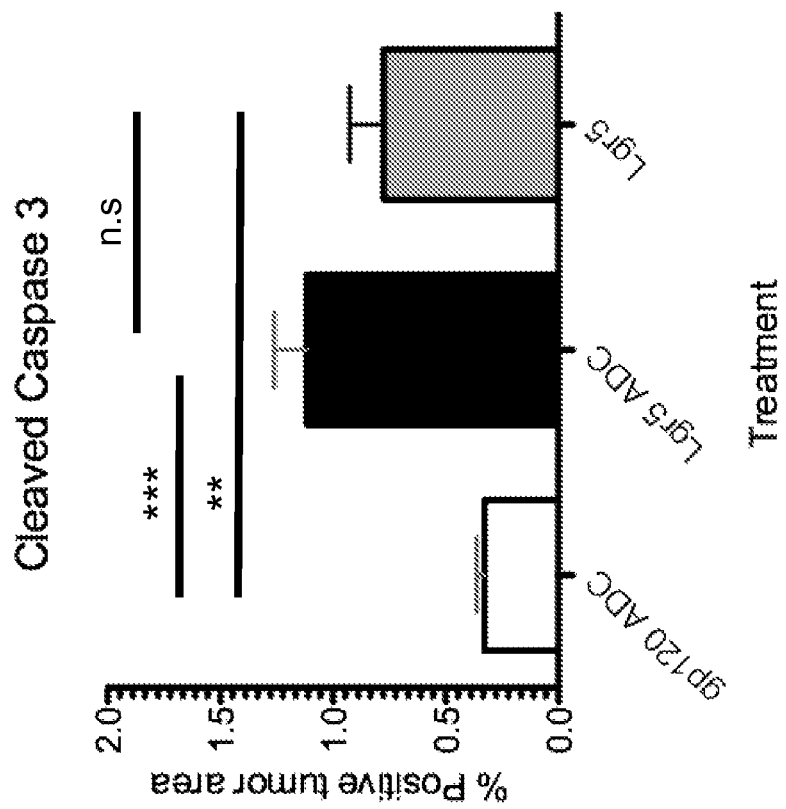
FIG. 18 shows percentage of tumor area that is positive for cleaved caspase 3 in AKV mice administered a control ADC, an anti-LgR5 ADC, or an anti-LgR5 antibody, as described in Example N.

The results of that experiment are shown in FIG. 18. Both anti-LgR5 antibody and anti-LgR5 ADC administration caused a statistically significant increase in the percentage of tumor area in AKV mice that was positive for the presence of cleaved caspase 3, compared to control ADC-treated AKV mice.

Figure 21:
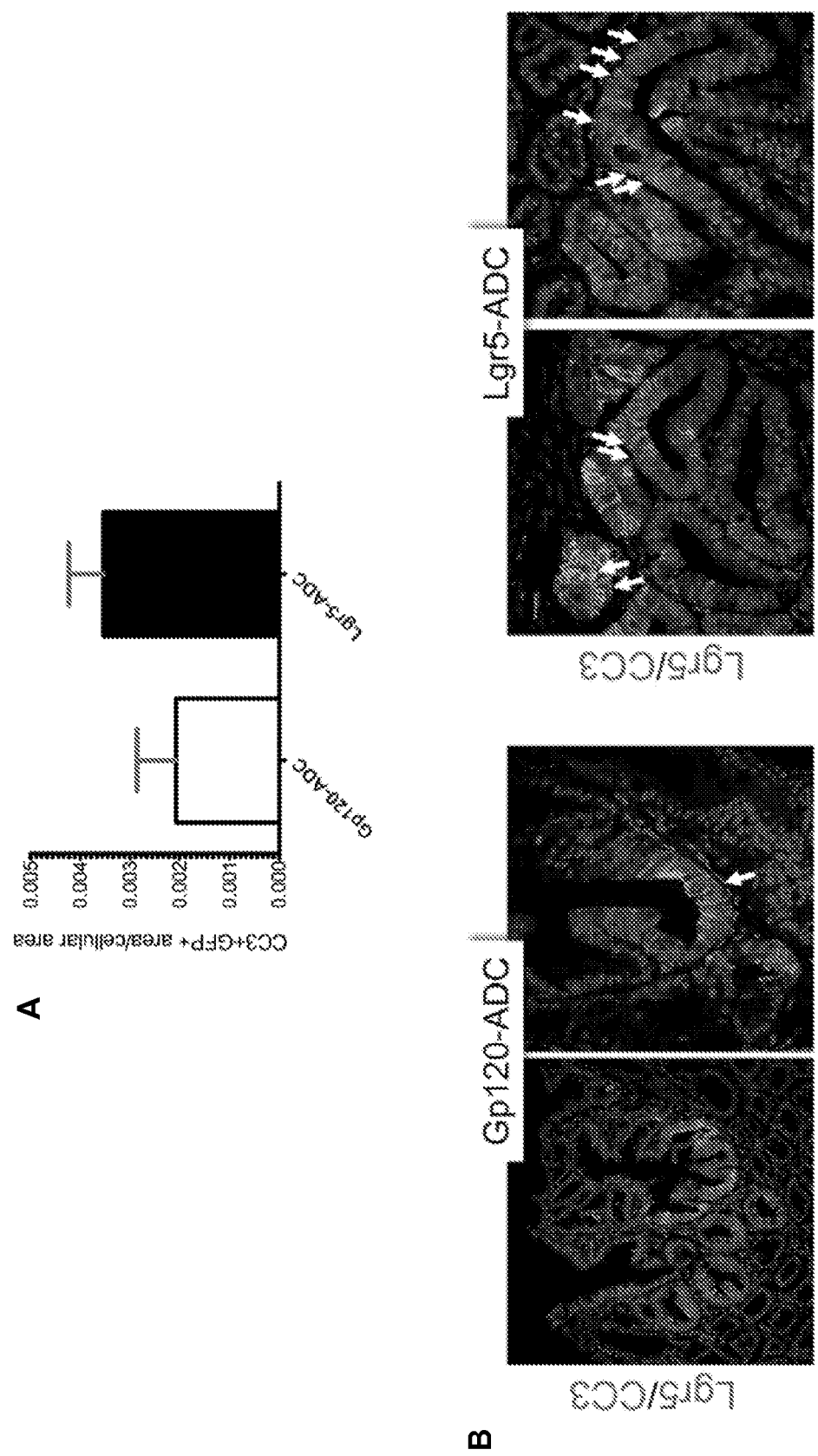
FIG. 21 shows (A) CC3+GFP+ area per cellular area in control ADC and anti-LgR5-ADC treated AKV LgR5$^{DTR/+}$ mice, and (B) exemplary immunohistochemistry staining in the control ADC and anti-LgR5-ADC treated AKV LgR5$^{DTR/+}$ mice, as described in Example N.

In order to demonstrate that the apoptosis is occurring in LgR5+cells, AKV Lgr5$^{DTR/+}$ mice were administered 15 mg/kg mu8E11-MC-vc-PAB-MMAE or 15 mg/kg control antibody anti-gp120-MC-vc-MMAE (day 1). On day 4, the mice were sacrificed and tumors from the gastrointestinal tract (small and large intestine) were visualized for expression of EGFP and cleaved caspase 3. The amount of CC3+ GFP+ area per total cellular area was then determined. As shown in FIG. 21A, anti-LgR5-ADC treated mice tended to have a greater proportion of CC3+GFP+ area than control treated mice, although not statistically significant in that experiment. FIG. 21B shows exemplary immunohistochemical staining from control ADC treated mice (left panels) and anti-LgR5-ADC treated mice (right panels). These results demonstrate a trend towards increased apoptosis in LgR5-expressing cells upon anti-LgR5-ADC treatment.

Figure 22:
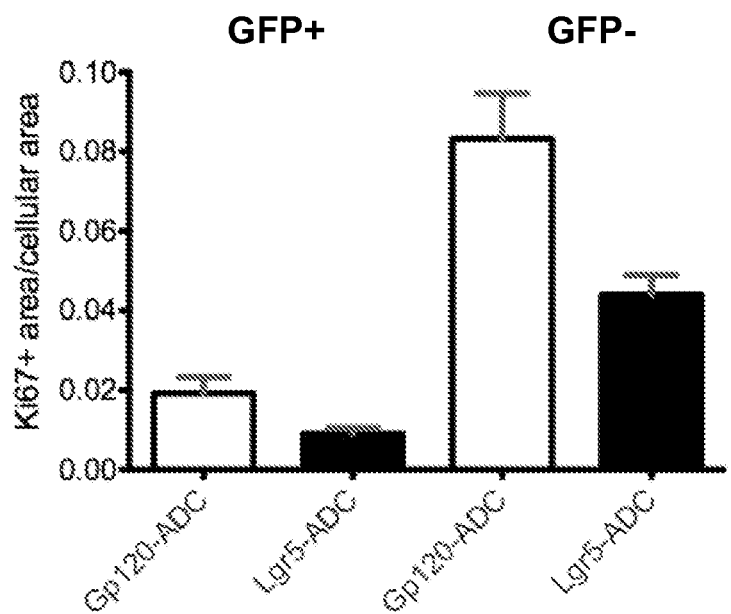
FIG. 22 shows Ki67+ area per cellular area (either GFP+ cells or GFP− cells) in control ADC and anti-LgR5-ADC treated AKV LgR5$^{DTR/+}$ mice, as described in Example N.

To determine whether cell proliferation of LgR5 expressing cells is affected by anti-LgR5 treatment, the Ki67+ area per cellular area was measured in the EGFP+ cell population and EGFP− cell population from the gastrointestinal tract of control-ADC treated and anti-LgR5-ADC treated AKV Lgr5$^{DTR/+}$ mice. Ki67 is a nuclear protein associated with cellular proliferation. Ki67 antibodies for immunohistochemical staining were obtained from Neomarker. The results of that experiment are shown in FIG. 22. There was significantly less proliferating cell area, as measured by Ki67 staining, in tumors from AKV Lgr5$^{DTR/+}$ mice treated with anti-LgR5-ADC than control ADC, in both the GFP+ and GFP− cell populations. These results suggest that anti-LgR5-ADC reduces proliferation and/or inhibits formation of proliferative progeny.

O. Efficacy of Anti-LgR5 Antibody Drug Conjugates in D5124 Pancreatic Cancer Xenograft The efficacy of the anti-LgR5 ADCs was investigated using a D5124 pancreatic cancer xenograft model, which has a β-catenin mutation. LgR5 is highly expressed in D5124 tumors, and was confirmed by microarray, TaqMan® quantitative RT-PCR, in situ hybridization, FACS, and Western blot. Twenty to 30 mm³ D5124 tumor fragments were implanted subcutaneously into the dorsal flank area of NCR nude mice and 22 days post-transplantation the mice were given a single intravenous injection of 2.62 mg/kg or 5.23 mg/kg huYW353-vcMMAE antibody-drug conjugate, 3 mg/kg or 6 mg/kg ch8E11-vcMMAE antibody-drug conjugate, or 3 mg/kg or 6 mg/kg hu8E11v2-vcMMAE antibody-drug conjugate; or 6 mg/kg humanized anti-gD 5B6-vcMMAE control antibody-drug conjugate; or with vehicle (histidine buffer: 20 mM histidine acetate, 240 mM sucrose, 0.02% Tween 20, pH5.5) alone (n=8 mice per group). The presence of the antibodies was confirmed by PK bleeds one and eight days post injection.

Figure 24:
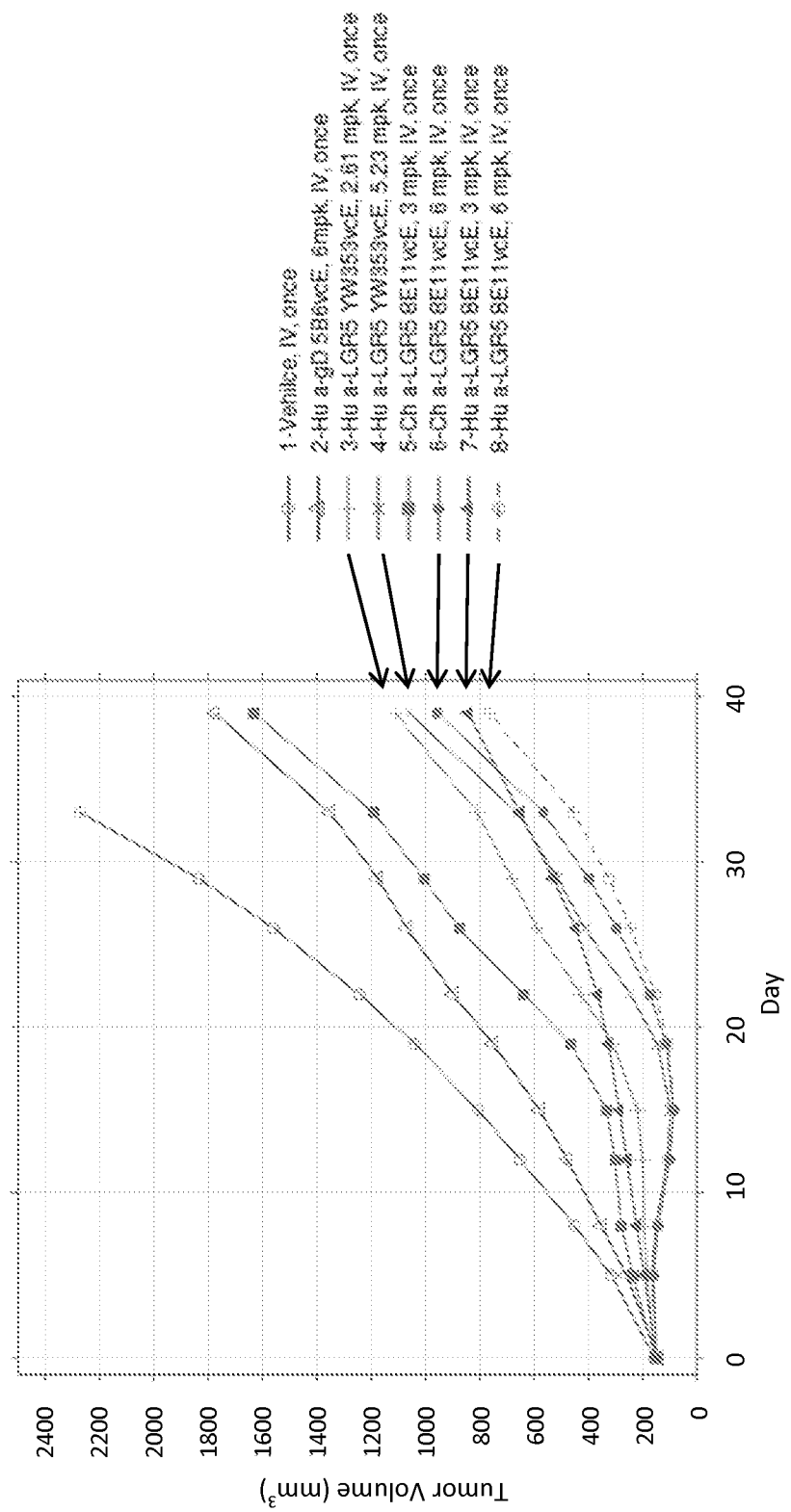
FIG. 24 shows that huYW353-vcMMAE, hu8E11v2-vcMMAE, and ch8E11-vcMMAE immunoconjugate demonstrates efficacy in D5124 pancreatic cancer xenografts, as described in Example O.

As shown in FIG. 24, substantial tumor growth inhibition was achieved at both doses of huYW353-vcMMAE, both doses of hu8E11v2-vcMMAE, and 6 mg/kg ch8E11v2-vcMMAE.

The efficacy of various doses of hu8E11v2-vcMMAE antibody-drug conjugate was then tested in the D5124 pancreatic cancer xenograft model described above. Twenty to 30 mm³ D5124 tumor fragments were implanted subcutaneously into the dorsal flank area of NCR nude mice and 26 days post-transplantation mice were given a single intravenous injection of 0.5 mg/kg, 1 mg/kg, 3 mg/kg, 6 mg/kg, or 12 mg/kg hu8E11v2-vcMMAE antibody-drug conjugate; or 15 mg/kg hu8E11v2; or 6.37 mg/kg or 12.73 mg/kg human anti-gD 5B6-vcMMAE control antibody-drug conjugate; or 15 mg/kg humanized anti-gD control antibody; or vehicle (histidine buffer: 20 mM histidine acetate, 240 mM sucrose, 0.02% Tween 20, pH5.5) alone (n=8 mice per group).

Figure 25:
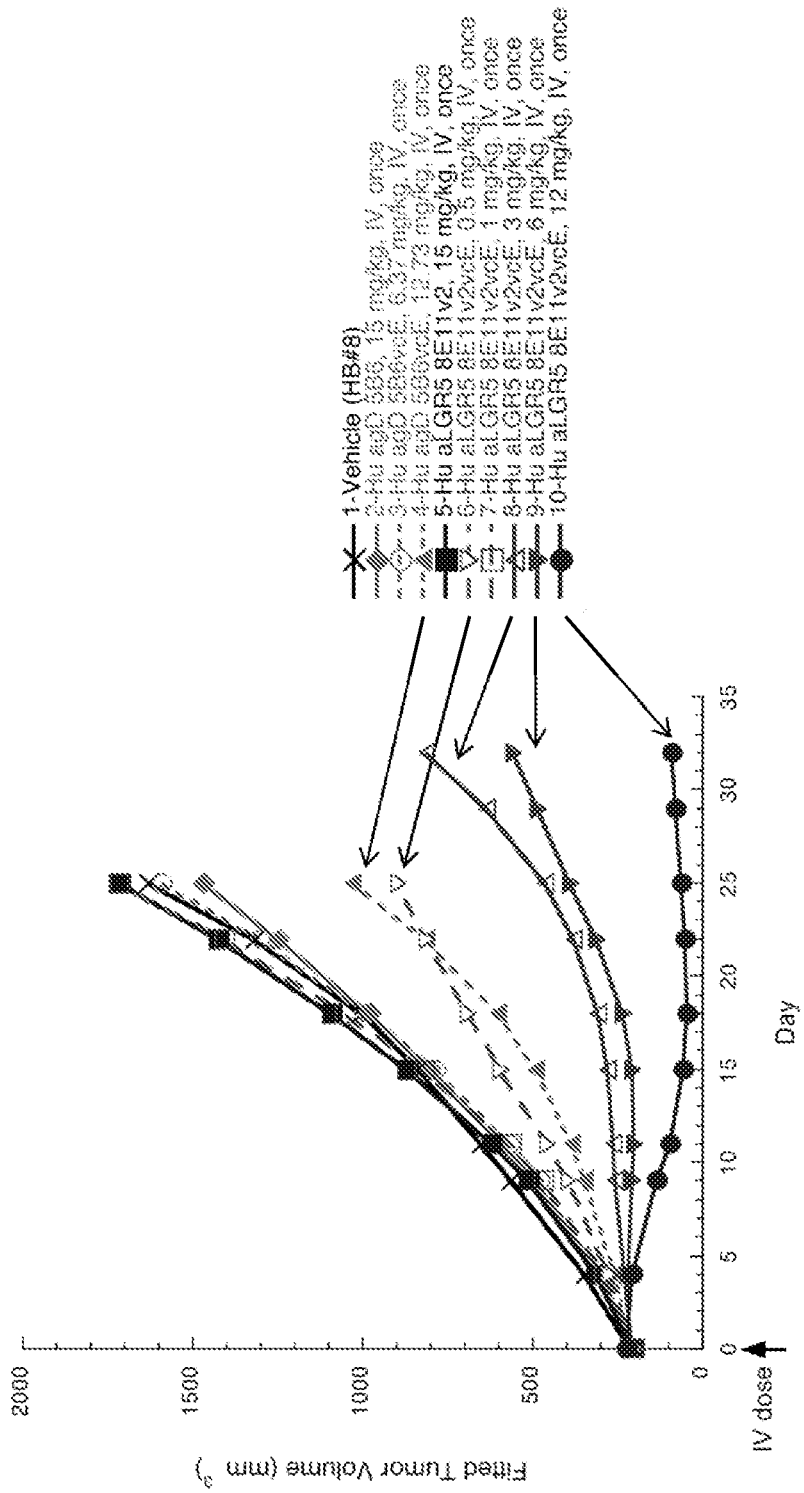
FIG. 25 shows that hu8E11v2-vcMMAE immunoconjugate demonstrates efficacy in D5124 pancreatic cancer xenografts, as described in Example O.

As shown in FIG. 25, substantial tumor growth inhibition was achieved at 3 mg/kg and 6 mg/kg hu8E11v2-vcMMAE, and tumor regression was achieved at 12 mg/kg hu8E11v2-vcMMAE.

P. Efficacy of Anti-LgR5 Antibody Drug Conjugates in LoVoX1.1 Colon Cancer Cell Line Xenograft The efficacy of the anti-LgR5 ADCs was investigated using a LoVo colon cancer xenograft model. LoVo cells are a colorectal adenocarcinoma cell line with an APC mutation (ATCC # CCL 229), and subline LoVoX1.1 was derived for optimal growth in mice. Briefly, mice were inoculated with LoVo cells. Once tumors were growing, a tumor with a desirable growth rate was harvested. The tumor was minced and grown in culture to establish cell line LoVoX1.1. LgR5 is expressed in LoVoX1.1 cells, and was confirmed by microarray, TaqMan® quantitative RT-PCR, in situ hybridization, FACS, and Western blot. Five million LoVoX1.1 cells in HBSS-matrigel were injected subcutaneously into the dorsal flank of C.B-17 SCID mice and 13 days post-inoculation mice were given a single intravenous injection of 3 mg/kg or 6 mg/kg huYW353-vcMMAE antibody-drug conjugate, 3 mg/kg or 6 mg/kg hu8E11v2-vcMMAE antibody-drug conjugate; 15 mg/kg hu8E11v2 antibody; 15 mg/kg humanized anti-gD 5B6 control antibody; or 6 mg/kg humanized anti-gD 5B6-vcMMAE control antibody-drug conjugate; or with vehicle (histidine buffer: 20 mM histidine acetate, 240 mM sucrose, 0.02% Tween 20, pH5.5) alone (n=10 mice per group).

Figure 26:
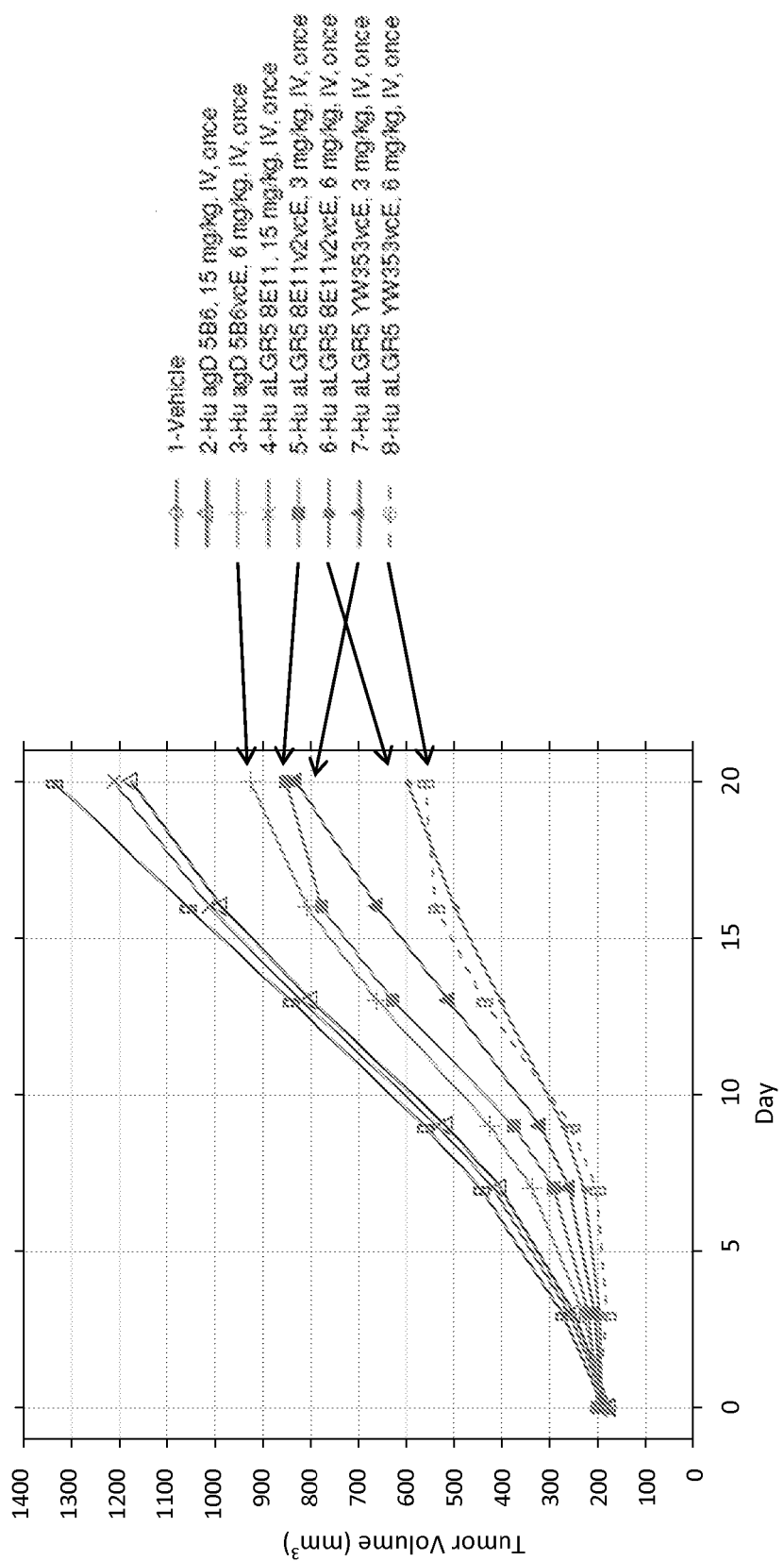
FIG. 26 shows that huYW353-vcMMAE and hu8E11v2-vcMMAE immunoconjugates demonstrate efficacy in LoVoX1.1 colon cancer xenografts, as described in Example P.

As shown in FIG. 26, substantial tumor growth inhibition was achieved at 6 mg/kg hu8E11v2-vcMMAE and 6 mg/kg huYW353-vcMMAE.

The efficacy of various doses of hu8E11v2-vcMMAE antibody-drug conjugate was then tested in the LoVoX1.1 colorectal adenocarcinoma xenograft model described above. Five million LoVoX1.1 cells in HBSS-matrigel were injected subcutaneously into the dorsal flank of C.B-17 SCID mice and 10 days post-inoculation mice were given a single intravenous injection of 1 mg/kg, 3 mg/kg, 6 mg/kg, 10 mg/kg, or 15 mg/kg hu8E11v2-vcMMAE antibody-drug conjugate; or 15 mg/kg hu8E11v2; or 6 mg/kg or 15 mg/kg humanized anti-gD 5B6-vcMMAE control antibody-drug conjugate; or vehicle (histidine buffer: 20 mM histidine acetate, 240 mM sucrose, 0.02% Tween 20, pH5.5) alone (n=9 mice per group). The presence of the antibodies was confirmed by PK bleeds one, seven, and 14 days post injection.

Figure 27:
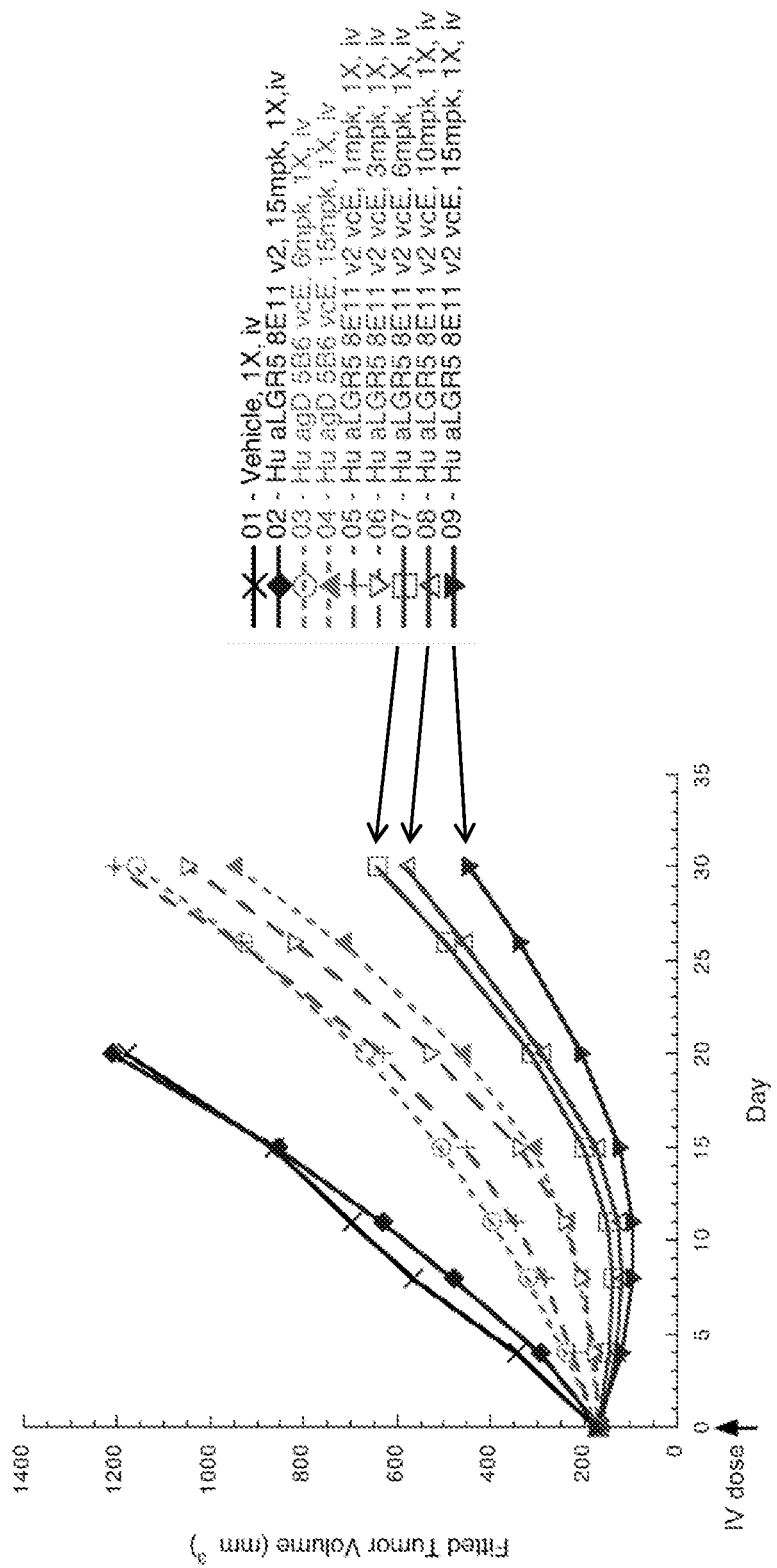
FIG. 27 shows that hu8E11v2-vcMMAE immunoconjugate demonstrates efficacy in LoVoX1.1 colon cancer xenografts, as described in Example P.

As shown in FIG. 27, substantial tumor growth inhibition was achieved at 6 mg/kg, 10 mg/kg, and 15 mg/kg hu8E11v2-vcMMAE.

Q. Efficacy of Anti-LgR5 Antibody Drug Conjugates in D5124 Pancreatic Cancer Xenograft The efficacy of the anti-LgR5 ADCs was investigated using a D5124 pancreatic cancer xenograft model, which has a β-catenin mutation. LgR5 is highly expressed in D5124 tumors, and was confirmed by microarray, TaqMan® quantitative RT-PCR, in situ hybridization, FACS, and Western blot. Twenty to 30 mm$^3$ D5124 tumor fragments were implanted subcutaneously into the dorsal flank area of NCR nude mice and 26 days post-transplantation the mice were given a single intravenous injection of 1 mg/kg huYW353-vcMMAE antibody-drug conjugate, 1 mg/kg huYW353-vcPNU antibody-drug conjugate, 1 mg/kg huYW353-PNU antibody-drug conjugate, 1 mg/kg huYW353-acetal-PNU antibody-drug conjugate; or 1 mg/kg humanized anti-gD 5B6-vcPNU control antibody-drug conjugate, 1 mg/kg humanized anti-gD 5B6-PNU control antibody-drug conjugate, or 1 mg/kg humanized anti-gD 5B6-acetal-PNU control antibody-drug conjugate; or with vehicle (histidine buffer: 20 mM histidine acetate, 240 mM sucrose, 0.02% Tween 20, pH5.5) alone (n=9 mice per group). The presence of the antibodies was confirmed by PK bleeds three, seven, and 14 days post injection.

Figure 28:
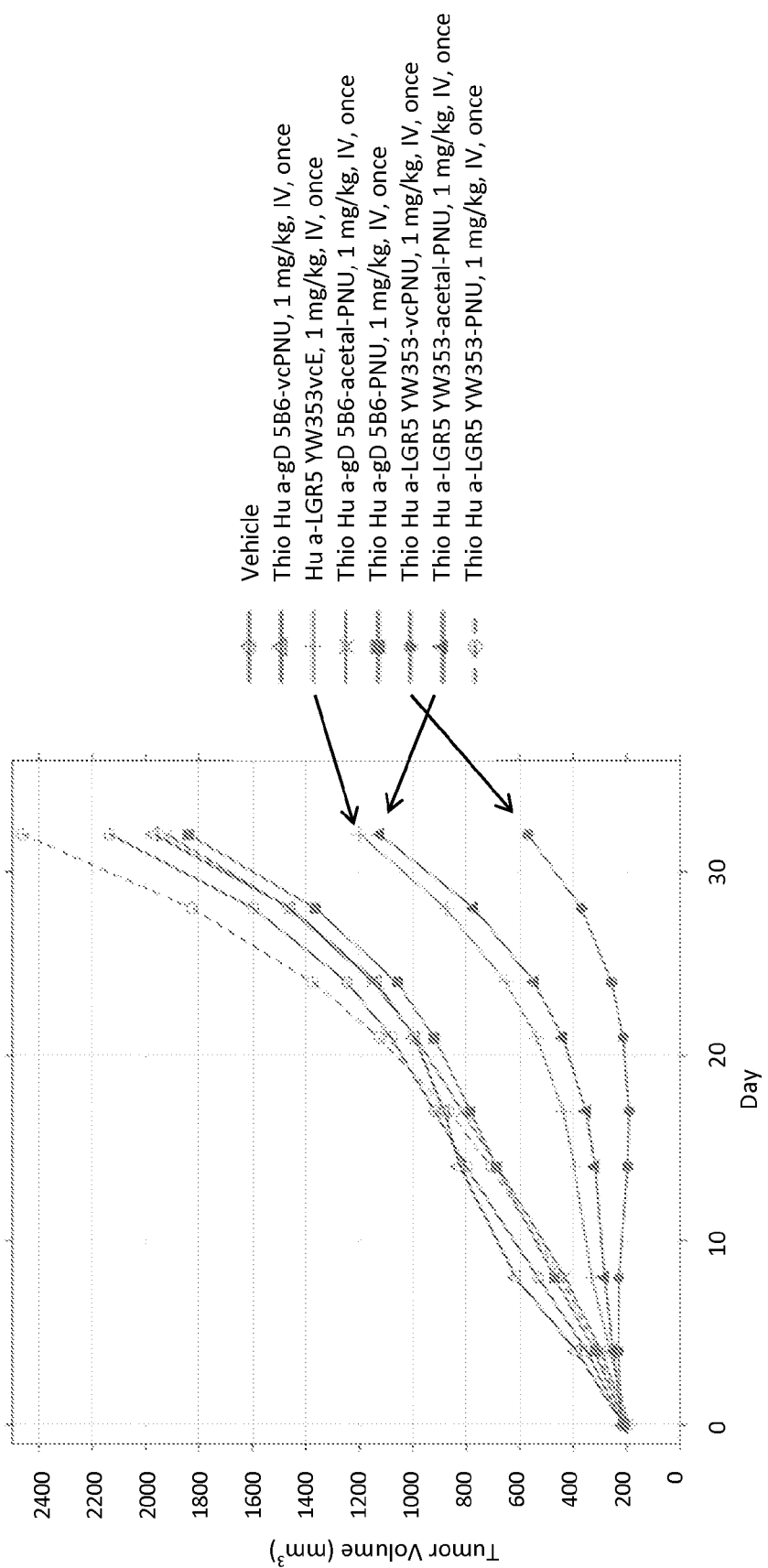
FIG. 28 shows that huYW353-vcMMAE, huYW353-acetal-PNU, and huYW353-vcPNU immunoconjugates demonstrate efficacy in D5124 pancreatic cancer xenografts, as described in Example Q.

As shown in FIG. 28, substantial tumor growth inhibition was achieved with 1 mg/kg huYW353-vcMMAE and 1 mg/kg huYW353-acetal-PNU, and almost complete tumor growth inhibition was achieved with 1 mg/kg huYW353-vcPNU. One of the mice treated with 1 mg/kg huYW353-acetal-PNU showed a complete response (i.e., the mouse had no detectable tumor at the end of the study). In addition, two of the mice treated with 1 mg/kg huYW353-vcPNU showed a partial response (i.e., >50% reduction of the initial tumor volume at day 0).

R. Efficacy of Anti-LgR5 Antibody Drug Conjugates in D5124 Pancreatic Cancer Xenograft The efficacy of various doses of hu8E11v2 antibody-drug conjugate was tested in the D5124 pancreatic cancer xenograft model. Twenty to 30 mm$^3$ D5124 tumor fragments were implanted subcutaneously into the dorsal flank area of NCR nude mice and 22 days post-transplantation mice were given a single intravenous injection of 2 mg/kg hu8E11v2-vcMMAE antibody-drug conjugate; or 2 mg/kg hu8E11v2-vcPNU; or 2 mg/kg or 10 mg/kg hu8E11v2-acetal-PNU; or 2 mg/kg or 10 mg/kg hu8E11v2-PNU; 2 mg/kg humanized anti-gD 5B6-vcPNU control antibody-drug conjugate, 10 mg/kg humanized anti-gD 5B6-acetal-PNU control antibody drug conjugate, or 10 mg/kg humanized anti-gD 5B6-PNU control antibody drug conjugate; or vehicle (histidine buffer: 20 mM histidine acetate, 240 mM sucrose, 0.02% Tween 20, pH5.5) alone (n=8 mice per group).

Figure 29:
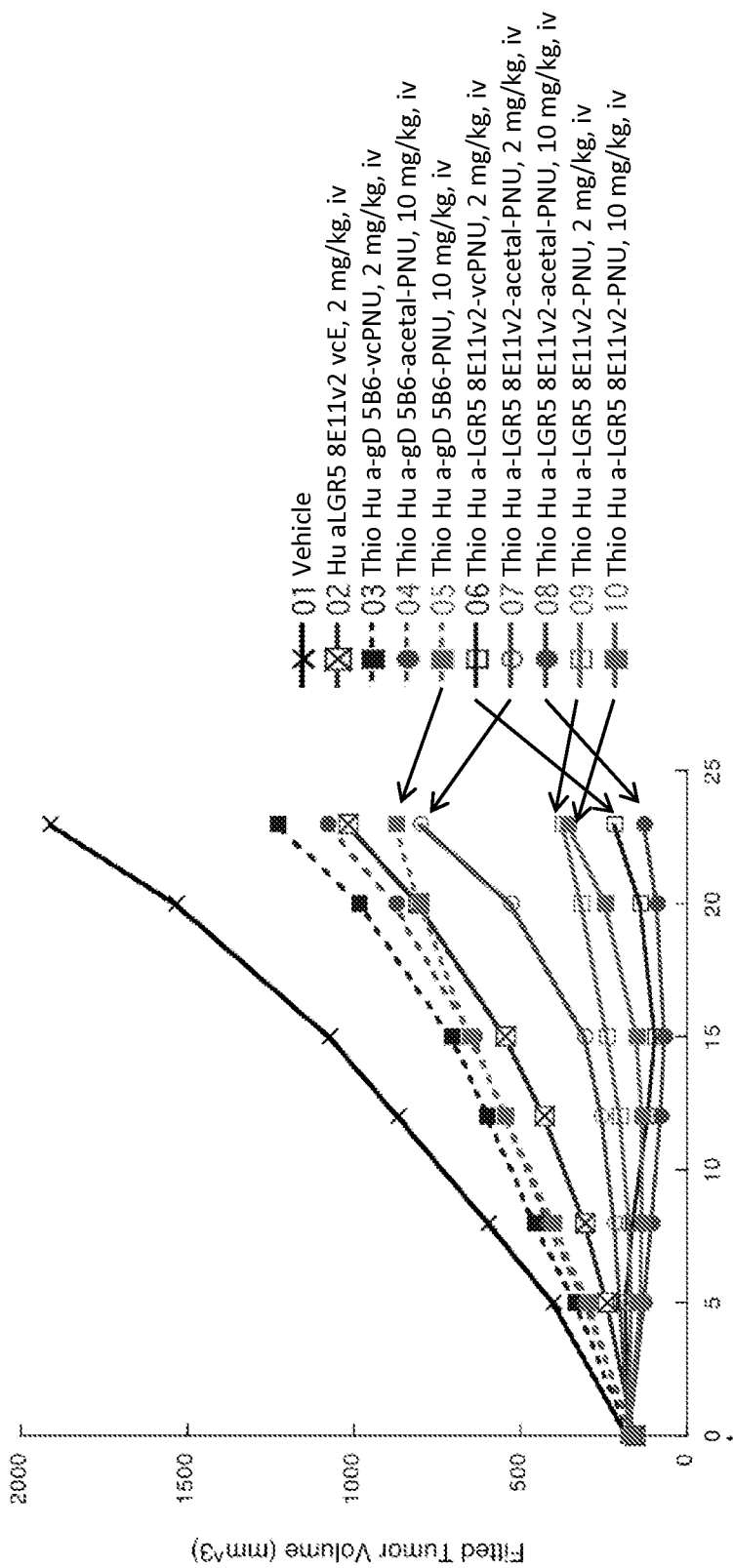
FIG. 29 shows that hu8E11v2-acetal-PNU, hu8E11v2-vcPNU, and hu8E11v2-PNU immunoconjugates demonstrate in D5124 pancreatic cancer xenografts, as described in Example R.

As shown in FIG. 29, substantial tumor growth inhibition was achieved at 2 mg/kg hu8E11v2-acetal-PNU, and almost complete tumor growth inhibition was achieved at 10 mg/kg hu8E11v2-acetal-PNU, 2 mg/kg hu8E11v2-vcPNU, and 2 mg/kg and 10 mg/kg hu8E11v2-PNU.

S. Efficacy of Anti-LgR5 Antibody Drug Conjugates in LoVo Colon Cancer Cell Line Xenograft The efficacy of the anti-LgR5 ADCs was investigated using a LoVo colon cancer xenograft model. LoVo cells are a colorectal adenocarcinoma cell line with an APC mutation (ATCC #CCL 229), and subline LoVoX1.1 was derived for optimal growth in mice. Briefly, mice were inoculated with LoVo cells. Once tumors were growing, a tumor with a desirable growth rate was harvested. The tumor was minced and grown in culture to establish cell line LoVoX1.1. LgR5 is expressed in LoVoX1.1 cells, and was confirmed by microarray, TaqMan® quantitative RT-PCR, in situ hybridization, FACS, and Western blot. Five million LoVoX1.1 cells in HBSS-matrigel were injected subcutaneously into the dorsal flank of C.B-17 SCID mice and 11 days post-inoculation mice were given a single intravenous injection of 2 mg/kg hu8E11v2-vcMMAE antibody-drug conjugate, 2 mg/kg hu8E11v2-vcPNU, 2 mg/kg hu8E11v2-acetal-PNU, or 2 mg/kg hu8E11v2-PNU; or 2 mg/kg humanized anti-gD 5B6-vcPNU control antibody-drug conjugate, 2 mg/kg humanized anti-gD 5B6-acetal-PNU control antibody drug conjugate, or 2 mg/kg humanized anti-gD 5B6-PNU control antibody drug conjugate; or with vehicle (histidine buffer: 20 mM histidine acetate, 240 mM sucrose, 0.02% Tween 20, pH5.5) alone (n=10 mice per group). The presence of the antibodies was confirmed by PK bleeds one, seven, and 14 days post injection.

Figure 30:
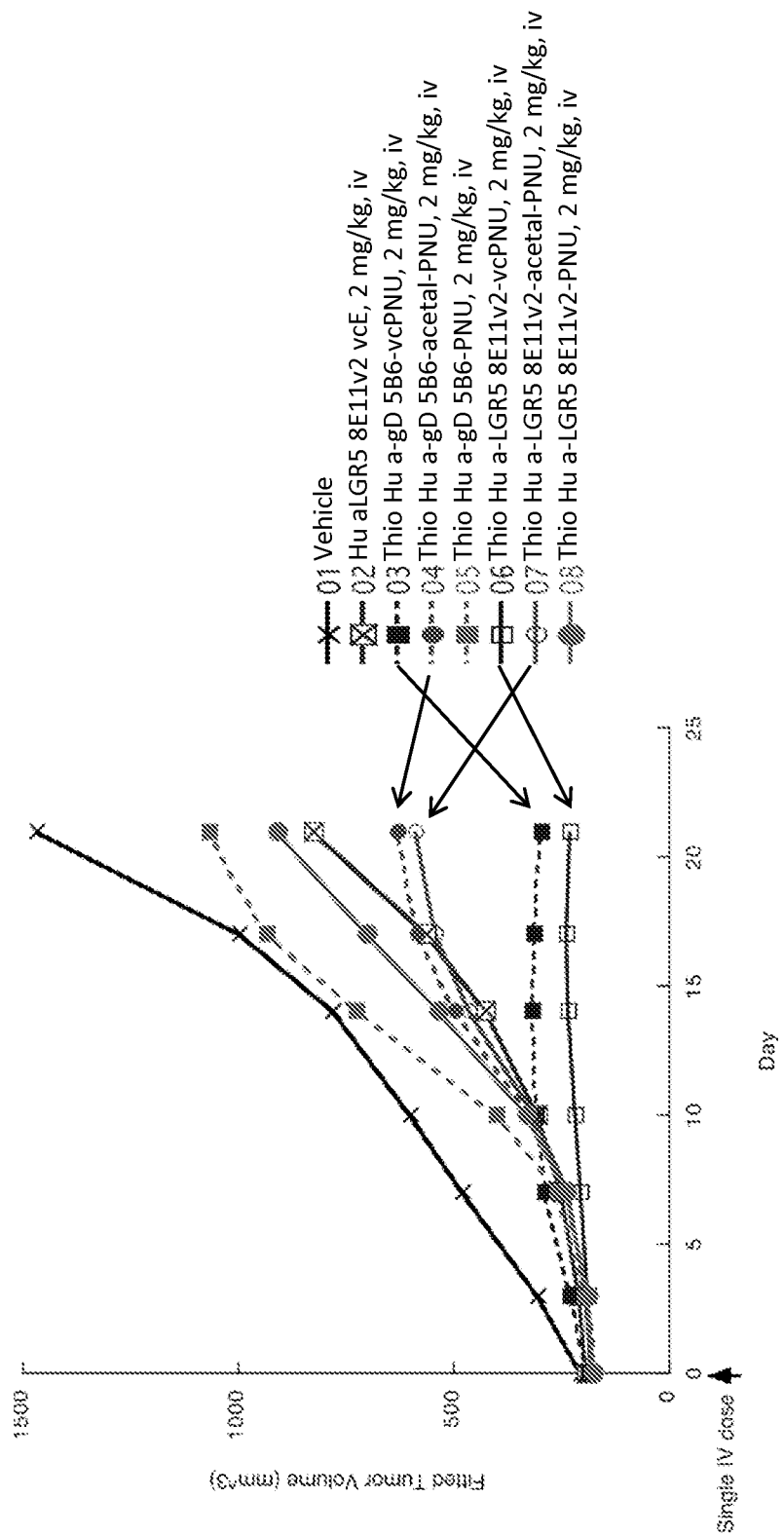
FIG. 30 shows the results of administering certain hu8E11v2 immunoconjugates and control antibody immunoconjugates in LoVoX1.1 colon cancer xenografts, as described in Example S.

As shown in FIG. 30, in this experiment, certain control antibodies appeared to show substantial tumor growth inhibition (see 2 mg/kg humanized anti-gD 5B6-vcPNU and 2 mg/kg humanized anti-gD 5B6-acetal-PNU control antibody drug conjugate).

Because of the apparent non-specific effects of the control antibody in the prior experiment, the LoVoX1.1 colorectal adenocarcinoma model was tested with a different control antibody-drug conjugate (that binds to a different antigen not expressed on the surface of LoVo cells), and with administration of an excess of anti-gD control antibody to block possible nonspecific antibody binding sites on the tumor cells. Five million LoVoX1.1 cells in HBSS-matrigel were injected subcutaneously into the dorsal flank of C.B-17 SCID mice and seven days post-inoculation mice were given a single intravenous injection of 10 mg/kg hu8E11v2-acetal-PNU antibody-drug conjugate; or 10 mg/kg thioAb-acetal-PNU control antibody-drug conjugate; or vehicle (50 mM sodium phosphate, 240 mM sucrose, 0.02% Tween20, pH 7) alone (n=5 mice per group). In addition, the mice were administered 30 mg/kg humanized anti-gD control antibody i.p. once per week until the end of the study, beginning on the same day as, but 4 hours prior to, administration of the test antibodies.

Figure 31:
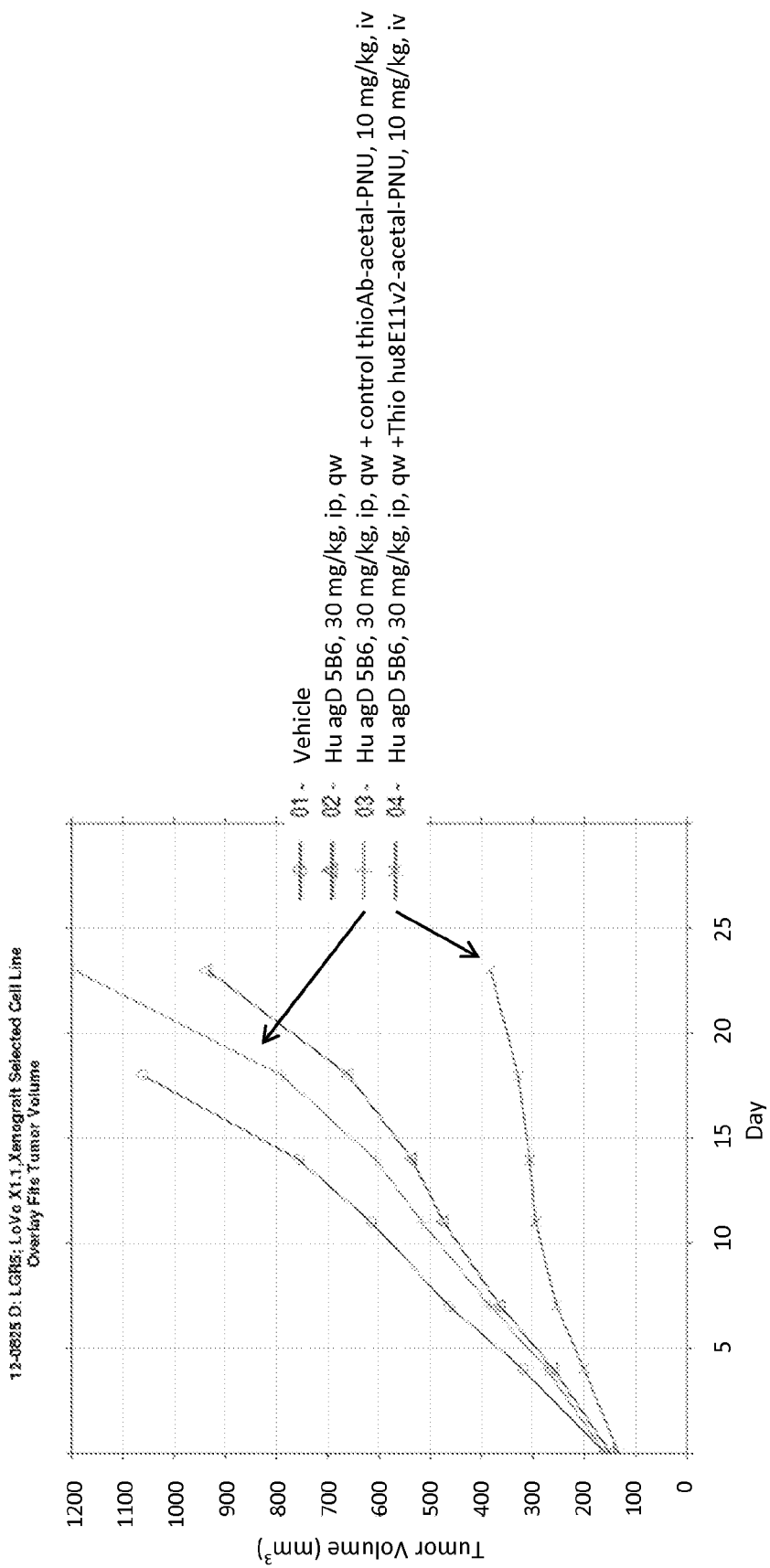
FIG. 31 that hu8E11v2-acetal-PNU immunoconjugate demonstrates efficacy in LoVoX1.1 colon cancer xenografts in mice coadministered excess control antibody, as described in Example S.

As shown in FIG. 31, substantial tumor growth inhibition was achieved with 10 mg/kg hu8E11v2-acetal-PNU and the control antibody did not inhibit tumor growth.

T. Efficacy of Anti-LgR5 Antibody Drug Conjugates in D5124 Pancreatic Cancer Xenograft The efficacy of the YW353 anti-LgR5 ADCs was investigated using the D5124 pancreatic cancer xenograft model, which has β-catenin mutation. LgR5 is highly expressed in D5124 tumors, and was confirmed by microarray, TaqMan® quantitative RT-PCR, in situ hybridization, FACS, and Western blot. Twenty to 30 mm³ D5124 tumor fragments were implanted subcutaneously into the dorsal flank area of NCR nude mice and 26 days post-transplantation the mice were given a single intravenous injection of 1 mg/kg huYW353-vcMMAE antibody-drug conjugate, 1 mg/kg huYW353-vcPBD antibody-drug conjugate; or 1 mg/kg humanized anti-gD 5B6-vcPBD control antibody-drug conjugate; or with vehicle (histidine buffer: 20 mM histidine acetate, 240 mM sucrose, 0.02% Tween 20, pH5.5) alone (n=9 mice per group). The presence of the antibodies was confirmed by PK bleeds one, seven, and fourteen days post injection.

Figure 32:
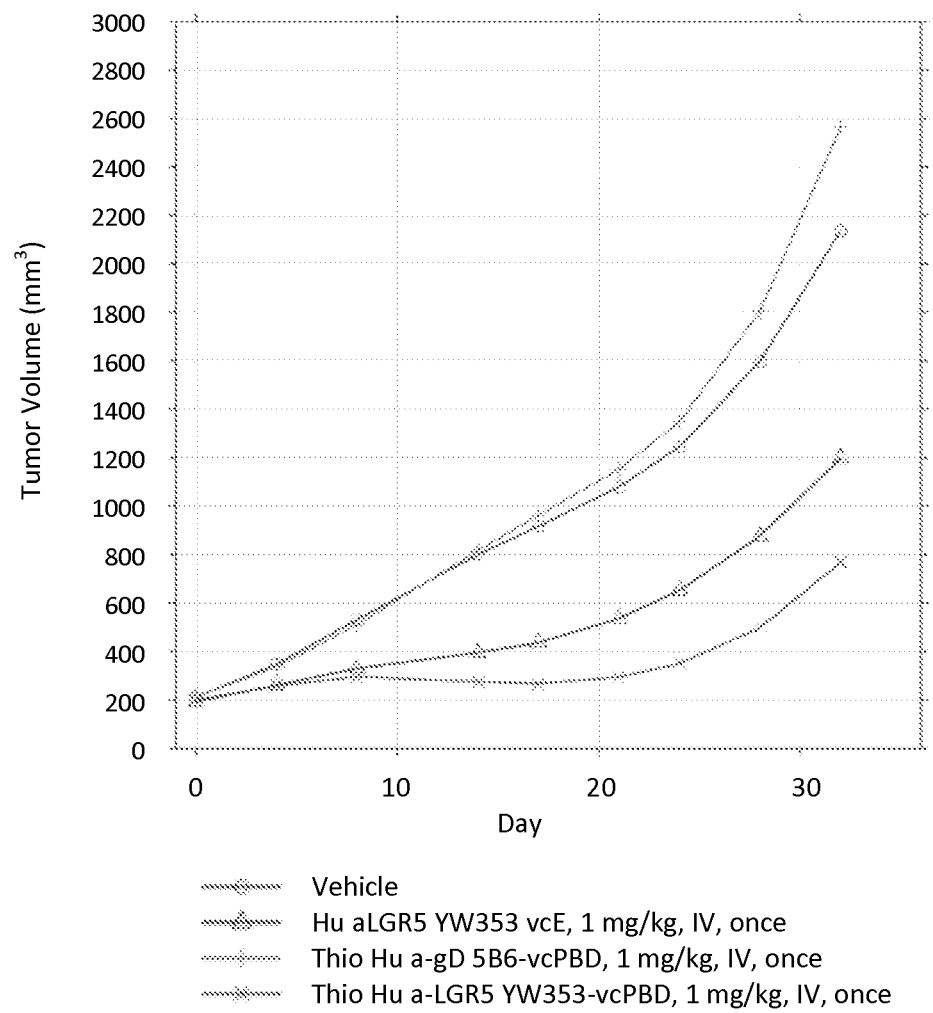
FIG. 32 shows that an anti-LgR5 huYW353 PBD immunoconjugate demonstrates efficacy in D5124 pancreatic cancer xenografts, as described in Example T.

As shown in FIG. 32, substantial tumor growth inhibition was achieved with 1 mg/kg huYW353-vcMMAE and 1 mg/kg huYW353-vcPBD. One of the mice treated with 1 mg/kg huYW353-vcPBD showed a complete response (i.e., the mouse had no detectable tumor at the end of the study).

In a separate experiment, efficacy of the hu8E11v2 anti-LgR5 ADCs was investigated using the D5124 pancreatic cancer xenograft model. Twenty to 30 mm³ D5124 tumor fragments were implanted subcutaneously into the dorsal flank area of NCR nude mice and 22 days post-transplantation the mice were given a single intravenous injection of 2 mg/kg hu8E11v2-vcMMAE antibody-drug conjugate, 2 mg/kg hu8E11v2-vcPBD antibody-drug conjugate; or 2 mg/kg humanized anti-gD 5B6-vcPBD control antibody-drug conjugate; or with vehicle (histidine buffer: 20 mM histidine acetate, 240 mM sucrose, 0.02% Tween 20, pH5.5) alone (n=8 mice per group).

Figure 33:
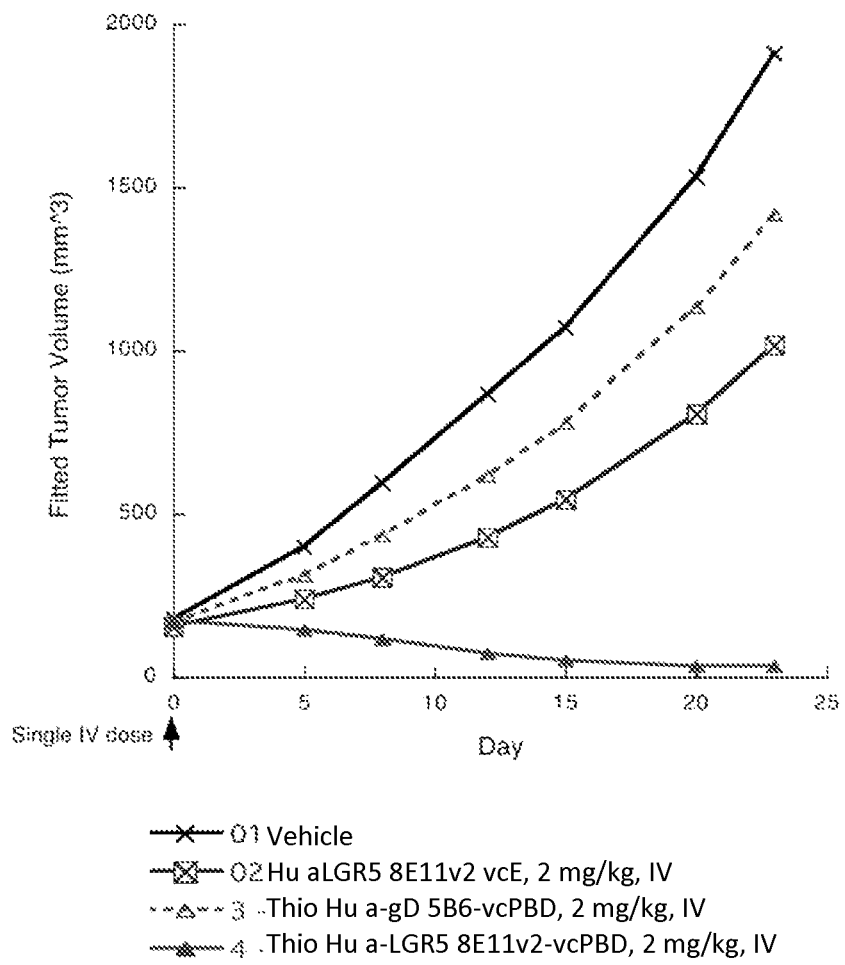
FIG. 33 shows that an anti-LgR5 hu8E11v2 PBD immunoconjugate demonstrates efficacy in D5124 pancreatic cancer xenografts, as described in Example T.

As shown in FIG. 33, substantial tumor growth inhibition was achieved with 2 mg/kg hu8E11v2-vcMMAE, and tumor regression was achieved with 2 mg/kg hu8E11v2-vcPBD.

U. Efficacy of Anti-LgR5 Antibody Drug Conjugates in LoVoX1.1 Colon Cancer Cell Line Xenograft The efficacy of the anti-LgR5 ADCs was investigated using a LoVoX1.1 colon cancer xenograft model. LoVo cells are a colorectal adenocarcinoma cell line with an APC mutation (ATCC #CCL 229), and subline LoVoX1.1 was derived for optimal growth in mice. Briefly, mice were inoculated with LoVo cells. Once tumors were growing, a tumor with a desirable growth rate was harvested. The tumor was minced and grown in culture to establish cell line LoVoX1.1. LgR5 is expressed in LoVoX1.1 cells, and was confirmed by microarray, TaqMan® quantitative RT-PCR, in situ hybridization, FACS, and Western blot. Five million LoVoX1.1 cells in HBSS-matrigel were injected subcutaneously into the dorsal flank of C.B-17 SCID mice and 11 days post-inoculation mice were given a single intravenous injection of 2 mg/kg hu8E11v2-vcMMAE antibody-drug conjugate, 2 mg/kg hu8E11v2-vcPBD antibody-drug conjugate; or 2 mg/kg humanized anti-gD 5B6-vcPBD control antibody-drug conjugate; or with vehicle (histidine buffer: 20 mM histidine acetate, 240 mM sucrose, 0.02% Tween 20, pH5.5) alone (n=10 mice per group). The presence of the antibodies was confirmed by PK bleeds one, seven, and 14 days post injection.

Figure 34:
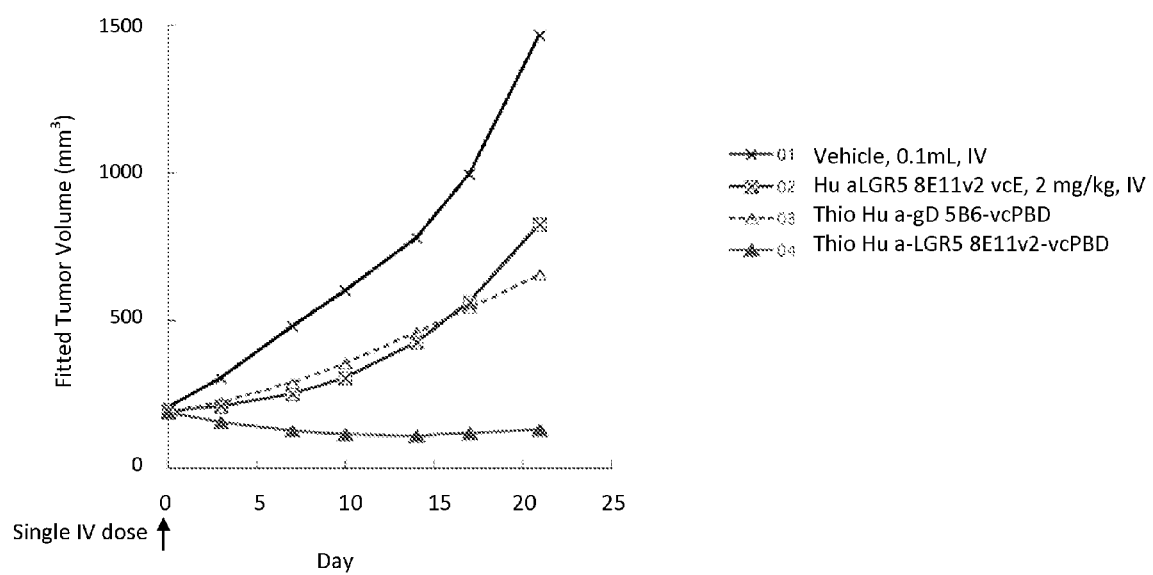
FIG. 34 shows that an anti-LgR5 hu8E11v2 PBD immunoconjugate demonstrates efficacy in a LoVoX1.1 colon cancer xenograft, as described in Example U.

As shown in FIG. 34, complete tumor growth inhibition was achieved with 2 mg/kg hu8E11v2-vcPBD.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

Table of Sequences

| SEQ ID NO | Description | Sequence |
|---|---|---|
| 1 | $huK_{IV}$ | DIVMTQSPDS LAVSLGERAT INCKSSQSVL YSSNNKNYLA WYQQKPGQPP KLLIYWASTR ESGVPDRFSG SGSGTDFTLT ISSLQAEDVA VYYCQQYYST PFTFGQGTKV EIKR |
| 2 | $huVH_1$ | EVQLVQSGAE VKKPGASVKV SCKASGYTFT SYYIHWVRQA PGQGLEWIGW INPGSGNTNY AQKFQGRVTI TRDTSTSTAY LELSSLRSED TAVYYCARFD YWGQGTLVTV SS |
| 3 | mu8E11 light chain variable region | NIVLTQSPAS LAVSLGQRAT ISCRASESVD NYGNSFMHWY QQKPGQPPKL LIYLASNLES GVPARFSGSG SRTDFTLTID PVEADDAATY YCQQNYEDPF TFGSGTKVEI KR |

Table of Sequences

| SEQ ID NO | Description | Sequence |
|---|---|---|
| 4 | mu8E11 heavy chain variable region | QVQLQQSGTE LMKPGASVKI SCKATGYTFS AYWIEWIKQR PGHGLEWIGE ILPGSDSTDY NEKFKVKATF SSDTSSNTVY IQLNSLTYED SAVYYCARGG HYGSLDYWGQ GTTLKVSS |
| 5 | hu8E11.v1 light chain variable region | DIVMTQSPDS LAVSLGERAT INCRASESVD NYGNSFMHWY QQKPGQPPKL LIYLASNLES GVPDRFSGSG SGTDFTLTIS SLQAEDVAVY YCQQNYEDPF TFGQGTKVEI KR |
| 6 | hu8E11.v1 heavy chain variable region | EVQLVQSGAE VKKPGASVKV SCKASGYTFS AYWIEWVRQA PGQGLEWIGE ILPGSDSTDY NEKFKVRVTI TSDTSTSTVY LELSSLRSED TAVYYCARGG HYGSLDYWGQ GTLVTVSS |
| 7 | hu8E11.v2 light chain variable region | DIVMTQSPDS LAVSLGERAT INCRASESVD NYGNSFMHWY QQKPGQPPKL LIYLASNLES GVPDRFSGSG SGTDFTLTIS SLQAEDVAVY YCQQNYEDPF TFGQGTKVEI KR |
| 8 | hu8E11.v2 heavy chain variable region | EVQLVQSGAE VKKPGASVKV SCKASGYTFS AYWIEWVRQA PGQGLEWIGE ILPGSDSTDY NEKFKVRATF TSDTSTSTVY LELSSLRSED TAVYYCARGG HYGSLDYWGQ GTLVTVSS |
| 9 | hu8E11.v3 light chain variable region | DIVMTQSPDS LAVSLGERAT INCRASESVD NYGNSFMHWY QQKPGQPPKL LIYLASNLES GVPDRFSGSG SRTDFTLTIS SLQAEDVAVY YCQQNYEDPF TFGQGTKVEI KR |
| 10 | hu8E11.v3 heavy chain variable region | EVQLVQSGAE VKKPGASVKV SCKASGYTFS AYWIEWVRQA PGQGLEWIGE ILPGSDSTDY NEKFKVRVTI TSDTSTSTVY LELSSLRSED TAVYYCARGG HYGSLDYWGQ GTLVTVSS |
| 11 | hu8E11.v4 light chain variable region | DIVMTQSPDS LAVSLGERAT INCRASESVD NYGNSFMHWY QQKPGQPPKL LIYLASNLES GVPDRFSGSG SRTDFTLTIS SLQAEDVAVY YCQQNYEDPF TFGQGTKVEI KR |
| 12 | hu8E11.v4 heavy chain variable region | EVQLVQSGAE VKKPGASVKV SCKASGYTFS AYWIEWVRQA PGQGLEWIGE ILPGSDSTDY NEKFKVRATF TSDTSTSTVY LELSSLRSED TAVYYCARGG HYGSLDYWGQ GTLVTVSS |
| 13 | hu8E11.v5 light chain variable region | DIVMTQSPDS LAVSLGERAT INCRASESVD NYGNSFMHWY QQKPGQPPKL LIYLASNLES GVPDRFSGSG SGTDFTLTIS SLQAEDVAVY YCQQNYEDPF TFGQGTKVEI KR |
| 14 | hu8E11.v5 heavy chain variable region | EVQLVQSGAE VKKPGASVKV SCKASGYTFS AYWIEWVRQA PGQGLEWIGE ILPGSDSTDY NEKFKVRVTI TRDTSTSTAY LELSSLRSED TAVYYCARGG HYGSLDYWGQ GTLVTVSS |
| 15 | hu8E11.v6 light chain variable region | DIVMTQSPDS LAVSLGERAT INCRASESVD NYGNSFMHWY QQKPGQPPKL LIYLASNLES GVPDRFSGSG SGTDFTLTIS SLQAEDVAVY YCQQNYEDPF TFGQGTKVEI KR |
| 16 | hu8E11.v6 heavy chain variable region | EVQLVQSGAE VKKPGASVKV SCKASGYTFS AYWIEWVRQA PGQGLEWIGE ILPGSDSTDY NEKFKVRVTI TADTSTSTAY LELSSLRSED TAVYYCARGG HYGSLDYWGQ GTLVTVSS |
| 17 | hu8E11.v7 light chain variable region | DIVMTQSPDS LAVSLGERAT INCRASESVD NYGNSFMHWY QQKPGQPPKL LIYLASNLES GVPDRFSGSG SRTDFTLTIS SLQAEDVAVY YCQQNYEDPF TFGQGTKVEI KR |
| 18 | hu8E11.v7 heavy chain variable region | EVQLVQSGAE VKKPGASVKV SCKASGYTFS AYWIEWVRQA PGQGLEWIGE ILPGSDSTDY NEKFKVRVTI TRDTSTSTAY LELSSLRSED TAVYYCARGG HYGSLDYWGQ GTLVTVSS |
| 19 | hu8E11.v8 light chain variable region | DIVMTQSPDS LAVSLGERAT INCRASESVD NYGNSFMHWY QQKPGQPPKL LIYLASNLES GVPDRFSGSG SRTDFTLTIS SLQAEDVAVY YCQQNYEDPF TFGQGTKVEI KR |
| 20 | hu8E11.v8 heavy chain variable region | EVQLVQSGAE VKKPGASVKV SCKASGYTFS AYWIEWVRQA PGQGLEWIGE ILPGSDSTDY NEKFKVRVTI TADTSTSTAY LELSSLRSED TAVYYCARGG HYGSLDYWGQ GTLVTVSS |
| 21 | mu3G12 light chain variable region | DVVMTQTPLS LPVSLGDQAS ISCRSSQSLV HSNGNTYLQW YLQKPGQSPK LLIYKVSNRF SGVPDRFSGS GSGTDFTLKI SRVEAEDLGI YFCSQSTHFP YTFGGGTKLE IKR |

Table of Sequences

| SEQ ID NO | Description | Sequence |
|---|---|---|
| 22 | mu3G12 heavy chain variable region | QVQLQQPGAE MVKPGASVKL SCKASVDTFN SYWMHWVKQR PGQGLEWIGE INPSNGRTNY IEKFKNRATV TVDKSSSTAF MQLSSLTSED SAVYYCATGW YFDVWGAGTT VTVSS |
| 23 | mu2H6 light chain variable region | DIVMTQSPSS LTVTAGEKVT MSCKSSQSLL NSGNQKNYLT WFQQKPGQPP KLLIYWASTR ESGVPDRFTG SGSGTDFTLT ISNVQAEDLA VYYCQNDYSF PFTFGQGTKV EIKR |
| 24 | mu2H6 heavy chain variable region | EVQLQQSGPE LVKPGTSMKI SCKASGYSFT GYTMNWVKQS HKNGLEWIGL INCYNGGTNY NQKFKGKATL TVDKSSSTAF MELLSLTSED SAVYYCARGG STMITPRFAY WGQGTLVTVS S |
| 25 | YW353 light chain variable region | DIQMTQSPSS LSASVGDRVT ITCRASQDVS TAVAWYQQKP GKAPKLLIYS ASFLYSGVPS RFSGSGSGTD FTLTISSLQP EDFATYYCQQ SYTTPPTFGQ GTKVEIKR |
| 26 | YW353 heavy chain variable region | EVQLVESGGG LVQPGGSLRL SCAASGFTFT SYSISWVRQA PGKGLEWVAE IYPPGGYTDY ADSVKGRFTI SADTSKNTAY LQMNSLRAED TAVYYCAKAR LFFDYWGQGT LVTVSS |
| 27 | nm8E11 HVR L1 | RASESVDNYG NSFMH |
| 28 | mu8E11 HVR L2 | LASNLES |
| 29 | mu8E11 HVR L3 | QQNYEDPFT |
| 30 | mu8E11 HVR H1 | GYTFSAYWIE |
| 31 | mu8E11 HVR H2 | EILPGSDSTD YNEKFKV |
| 32 | mu8E11 HVR H3 | GGHYGSLDY |
| 33 | Hu8E11 light chain (LC) framework 1 (FR1) | DIVMTQSPDS LAVSLGERAT INC |
| 34 | Hu8E11 LC FR2 | WYQQKPGQPP KLLIY |
| 35 | Hu8E11.v1 LC FR3 Hu8E11.v2 LC FR3 Hu8E11.v5 LC FR3 Hu8E11.v6 LC FR3 | GVPDRFSGSG SGTDFTLTIS SLQAEDVAVY YC |
| 36 | Hu8E11.v3 LC FR3 Hu8E11.v4 LC FR3 Hu8E11.v7 LC FR3 Hu8E11.v8 LC FR3 | GVPDRFSGSG SRTDFTLTIS SLQAEDVAVY YC |
| 37 | Hu8E11 LC FR4 | FGQGTKVEIK R |
| 38 | Hu8E11 heavy chain (HC) framework1 (FR1) | EVQLVQSGAE VKKPGASVKV SCKAS |
| 39 | Hu8E11 HC FR2 | WVRQAPGQGL EWIG |
| 40 | Hu8E11.v1 HC FR3 Hu8E11.v3 HC FR3 | RVTITSDTST STVYLELSSL RSEDTAVYYC AR |

Table of Sequences

| SEQ ID NO | Description | Sequence |
|---|---|---|
| 41 | Hu8E11.v2 HC FR3<br>Hu8E11.v4 HC FR3 | RATFTSDTST STVYLELSSL RSEDTAVYYC AR |
| 42 | Hu8E11.v5 HC FR3<br>Hu8E11.v7 HC FR3 | RVTITRDTST STAYLELSSL RSEDTAVYYC AR |
| 43 | Hu8E11.v6 HC FR3<br>Hu8E11.v8 HC FR3 | RVTITADTST STAYLELSSL RSEDTAVYYC AR |
| 44 | Hu8E11 HC FR4 | WGQGTLVTVS S |
| 45 | mu3G12 HVR L1 | RSSQSLVHSN GNTYLQ |
| 46 | mu3G12 HVR L2 | KVSNRFS |
| 47 | mu3G12 HVR L3 | SQSTHFPYT |
| 48 | mm3G12 HVR H1 | VDTFNSYWMH |
| 49 | mu3G12 HVR H2 | EINPSNGRTN YIEKFKN |
| 50 | mu3G12 HVR H3 | GWYFDV |
| 51 | mu2H6 HVR L1 | KSSQSLLNSG NQKNYLT |
| 52 | mu2H6 HVR L2 | WASTRES |
| 53 | mu2H6 HVR L3 | QNDYSFPFT |
| 54 | mu2H6 HVR H1 | GYSFTGYTMN |
| 55 | mu2H6 HVR H2 | LINCYNGGTN YNQKFKG |
| 56 | mu2H6 HVR H3 | GGSTMITPRF AY |
| 57 | YW353 HVR L1 | RASQDVSTAV A |
| 58 | YW353 HVR L2 | SASFLYS |
| 59 | YW353 HVR L3 | QQSYTTPPT |
| 60 | YW353 HVR H1 | GFTFTSYSIS |
| 61 | YW353 HVR H2 | EIYPPGGYTD YADSVKG |
| 62 | YW353 HVR H3 | ARLFFDY |
| 63 | hu8E11.v2 light chain | DIVMTQSPDS LAVSLGERAT INCRASESVD NYGNSFMHWY QQKPGQPPKL LIYLASNLES GVPDRFSGSG SGTDFTLTIS SLQAEDVAVY YCQQNYEDPF TFGQGTKVEI KRTVAAPSVF IFPPSDEQLK SGTASVVCLL NNFYPREAKV QWKVDNALQS GNSQESVTEQ DSKDSTYSLS STLTLSKADY EKHKVYACEV THQGLSSPVT KSFNRGEC |
| 64 | hu8E11.v2 heavy chain | EVQLVQSGAE VKKPGASVKV SCKASGYTFS AYWIEWVRQA PGQGLEWIGE ILPGSDSTDY NEKFKVRATF TSDTSTSTVY LELSSLRSED TAVYYCARGG HYGSLDYWGQ GTLVTVSSAS TKGPSVFPLA PSSKSTSGGT AALGCLVKDY FPEPVTVSWN SGALTSGVHT FPAVLQSSGL YSLSSVVTVP SSSLGTQTYI CNVNHKPSNT KVDKKVEPKS CDKTHTCPPC PAPELLGGPS VFLFPPKPKD TLMISRTPEV TCVVVDVSHE DPEVKFNWYV DGVEVHNAKT KPREEQYNST YRVVSVLTVL HQDWLNGKEY KCKVSNKALP APIEKTISKA KGQPREPQVY TLPPSREEMT KNQVSLTCLV KGFYPSDIAV EWESNGQPEN NYKTTPPVLD SDGSFFLYSK LTVDKSRWQQ GNVFSCSVMH EALHNHYTQK SLSLSPGK |

Table of Sequences

| SEQ ID NO | Description | Sequence |
|---|---|---|
| 65 | YW353 light chain | DIQMTQSPSS LSASVGDRVT ITCRASQDVS TAVAWYQQKP GKAPKLLIYS ASFLYSGVPS RFSGSGSGTD FTLTISSLQP EDFATYYCQQ SYTTPPTFGQ GTKVEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 66 | YW353 heavy chain | EVQLVESGGG LVQPGGSLRL SCAASGFTFT SYSISWVRQA PGKGLEWVAE IYPPGGYTDY ADSVKGRFTI SADTSKNTAY LQMNSLRAED TAVYYCAKAR LFFDYWGQGT LVTVSSASTK GPSVFPLAPS SKSTSGGTAA LGCLVKDYFP EPVTVSWNSG ALTSGVHTFP AVLQSSGLYS LSSVVTVPSS SLGTQTYICN VNHKPSNTKV DKKVEPKSCD KTHTCPPCPA PELLGGPSVF LFPPKPKDTL MISRTPEVTC VVVDVSHEDP EVKFNWYVDG VEVHNAKTKP REEQYNSTYR VVSVLTVLHQ DWLNGKEYKC KVSNKALPAP IEKTISKAKG QPREPQVYTL PPSREEMTKN QVSLTCLVKG FYPSDIAVEW ESNGQPENNY KTTPPVLDSD GSFFLYSKLT VDKSRWQQGN VFSCSVMHEA LHNHYTQKSL SLSPGK |
| 67 | Human LgR5 precursor; LGR5_human NP_003658; signal sequence = amino acids 1-21 | MDTSRLGVLL SLPVLLQLAT GGSSPRSGVL LRGCPTHCHC EPDGRMLLRV DCSDLGLSEL PSNLSVFTSY LDLSMNNISQ LLPNPLPSLR FLEELRLAGN ALTYIPKGAF TGLYSLKVLM LQNNQLRHVP TEALQNLRSL QSLRLDANHI SYVPPSCFSG LHSLRHLWLD DNALTEIPVQ AFRSLSALQA MTLALNKIHH IPDYAFGNLS SLVVLHLHNN RIHSLGKKCF DGLHSLETLD LNYNNLDEFP TAIRTLSNLK ELGFHSNNIR SIPEKAFVGN PSLITIHFYD NPIQFVGRSA FQHLPELRTL TLNGASQITE FPDLTGTANL ESLTLTGAQI SSLPQTVCNQ LPNLQVLDLS YNLLEDLPSF SVCQKLQKID LRHNEIYEIK VDTFQQLLSL RSLNLAWNKI AIIHPNAFST LPSLIKLDLS SNLLSSFPIT GLHGLTHLKL TGNHALQSLI SSENFPELKV IEMPYAYQCC AFGVCENAYK ISNQWNKGDN SSMDDLHKKD AGMFQAQDER DLEDFLLDFE EDLKALHSVQ CSPSPGPFKP CEHLLDGWLI RIGVWTIAVL ALTCNALVTS TVFRSPLYIS PIKLLIGVIA AVNMLTGVSS AVLAGVDAFT FGSFARHGAW WENGVGCHVI GFLSIFASES SVFLLTLAAL ERGFSVKYSA KFETKAPFSS LKVIILLCAL LALTMAAVPL LGGSKYGASP LCLPLPFGEP STMGYMVALI LLNSLCFLMM TIAYTKLYCN LDKGDLENIW DCSMVKHIAL LLFTNCILNC PVAFLSFSSL INLTFISPEV IKFILLVVVP LPACLNPLLY ILFNPHFKED LVSLRKQTYV WTRSKHPSLM SINSDDVEKQ SCDSTQALVT FTSSSITYDL PPSSVPSPAY PVTESCHLSS VAFVPCL |
| 68 | Human LgR5 mature, without signal sequence; amino acids 22 to 907 | GSSPRSGVL LRGCPTHCHC EPDGRMLLRV DCSDLGLSEL PSNLSVFTSY LDLSMNNISQ LLPNPLPSLR FLEELRLAGN ALTYIPKGAF TGLYSLKVLM LQNNQLRHVP TEALQNLRSL QSLRLDANHI SYVPPSCFSG LHSLRHLWLD DNALTEIPVQ AFRSLSALQA MTLALNKIHH IPDYAFGNLS SLVVLHLHNN RIHSLGKKCF DGLHSLETLD LNYNNLDEFP TAIRTLSNLK ELGFHSNNIR SIPEKAFVGN PSLITIHFYD NPIQFVGRSA FQHLPELRTL TLNGASQITE FPDLTGTANL ESLTLTGAQI SSLPQTVCNQ LPNLQVLDLS YNLLEDLPSF SVCQKLQKID LRHNEIYEIK VDTFQQLLSL RSLNLAWNKI AIIHPNAFST LPSLIKLDLS SNLLSSFPIT GLHGLTHLKL TGNHALQSLI SSENFPELKV IEMPYAYQCC AFGVCENAYK ISNQWNKGDN SSMDDLHKKD AGMFQAQDER DLEDFLLDFE EDLKALHSVQ CSPSPGPFKP CEHLLDGWLI RIGVWTIAVL ALTCNALVTS TVFRSPLYIS PIKLLIGVIA AVNMLTGVSS AVLAGVDAFT FGSFARHGAW WENGVGCHVI GFLSIFASES SVFLLTLAAL ERGFSVKYSA KFETKAPFSS LKVIILLCAL LALTMAAVPL LGGSKYGASP LCLPLPFGEP STMGYMVALI LLNSLCFLMM TIAYTKLYCN LDKGDLENIW DCSMVKHIAL LLFTNCILNC PVAFLSFSSL INLTFISPEV IKFILLVVVP LPACLNPLLY ILFNPHFKED LVSLRKQTYV WTRSKHPSLM SINSDDVEKQ SCDSTQALVT FTSSSITYDL PPSSVPSPAY PVTESCHLSS VAFVPCL |
| 69 | Cynomolgus monkey LgR5 partial sequence, predicted; | GCPTHCHCEP DGRMLLRVDC SDLGLSELPS NLSVFTSYLD LSMNNISQLL PNPLPSLRFL EELRLAGNAL TYIPKGAFTG LYSLKVLMLQ NNQLRQVPTE ALQNLRSLQS LRLDANHISY VPPSCFSGLH SLRHLWLDDN ALTEIPVQAF RSLSALQAMT |

Table of Sequences

| SEQ ID NO | Description | Sequence |
|---|---|---|
| | predicted to correspond to amino acids 33 to 907 of full-length precursor | LALNKIHHIP DYAFGNLSSL VVLHLHNNRI HSLGKKCFDG LHSLETLDLN YNNLDEFPTA IRTLSNLKEL GFHSNNIRSI PEKAFVGNPS LITIHFYDNP IQFVGRSAFQ HLPELRTLTL NGASQITEFP DLTGTANLES LTLTGAQISS LPQTVCNQLP NLQVLDLSYN LLEDLPSFSV CQKLQKIDLR HNEIYEIKVD TFQQLLSLRS LNLAWNKIAI IHPNAFSTLP SLIKLDLSSN LLSSFPVTGL HGLTHLKLTG NHALQSLISS ENFPELKIIE MPYAYQCCAF GVCENAYKIS NQWNKGDNSS MDDLHKKDAG MFQVQDERDL EDFLLDFEED LKALHSVQCS PSPGPFKPCE HLLDGWLIRI GVWTIAVLAL TCNALVTSTV FRSPLYISPI KLLIGVIAVV NMLTGVSSAV LAGVDAFTFG SFARHGAWWE NGVGCQVIGF LSIFASESSV FLLTLAALER GFSVKCSAKF ETKAPFSSLK VIILLCALLA LTMAAVPLLG GSEYGASPLC LPLPFGEPST TGYMVALILL NSLCFLMMTI AYTKLYCNLD KGDLENIWDC SMVKHIALLL FTNCILYCPV AFLSFSSLLN LTFISPEVIK FILLVIVPLP ACLNPLLYIL FNPHFKEDLV SLGKQTYFWT RSKHPSLMSI NSDDVEKQSC DSTQALVTFT SSSIAYDLPP SSVPSPAYPV TESCHLSSVA FVPCL |
| 70 | Rat LgR5 precursor; LGR5_rat NP_001100254; signal sequence = amino acids 1-21 | MDTSRVRMLL SLLALLQLVA AGSPPRPDTM PRGCPSYCHC ELDGRMLLRV DCSDLGLSEL PSNLSVFTSY LDLSMNNISQ LPASLLHRLR FLEELRLAGN ALTHIPKGAF AGLHSLKVLM LQNNQLRQVP EEALQNLRSL QSLRLDANHI SYVPPSCFSG LHSLRHLWLD DNALTDVPVQ AFRSLSALQA MTLALNKIHH IADHAFGNLS SLVVLHLHNN RIHSLGKKCF DGLHSLETLD LNYNNLDEFP TAIKTLSNLK ELGFHSNNIR SIPERAFVGN PSLITIHFYD NPIQFVGISA FQHLPELRTL TLNGASQITE FPDLTGTATL ESLTLTGAKI SSLPQTVCDQ LPNLQVLDLS YNLLEDLPSL SGCQKLQKID LRHNEIYEIK GGTFQQLFNL RSLNLARNKI AIIHPNAFST LPSLIKLDLS SNLLSSFPVT GLHGLTHLKL TGNRALQSLI PSANFPELKI IEMPYAYQCC AFGGCENVYK IPNQWNKDDS SSVDDLRKKD AGLFQVQDER DLEDFLLDFE EDLKVLHSVQ CSPPPGPFKP CEHLFGSWLI RIGVWTTAVL ALSCNALVAF TVFRTPLYIS SIKLLIGVIA VVDILMGVSS AILAVVDTFT FGSFAQHGAW WEGGIGCQIV GFLSIFASES SVFLLTLAAL ERGFSVKCSS KFEMKAPLSS LKAIILLCVL LALTIATVPL LGGSEYNASP LCLPLPFGEP STTGYMVALV LLNSLCFLIM TIAYTRLYCS LEKGELENLW DCSMVKHTAL LLFTNCILYC PVAFLSFSSL LNLTFISPEV IKFILLVIVP LPACLNPLLY IVFNPHFKED MGSLGKQTRF WTRAKHPSLL SINSDDVEKR SCDSTQALVS FTHASIAYDL PSDSGSSPAY PMTESCHLSS VAFVPCL |
| 71 | Rat LgR5 mature, without signal sequence; amino acids 22 to 907 | GSPPRPDTM PRGCPSYCHC ELDGRMLLRV DCSDLGLSEL PSNLSVFTSY LDLSMNNISQ LPASLLHRLR FLEELRLAGN ALTHIPKGAF AGLHSLKVLM LQNNQLRQVP EEALQNLRSL QSLRLDANHI SYVPPSCFSG LHSLRHLWLD DNALTDVPVQ AFRSLSALQA MTLALNKIHH IADHAFGNLS SLVVLHLHNN RIHSLGKKCF DGLHSLETLD LNYNNLDEFP TAIKTLSNLK ELGFHSNNIR SIPERAFVGN PSLITIHFYD NPIQFVGISA FQHLPELRTL TLNGASQITE FPDLTGTATL ESLTLTGAKI SSLPQTVCDQ LPNLQVLDLS YNLLEDLPSL SGCQKLQKID LRHNEIYEIK GGTFQQLFNL RSLNLARNKI AIIHPNAFST LPSLIKLDLS SNLLSSFPVT GLHGLTHLKL TGNRALQSLI PSANFPELKI IEMPYAYQCC AFGGCENVYK IPNQWNKDDS SSVDDLRKKD AGLFQVQDER DLEDFLLDFE EDLKVLHSVQ CSPPPGPFKP CEHLFGSWLI RIGVWTTAVL ALSCNALVAF TVFRTPLYIS SIKLLIGVIA VVDILMGVSS AILAVVDTFT FGSFAQHGAW WEGGIGCQIV GFLSIFASES SVFLLTLAAL ERGFSVKCSS KFEMKAPLSS LKAIILLCVL LALTIATVPL LGGSEYNASP LCLPLPFGEP STTGYMVALV LLNSLCFLIM TIAYTRLYCS LEKGELENLW DCSMVKHTAL LLFTNCILYC PVAFLSFSSL LNLTFISPEV IKFILLVIVP LPACLNPLLY IVFNPHFKED MGSLGKQTRF WTRAKHPSLL SINSDDVEKR SCDSTQALVS FTHASIAYDL PSDSGSSPAY PMTESCHLSS VAFVPCL |
| 72 | Mouse LgR5 precursor; LGR5_mouse NP_034325; signal sequence = amino acids 1-21 | MDTSCVHMLL SLLALLQLVA AGSPGPDAI PRGCPSHCHC ELDGRMLLRV DCSDLGLSEL PSNLSVFTSY LDLSMNNISQ LPASLLHRLC FLEELRLAGN ALTHIPKGAF TGLHSLKVLM LQNNQLRQVP EEALQNLRSL QSLRLDANHI SYVPPSCFSG LHSLRHLWLD DNALTDVPVQ AFRSLSALQA MTLALNKIHH IADYAFGNLS SLVVLHLHNN RIHSLGKKCF DGLHSLETLD |

| SEQ ID NO | Description | Sequence |
|---|---|---|
| | | LNYNNLDEFP TAIKTLSNLK ELGFHSNNIR SIPERAFVGN PSLITIHFYD NPIQFVGVSA FQHLPELRTL TLNGASHITE FPHLTGTATL ESLTLTGAKI SSLPQAVCDQ LPNLQVLDLS YNLLEDLPSL SGCQKLQKID LRHNEIYEIK GSTFQQLFNL RSLNLAWNKI AIIHPNAFST LPSLIKLDLS SNLLSSFPVT GLHGLTHLKL TGNRALQSLI PSANFPELKI IEMPSAYQCC AFGGCENVYK ISNQWNKDDG NSVDDLHKKD AGLFQVQDER DLEDFLLDFE EDLKALHSVQ CSPSPGPFKP CEHLFGSWLI RIGVWTTAVL ALSCNALVAL TVFRTPLYIS SIKLLIGVIA VVDILMGVSS AVLAAVDAFT FGRFAQHGAW WEDGIGCQIV GFLSIFASES SIFLLTLAAL ERGFSVKCSS KFEVKAPLFS LRAIVLLCVL LALTIATIPL LGGSKYNASP LCLPLPFGEP STTGYMVALV LLNSLCFLIM TIAYTKLYCS LEKGELENLW DCSMVKHIAL LLFANCILYC PVAFLSFSSL LNLTFISPDV IKFILLVIVP LPSCLNPLLY IVFNPHFKED MGSLGKHTRF WMRSKHASLL SINSDDVEKR SCESTQALVS FTHASIAYDL PSTSGASPAY PMTESCHLSS VAFVPCL |
| 73 | Mouse LgR5 mature, without signal sequence; amino acids 22 to 907 | GSSPGPDAI PRGCPSHCHC ELDGRMLLRV DCSDLGLSEL PSNLSVFTSY LDLSMNNISQ LPASLLHRLC FLEELRLAGN ALTHIPKGAF TGLHSLKVLM LQNNQLRQVP EEALQNLRSL QSLRLDANHI SYVPPSCFSG LHSLRHLWLD DNALTDVPVQ AFRSLSALQA MTLALNKIHH IADYAFGNLS SLVVLHLHNN RIHSLGKKCF DGLHSLETLD LNYNNLDEFP TAIKTLSNLK ELGFHSNNIR SIPERAFVGN PSLITIHFYD NPIQFVGVSA FQHLPELRTL TLNGASHITE FPHLTGTATL ESLTLTGAKI SSLPQAVCDQ LPNLQVLDLS YNLLEDLPSL SGCQKLQKID LRHNEIYEIK GSTFQQLFNL RSLNLAWNKI AIIHPNAFST LPSLIKLDLS SNLLSSFPVT GLHGLTHLKL TGNRALQSLI PSANFPELKI IEMPSAYQCC AFGGCENVYK ISNQWNKDDG NSVDDLHKKD AGLFQVQDER DLEDFLLDFE EDLKALHSVQ CSPSPGPFKP CEHLFGSWLI RIGVWTTAVL ALSCNALVAL TVFRTPLYIS SIKLLIGVIA VVDILMGVSS AVLAAVDAFT FGRFAQHGAW WEDGIGCQIV GFLSIFASES SIFLLTLAAL ERGFSVKCSS KFEVKAPLFS LRAIVLLCVL LALTIATIPL LGGSKYNASP LCLPLPFGEP STTGYMVALV LLNSLCFLIM TIAYTKLYCS LEKGELENLW DCSMVKHIAL LLFANCILYC PVAFLSFSSL LNLTFISPDV IKFILLVIVP LPSCLNPLLY IVFNPHFKED MGSLGKHTRF WMRSKHASLL SINSDDVEKR SCESTQALVS FTHASIAYDL PSTSGASPAY PMTESCHLSS VAFVPCL |
| 74 | hu8E11.v2 V205C cysteine engineered light chain (Igκ) | DIVMTQSPDS LAVSLGERAT INCRASESVD NYGNSFMHWY QQKPGQPPKL LIYLASNLES GVPDRFSGSG SGTDFTLTIS SLQAEDVAVY YCQQNYEDPF TFGQGTKVEI KRTVAAPSVF IFPPSDEQLK SGTASVVCLL NNFYPREAKV QWKVDNALQS GNSQESVTEQ DSKDSTYSLS STLTLSKADY EKHKVYACEV THQGLSSPCT KSFNRGEC |
| 75 | hu8E11.v2 A118C cysteine engineered heavy chain (IgG1) | EVQLVQSGAE VKKPGASVKV SCKASGYTFS AYWIEWVRQA PGQGLEWIGE ILPGSDSTDY NEKFKVRATF TSDTSTSTVY LELSSLRSED TAVYYCARGG HYGSLDYWGQ GTLVTVSSCS TKGPSVFPLA PSSKSTSGGT AALGCLVKDY FPEPVTVSWN SGALTSGVHT FPAVLQSSGL YSLSSVVTVP SSSLGTQTYI CNVNHKPSNT KVDKKVEPKS CDKTHTCPPC PAPELLGGPS VFLFPPKPKD TLMISRTPEV TCVVVDVSHE DPEVKFNWYV DGVEVHNAKT KPREEQYNST YRVVSVLTVL HQDWLNGKEY KCKVSNKALP APIEKTISKA KGQPREPQVY TLPPSREEMT KNQVSLTCLV KGFYPSDIAV EWESNGQPEN NYKTTPPVLD SDGSFFLYSK LTVDKSRWQQ GNVFSCSVMH EALHNHYTQK SLSLSPGK |
| 76 | hu8E11.v2 S400C cysteine engineered heavy chain (IgG1) | EVQLVQSGAE VKKPGASVKV SCKASGYTFS AYWIEWVRQA PGQGLEWIGE ILPGSDSTDY NEKFKVRATF TSDTSTSTVY LELSSLRSED TAVYYCARGG HYGSLDYWGQ GTLVTVSSAS TKGPSVFPLA PSSKSTSGGT AALGCLVKDY FPEPVTVSWN SGALTSGVHT FPAVLQSSGL YSLSSVVTVP SSSLGTQTYI CNVNHKPSNT KVDKKVEPKS CDKTHTCPPC PAPELLGGPS VFLFPPKPKD TLMISRTPEV TCVVVDVSHE DPEVKFNWYV DGVEVHNAKT KPREEQYNST YRVVSVLTVL HQDWLNGKEY KCKVSNKALP APIEKTISKA KGQPREPQVY TLPPSREEMT |

| SEQ ID NO | Description | Sequence |
|---|---|---|
| | | KNQVSLTCLV KGFYPSDIAV EWESNGQPEN NYKTTPPVLD CDGSFFLYSK LTVDKSRWQQ GNVFSCSVMH EALHNHYTQK SLSLSPGK |
| 77 | YW353 V205C cysteine engineered light chain (Igκ) | DIQMTQSPSS LSASVGDRVT ITCRASQDVS TAVAWYQQKP GKAPKLLIYS ASFLYSGVPS RFSGSGSGTD FTLTISSLQP EDFATYYCQQ SYTTPPTFGQ GTKVEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPCTKSFN RGEC |
| 78 | YW353 A118C cysteine engineered heavy chain (IgG1) | EVQLVESGGG LVQPGGSLRL SCAASGFTFT SYSISWVRQA PGKGLEWVAE IYPPGGYTDY ADSVKGRFTI SADTSKNTAY LQMNSLRAED TAVYYCAKAR LFFDYWGQGT LVTVSSCSTK GPSVFPLAPS SKSTSGGTAA LGCLVKDYFP EPVTVSWNSG ALTSGVHTFP AVLQSSGLYS LSSVVTVPSS SLGTQTYICN VNHKPSNTKV DKKVEPKSCD KTHTCPPCPA PELLGGPSVF LFPPKPKDTL MISRTPEVTC VVVDVSHEDP EVKFNWYVDG VEVHNAKTKP REEQYNSTYR VVSVLTVLHQ DWLNGKEYKC KVSNKALPAP IEKTISKAKG QPREPQVYTL PPSREEMTKN QVSLTCLVKG FYPSDIAVEW ESNGQPENNY KTTPPVLDSD GSFFLYSKLT VDKSRWQQGN VFSCSVMHEA LHNHYTQKSL SLSPGK |
| 79 | YW353 S400C cysteine engineered heavy chain (IgG1) | EVQLVESGGG LVQPGGSLRL SCAASGFTFT SYSISWVRQA PGKGLEWVAE IYPPGGYTDY ADSVKGRFTI SADTSKNTAY LQMNSLRAED TAVYYCAKAR LFFDYWGQGT LVTVSSASTK GPSVFPLAPS SKSTSGGTAA LGCLVKDYFP EPVTVSWNSG ALTSGVHTFP AVLQSSGLYS LSSVVTVPSS SLGTQTYICN VNHKPSNTKV DKKVEPKSCD KTHTCPPCPA PELLGGPSVF LFPPKPKDTL MISRTPEVTC VVVDVSHEDP EVKFNWYVDG VEVHNAKTKP REEQYNSTYR VVSVLTVLHQ DWLNGKEYKC KVSNKALPAP IEKTISKAKG QPREPQVYTL PPSREEMTKN QVSLTCLVKG FYPSDIAVEW ESNGQPENNY KTTPPVLDCD GSFFLYSKLT VDKSRWQQGN VFSCSVMHEA LHNHYTQKSL SLSPGK |
| 80 | V205C cysteine engineered light chain constant region (Igκ) | TVAAPSVFIF PPSDEQLKSG TASVVCLLNN FYPREAKVQW KVDNALQSGN SQESVTEQDS KDSTYSLSST LTLSKADYEK HKVYACEVTH QGLSSPCTKS FNRGEC |
| 81 | A118C cysteine engineered heavy chain constant region (IgG1) | CSTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPELLGG PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSREE MTKNQVSLTC LVKGFYPSDI AVEWESNGQP ENNYKTTPPV LDSDGSFFLY SKLTVDKSRW QQGNVFSCSV MHEALHNHYT QKSLSLSPGK |
| 82 | S400C cysteine engineered heavy chain constant region (IgG1) | ASTKGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPELLGG PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSREE MTKNQVSLTC LVKGFYPSDI AVEWESNGQP ENNYKTTPPV LDCDGSFFLY SKLTVDKSRW QQGNVFSCSV MHEALHNHYT QKSLSLSPGK |

What is claimed is:

1. An immunoconjugate comprising an isolated antibody that binds to LgR5, wherein the antibody comprises:
   a) HVR-H1 comprising the amino acid sequence of SEQ ID NO: 30, HVR-H2 comprising the amino acid sequence of SEQ ID NO: 31, HVR-H3 comprising the amino acid sequence of SEQ ID NO: 32, HVR-L1 comprising the amino acid sequence of SEQ ID NO: 27, HVR-L2 comprising the amino acid sequence of SEQ ID NO: 28, and HVR-L3 comprising the amino acid sequence of SEQ ID NO: 29; or
   b) HVR-H1 comprising the amino acid sequence of SEQ ID NO: 60, HVR-H2 comprising the amino acid sequence of SEQ ID NO: 61, HVR-H3 comprising the amino acid sequence of SEQ ID NO: 62, HVR-L1 comprising the amino acid sequence of SEQ ID NO: 57, HVR-L2 comprising the amino acid sequence of SEQ ID NO: 58, and HVR-L3 comprising the amino acid sequence of SEQ ID NO: 59.

2. The immunoconjugate of claim 1, wherein the antibody is a monoclonal antibody.

3. The immunoconjugate of claim 1, wherein the antibody is a human, humanized, or chimeric antibody.

4. The immunoconjugate of claim 1, wherein the antibody is an antibody fragment that binds LgR5.

5. The immunoconjugate of claim 1, wherein LgR5 is human LgR5 of SEQ ID NO: 67.

6. The immunoconjugate of claim 1, wherein the antibody comprises:
   a) heavy chain framework FR3 sequence of SEQ ID NO: 40;
   b) heavy chain framework FR3 sequence of SEQ ID NO: 41;
   c) heavy chain framework FR3 sequence of SEQ ID NO: 42; or
   d) heavy chain framework FR3 sequence of SEQ ID NO: 43.

7. The immunoconjugate of claim 1, wherein the antibody comprises a light chain framework FR3 sequence of SEQ ID NO: 35.

8. The immunoconjugate of claim 1, wherein the antibody comprises:
   a) a VH sequence having at least 95% sequence identity to the amino acid sequence of SEQ ID NO: 6;
   b) a VL sequence having at least 95% sequence identity to the amino acid sequence of SEQ ID NO: 5;
   c) a VH sequence as in (a) and a VL sequence as in (b);
   d) a VH sequence having at least 95% sequence identity to the amino acid sequence of SEQ ID NO: 8;
   e) a VL sequence having at least 95% sequence identity to the amino acid sequence of SEQ ID NO: 7;
   f) a VH sequence as in (d) and a VL sequence as in (e);
   g) a VH sequence having at least 95% sequence identity to the amino acid sequence of SEQ ID NO: 10;
   h) a VL sequence having at least 95% sequence identity to the amino acid sequence of SEQ ID NO: 9;
   i) a VH sequence as in (g) and a VL sequence as in (h);
   j) a VH sequence having at least 95% sequence identity to the amino acid sequence of SEQ ID NO: 12;
   k) a VL sequence having at least 95% sequence identity to the amino acid sequence of SEQ ID NO: 11;
   l) a VH sequence as in (j) and a VL sequence as in (k);
   m) a VH sequence having at least 95% sequence identity to the amino acid sequence of SEQ ID NO: 14;
   n) a VL sequence having at least 95% sequence identity to the amino acid sequence of SEQ ID NO: 13;
   o) a VH sequence as in (m) and a VL sequence as in (n);
   p) a VH sequence having at least 95% sequence identity to the amino acid sequence of SEQ ID NO: 16;
   q) a VL sequence having at least 95% sequence identity to the amino acid sequence of SEQ ID NO: 15;
   r) a VH sequence as in (p) and a VL sequence as in (q);
   s) a VH sequence having at least 95% sequence identity to the amino acid sequence of SEQ ID NO: 18;
   t) a VL sequence having at least 95% sequence identity to the amino acid sequence of SEQ ID NO: 17;
   u) a VH sequence as in (s) and a VL sequence as in (t);
   v) a VH sequence having at least 95% sequence identity to the amino acid sequence of SEQ ID NO: 20;
   w) a VL sequence having at least 95% sequence identity to the amino acid sequence of SEQ ID NO: 19;
   x) a VH sequence as in (v) and a VL sequence as in (w);
   y) a VH sequence having at least 95% sequence identity to the amino acid sequence of SEQ ID NO: 26;
   z) a VL sequence having at least 95% sequence identity to the amino acid sequence of SEQ ID NO: 25; or
   aa) a VH sequence as in (y) and a VL sequence as in (z).

9. The immunoconjugate of claim 8, comprising a VH sequence selected from SEQ ID NOs: 6, 8, 10, 12, 14, 16, 18, 20, and 26.

10. The immunoconjugate of claim 8, comprising a VL sequence selected from SEQ ID NOs: 5, 7, 9, 11, 13, 15, 17, 19, and 25.

11. An immunoconjugate comprising:
   a) a VH sequence of SEQ ID NO: 6 and a VL sequence of SEQ ID NO: 5;
   b) a VH sequence of SEQ ID NO: 8 and a VL sequence of SEQ ID NO: 7;
   c) a VH sequence of SEQ ID NO: 10 and a VL sequence of SEQ ID NO: 9;
   d) a VH sequence of SEQ ID NO: 12 and a VL sequence of SEQ ID NO: 11;
   e) a VH sequence of SEQ ID NO: 14 and a VL sequence of SEQ ID NO: 13;
   f) a VH sequence of SEQ ID NO: 16 and a VL sequence of SEQ ID NO: 15;
   g) a VH sequence of SEQ ID NO: 18 and a VL sequence of SEQ ID NO: 17;
   h) a VH sequence of SEQ ID NO: 20 and a VL sequence of SEQ ID NO: 19; or
   i) a VH sequence of SEQ ID NO: 26 and a VL sequence of SEQ ID NO: 25;
and a cytotoxic agent.

12. The immunoconjugate of claim 1, which is an IgG1, IgG2a or IgG2b antibody.

13. The immunoconjugate of claim 1 having the formula Ab-(L-D)p, wherein:

(a) Ab is the antibody;

(b) L is a linker;

(c) D is a drug selected from a maytansinoid, an auristatin, a calicheamicin, a pyrrolobenzodiazepine, and a nemorubicin derivative; and (d) p ranges from 1-8.

14. The immunoconjugate of claim 13, wherein D is an auristatin.

15. The immunoconjugate of claim 14, wherein D has formula $D_E$

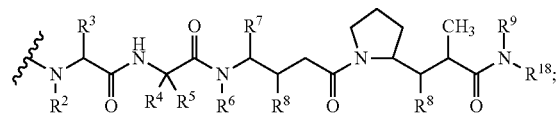

and wherein $R^2$ and $R^6$ are each methyl, $R^3$ and $R^4$ are each isopropyl, $R^5$ is H, $R^7$ is sec-butyl, each $R^8$ is independently selected from $CH_3$, $O-CH_3$, OH, and H; $R^9$ is H; and $R^{18}$ is $-C(R^8)_2-C(R^8)_2$-aryl.

16. The immunoconjugate of claim 13, wherein the drug is MMAE.

17. The immunoconjugate of claim 13, wherein D is a pyrrolobenzodiazepine of Formula A:

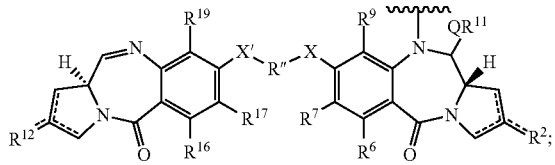

wherein the dotted lines indicate the optional presence of a double bond between C1 and C2 or C2 and C3;

$R^2$ is independently selected from H, OH, =O, =CH$_2$, CN, R, OR, =CH—$R^D$, =C($R^D$)$_2$, O—SO$_2$—R, CO$_2$R and COR, and optionally further selected from halo or dihalo, wherein $R^D$ is independently selected from R, CO$_2$R, COR, CHO, CO$_2$H, and halo;

$R^6$ and $R^9$ are independently selected from H, R, OH, OR, SH, SR, NH$_2$, NHR, NRR', NO$_2$, Me$_3$Sn and halo;

$R^7$ is independently selected from H, R, OH, OR, SH, SR, NH$_2$, NHR, NRR', NO$_2$, Me$_3$Sn and halo;

Q is independently selected from O, S and NH;

$R^{11}$ is either H, or R or, where Q is O, SO$_3$M, where M is a metal cation;

R and R' are each independently selected from optionally substituted $C_{1-8}$ alkyl, $C_{3-8}$ heterocyclyl and $C_{5-20}$ aryl groups, and optionally in relation to the group NRR', R and R' together with the nitrogen atom to which they are attached form an optionally substituted 4-, 5-, 6- or 7-membered heterocyclic ring;

$R^{12}$, $R^{16}$, $R^{19}$ and $R^{17}$ are as defined for $R^2$, $R^6$, $R^9$ and $R^7$ respectively;

R" is a $C_{3-12}$ alkylene group, which chain may be interrupted by one or more heteroatoms and/or aromatic rings that are optionally substituted; and X and X' are independently selected from O, S and N(H).

18. The immunoconjugate of claim 17, wherein D has the structure:

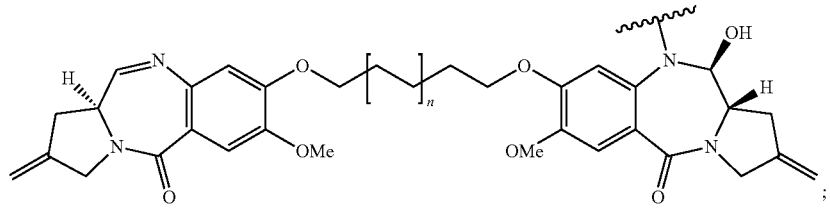

(A(II))

wherein n is 0 or 1.

19. The immunoconjugate of claim 17, wherein D has a structure selected from:

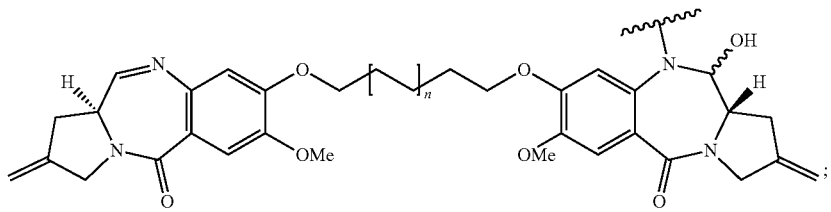

A(I)

-continued

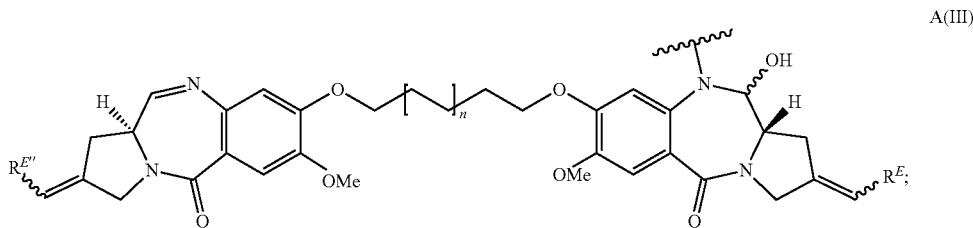
A(III)

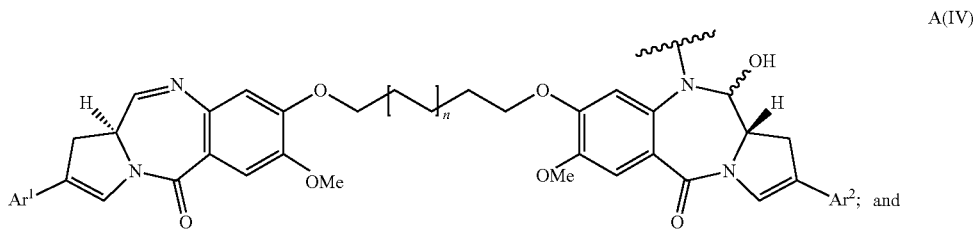
A(IV); and

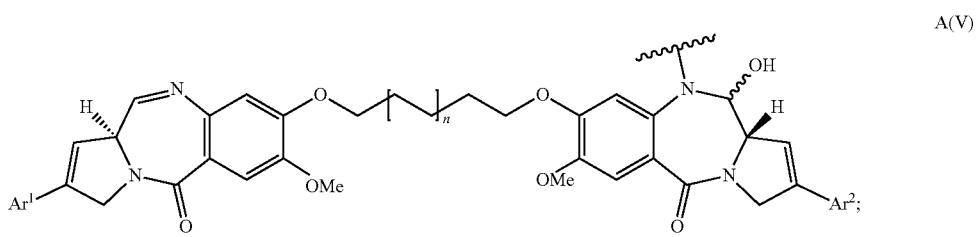
A(V);

wherein $R^E$ and $R^{E''}$ are each independently selected from H or $R^D$, wherein $R^D$ is independently selected from R, $CO_2R$, COR, CHO, $CO_2H$, and halo;

wherein $Ar^1$ and $Ar^2$ are each independently optionally substituted $C_{5-20}$ aryl; and wherein n is 0 or 1.

20. The immunoconjugate of claim 13, wherein D is a pyrrolobenzodiazepine of Formula B:

wherein the horizontal wavy line indicates the covalent attachment site to the linker;

$R^{V1}$ and $R^{V2}$ are independently selected from H, methyl, ethyl, phenyl, fluoro-substituted phenyl, and $C_{5-6}$ heterocyclyl; and n is 0 or 1.

21. The immunoconjugate of claim 13, wherein D is a nemorubicin derivative.

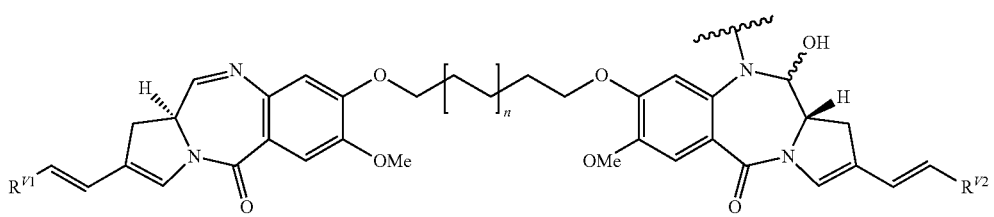

22. The immunoconjugate of claim 21, wherein D has a structure selected from:

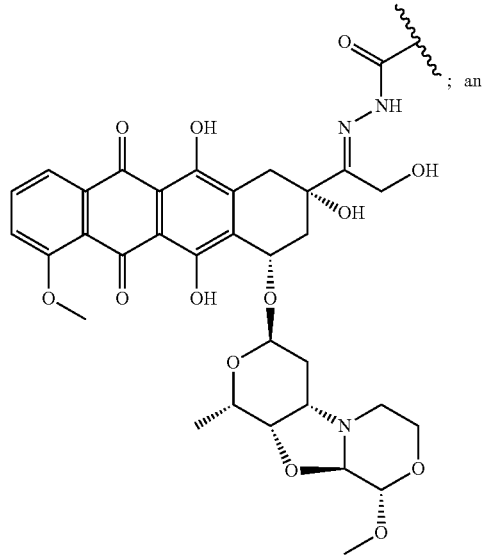

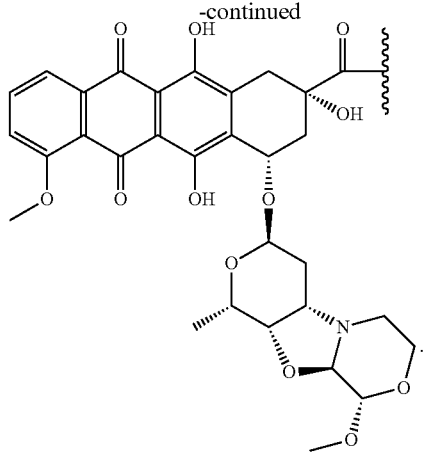

23. The immunoconjugate of claim 13, wherein the linker is cleavable by a protease.
24. The immunoconjugate of claim 23, wherein the linker comprises a val-cit dipeptide or a Phe-Lys dipeptide.
25. The immunoconjugate of claim 13, wherein the linker is acid-labile.
26. The immunoconjugate of claim 25, wherein the linker comprises hydrazone.
27. The immunoconjugate of claim 15 having the formula:

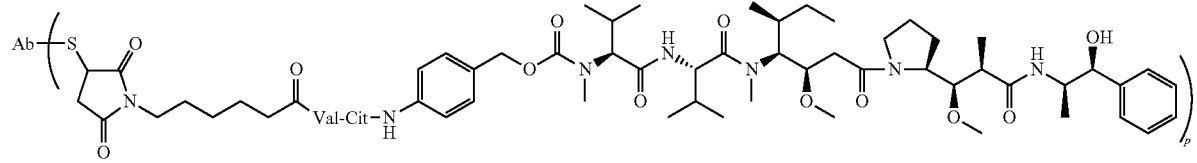

wherein S is a sulfur atom.
28. The immunoconjugate of claim 18 having the formula:

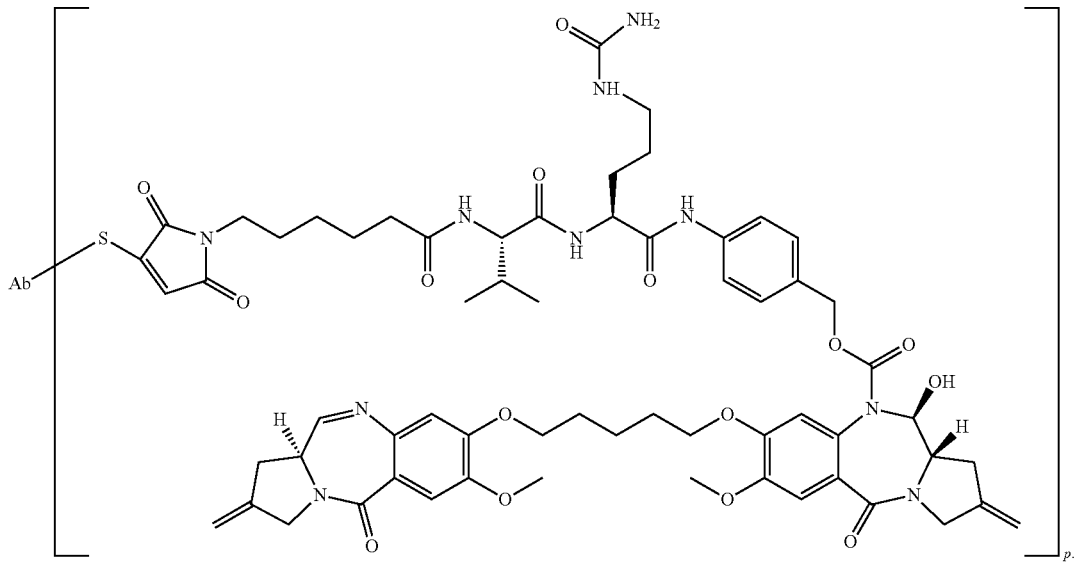

29. The immunoconjugate of claim 22 having a formula selected from:
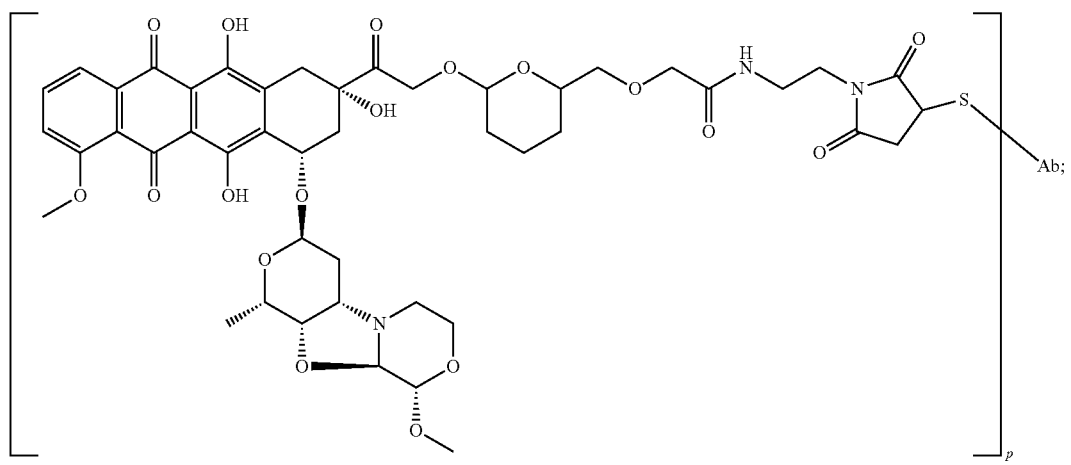
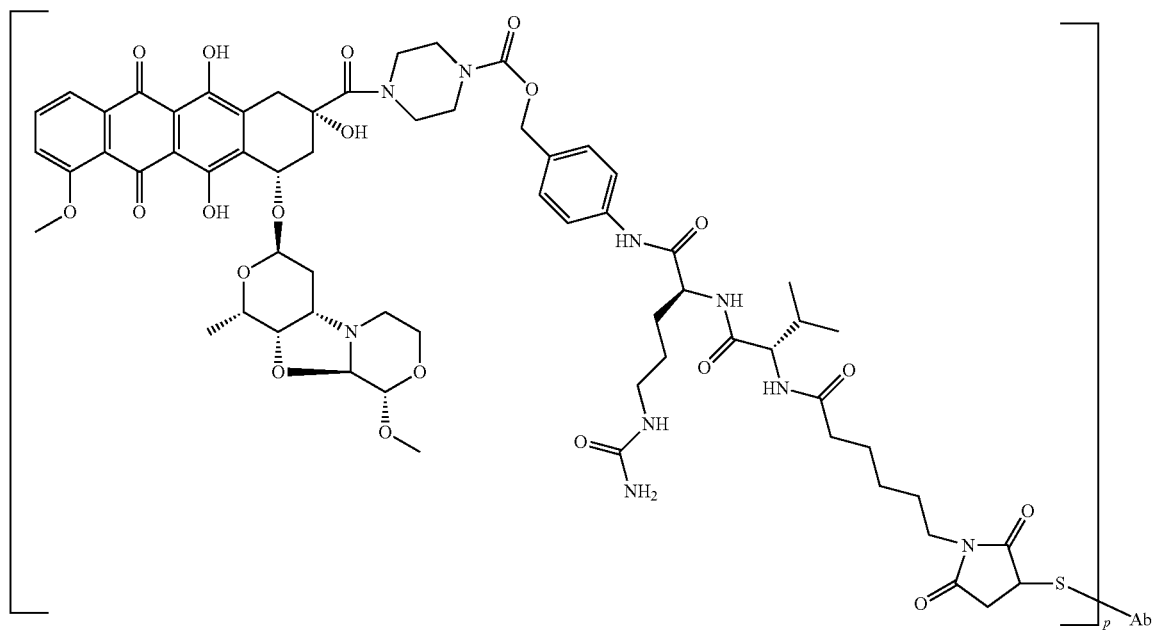
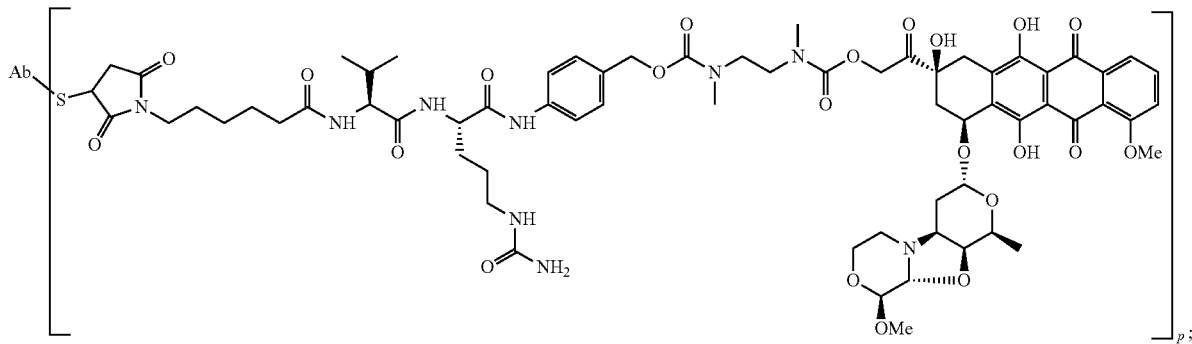

-continued
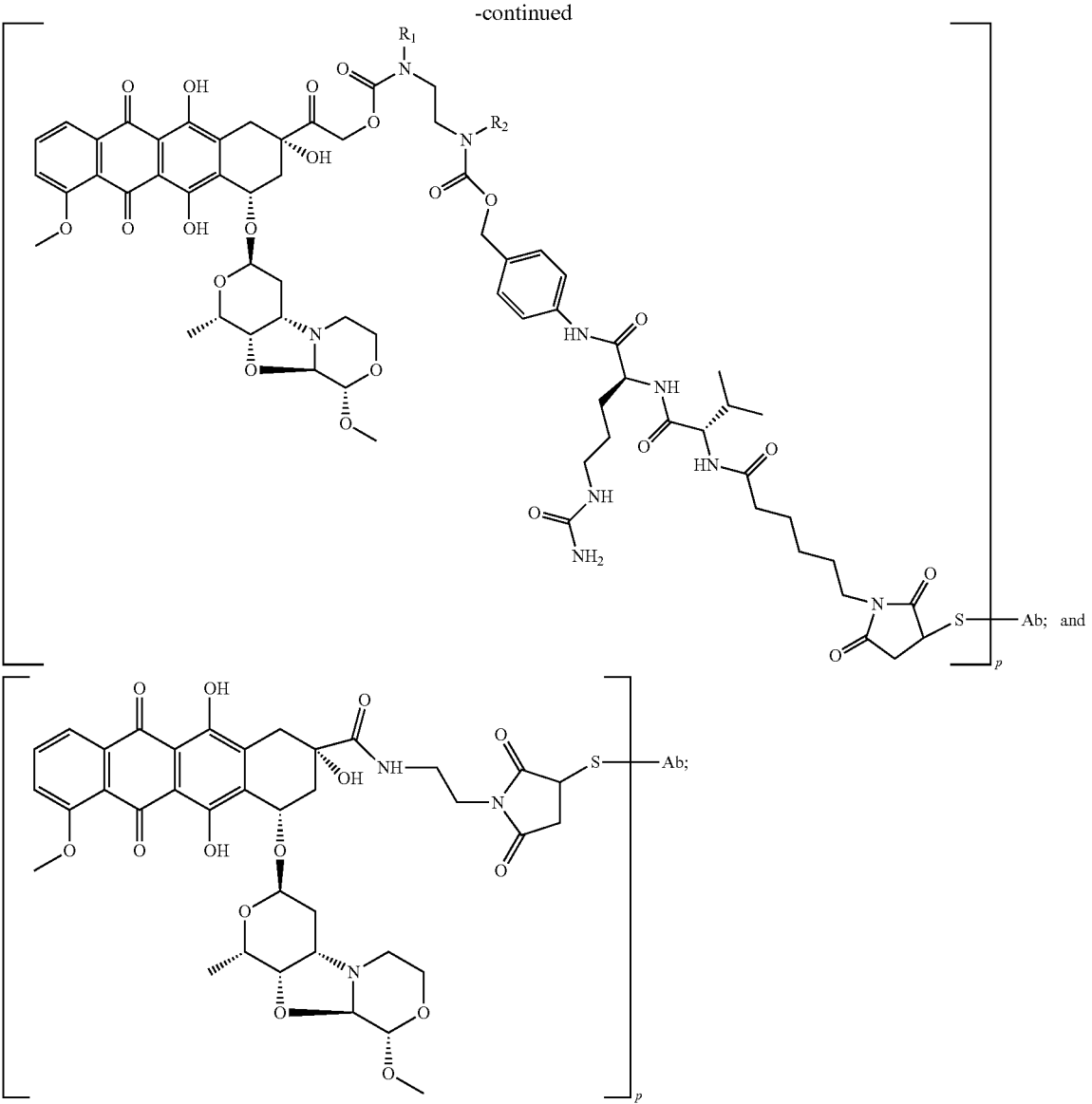
wherein $R_1$ and $R_2$ are independently selected from H and $C_1$-$C_6$ alkyl.
30. The immunoconjugate of claim 13, wherein p ranges from 2-5.
31. A pharmaceutical formulation comprising the immunoconjugate of claim 13 and a pharmaceutically acceptable carrier.
* * * * *